United States Patent
Yancopoulos et al.

(10) Patent No.: US 10,519,240 B2
(45) Date of Patent: Dec. 31, 2019

(54) ANTI-FGFR1C ANTIBODY-FGF21 FUSION PROTEINS

(71) Applicant: Regeneron Pharmaceuticals, Inc., Tarrytown, NY (US)

(72) Inventors: George D. Yancopoulos, Yorktown Heights, NY (US); Andrew J. Murphy, Croton-on-Hudson, NY (US); Jesper Gromada, Scarsdale, NY (US); David R. Buckler, Sleepy Hollow, NY (US); Kihwa Kang, Montvale, NJ (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 48 days.

(21) Appl. No.: 15/128,897

(22) PCT Filed: Mar. 25, 2015

(86) PCT No.: PCT/US2015/022548
§ 371 (c)(1),
(2) Date: Sep. 23, 2016

(87) PCT Pub. No.: WO2015/148708
PCT Pub. Date: Oct. 1, 2015

(65) Prior Publication Data
US 2017/0174769 A1 Jun. 22, 2017

Related U.S. Application Data

(60) Provisional application No. 61/970,002, filed on Mar. 25, 2014.

(51) Int. Cl.
| | |
|---|---|
| C07K 14/50 | (2006.01) |
| C07K 16/28 | (2006.01) |
| A61K 38/18 | (2006.01) |
| A61K 39/395 | (2006.01) |
| C07K 16/22 | (2006.01) |
| C07K 16/40 | (2006.01) |
| A61K 38/00 | (2006.01) |
| A61K 39/00 | (2006.01) |

(52) U.S. Cl.
CPC ......... *C07K 16/2863* (2013.01); *C07K 14/50* (2013.01); *C07K 16/22* (2013.01); *C07K 16/40* (2013.01); *C12Y 302/01031* (2013.01); *A61K 38/00* (2013.01); *A61K 2039/505* (2013.01); *C07K 2317/31* (2013.01); *C07K 2317/33* (2013.01); *C07K 2317/52* (2013.01); *C07K 2317/524* (2013.01); *C07K 2317/526* (2013.01); *C07K 2317/56* (2013.01); *C07K 2317/565* (2013.01); *C07K 2317/622* (2013.01); *C07K 2317/75* (2013.01); *C07K 2317/92* (2013.01); *C07K 2319/75* (2013.01)

(58) Field of Classification Search
None
See application file for complete search history.

(56) References Cited

U.S. PATENT DOCUMENTS

| | | | |
|---|---|---|---|
| 7,700,558 B2 | 4/2010 | Thomason et al. | |
| 7,704,952 B2 | 4/2010 | Thomason et al. | |
| 7,727,742 B2 | 6/2010 | Thomason et al. | |
| 8,093,356 B2 | 1/2012 | Hays et al. | |
| 8,361,963 B2 | 1/2013 | Belouski et al. | |
| 8,410,051 B2 | 4/2013 | Belouski et al. | |
| 8,618,053 B2 | 12/2013 | Belouski et al. | |
| 9,085,626 B2* | 7/2015 | Sonoda | C07K 16/28 |
| 9,517,264 B2* | 12/2016 | Fachini | C07K 16/2863 |
| 2011/0135657 A1 | 6/2011 | Hy et al. | |
| 2012/0009200 A1 | 1/2012 | Sun et al. | |
| 2012/0121609 A1 | 5/2012 | Sun et al. | |
| 2012/0219563 A1 | 8/2012 | Sun et al. | |
| 2012/0294861 A1 | 11/2012 | Sondoa et al. | |
| 2013/0129725 A1* | 5/2013 | Fachin | C07K 16/2863 424/134.1 |
| 2013/0330336 A1 | 12/2013 | Darling et al. | |
| 2015/0218276 A1 | 8/2015 | Chen et al. | |

FOREIGN PATENT DOCUMENTS

| | | |
|---|---|---|
| CA | 2782814 A1 | 6/2011 |
| EP | 1680140 B1 | 7/2006 |
| EP | 2060270 A2 | 5/2009 |
| WO | 2010/006214 A1 | 1/2010 |
| WO | 2011/071783 A1 | 6/2011 |
| WO | 2011/130417 A2 | 10/2011 |
| WO | 2012/140086 A2 | 11/2011 |
| WO | 2012/066075 A1 | 5/2012 |
| WO | 2012/154263 A1 | 11/2012 |
| WO | 2012/170438 A2 | 12/2012 |
| WO | 2013/033452 A2 | 3/2013 |
| WO | 2015/148708 A1 | 10/2015 |

OTHER PUBLICATIONS

Vajdos et al. J. Mol. Biol. 320(2): 415-428, 2002.*
Foltz, et al., "Treating Diabetes and Obesity with an FGF21-Mimetic Antibody Activating the βKlotho/FGFR1c Receptor Complex," Science Translational Medicine, US, vol. 4 (No. 162); (Nov. 28, 2012); pp. 1-10.
Ogawa, Y., et al., "βKlotho is required for metabolic activity of fibroblast growth factor 21," Proceedings of the National Academy of Sciences, vol. 104 (No. 18); (May 1, 2007); pp. 7432-7437.
Yie et al., "Understanding the Physical Interactions in the FGF21/FGF/ β-Klotho Complex: Structural Requirements and Implications in FGF21 Signaling," Chemical Biology & Drug Design, vol. 79 (No. 4); (Apr. 1, 2012); pp. 398-410.

(Continued)

*Primary Examiner* — Christine J Saoud
(74) *Attorney, Agent, or Firm* — Schwabe, Williamson & Wyatt PC; Christopher Westberg

(57) ABSTRACT

The present invention provides agonists of FGF21 signaling. In particular, the present invention provides FGF21 receptor (FGF21R) agonists that are capable of simultaneously binding βKlotho (KLB) and/or FGFR1c to mimic the signaling activity of FGF21. The present invention also provides anti-FGF21 and anti-KLB/FGFR1c antibodies and antigen-binding fragments thereof. Also provided are methods of treating various metabolic disorders by administering the FGF21R agonists and/or anti-FGF21 antibodies to a subject in need thereof.

10 Claims, 8 Drawing Sheets

Specification includes a Sequence Listing.

(56) References Cited

OTHER PUBLICATIONS

Kharitonenkov, et al., "FGF-21 as a novel metabolic regulator"; (2005), J. Clin. Invest. 115: 1627-1635.
Kharitonenkov, et al., "The Metabolic State of Diabetic Monkeys Is Regulated by Fibroblast Growth Factor 21"; (2007), Endocrinology 148: 774-781.
Long and Kharitonenkov, "Hormone-like fibroblast growth factors and metabolic regulation"; (2011), Biochim. Biophys, Acta. 1812: 791-795.
Suzuki, et al., "βKlotho is Required for Fibroblast Growth Factor (FGF) 21 Signaling through FGF Receptor (FGFR) 1c and FGFR3c"; (2008), Molecular Endocrinology 22: 1006-1014.
Adams, et al., "The breadth of FGF21's metabolic actions are governed by FGFR1 in adipose tissue"; (2013) Molecular Metabolism 2:31-37.
Badman et al., "Hepatic Fibroblast Growth Factor 21 is Regulated by PPARa and is a Key Mediator of Hepatic Lipid Metabolism in Ketotic States"; (2007) Cell Metabolism 5(6):426-37.
Gaich, et al., "The Effects on LY2405319, an FGF21 Analog, in Obese Human Subjects with Type 2 Diabetes", (2013) Cell Metabolism18 (3):333-40.
Goetz et al. "Molecular Insights into the Klotho-Dependent, Endocrine Mode of Action of Fibroblast Growth Factor 19 Subfamily Members"; Molecular and Cellular Biology, May 2007, vol. 27, No. 9; pp. 3417-3428.
Goetz, et al., "Conversion of a Paracrine Fibroblast Growth Factor into an Endocrine Fibroblast Growth Factor"; (2012) Journal of Biological Chemistry 287( 34): 29134-29146.
Iglesias, et al., "Biological role, clinical significance, and therapeutic possibilities of the recently discovered metabolic hormone fibroblastic growth factor 21"; (2012) European Journal of Endocrinology 167:301-309.
Kharitonenkov and Adams, "Inventing new medicines: The FGF21 story", (Jun. 2014) Molecular Metabolism 3(3):221-229.
Micanovic, et al., "Different Roles of N- and C-Termini in the Functional Activity of FGF21", (2009) Journal of Cellular Physiology 219: 227-234.
Ming et al., "Dynamics and Distribution of Klothoβ (KLB) and Fibroblast Growth Factor Receptor-1 (FGFR1) in Living Cells Reveal the Fibroblast Growth Factor-21 (FGF21)-induced Receptor Complex"; Journal of Biological Chemistry (2012) 287:19997-20006.
Mohammadi, et al., "Structural basis for fibroblast growth factor receptor activation"; (2005) Cytokine & Growth Factor Reviews 16:107-137.
Yie, J. et al., "FGF21 N- and C-termini play different roles in receptor interaction and activation"; (2009) FEBS Letters 583:19-24.
WIPO Application No. PCT/US2015/022548, PCT International Preliminary Report on Patentability dated Sep. 27, 2016; 8 pages.
WIPO Application No. PCT/US2015/022548, PCT International Search Report and Written Opinion of the International Searching Authority dated Jul. 3, 2015; 12 pages.

\* cited by examiner (A) 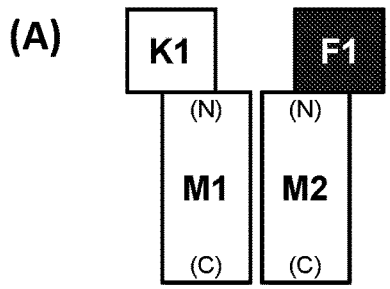

K1 = anti-KLB scFV, or
portion of FGF21 that binds KLB, or
anti-FGF21 scFv (binding FGFR1c site)

F1 = anti-FGFR1c scFV, or
portion of FGF21 that binds FGFR1c, or
anti-FGF21 scFv (binding KLB site)

(B) 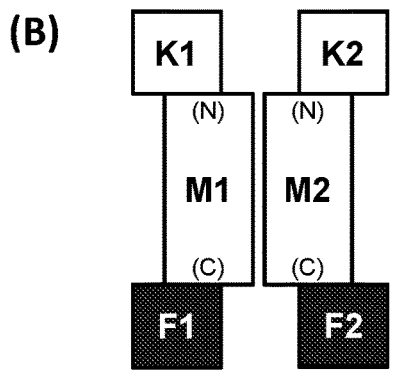

K1 & K2 = anti-KLB scFV, or
portion of FGF21 that binds KLB, or
anti-FGF21 scFv (binding FGFR1c site)

F1 & F2 = anti-FGFR1c scFV, or
portion of FGF21 that binds FGFR1c, or
anti-FGF21 scFv (binding KLB site)

(C) 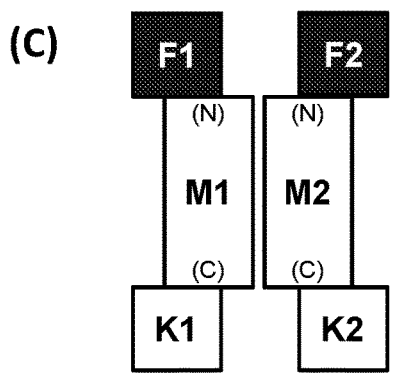

F1 & F2 = anti-FGFR1c scFV, or
portion of FGF21 that binds FGFR1c, or
anti-FGF21 scFv (binding KLB site)

K1 & K2 = anti-KLB scFV, or
portion of FGF21 that binds KLB, or
anti-FGF21 scFv (binding FGFR1c site)

Figure 1

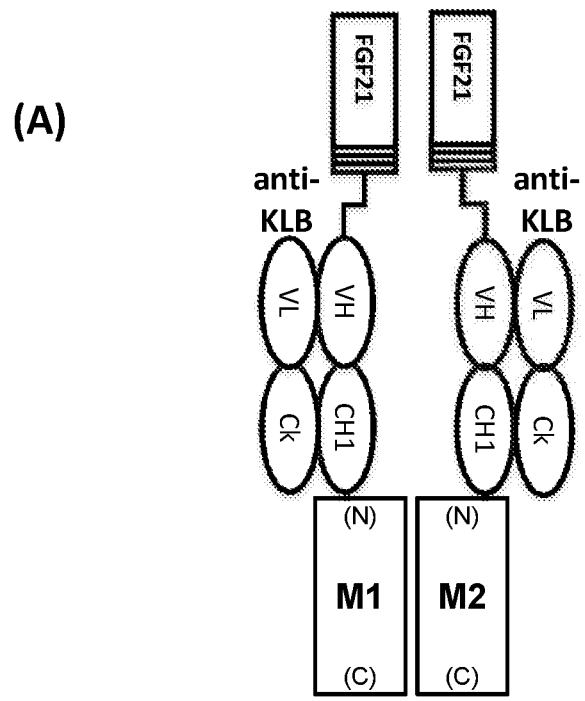
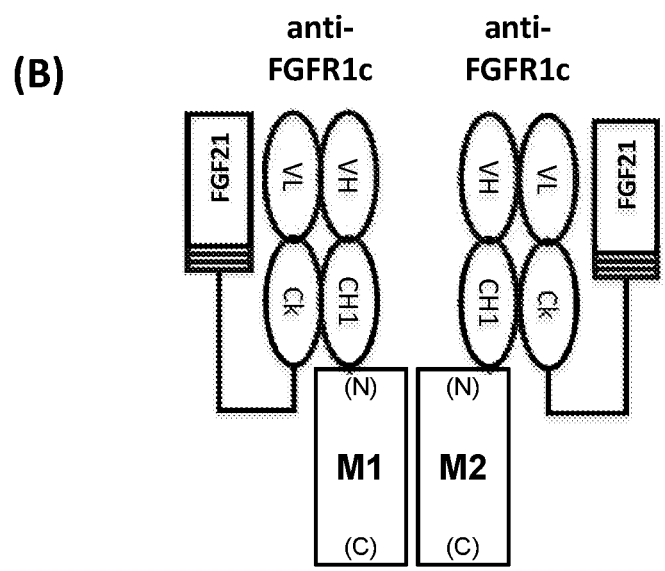
Figure 5

ANTI-FGFR1C ANTIBODY-FGF21 FUSION PROTEINS

CROSS-REFERENCE TO RELATED APPLICATIONS

This application is a US national stage of International Application No. PCT/US2015/022548, filed Mar. 25, 2015, which claims the benefit under 35 U.S.C. § 119(e) of U.S. Provisional Patent Application No. 61/970,002, filed Mar. 25, 2014, each of which is incorporated herein by reference in its entirety for all purposes.

SEQUENCE LISTING

This application incorporates by reference the Sequence Listing submitted in Computer Readable Form as filename 1750_substitute_2_seqlisting.txt created on Jul. 10, 2019 (264902 bytes).

FIELD OF THE INVENTION

The present invention relates to agonists of the fibroblast growth factor 21 (FGF21) signaling pathway. In particular, the present invention provides agonist molecules capable of binding or interacting with βKlotho and FGF receptor 1c (FGFR1c) to thereby mimic the signaling activity of FGF21. The present invention further relates to antibodies, bispecific antibodies, and antigen-binding fragments thereof, which are specific for human FGF21 or KLB/FGFR1c, and methods of use thereof.

BACKGROUND

Fibroblast growth factor 21 (FGF21) is a member of the FGF family which produces beneficial effects on lipid levels, body weight and glucose metabolism in animals. For example, overexpression of FGF21 in transgenic mice has been shown to result in reduced glucose and triglyceride levels, and resistance to diet-induced obesity. (Kharitonenkov et al. (2005), *J. Clin. Invest.* 115; 1627-1635). Moreover, the administration of exogenous FGF21 to rodents and primates results in normalization of blood glucose levels, reduced triglyceride and cholesterol levels, improved glucose tolerance and improved insulin sensitivity. (Kharitonenkov et al. (2007), *Endocrinol.* 148:774-781) FGF21 administration in experimental animal models has been shown to reduce body weight and body fat by increasing energy expenditure, physical activity, and metabolic rate. (Long and Kharitonenkov (2011) *Biochim. Biophys. Acta* 1812:791-795).

FGF21 signaling is mediated through its interaction with a receptor complex that includes βKlotho (KLB) and one of three different FGF receptors (FGFR1c, FGFR2c or FGFR3c). (Ogawa et al. (2007), *Proc. Natl. Acad. Sci. USA* 104:7432-7437; Suzuki et al. (2008), Mol. Endocrinol. 22:1006-1014). It is believed that the main functional receptor for FGF21 signaling in vivo is the KLB/FGFR1c complex (this complex is referred to herein as "FGF21R").

Pharmacological activation of FGF21 signaling has been proposed for the treatment of various diseases and disorders in humans including type-2 diabetes, obesity, dyslipidemia, and other metabolic conditions. Proposed therapeutic strategies for activating FGF21 signaling include administration of recombinant FGF21, and the use of agonistic antibodies that bind FGFR1 or the KLB/FGFR1c complex (US2011/0135657; US2012/0294861; US2013/0330336; WO 2011/130417; WO2012/170438; WO2013/033452). Nonetheless, there exists a need in the art for novel avidity-driven therapeutic approaches that take advantage of FGF21's beneficial metabolic properties.

BRIEF SUMMARY OF THE INVENTION

The present invention provides FGF21 receptor (FGF21R) agonists that are capable of simultaneously binding βKlotho (KLB) and FGFR1c to mimic the signaling activity of FGF21. The FGF21R agonists of the present invention comprise: a KLB-interacting domain (K1); an FGFR1c-interacting domain (F1); a first multimerizing domain (M1); and a second multimerizing domain (M2). According to certain embodiments, individual components of the FGF21R agonists are arranged such that K1 is attached to M1 or M2, and F1 is attached to M1 or M2. According to certain embodiments, a second KLB-interacting domain (K2) is attached to M1 or M2; and/or a second FGFR1c-interacting domain (F2) is attached to M1 or M2. Numerous arrangements and configurations of the K1, K2, F1, F2, M1 and M2 components are contemplated within the scope of the present invention, examples of which are described herein.

Various molecules can serve as KLB- or FGFR1c-interacting domains that can be included within the FGF21R agonists of the present invention. According to certain embodiments of the invention, the K1 and/or K2 components may comprise one or more molecules selected from: (a) an antigen-binding protein that specifically binds KLB; (b) a polypeptide comprising a KLB-binding portion of FGF21; or (c) an antigen-binding protein that specifically binds FGF21 at an epitope within the FGFR1c-interacting portion of FGF21. According to certain embodiments of the invention, the F1 and/or F2 components may comprise one or more molecule selected from: (a) an antigen-binding protein that specifically binds FGFR1c; (b) a polypeptide comprising an FGFR1c-binding portion of FGF21; or (c) an antigen-binding protein that specifically binds FGF21 at an epitope within the KLB-interacting portion of FGF21.

The present invention also includes pharmaceutical compositions comprising any of the FGF21R agonists described herein and therapeutic methods comprising administering such pharmaceutical compositions to subjects in need thereof. In certain embodiments, an additional therapeutically active component is formulated with, or administered in combination with an FGF21R agonist of the present invention.

The present invention also includes pharmaceutical compositions comprising any of the anti-KLB/FGFR1c antibodies or bispecific antibodies or antigen-binding fragments thereof described herein and therapeutic methods comprising administering such pharmaceutical compositions to subjects in need thereof. In certain embodiments, an additional therapeutically active component is formulated with, or administered in combination with an anti-KLB/FGFR1c antibody of the present invention.

In various methods or uses of the present invention, administration of an anti-KLB/FGFR1c bispecific antibody to a subject at a dose of at least about 1 to 10 mg/kg causes a reduction in blood glucose levels in the subject by about day 2 after administration of the bispecific antibody to the subject as compared to levels in a subject that has not received the bispecific antibody. In some cases, the reduced blood glucose remains controlled up to at least about 7 days after administration of a single dose of at least about 1 to 10 mg/kg of the bispecific antibody to the subject.

The present invention includes the use of an anti-KLB/anti-FGFR1c bispecific antigen-binding molecule of the invention for regulating glucose, and in the manufacture of a medicament for the treatment of a disease or disorder related to or caused by glucose intolerance or diabetes. In some cases, the bispecific antibody of the present invention is used in the manufacture of a medicament for treating or preventing glucose intolerance or diabetes in a subject, wherein the bispecific antibody comprises a first antigen-binding domain that binds human KLB, a second antigen-binding domain that binds human FGFR1c, and a multimerizing domain tethered to each or both of the first and second antigen-binding domains, and the treating or preventing glucose intolerance or diabetes comprises: (a) lowering blood glucose levels; (b) regulating glucose levels in the subject, (c) mediating glycemic control in the subject, (d) improving glucose tolerance in the subject, (e) activating glucose uptake in the subject, or (f) increasing insulin sensitivity in the subject.

Other embodiments will become apparent from a review of the ensuing detailed description.

BRIEF DESCRIPTION OF THE FIGURES

FIG. 1 shows three exemplary arrangements of the individual components of the FGF21R agonists relative to one another. Panel A shows an arrangement in which a KLB-interacting domain (K1) is attached to the N-terminus of a first multimerizing domain (M1), and a FGFR1c-interacting domain (F1) is attached to the N-terminus of a second multimerizing domain (M2). Panel B shows an arrangement in which a first KLB-interacting domain (K1) is attached to the N-terminus of a first multimerizing domain (M1), a second KLB-interacting domain (K2) is attached to the N-terminus of a second multimerizing domain (M2), a first FGFR1c-interacting domain (F1) is attached to the C-terminus of M1, and a second FGFR1c-interacting domain (F2) is attached to the C-terminus of M2. Panel C shows an arrangement in which a first FGFR1c-interacting domain (F1) is attached to the N-terminus of a first multimerizing domain (M1), a second FGFR1c-interacting domain (F2) is attached to the N-terminus of a second multimerizing domain (M2), a first KLB-interacting domain (K1) is attached to the C-terminus of M1, and a second KLB-interacting domain (K2) is attached to the C-terminus of M2. Specific exemplary K1, K2, F1 and F2 components are indicated next to the corresponding structures.

FIG. 5 shows additional examples of how the different components of the FGF21R agonists of the invention may be arranged relative to one another. In Panel A, a portion of FGF21 comprising the FGFR1c-interacting domain (N-terminus) is attached to the N-terminus of the heavy chain of an anti-KLB antibody. In Panel B, a portion of FGF21 comprising the KLB-interacting domain (C-terminus) is attached at the C-terminus of the light chain of an anti-FGFR1c antibody.

DETAILED DESCRIPTION

Figure 2:
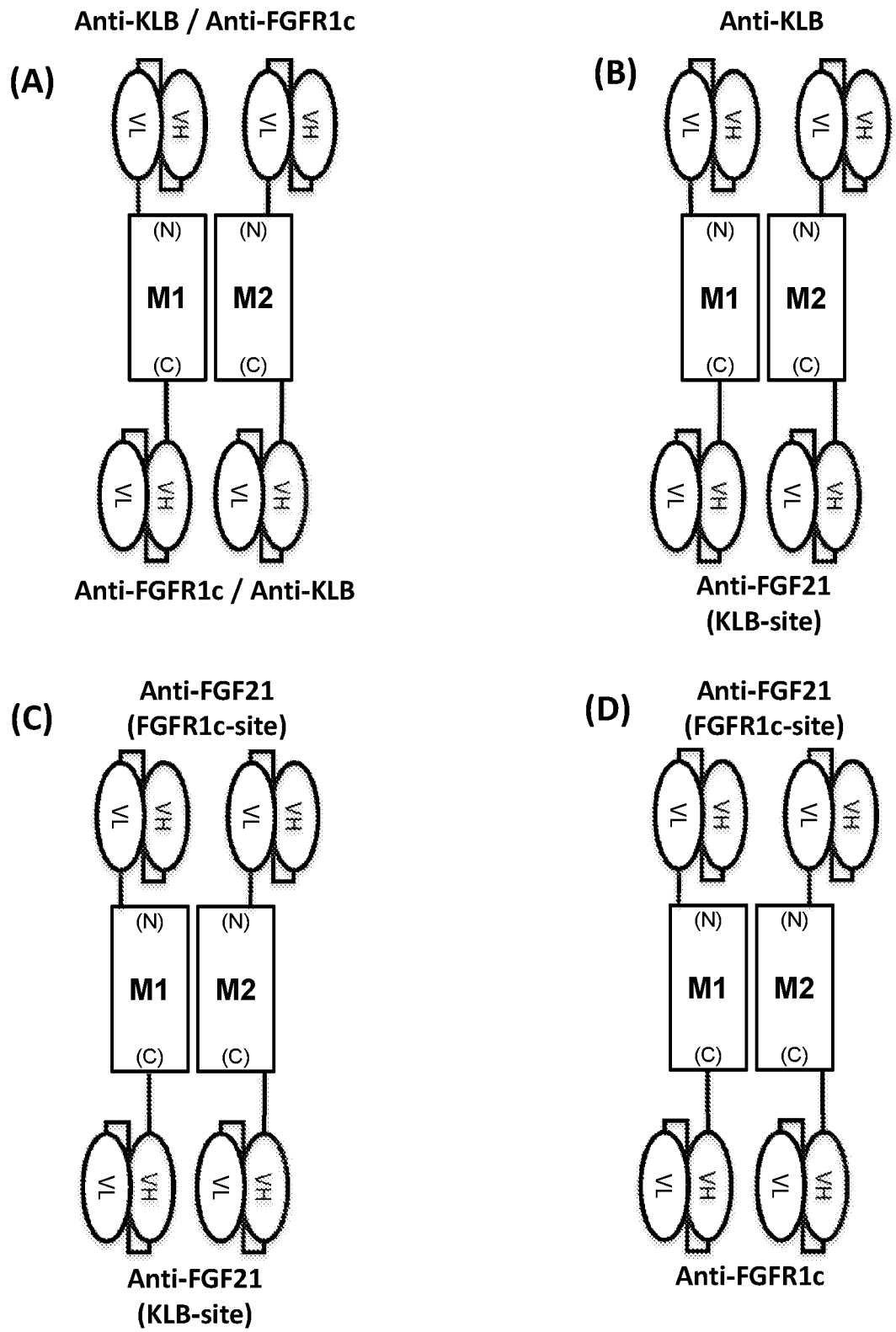
FIG. 2 illustrates four specific exemplary FGF21R agonists, each comprising two identical KLB-interacting domains (K1 and K2) and two identical FGFR1c-interacting domains (F1 and F2). In Panel A, a first anti-KLB scFv is attached to the N-terminus of M1, a second (identical) anti-KLB-scFv is attached to the N-terminus of M2, a first anti-FGFR1c scFv is attached to the C-terminus of M1, and a second (identical) anti-FGFR1c scFv is attached to the C-terminus of M2. Alternatively, a first anti-FGFR1c scFv is attached to the N-terminus of M1, a second (identical) anti-FGFR1c-scFv is attached to the N-terminus of M2, a first anti-KLB scFv is attached to the C-terminus of M1, and a second (identical) anti-KLB scFv is attached to the C-terminus of M2. In Panel B, a first anti-KLB scFv is attached to the N-terminus of M1, a second (identical) anti-KLB-scFv is attached to the N-terminus of M2, a first anti-FGF21 scFv which specifically binds the KLB-binding site of FGF21 is attached to the C-terminus of M1, and a second (identical) anti-FGF21 scFv is attached to the C-terminus of M2. In Panel C, a first anti-FGF21 scFv which specifically binds the FGFR1c-binding site of FGF21 is attached to the N-terminus of M1, a second (identical) anti-FGF21 scFv is attached to the N-terminus of M2, a first anti-FGF21 scFv which specifically binds the KLB-binding site of FGF21 is attached to the C-terminus of M1, and a second (identical) anti-FGF21 scFv is attached to the C-terminus of M2. In Panel D, a first anti-FGF21 scFv which specifically binds the FGFR1c-binding site of FGF21 is attached to the N-terminus of M1, a second (identical) anti-FGF21 scFv is attached to the N-terminus of M2, a first anti-FGFR1c scFv is attached to the C-terminus of M1, and a second (identical) anti-FGFR1c scFv is attached to the C-terminus of M2.

Before the present invention is described, it is to be understood that this invention is not limited to particular methods and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. As used herein, the term "about," when used in reference to a particular recited numerical value, means that the value may vary from the recited value by no more than 1%. For example, as used herein, the expression "about 100" includes 99 and 101 and all values in between (e.g., 99.1, 99.2, 99.3, 99.4, etc.).

Although any methods and materials similar or equivalent to those described herein can be used in the practice or testing of the present invention, the preferred methods and materials are now described. All patents, applications and non-patent publications mentioned in this specification are incorporated herein by reference in their entireties.

FGF21 Receptor Agonists

As used herein, an "FGF21 receptor" (FGF21R) is a cell-surface complex comprising an βKlotho (KLB) molecule and an FGFR1c molecule.

As used herein, "βKlotho" or KLB means a polypeptide comprising the amino acid sequence of SEQ ID NO:434 or the amino acid sequence of GenBank accession No. NP_783864.

As used herein, "FGFR1c" means a polypeptide comprising the amino acid sequence of SEQ ID NO:433 or the amino acid sequence of GenBank accession No. NP_075593.

As used herein, "FGF21" means a polypeptide comprising the amino acid sequence of GenBank accession No. NP_061986 (SEQ ID NO:435), or the amino acid sequence of UniProtKB/Swiss-Prot Q9NSA1 (SEQ ID NO:447).

FGF21 is believed to exert its signaling effects by simultaneously binding βKlotho (KLB) and FGFR1c on the surface of cells. Evidence suggests that the N-terminal portion of FGF21 (e.g., amino acids from about 29 to about 36) interacts with FGFR1c, while the C-terminal portion of FGF21 (e.g., amino acids from about 196 to about 209) interacts with KLB. (Yie et al. (2009), *FEBS Lett.* 583(1): 19-24; Micanovic et al. (2009), *J. Cell. Physiol.* 219(2):227-234). The present invention provides FGF21R agonists that are capable of simultaneously binding KLB and FGFR1c to mimic the signaling activity of FGF21.

The inventors have discovered antibodies that interact with KLB and/or FGFR1c, and used their insight to engineer various antibody formats that mimic the signaling activity of FGF21 in an advantageous manner. The inventors show that their approach achieves higher avidity as it translates to greater in vitro potency of the antibodies, thus leading to greater therapeutic efficacy.

The FGF21R agonists of the present invention comprise a KLB-interacting domain (K1) and an FGFR1c-interacting domain (F1). The KLB- and FGFR1c-interacting domains are associated with one another through the interaction of two multimerizing domains (M1 and M2). The individual components may be arranged relative to one another in a variety of ways that result in functional agonist molecules that can simultaneously bind KLB and FGFR1c and thereby mimic the signaling activity of FGF21. In certain embodiments, K1 is attached to M1 or M2, and F1 is attached to M1 or M2. In certain embodiments, a second KLB-interacting domain is attached to M1 or M2, and/or a second FGFR1c-interacting domain is attached to M1 or M2. Specific exemplary arrangements of the various components of the FGF21R agonists of the present invention are described elsewhere herein.

As used herein, the term "attached", in the context of a first polypeptide component being "attached" to a second polypeptide component (e.g., "K1 is attached to M1 or M2," "F1 is attached to M1 or M2," etc.), means that the first component is physically connected to the second component either directly or indirectly. As an example of a direct attachment between two polypeptide components, the C-terminal amino acid of the first component may be connected via a peptide bond to the N-terminal amino acid of the second component, or the N-terminal amino acid of the first component may be connected via a peptide bond to the C-terminal amino acid of the second component. Indirect attachment, on the other hand, means that the first and second components are each connected physically to different parts of an intervening structure which serves as a link between the first and second components. The intervening structure may be, e.g., a single amino acid, a peptide linker, or another polypeptide component (e.g., another KLB-interacting domain, another FGFR1c-interacting domain, etc.). For example, in the arrangement K1-F1-M1 (wherein a KLB-interacting domain [K1] is attached to an FGFR1c-interacting domain [F1] which in turn is connected to a first multimerizing domain [M1]), K1 is regarded as being "attached" to M1, even though the attachment is indirect with F1 serving as an intervening structure. Similarly, in a tandem arrangement such as K1-K2-F1-M1, involving two KLB-interacting domains, K1 is nonetheless regarded as being "attached" to M1, even though there are two intervening domains (K2 and F1) between K1 and M1.

The present invention includes FGF21R agonists that are bispecific antibodies; e.g., bispecific antibodies comprising an antigen-binding arm that specifically binds KLB and an antigen-binding arm that specifically binds FGFR1c. Methods for making bispecific antibodies are known in the art and may be used to construct various FGF21R agonists of the present invention. Exemplary bispecific formats that can be used in the context of the present invention include, without limitation, e.g., scFv-based or diabody bispecific formats, IgG-scFv fusions, dual variable domain (DVD)-Ig, Quadroma, knobs-into-holes, common light chain (e.g., common light chain with knobs-into-holes, etc.), CrossMab, CrossFab, (SEED)body, leucine zipper, Duobody, IgG1/IgG2, dual acting Fab (DAF)-IgG, and Mabe bispecific formats (see, e.g., Klein et al. 2012, mAbs 4:6, 1-11, and references cited therein, for a review of the foregoing formats).

One aspect of the invention relates to FGF21R agonists that are bispecific antibodies comprising two ScFv antigen-binding arms or domains. In some examples, the first ScFv antigen-binding domain specifically binds KLB (such as K1) and the second ScFv antigen-binding domain binds specifically FGFR1c (such as F1).

In some embodiments, the first ScFv antigen-binding domain comprises, from 5' to 3': HCVR-linker-LCVR, wherein the antigen-binding domain is a KLB-interacting domain.

In another embodiment, the second ScFv antigen-binding domain comprises, from 5' to 3': HCVR-linker-LCVR, wherein the antigen-binding domain is an FGFR1c-interacting domain.

Standard molecular biological techniques (e.g., recombinant DNA technology) may be used to construct any of the FGF21R agonists of the invention or variants thereof.

Klb-Interacting Domain

The FGF21R agonists of the present invention comprise at least one βKlotho (KLB)-interacting domain (sometimes referred to herein by the designation "K," "K1," "K2," etc.). A "KLB-interacting domain," as used herein, means any macromolecule that is capable of directly or indirectly interacting with KLB. For example, a KLB-interacting domain may comprise a protein or polypeptide (e.g., an antigen-binding protein) that specifically binds KLB. In certain embodiments, one or more of the KLB-interacting domains is an antigen-binding protein that specifically binds an epitope of KLB on a surface or region of KLB that ordinarily interacts with FGF21. Specific types of antigen-binding proteins are described elsewhere herein.

In certain embodiments, one or more of the KLB-interacting domains is a nucleic acid molecule that specifically binds KLB (e.g., an anti-KLB aptamer) rather than an antigen-binding protein.

In certain embodiments, one or more of the KLB-interacting domains comprises a polypeptide comprising a KLB-binding portion of FGF21. For example, one or more of the KLB-interacting domains may comprise a portion of the C-terminal region of FGF21 (e.g., the C-terminal 5, 10, 15, 20, 25, 30, 40, 50, 75, 100 or more amino acids of FGF21) that is capable of interacting with KLB.

Alternatively, a KLB-interacting domain may comprise an antigen-binding protein that does not itself directly interact with KLB, but instead interacts with an intermediary protein that directly interacts with KLB. One such intermediary protein is FGF21. Thus, in the context of an FGF21R agonist of the present invention, one or more of the KLB-interacting domains may comprise an antigen-binding protein that binds FGF21. Preferably, the KLB-interacting domain will bind an epitope on FGF21 that does not interfere with the binding of FGF21 to KLB; for example, a KLB-interacting domain may be an antigen-binding protein that binds an epitope within the FGFR1c-interacting portion (e.g., N-terminal portion) of FGF21. In this manner the "KLB-interacting domain" indirectly interacts with KLB through a direct interaction with FGF21 as an intermediary structure.

An FGF21R agonist of the present invention may comprise multiple KLB-interacting domains (referred to as, e.g., "K1," "K2," etc.). For example, in embodiments in which an FGF21R agonist comprises two KLB-interacting domains (K1 and K2), K1 and K2 may be distinct from one another; e.g., K1 and K2 may have different amino acid sequences or may be different types of molecules. For example, K1 may comprise an antigen-binding portion of an antibody that specifically binds KLB, while K2 may comprise a portion of FGF21 that interacts with KLB. Alternatively, in arrangements comprising multiple KLB-interacting domains, each KLB-interacting domain may be identical to the other KLB-interacting domain(s). For example, in embodiments in which an FGF21R agonist comprises two KLB-interacting domains (K1 and K2), K1 and K2 may comprise the same amino acid sequence and have the same binding specificity for KLB.

In some embodiments, the KLB-interacting domain comprises, from 5' to 3': HCVR-linker-LCVR. In other embodiments, the KLB-interacting domain comprises an HCVR/LCVR sequence pair comprising an amino acid HCVR/LCVR sequence pair selected from Table 7A. In still other embodiments, the KLB-interacting domain comprises an HCVR/LCVR sequence pair comprising the amino acid sequences selected from the group consisting of: SEQ ID NO: 98/106; 130/138; 146/154; 162/170; 194/202; 242/250; 338/346; 354/362; and 370/378.

FGFR1c-Interacting Domain

The FGF21R agonists of the present invention comprise at least one FGF21R-interacting domain (sometimes referred to herein by the designation "F," "F1," "F2," etc.). An "FGFR1c-interacting domain," as used herein, means any macromolecule that is capable of directly or indirectly interacting with FGFR1c. For example, an FGFR1c-interacting domain may comprise a protein or polypeptide (e.g., an antigen-binding protein) that specifically binds FGFR1c. In certain embodiments, one or more of the FGFR1c-interacting domains is an antigen-binding protein that specifically binds an epitope of FGFR1c on a surface or region of FGFR1c that ordinarily interacts with FGF21. Specific types of antigen-binding proteins are described elsewhere herein.

In certain embodiments, one or more of the FGFR1c-interacting domains is a nucleic acid molecule that specifically binds FGFR1c (e.g., an anti-FGFR1c aptamer).

In certain embodiments, one or more of the FGFR1c-interacting domains comprises a polypeptide comprising a FGFR1c-binding portion of FGF21. For example, one or more of the FGFR1c-interacting domains may comprise a portion of the N-terminal region of FGF21 (e.g., the N-terminal 5, 10, 15, 20, 25, 30, 40, 50, 75, 100 or more amino acids of FGF21) that is capable of interacting with FGFR1c.

Alternatively, one or more of the FGFR1c-interacting domains may comprise an antigen-binding protein that does not itself directly interact with FGFR1c, but instead interacts with an intermediary protein that directly interacts with FGFR1c. One such intermediary protein is FGF21. Thus, in the context of an FGF21R agonist of the present invention, one or more of the FGFR1c-interacting domains may comprise an antigen-binding protein that binds FGF21. Preferably, in this context, the FGFR1c-interacting domain will bind an epitope on FGF21 that does not interfere with the binding of FGF21 to FGFR1c; for example, an FGFR1c-interacting domain may be an antigen-binding protein that binds an epitope within the KLB-interacting portion (e.g., C-terminal portion) of FGF21. In this manner the "FGFR1c-interacting domain" indirectly interacts with FGFR1c through a direct interaction with FGF21 as an intermediary structure.

An FGF21R agonist of the present invention may comprise multiple FGFR1c-interacting domains (referred to as, e.g., "F1," "F2," etc.). For example, in embodiments in which an FGF21R agonist comprises two FGFR1c-interacting domains (F1 and F2), F1 and F2 may be distinct from one another; e.g., F1 and F2 may have different amino acid sequences or may be different types of molecules. For example, F1 may comprise an antigen-binding portion of an antibody that specifically binds FGFR1c, while F2 may comprise a portion of FGF21 that interacts with FGFR1c. Alternatively, when the FGF21R agonist comprises multiple FGFR1c-interacting domains, each FGFR1c-interacting domain may be identical to the other FGFR1c-interacting domains. For example, in embodiments in which an FGF21R agonist comprises two FGFR1c-interacting domains (F1 and F2), F1 and F2 may comprise the same amino acid sequence and have the same binding specificity for FGFR1c.

In some embodiments, the FGFR1c-interacting domain comprises, from 5' to 3': HCVR-linker-LCVR. In other embodiments, the FGFR1c-interacting domain comprises an HCVR/LCVR sequence pair comprising an amino acid HCVR/LCVR sequence pair selected from Table 7A. In still other embodiments, the FGFR1c-interacting domain comprises the HCVR/LCVR sequence pair comprising the amino acid sequences selected from the group consisting of: 290/298 and 306/314.

FGF21 Signaling Activity

The interaction between FGF21 and FGF21R, and hence the interaction between the antigen-binding molecules of the invention and FGF21R, can be measured by a number of in vitro (e.g. as in a test tube or plate), ex vivo (e.g. as in a cell culture from a living animal) and in vivo (e.g. as in a living animal) bioassays known to the skilled person in the relevant art.

Stimulation of KLB/FGFR1c (FGF21R) by FGF21 leads to activation of the mitogen-activated protein kinase (MAPK) pathway. Assays to measure MAPK activation are known in the art. Some MAPK assays are designed to monitor the activity of Serum Response Factor (SRF)-mediated signal transduction pathways in receptor-expressing cells. Elk-1 protein is phosphorylated by MAPK and Elk-1 in turn forms a complex with the SRF over the serum response element (SRE), and activates gene expression. Expression of luciferase is thus controlled by phosphorylation of Elk-1 by MAPK in a SRE-luciferase reporter system. Such SRE-luciferase kits are commercially available (e.g. Cignal™ SRE Reporter (luc) Kit, SA Biosciences, Valencia, Calif.; and SRE Reporter Kit, BPS Bioscience, San Diego, Calif.).

MAPK was originally identified as an extracellular signal-regulated kinase or "ERK". In certain assays, phosphorylated (pERK) cellular response may also be a measure of FGF21-induced signaling through KLB/FGFR1c (Ming, A. Y. K. et al. 2012, *J. Biol. Chem.*, 287:19997-20006, epub Apr. 20, 2012). Endogenous extracellular signal-regulated kinase 1 (ERK1 or MAP3K) and 2 (ERK2 or MAP4K) belong to a conserved family of serine/threonine protein kinases and are involved cellular signaling events associated with a range of stimuli. The kinase activity of ERK proteins is regulated by dual phosphorylation at Threonine 202/Tyrosine 204 in ERK1, and Threonine 185/Tyrosine 187 in ERK2. Many downstream targets of ERK 1/2 have also been identified, including other kinases, and transcription factors. In one example, a pERK 1/2 assay utilizes an enzyme-linked immunosorbent assay (ELISA) method to measure specific phosphorylation of ERK 1 in cellular lysates of cell cultures expressing recombinant or endogenous receptors. In another example, the pERK 1/2 assay uses a primary (non-conjugated) antibody which recognizes phosphorylated Thr202/Tyr204 in ERK1 or phos-Thr185/Tyr187 in ERK2 and a secondary conjugated antibody that recognizes the primary antibody, whereas the secondary conjugated mAb provides a method of detection such as a conjugate reacts with an exogenously added substrate. Various commercial kits and antibodies for ELISA are available, such as p44/42 MAPK (ERK1/2) antibodies (Cell Signaling Technology, Danvers, Mass., USA), AlphaScreen® SureFire™ (PerkinElmer), ThermoScientific (Waltham, Mass., USA), Sigma Aldrich (St. Louis, Mo., USA), ELISAOne (TGR BioSciences (South Australia, Australia) etc.).

Additional cellular functions may be measured to indicate that an KLB/FGFR1c binding molecule mimics FGF21-induced cell signaling. Certain assays, such as ERK phosphorylation, apoptosis inhibition, glucose transporter upregulation, and other assays are performed using KLB-expressing fibroblast cells (adipocytes) or the like, and are well-known to the person skilled in the relevant art (see e.g. Micanovic et al., 2009, *J. Cell. Physiol.* 219(2):227-234).

Biological Characteristics of the Antibodies and Bispecific Antigen-Binding Molecules The present invention includes antibodies and antigen-binding fragments thereof that bind KLB/FGFR1c and induce mitogen-activated protein kinase (MAPK) signaling. For example, the present invention includes anti-KLB/FGFR1c antibodies that induce MAPK signaling with an $EC_{50}$ value of less than about 23 nM, as measured by an in vitro serum response element (SRE) reporter assay, e.g., using the assay format as defined in Examples 9, 10, 11 herein (e.g., assessing MAPK phosphorylation activity in the presence of anti-KLB/FGFR1c antibodies), or a substantially similar assay. In certain embodiments, the antibodies or antigen-binding fragments of the present invention induce MAPK signaling (e.g., phosphorylation of Elk-1 by MAPK in a SRE-luciferase reporter system or other reporter system) with an $EC_{50}$ value of less than about 20 nM, less than about 10 nM, less than about 5 nM, less than about 1 nM, less than about 800 pM, less than about 600 pM, less than about 500 pM, less than about 400 pM, less than about 300 pM, less than about 200 pM, less than about 180 pM, less than about 160 pM, less than about 140 pM, less than about 120 pM, less than about 110 pM, less than about 100 pM, less than about 75 pM, less than about 50 pM, or less than about 20 pM as measured by an in vitro reporter assay, e.g., using the assay format as defined in Examples 9, 10, and 11 herein, or a substantially similar assay.

The present invention includes antibodies and antigen-binding fragments thereof that bind KLB/FGFR1c and inhibit FGF21-induced MAPK signaling. For example, the present invention includes anti-KLB/FGFR1c antibodies that inhibit FGF21-induced MAPK signaling with an $IC_{50}$ value of less than about 15 nM, as measured by an in vitro serum response element (SRE) reporter assay, e.g., using the assay format as defined in Examples 9, 10, 11 herein (e.g., assessing MAPK phosphorylation activity in the presence of FGF21 and anti-KLB/FGFR1c antibodies), or a substantially similar assay. In certain embodiments, the antibodies or antigen-binding fragments of the present invention inhibit MAPK signaling (e.g., phosphorylation of Elk-1 by MAPK in a SRE-luciferase reporter system or other reporter system) with an $IC_{50}$ value of less than about 10 nM, less than about 5 nM, less than about 1 nM, less than about 800 pM, less than about 600 pM, less than about 500 pM, less than about 400 pM, less than about 300 pM, less than about 200 pM, less than about 180 pM, less than about 160 pM, less than about 140 pM, less than about 120 pM, less than about 110 pM, less than about 100 pM, less than about 50 pM, or less than about 30 pM, as measured by an in vitro reporter assay, e.g., using the assay format as defined in Examples 9, 10, and 11 herein, or a substantially similar assay.

The present invention includes antibodies and bispecific antigen-binding fragments thereof that bind KLB and/or FGFR1c with high affinity. The present invention also includes antibodies and antigen-binding fragments thereof that bind KLB and/or FGFR1c with medium or low affinity, depending on the therapeutic context and particular targeting properties that are desired. For example, in the context of a bispecific antigen-binding molecule, wherein one arm binds KLB and another arm binds FGFR1c, it may be desirable for the anti-KLB arm to bind the KLB with high affinity while the anti-FGFR1c arm binds FGFR1c with only moderate or low affinity. In this manner, preferential targeting of the antigen-binding molecule to cells expressing the target antigen may be achieved while avoiding general/untargeted KLB binding and the consequent adverse side effects associated therewith.

According to certain embodiments, the present invention includes antibodies and bispecific antigen-binding fragments of antibodies that bind human KLB (e.g., at 25° C. or 37° C.) with a $K_D$ of less than about 10.9 nM as measured by surface plasmon resonance, e.g., using an assay format as defined in Example 15 herein. In certain embodiments, the antibodies or bispecific antigen-binding fragments of the present invention bind KLB with a $K_D$ of less than about 7 nM, less than about 5 nM, less than about 1 nM, less than about 800 pM, less than about 600 pM, less than about 500 pM, less than about 400 pM, less than about 300 pM, less than about 200 pM, less than about 180 pM, less than about 160 pM, less than about 140 pM, less than about 120 pM, less than about 110 pM, or less than about 100 pM, as measured by surface plasmon resonance, e.g., using an assay format as defined in Example 15 herein (e.g., antigen-capture format), or a substantially similar assay.

The present invention also includes antibodies and bispecific antigen-binding fragments thereof that bind KLB with a dissociative half-life (t½) of greater than about 4 minutes as measured by surface plasmon resonance at 25° C. or 37° C., e.g., using an assay format as defined in Example 15 herein, or a substantially similar assay. In certain embodiments, the antibodies or bispecific antigen-binding fragments of the present invention bind KLB with a t½ of greater than about 12 minutes, greater than about 20 minutes, greater than about 30 minutes, greater than about 40 minutes, greater than about 50 minutes, greater than about 100 minutes, greater than about 200 minutes, greater than about 900 minutes, greater than about 293 minutes, or greater than about 300 minutes, as measured by surface plasmon resonance at 25° C. or 37° C., e.g., using an assay format as defined in Example 15 herein (e.g., antigen-capture format), or a substantially similar assay.

The present invention includes antibodies and antigen-binding fragments of antibodies that bind human FGFR1c (e.g., at 25° C. or 37° C.) with a $K_D$ of less than about 352 nM as measured by surface plasmon resonance, e.g., using an assay format as defined in Example 15 herein. In certain embodiments, the antibodies or bispecific antigen-binding fragments of the present invention bind FGFR1c with a $K_D$ of less than about 350 nM, less than about 300 nM, less than about 200 nM, less than about 100 nM, less than about 50 nM, less than about 1 nM, less than about 500 pM, less than about 200 pM, or less than about 100 pM, as measured by surface plasmon resonance, e.g., using an assay format as defined in Example 15 herein (e.g., antigen-capture format), or a substantially similar assay.

The present invention further includes anti-KLB/FGFR1c or anti-KLB or anti-FGFR1c antibodies that bind to the same epitope as any of the specific exemplary antibodies described herein (e.g. antibodies comprising any of the amino acid sequences as set forth in Table 7A herein). Likewise, the present invention also includes anti-KLB/FGFR1c or anti-KLB antibodies that compete for binding to KLB with any of the specific exemplary antibodies described herein (e.g. antibodies comprising any of the amino acid sequences as set forth in Table 7A herein). In certain embodiments, an antibody or antigen-binding fragment of the invention binds to the same epitope as, or competes for binding to KLB with, any of the specific exemplary antibodies described herein, as measured by cross-competition binding assay, e.g., using an assay format as defined in Example 16 herein (e.g., antigen-capture format), or a substantially similar assay.

Antigen-Binding Proteins

The KLB-interacting domains and/or the FGFR1c-interacting domains of the FGF21R agonists of the present invention, in certain embodiments, may comprise or consist of antigen-binding proteins. For example, a KLB-interacting domain may comprise or consist of an antigen-binding protein that specifically binds KLB; likewise, an FGFR1c-interacting domain may comprise or consist of an antigen-binding protein that specifically binds FGFR1c.

As used herein, the expression "antigen-binding protein" or "antigen-binding domain" means any peptide, polypeptide or polypeptide-containing construct that is capable of specifically binding a particular antigen of interest. Exemplary categories of antigen-binding proteins that can be used in the context of the present invention include antibodies, antigen-binding portions of antibodies, peptides that specifically interact with a particular antigen (e.g., peptibodies), receptor molecules that specifically interact with a particular antigen, proteins comprising a ligand-binding portion of a receptor that specifically binds a particular antigen, or ligands (or portions thereof) that specifically bind a receptor molecule of interest.

The term "specifically binds," or the like, means that the antigen-binding protein forms a complex with a target antigen that is relatively stable under physiologic conditions. Methods for determining whether an antigen-binding protein specifically binds to an antigen are well known in the art and include, for example, equilibrium dialysis, surface plasmon resonance, and the like. For example, an antigen-binding protein that "specifically binds" a target antigen, as used in the context of the present invention, includes antigen-binding molecules that bind the target antigen or portion thereof with a $K_D$ of less than about 10 nM, less than about 5 nM, less than about 4 nM, less than about 3 nM, less than about 2 nM, less than about 1 nM or less than about 0.5 nM, as measured in a surface plasmon resonance assay.

Specificity of the antigen-binding molecules of the invention may be determined based on affinity and/or avidity. Affinity, represented by the equilibrium constant for the dissociation of an antigen with an antibody ($K_D$) measures the binding strength between an antigen and its binding site. Avidity is the measure of the strength of binding between an antibody and its antigen, therefore avidity is related to both the affinity between an epitope with its antigen binding site on the antibody as well as the valence of the antibody (i.e. the number of binding sites of a particular epitope). Hence, certain FGF21R agonists are advantageously avidity-driven, meaning that a greater accumulated strength of multiple binding affinities, thus higher functional avidity is observed. Without being bound by any one theory, functional avidity assessment typically leads to better prediction of efficacy. The functional avidity of an antibody, in particular FGF21R agonists of the invention, inversely correlates with the dose that is required for a particular effect. For example, the valency of a molecular interaction (monospecific antibody binding versus avidity binding) can influence antibody/coreceptor interactions such that avidity effects translate low intrinsic affinities into more significant functional outcomes.

The term "surface plasmon resonance", as used herein, refers to an optical phenomenon that allows for the analysis of real-time interactions by detection of alterations in protein concentrations within a biosensor matrix, for example using the BIAcore™ system (Biacore Life Sciences division of GE Healthcare, Piscataway, N.J.).

The term "$K_D$", as used herein, means the equilibrium dissociation constant of a particular protein-protein interaction (e.g., antibody-antigen interaction). Unless indicated otherwise, the $K_D$ values disclosed herein refer to $K_D$ values determined by surface plasmon resonance assay at 25° C.

The present invention includes FGF21R agonists comprising a KLB-interacting domain with low affinity for KLB and/or an FGFR1c-interacting domain with low affinity for FGFR1c. In certain embodiments of the present invention, the affinity of the KLB-interacting domain for KLB is lower than the affinity of the FGFR1c-interacting domain for FGFR1c. Alternatively, in certain other embodiments, the affinity of the FGFR1c-interacting domain for FGFR1c is lower than the affinity of the KLB-interacting domain for KLB. As used herein, the affinity of a first antigen-binding protein for its antigen is "lower" than the affinity of a second antigen-binding protein for its antigen if the binding affinity of the first antigen-binding protein to its antigen is at least 10% weaker (e.g., 15% weaker, 25% weaker, 50% weaker, 75% weaker, 90% weaker, etc.) than the binding affinity of the second antigen-binding protein to its antigen. In certain embodiments, "low affinity" binding means that the antigen-binding protein interacts with its antigen with a $K_D$ of greater than about 10 nM to about 1 pM as measured in a surface plasmon resonance assay at about 25° C. Thus, the lesser the value of the affinity ($K_D$), the stronger the binding strength between the epitope and the antibody (for example, 10 nM $K_D$ indicates a stronger binding strength compared to 1 pM $K_D$).

Antibodies and Antigen-Binding Fragments of Antibodies

As indicated above, a KLB-interacting domain and/or an FGFR1c-interacting domain can comprise or consist of an antibody or antigen-binding fragment of an antibody. The term "antibody," as used herein, means any antigen-binding molecule or molecular complex comprising at least one complementarity determining region (CDR) that specifically binds to or interacts with a particular antigen (e.g., KLB or FGFR1c). The term "antibody" includes immunoglobulin molecules comprising four polypeptide chains, two heavy (H) chains and two light (L) chains inter-connected by disulfide bonds, as well as multimers thereof (e.g., IgM). Each heavy chain comprises a heavy chain variable region (abbreviated herein as HCVR or VH) and a heavy chain constant region. The heavy chain constant region comprises three domains, CH1, CH2 and CH3. Each light chain comprises a light chain variable region (abbreviated herein as LCVR or VL) and a light chain constant region. The light chain constant region comprises one domain (CL1). The VH and VL regions can be further subdivided into regions of hypervariability, termed complementarity determining regions (CDRs), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. In different embodiments of the invention, the FRs of the antibodies of the invention (or antigen-binding portion thereof) may be identical to the human germline sequences, or may be naturally or artificially modified. An amino acid consensus sequence may be defined based on a side-by-side analysis of two or more CDRs.

The KLB-interacting domains and/or FGFR1c-interacting domains of the FGF21R agonists of the present invention may comprise or consist of antigen-binding portions of full antibody molecules. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of such antigen-binding proteins include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding protein," as used herein.

An antigen-binding fragment of an antibody will typically comprise at least one variable domain. The variable domain may be of any size or amino acid composition and will generally comprise at least one CDR which is adjacent to or in frame with one or more framework sequences. In antigen-binding fragments having a VH domain associated with a VL domain, the VH and VL domains may be situated relative to one another in any suitable arrangement. For example, the variable region may be dimeric and contain VH-VH, VH-VL or VL-VL dimers. Alternatively, the antigen-binding fragment of an antibody may contain a monomeric VH or VL domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present invention include: (i) VH-CH1; (ii) VH-CH2; (iii) VH-CH3; (iv) VH-CH1-CH2; (v) VH-CH1-CH2-CH3; (vi) VH-CH2-CH3; (vii) VH-CL; (viii) VL-CH1; (ix) VL-CH2; (x) VL-CH3; (xi) VL-CH1-CH2; (xii) VL-CH1-CH2-CH3; (xiii) VL-CH2-CH3; and (xiv) VL-CL. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids which result in a flexible or semi-flexible linkage between adjacent variable and/or constant domains in a single polypeptide molecule. Moreover, an antigen-binding fragment may comprise a homo-dimer or hetero-dimer (or other multimer) of any of the variable and constant domain configurations listed above in non-covalent association with one another and/or with one or more monomeric VH or VL domain (e.g., by disulfide bond(s)).

The FGF21R agonists of the present invention may comprise or consist of human antibodies and/or recombinant human antibodies, or fragments thereof. The term "human antibody", as used herein, includes antibodies having variable and constant regions derived from human germline immunoglobulin sequences. Human antibodies may nonetheless include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include antibodies in which CDR sequences derived from the germline of another mammalian species, such as a mouse, have been grafted onto human framework sequences.

The FGF21R agonists of the present invention may comprise or consist of recombinant human antibodies or antigen-binding fragments thereof. The term "recombinant human antibody", as used herein, is intended to include all human antibodies that are prepared, expressed, created or isolated by recombinant means, such as antibodies expressed using a recombinant expression vector transfected into a host cell (described further below), antibodies isolated from a recombinant, combinatorial human antibody library (described further below), antibodies isolated from an animal (e.g., a mouse) that is transgenic for human immunoglobulin genes (see e.g., Taylor et al. (1992) Nucl. Acids Res. 20:6287-6295) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

Multimerizing Domain

The FGF21R agonists of the present invention also comprise at least one multimerizing domain (sometimes referred to herein by the abbreviation "M," "M1", "M2", etc.). In general terms, the multimerizing domains of the present invention function to connect the various components of the targeting constructs (e.g., the KLB-interacting domain(s) and the FGFR1c-interacting domain(s)) with one another. As used herein, a "multimerizing domain" is any macromolecule that has the ability to associate (covalently or non-covalently) with a second macromolecule of the same or similar structure or constitution. For example, a multimerizing domain may be a polypeptide comprising an immunoglobulin $C_H3$ domain. A non-limiting example of a multimerizing domain is an Fc portion of an immunoglobulin, e.g., an Fc domain of an IgG selected from the isotypes IgG1, IgG2, IgG3, and IgG4, as well as any allotype within each isotype group. In certain embodiments, the multimerizing domain is an Fc fragment or an amino acid sequence of 1 to about 200 amino acids in length containing at least one cysteine residue. In other embodiments, the multimerizing domain is a cysteine residue or a short cysteine-containing peptide. Other multimerizing domains include peptides or polypeptides comprising or consisting of a leucine zipper, a helix-loop motif, or a coiled-coil motif.

In certain embodiments, the FGF21R agonists of the present invention comprise two multimerizing domains, M1 and M2, wherein M1 and M2 are identical to one another. For example, M1 can be an Fc domain having a particular amino acid sequence, and M2 is an Fc domain with the same amino acid sequence as M1.

Alternatively, M1 and M2 may differ from one another at one or more amino acid position. For example, M1 may comprise a first immunoglobulin (Ig) $C_H3$ domain and M2 may comprise a second Ig $C_H3$ domain, wherein the first and second Ig $C_H3$ domains differ from one another by at least one amino acid, and wherein at least one amino acid difference reduces binding of the targeting construct to Protein A as compared to a reference construct having identical M1 and M2 sequences. In one embodiment, the Ig $C_H3$ domain of M1 binds Protein A and the Ig $C_H3$ domain of M2 contains a mutation that reduces or abolishes Protein A binding such as an H95R modification (by IMGT exon numbering; H435R by EU numbering). The $C_H3$ of M2 may further comprise a Y96F modification (by IMGT; Y436F by EU). Further modifications that may be found within the $C_H3$ of M2 include: D16E, L18M, N44S, K52N, V57M, and V82I (by IMGT; D356E, L358M, N384S, K392N, V397M, and V422I by EU) in the case of an IgG1 Fc domain; N44S, K52N, and V82I (IMGT; N384S, K392N, and V422I by EU) in the case of an IgG2 Fc domain; and Q15R, N44S, K52N, V57M, R69K, E79Q, and V82I (by IMGT; Q355R, N384S, K392N, V397M, R409K, E419Q, and V422I by EU) in the case of an IgG4 Fc domain.

According to certain embodiments of the present invention, M1 and/or M2 of the FGF21R agonists comprise an Fc domain comprising one or more mutations which enhance or diminish antibody binding to the FcRn receptor, e.g., at acidic pH as compared to neutral pH. For example, the present invention includes FGF21R agonists comprising a mutation in the $C_H2$ or a $C_H3$ region of the Fc domain, wherein the mutation(s) increases the affinity of the Fc domain to FcRn in an acidic environment (e.g., in an endosome where pH ranges from about 5.5 to about 6.0). Such mutations may result in an increase in serum half-life of the FGF21R agonists when administered to an animal. Non-limiting examples of such Fc modifications include, e.g., a modification at position 250 (e.g., E or Q); 250 and 428 (e.g., L or F); 252 (e.g., L/Y/F/W or T), 254 (e.g., S or T), and 256 (e.g., S/R/Q/E/D or T); or a modification at position 428 and/or 433 (e.g., H/L/R/S/P/Q or K) and/or 434 (e.g., H/F or Y); or a modification at position 250 and/or 428; or a modification at position 307 or 308 (e.g., 308F, V308F), and 434. In one embodiment, the modification comprises a 428L (e.g., M428L) and 434S (e.g., N434S) modification; a 428L, 259I (e.g., V259I), and 308F (e.g., V308F) modification; a 433K (e.g., H433K) and a 434 (e.g., 434Y) modification; a 252, 254, and 256 (e.g., 252Y, 254T, and 256E) modification; a 250Q and 428L modification (e.g., T250Q and M428L); and a 307 and/or 308 modification (e.g., 308F or 308P).

For example, the present invention includes FGF21R agonists comprising an Fc domain comprising one or more pairs or groups of mutations selected from the group consisting of: 250Q and 248L (e.g., T250Q and M248L); 252Y, 254T and 256E (e.g., M252Y, S254T and T256E); 428L and 434S (e.g., M428L and N434S); and 433K and 434F (e.g., H433K and N434F).

The present invention also includes FGF21R agonists comprising chimeric heavy chain constant ($C_H$) regions (e.g. M1 and/or M2), wherein the chimeric $C_H$ region comprises segments derived from the CH regions of more than one immunoglobulin isotype. For example, the FGF21R agonists of the invention may comprise a chimeric CH region comprising part or all of a $C_H2$ domain derived from a human IgG1, human IgG2 or human IgG4 molecule, combined with part or all of a CH3 domain derived from a human IgG1, human IgG2 or human IgG4 molecule. According to certain embodiments, the FGF21R agonists of the invention comprise a chimeric $C_H$ region having a chimeric hinge region. For example, a chimeric hinge may comprise an "upper hinge" amino acid sequence (amino acid residues from positions 216 to 227 according to EU numbering) derived from a human IgG1, a human IgG2 or a human IgG4 hinge region, combined with a "lower hinge" sequence (amino acid residues from positions 228 to 236 according to EU numbering) derived from a human IgG1, a human IgG2 or a human IgG4 hinge region. According to certain embodiments, the chimeric hinge region comprises amino acid residues derived from a human IgG1 or a human IgG4 upper hinge and amino acid residues derived from a human IgG2 lower hinge. An FGF21R agonist comprising a chimeric $C_H$ region as described herein may, in certain embodiments, exhibit modified Fc effector functions without adversely affecting the therapeutic or pharmacokinetic properties of the antibody. (See, e.g., PCT International Publication. No. WO/2014/121087, published Aug. 7, 2014, the disclosure of which is hereby incorporated by reference in its entirety).

All possible combinations of the foregoing Fc domain mutations, and other mutations within the antibody variable domains disclosed herein, are contemplated within the scope of the present invention.

Orientation and Arrangement of the Components of the FGF21R Agonists

The individual components of the FGF21R agonists of the present invention (e.g., K1, K2, F1, F2, M1, M2, etc.) can be arranged relative to one another in a variety of ways. Exemplary arrangements of the individual components are illustrated generically in FIGS. 1-5 and in Table 1.

According to certain embodiments, a KLB-interacting domain (K1) is attached to a first multimerizing domain (M1), and an FGFR1c-interacting domain (F1) is attached to a second multimerizing domain (M2). In other embodiments, a KLB-interacting domain (K1) and an FGFR1c-interacting domain (F1) are both attached to a single multimerizing domain (M1).

In certain embodiments, one or more additional KLB-interacting domains (K2, K3, K4, etc.) and/or one or more additional FGFR1c-interacting domains (F2, F3, F4, etc.) are attached to M1 and/or M2. In exemplary arrangements, a first KLB-interacting domain (K1) is attached to M1, a first FGFR1c-interacting domain (F1) is attached to M1, a second KLB-interacting domain (K2) is attached to M2, and a second FGFR1c-interacting domain (F2) is attached to M2. In other exemplary arrangements, a first KLB-interacting domain (K1) is attached to M1, a second KLB-interacting domain (K2) is attached to M1, a first FGFR1c-interacting domain is attached to M2, and a second FGFR1c-interacting domain is attached to M2. Numerous variations of these arrangements are set out in Table 1 and are included within the scope of the present invention.

The KLB-interacting domains and the FGFR1c-interacting domains can be attached to either the N-terminus or the C-terminus of the multimerizing domains (M1 and/or M2), (e.g., in embodiments in which the multimerizing components are polypeptides such as Fc portions of an immunoglobulin molecule). For example, in certain embodiments, the KLB-interacting domain (K1, K2) is attached to the N-terminus of a multimerizing domain. In other embodiments, the KLB-interacting domain (K1, K2) is attached to the C-terminus of a multimerizing domain. Similarly, in certain embodiments, the FGFR1c-interacting domain (F1, F2) may be attached to the N-terminus of a multimerizing domain. In other embodiments, the FGFR1c-interacting domain (F1, F2) is attached to the C-terminus of a multimerizing domain.

Table 1 illustrates various exemplary component arrangements that are encompassed within the present invention, with the KLB-interacting domains (K1, K2) and the FGFR1c-interacting domains (F1, F2) attached to either the N-terminus or the C-terminus of the multimerizing domains (M1, M2) as shown under the corresponding columns.

TABLE 1

Exemplary Arrangements of Components

| No. | M1 N-Terminus | M1 C-Terminus | M2 N-Terminus | M2 C-Terminus |
|---|---|---|---|---|
| 1 | K1 | F1 | — | — |
| 2 | K1 | — | F1 | — |
| 3 | K1 | — | — | F1 |
| 4 | F1 | K1 | — | — |
| 5 | — | K1 | F1 | — |
| 6 | — | K1 | — | F1 |
| 7 | F1 | — | K1 | — |
| 8 | — | F1 | K1 | — |
| 9 | — | — | K1 | F1 |
| 10 | F1 | — | — | K1 |
| 11 | — | F1 | — | K1 |
| 12 | — | — | F1 | K1 |
| 13 | K1 | F1 | K2 | — |
| 14 | K1 | F1 | — | K2 |
| 15 | K1 | K2 | F1 | — |
| 16 | K1 | — | F1 | K2 |
| 17 | K1 | K2 | — | F1 |
| 18 | K1 | — | K2 | F1 |
| 19 | F1 | K1 | K2 | — |
| 20 | F1 | K1 | — | K2 |
| 21 | — | K1 | F1 | K2 |
| 22 | — | K1 | K2 | F1 |
| 23 | F1 | — | K1 | K2 |
| 24 | — | F1 | K1 | K2 |
| 25 | K1 | F1 | F2 | — |
| 26 | K1 | F1 | — | F2 |
| 27 | K1 | — | F1 | F2 |
| 28 | F1 | K1 | F2 | — |
| 29 | F1 | K1 | — | F2 |
| 30 | — | K1 | F1 | F2 |
| 31 | F1 | F2 | K1 | — |
| 32 | — | F1 | K1 | F2 |
| 33 | F1 | F2 | — | K1 |
| 34 | F1 | — | F2 | K1 |
| 35 | K1 | K2 | F1 | F2 |
| 36 | K1 | F1 | K2 | F2 |
| 37 | K1 | F1 | F2 | K2 |
| 38 | F1 | K1 | K2 | F2 |
| 39 | F1 | K1 | F2 | K2 |

Arrangements 1-12 in Table 1 represent embodiments in which the FGF21R agonist comprises a single KLB-interacting domain (K1) and a single FGFR1c-interacting domain (F1). For example, arrangement No. 1 in Table 1 represents an FGF21R agonist comprising a K1 component attached to the N-terminus of M1 and an F1 component attached to the C-terminus of M1.

Arrangements 13-24 in Table 1 represent embodiments in which the FGF21R agonist comprises two KLB-interacting domains (K1 and K2) and a single FGFR1c-interacting domain (F1). For example, arrangement No. 13 in Table 1 represents an FGF21R agonist comprising a K1 component attached to the N-terminus of M1, an F1 component attached to the C-terminus of M1, and a K2 component attached to the N-terminus of M2.

Arrangements 25-34 in Table 1 represent embodiments in which the FGF21R agonist comprises a single KLB-interacting domain (K1) and two FGFR1c-interacting domains (F1 and F2). For example, arrangement No. 25 in Table 1 represents an FGF21R agonist comprising a K1 component attached to the N-terminus of M1, an F1 component attached to the C-terminus of M1, and an F2 component attached to the N-terminus of M2.

Arrangements 35-39 in Table 1 represent embodiments in which the FGF21 agonist comprises two KLB-interacting domains (K1 and K2) and two FGFR1c-interacting domains (F1 and F2). For example, arrangement 35 in Table 1 represents an FGF21R agonist comprising a K1 component attached to the N-terminus of M1, a K2 component attached to the C-terminus of M1, an F1 component attached to the N-terminus of M2, and an F2 component attached to the C-terminus of M2.

The KLB-interacting domains and/or FGFR1c-interacting domains of the FGF21R agonists of the present invention, in certain embodiments, may be attached in tandem to a multimerizing domain. As used herein, two or more components are "attached in tandem" to a multimerizing domain if only one of the components is directly attached to the multimerizing domain while the other component(s) is/are attached to one another without being directly attached directly to the multimerizing domain. For example, a tandem arrangement of two KLB-interacting domains may be represented (from N-terminus to C-terminus) as K1-K2-M1; a tandem arrangement of two FGFR1c-interacting domains may be represented (from N-terminus to C-terminus) as F1-F2-M1; and a tandem arrangement of a KLB-interacting domain and an FGFR1c-interacting domain may be represented (from N-terminus to C-terminus) as K1-F1-M1 or F1-K1-M1. Other tandem arrangements of the various components are contemplated within the scope of the present invention and will be apparent to a person of ordinary skill in the art in light of the present disclosure.

The present invention includes FGF21R agonists in which a heavy chain variable region of an anti-KLB antibody is paired with a light chain variable region of an anti-KLB antibody, wherein an FGFR1c-binding domain (e.g., a polypeptide comprising the FGFR1c-binding portion of FGF21) is attached to the N-terminus of the anti-KLB antibody heavy chain variable region. An example of this type of structure is illustrated in FIG. 5A.

In another contemplated configuration, a heavy chain variable region of an anti-FGFR1c antibody is paired with a light chain variable region of an anti-FGFR1c antibody, wherein a KLB-binding domain (e.g., a polypeptide comprising the KLB-binding portion of FGF21) is attached to the C-terminus of the anti-FGFR1c light chain. An example of this type of structure is illustrated in FIG. 5B.

Linkers

The individual components of the FGF21 agonists of the present invention (K1, K2, F1, F2, M1, M2, etc.) may be attached to one another directly (e.g., a K1 may be directly attached to M1, etc.); alternatively, the individual components may be attached to one another via a linker component (e.g., K1 may be attached to M1 via a linker oriented between K1 and M1). In any of the arrangements disclosed herein, wherein one component is described as being "attached" to another component, the attachment may be through a linker (even if not specifically designated as such). As used herein, a "linker" is any molecule that joins two polypeptide components together. For example, a linker may be a peptide comprising from 1 to 20 amino acids connected together via peptide bonds. (A peptide bond per se, however, is not considered a "linker" for purposes of the present disclosure). In certain embodiments, the linker comprises sterically unhindered amino acids such as glycine and alanine. In certain embodiments, the linker is a flexible chain of amino acids that is resistant to proteolytic degradation. A linker may comprise two molecular structures that interact with one another. For example, in certain embodiments a linker may comprise a streptavidin component and a biotin component; the association between streptavidin (attached to one component) and biotin (attached to another component) serves as an attachment between individual components of the FGF21R agonists. Other similar linker arrangements and configurations involving linkers are contemplated within the scope of the present invention.

Peptide linkers may also be used to produce single chain antibodies of the invention. Peptide linkers are considered flexible peptides selected to assure that the proper three-dimensional folding of the VL and VH domains occurs. The portion of an antibody consisting of VL and VH domains is designated Fv (Fragment variable) and constitutes the antigen binding site. Single chain Fv (scFv) is an antibody fragment containing a VL domain and a VH domain on one polypeptide chain, wherein the N terminus of one domain and the C terminus of the other domain are joined by such a flexible linker (see, e.g., U.S. Pat. No. 4,946,778 (Ladner et al.); WO 88/09344, (Huston et al.). The linker is generally 10 to 50 amino acid residues, or about 10 to 30 amino acid residues, or about 12 to 30 amino acid residues, or about 15 to 25 amino acid residues. In one example, the linker is several repeats of Gly-Gly-Gly-Ser (SEQ ID NO: 468), such as (Gly-Gly-Gly-Ser)4 (SEQ ID NO: 446).

Additional examples of linkers are known in the art. These include polyGlycine linkers, such as Gly-Gly, Gly-Gly-Gly (3Gly), 4Gly, 5Gly, 6Gly, 7Gly, 8Gly or 9Gly. Examples of linkers also include Gly-Ser peptide linkers such as Ser-Gly, Gly-Ser, Gly-Gly-Ser, Ser-Gly-Gly, Gly-Gly-Gly-Ser (SEQ ID NO: 468), Ser-Gly-Gly-Gly (SEQ ID NO: 469), Gly-Gly-Gly-Gly-Ser (SEQ ID NO: 470), Ser-Gly-Gly-Gly-Gly (SEQ ID NO: 471), Gly-Gly-Gly-Gly-Gly-Ser (SEQ ID NO: 472), Ser-Gly-Gly-Gly-Gly-Gly (SEQ ID NO: 473), Gly-Gly-Gly-Gly-Gly-Gly-Ser (SEQ ID NO: 474), Ser-Gly-Gly-Gly-Gly-Gly-Gly (SEQ ID NO: 475), (Gly-Gly-Gly-Ser)n, which corresponds to SEQ ID NO: 468 repeated n times, wherein n=1 to 10, and (Ser-Gly-Gly-Gly)n, which corresponds to SEQ ID NO: 469 repeated n times, wherein n=1 to 10. (Gly-Gly-Gly-Ser)n and (Ser-Gly-Gly-Gly)n, which correspond to SEQ ID NOs: 468 and 469, respectively, repeated n times, are also known as (G3S)n and (S3G)n, respectively.

Anti-FGF21 Antibodies and Antigen-Binding Fragments Thereof

The present invention also comprises antibodies that specifically bind FGF21 and antigen-binding fragments thereof. Such anti-FGF21 antibodies and fragments may be included as components of the FGF21R agonists; e.g., wherein a KLB-interacting domain and/or an FGFR1c-interacting domain indirectly interacts with KLB or FGFR1c through FGF21. In such embodiments the KLB-interacting domain may bind an epitope on FGF21 located within the FGFR1c binding portion of FGF21, thereby allowing the KLB binding portion of FGF21 to interact with KLB. In this way FGF21 serves as a "bridge" or intermediary structure between the KLB-interacting domain and KLB. Similarly, the FGFR1c-interacting domain may bind an epitope on FGF21 located within the KLB binding portion of FGF21, thereby allowing the FGFR1c binding portion of FGF21 to interact with FGFR1c. Here, FGF21 serves as a "bridge" or intermediary structure between the FGFR1c-interacting domain and FGFR1c.

Exemplary anti-FGF21 antibodies, and antigen-binding portions thereof, that can be used to construct an anti-FGF21R agonist of the present invention are shown in Examples 1-5 herein. For example, any of the CDRs and/or heavy and light chain variable domains of the exemplary anti-FGF21 antibodies set forth in Table 2 may be included in the FGF21R agonists of the present invention.

The anti-FGF21 antibodies disclosed herein may also be used for various therapeutic and diagnostic applications on their own, i.e., not in the context of an FGF21R agonist but instead as independent molecular entities. For example, the present invention includes anti-FGF21 antibodies that are capable of stabilizing FGF21 in vivo (see Example 5 herein).

The present invention provides anti-FGF21 antibodies, or FGF21R agonists comprising an FGF21-binding domain comprising a heavy chain variable region (HCVR) having an amino acid sequence selected from the group consisting of SEQ ID NO: 2, 18, 34, 50 and 66, or a substantially similar sequence thereof having at least 90%, at least 95%, at least 98% or at least 99% sequence identity.

The present invention also provides anti-FGF21 antibodies, or FGF21R agonists comprising an FGF21-binding domain comprising a light chain variable region (LCVR) having an amino acid sequence selected from the group consisting of SEQ ID NO: 10, 26, 42, 58 and 74, or a substantially similar sequence thereof having at least 90%, at least 95%, at least 98% or at least 99% sequence identity.

The present invention also provides anti-FGF21 antibodies, or FGF21R agonists comprising an FGF21-binding domain comprising a HCVR and LCVR (HCVR/LCVR) sequence pair selected from the group consisting of SEQ ID NO: 2/10, 18/26, 34/42, 50/58 and 66/74.

The present invention also provides anti-FGF21 antibodies, or FGF21R agonists comprising an FGF21-binding domain comprising a heavy chain CDR3 (HCDR3) domain having an amino acid sequence selected from the group consisting of SEQ ID NO: 8, 24, 40, 56 and 72, or a substantially similar sequence thereof having at least 90%, at least 95%, at least 98% or at least 99% sequence identity; and a light chain CDR3 (LCDR3) domain having an amino acid sequence selected from the group consisting of SEQ ID NO: 16, 32, 48, 64 and 80, or a substantially similar sequence thereof having at least 90%, at least 95%, at least 98% or at least 99% sequence identity.

In certain embodiments, the antibody or antigen-binding portion of an antibody comprises a HCDR3/LCDR3 amino acid sequence pair selected from the group consisting of SEQ ID NO: 8/16, 24/32, 40/48, 56/64 and 72/80.

The present invention also provides anti-FGF21 antibodies, or FGF21R agonists comprising an FGF21-binding domain comprising a heavy chain CDR1 (HCDR1) domain having an amino acid sequence selected from the group consisting of SEQ ID NO: 4, 20, 36, 52 and 68, or a substantially similar sequence thereof having at least 90%, at least 95%, at least 98% or at least 99% sequence identity; a heavy chain CDR2 (HCDR2) domain having an amino acid sequence selected from the group consisting of SEQ ID NO: 6, 22, 38, 54 and 70, or a substantially similar sequence thereof having at least 90%, at least 95%, at least 98% or at least 99% sequence identity; a light chain CDR1 (LCDR1) domain having an amino acid sequence selected from the group consisting of SEQ ID NO: 12, 28, 44, 60 and 76, or a substantially similar sequence thereof having at least 90%, at least 95%, at least 98% or at least 99% sequence identity; and a light chain CDR2 (LCDR2) domain having an amino acid sequence selected from the group consisting of SEQ ID NO: 14, 30, 46, 62 and 78, or a substantially similar sequence thereof having at least 90%, at least 95%, at least 98% or at least 99% sequence identity.

Certain non-limiting, exemplary antibodies and antigen-binding fragments of the invention comprise HCDR1-HCDR2-HCDR3-LCDR1-LCDR2-LCDR3 domains, respectively, having the amino acid sequences selected from the group consisting of: SEQ ID NOs: 4-6-8-12-14-16 (e.g. H2M6499N); 20-22-24-28-30-32 (e.g. H2M6504N); 36-38-40-44-46-48 (e.g. H2M6509N); 52-54-56-60-62-64 (e.g. H4H6879P); 68-70-72-76-78-80 (e.g. H4H6915P).

In a related embodiment, the present invention includes anti-FGF21 antibodies, or FGF21R agonists comprising an FGF21-binding domain, wherein the antibody or fragment comprises the heavy and light chain CDR domains contained within heavy and light chain variable region (HCVR/LCVR) sequences selected from the group consisting of SEQ ID NO: 2/10, 18/26, 34/42, 50/58 and 66/74. Methods and techniques for identifying CDRs within HCVR and LCVR amino acid sequences are well known in the art and can be used to identify CDRs within the specified HCVR and/or LCVR amino acid sequences disclosed herein. Exemplary conventions that can be used to identify the boundaries of CDRs include, e.g., the Kabat definition, the Chothia definition, and the AbM definition. In general terms, the Kabat definition is based on sequence variability, the Chothia definition is based on the location of the structural loop regions, and the AbM definition is a compromise between the Kabat and Chothia approaches. See, e.g., Kabat, "Sequences of Proteins of Immunological Interest," National Institutes of Health, Bethesda, Md. (1991); Al-Lazikani et al., *J. Mol. Biol.* 273:927-948 (1997); and Martin et al., *Proc. Natl. Acad. Sci. USA* 86:9268-9272 (1989). Public databases are also available for identifying CDR sequences within an antibody.

In another aspect, the invention provides nucleic acid molecules encoding anti-FGF21 antibodies or antigen-binding fragments thereof. Recombinant expression vectors carrying the nucleic acids of the invention, and host cells into which such vectors have been introduced, are also encompassed by the invention, as are methods of producing the antibodies by culturing the host cells under conditions permitting production of the antibodies, and recovering the antibodies produced.

In one embodiment, the invention provides anti-FGF21 antibodies, or FGF21R agonists comprising an FGF21-binding domain comprising a HCVR encoded by a nucleic acid sequence selected from the group consisting of SEQ ID NO: 1, 17, 33, 49 and 65, or a substantially identical sequence having at least 90%, at least 95%, at least 98%, or at least 99% homology thereof.

The present invention also provides anti-FGF21 antibodies, or FGF21R agonists comprising an FGF21-binding domain comprising a LCVR encoded by a nucleic acid sequence selected from the group consisting of SEQ ID NO: 9, 25, 41, 57 and 73, or a substantially identical sequence having at least 90%, at least 95%, at least 98%, or at least 99% homology thereof.

The present invention also provides anti-FGF21 antibodies, or FGF21R agonists comprising an FGF21-binding domain comprising a HCDR3 domain encoded by a nucleotide sequence selected from the group consisting of SEQ ID NO: 7, 23, 39, 55 and 71, or a substantially identical sequence having at least 90%, at least 95%, at least 98%, or at least 99% homology thereof; and a LCDR3 domain encoded by a nucleotide sequence selected from the group consisting of SEQ ID NO: 15, 31, 47, 63 and 79, or a substantially identical sequence having at least 90%, at least 95%, at least 98%, or at least 99% homology thereof.

The present invention also provides anti-FGF21 antibodies, or FGF21R agonists comprising an FGF21-binding domain further comprising a HCDR1 domain encoded by a nucleotide sequence selected from the group consisting of SEQ ID NO: 3, 19, 35, 51 and 67, or a substantially identical sequence having at least 90%, at least 95%, at least 98%, or at least 99% homology thereof; a HCDR2 domain encoded by a nucleotide sequence selected from the group consisting of SEQ ID NO: 5, 21, 37, 53 and 69, or a substantially identical sequence having at least 90%, at least 95%, at least 98%, or at least 99% homology thereof; a LCDR1 domain encoded by a nucleotide sequence selected from the group consisting of SEQ ID NO: 11, 27, 43, 59 and 75, or a substantially identical sequence having at least 90%, at least 95%, at least 98%, or at least 99% homology thereof; and a LCDR2 domain encoded by a nucleotide sequence selected from the group consisting of SEQ ID NO: 13, 29, 45, 61 and 77, or a substantially identical sequence having at least 90%, at least 95%, at least 98%, or at least 99% homology thereof.

According to certain embodiments, the antibody or fragment thereof comprises the heavy and light chain CDR sequences encoded by the nucleic acid sequences of SEQ ID NOs: 1 and 9 (e.g. H2M6499N), 17 and 25 (e.g. H2M6504N), 33 and 41 (e.g. H2M6509N), 49 and 57 (e.g. H4H6879P) or 65 and 73 (e.g. H4H6915P).

Anti-FGF21R Antibodies and Antigen-Binding Fragments Thereof

The present invention also comprises antibodies that specifically bind FGF21R (herein referred to as KLB/FGFR1c) and antigen-binding fragments thereof. Such anti-KLB/FGFR1c antibodies and fragments may be included as components of the FGF21R agonists; e.g., wherein the anti-KLB/FGFR1c antibodies and fragments have a KLB-interacting domain and/or an FGFR1c-interacting domain which directly or indirectly interacts with KLB or FGFR1c or the KLB/FGFR1c coreceptor. In such embodiments the anti-KLB/FGFR1c antibody or antigen-binding portion thereof may bind an epitope on KLB. In another embodiment, the anti-KLB/FGFR1c antibody or antigen-binding portion thereof may bind an epitope on FGFR1c. In another embodiment, the anti-KLB/FGFR1c antibody or antigen-binding portion thereof may bind an epitope on that bridges the KLB/FGFR1c coreceptor.

Exemplary anti-KLB/FGFR1c antibodies, and antigen-binding portions thereof, that can be used to construct an anti-FGF21R agonist of the present invention are shown in Examples 6-16 herein. For example, any of the CDRs and/or heavy and light chain variable domains of the exemplary anti-KLB/FGFR1c antibodies set forth in Tables 7A and 7B may be included in the FGF21R agonists of the present invention.

The anti-KLB/FGFR1c antibodies disclosed herein may also be used for various therapeutic and diagnostic applications on their own, i.e., not in the context of an FGF21R agonist but instead as independent molecular entities. For example, the present invention includes anti-KLB/FGFR1c antibodies that are capable of binding both KLB/FGFR1c (see Example 8 herein). In other examples, the present invention includes anti-KLB/FGFR1c antibodies that are capable of activating MAPK signaling in KLB/FGFR1c-expressing cells in vitro, thereby mimicking FGF21 signaling (see Examples 9, 10 and 11 herein). In still other examples, the present invention includes anti-KLB/FGFR1c antibodies that are capable of inhibiting MAPK signaling by FGF21 in KLB/FGFR1c-expressing cells in vitro, thereby blocking FGF21 signaling (see Examples 9, 10 and 11 herein).

The present invention provides anti-KLB/FGFR1c antibodies, or FGF21R agonists, comprising a KLB-binding domain and/or an FGFR1c-binding domain comprising a heavy chain variable region (HCVR) having an amino acid sequence selected from the group consisting of SEQ ID NO: 82, 98, 114, 130, 146, 162, 178, 194, 210, 226, 242, 258, 274, 290, 306, 322, 338, 354, 370, 386, 402, and 418, or a substantially similar sequence thereof having at least 90%, at least 95%, at least 98% or at least 99% sequence identity.

The present invention provides anti-KLB/FGFR1c antibodies, or FGF21R agonists, comprising a KLB-binding domain and/or an FGFR1c-binding domain comprising a light chain variable region (LCVR) having an amino acid sequence selected from the group consisting of SEQ ID NO: 90, 106, 122, 138, 154, 170, 186, 202, 218, 234, 250, 266, 282, 298, 314, 330, 346, 362, 378, 394, 410, and 426, or a substantially similar sequence thereof having at least 90%, at least 95%, at least 98% or at least 99% sequence identity.

The present invention also provides anti-KLB/FGFR1c antibodies, or FGF21R agonists, comprising a KLB-binding domain and/or an FGFR1c-binding domain comprising a HCVR and LCVR (HCVR/LCVR) sequence pair selected from the group consisting of SEQ ID NO: 82/90, 98/106, 114/122, 130/138, 146/154, 162/170, 178/186, 194/202, 210/218, 226/234, 242/250, 258/266, 274/282, 290/298, 306/314, 322/330, 338/346, 354/362, 370/378, 386/394, 402/410, and 418/426.

The present invention also provides anti-KLB/FGFR1c antibodies, or FGF21R agonists, comprising a KLB-binding domain and/or an FGFR1c-binding domain comprising a heavy chain CDR3 (HCDR3) domain having an amino acid sequence selected from the group consisting of SEQ ID NO: 88, 104, 120, 136, 152, 168, 184, 200, 216, 232, 248, 264, 280, 296, 312, 328, 344, 360, 376, 392, 408, and 424, or a substantially similar sequence thereof having at least 90%, at least 95%, at least 98% or at least 99% sequence identity; and a light chain CDR3 (LCDR3) domain having an amino acid sequence selected from the group consisting of SEQ ID NO: 96, 112, 128, 144, 160, 176, 192, 208, 224, 240, 256, 272, 288, 304, 320, 336, 352, 368, 384, 400, 416, and 432, or a substantially similar sequence thereof having at least 90%, at least 95%, at least 98% or at least 99% sequence identity.

In certain embodiments, the antibody or antigen-binding portion of an antibody comprises a HCDR3/LCDR3 amino acid sequence pair selected from the group consisting of SEQ ID NO: 88/96, 104/112, 120/128, 136/144, 152/160, 168/176, 184/192, 200/208, 216/224, 232/240, 248/256, 264/272, 280/288, 296/304, 312/320, 328/336, 344/352, 360/368, 376/384, 392/400, 408/416, and 424/432.

The present invention also provides anti-KLB/FGFR1c antibodies, or FGF21R agonists, comprising a KLB-binding domain and/or an FGFR1c-binding domain comprising a heavy chain CDR1 (HCDR1) domain having an amino acid sequence selected from the group consisting of SEQ ID NO: 84, 100, 116, 132, 148, 164, 180, 196, 212, 228, 244, 260, 276, 292, 308, 324, 340, 356, 372, 388, 404, and 420, or a substantially similar sequence thereof having at least 90%, at least 95%, at least 98% or at least 99% sequence identity; a heavy chain CDR2 (HCDR2) domain having an amino acid sequence selected from the group consisting of SEQ ID NO: 86, 102, 118, 134, 150, 166, 182, 198, 214, 230, 246, 262, 278, 294, 310, 326, 342, 358, 374, 390, 406, and 422, or a substantially similar sequence thereof having at least 90%, at least 95%, at least 98% or at least 99% sequence identity; a light chain CDR1 (LCDR1) domain having an amino acid sequence selected from the group consisting of SEQ ID NO: 92, 108, 124, 140, 156, 172, 188, 204, 220, 236, 252, 268, 284, 300, 316, 332, 348, 364, 380, 396, 412, and 428, or a substantially similar sequence thereof having at least 90%, at least 95%, at least 98% or at least 99% sequence identity; and a light chain CDR2 (LCDR2) domain having an amino acid sequence selected from the group consisting of SEQ ID NO: 94, 110, 126, 142, 158, 174, 190, 206, 222, 238, 254, 270, 286, 302, 318, 334, 350, 366, 382, 398, 414, and 430, or a substantially similar sequence thereof having at least 90%, at least 95%, at least 98% or at least 99% sequence identity.

Certain non-limiting, exemplary antibodies and antigen-binding fragments of the invention comprise HCDR1-HCDR2-HCDR3-LCDR1-LCDR2-LCDR3 domains, respectively, having the amino acid sequences selected from the group consisting of: SEQ ID NOs: 84-86-88-92-94-96 (e.g. 8898P); 100-102-104-108-110-112 (e.g. 8115N); 116-118-120-124-126-128 (e.g. 8091N); 132-134-136-140-142-144 (e.g. 8092N); 148-150-152-156-158-160 (e.g. 8093N); 164-166-168-172-174-176 (e.g. 8096N); 180-182-184-188-190-192 (e.g. 8098N); 196-198-200-204-206-208 (e.g. 8109N); 212-214-216-220-222-224 (e.g. 8832N); 228-230-232-236-238-240 (e.g. 8833N); 244-246-248-252-254-256 (e.g. 8837P); 260-262-264-268-270-272 (e.g. 8852P); 276-278-280-284-286-288 (e.g. 8856P); 292-294-296-300-302-304 (e.g. 8859P); 308-310-312-316-318-320 (e.g. 8870P); 324-326-328-332-334-336 (e.g. 8871P); 340-342-344-348-350-352 (e.g. 8878P); 356-358-360-364-366-368 (e.g. 8880P); 372-374-376-380-382-384 (e.g. 8881P); 388-390-392-396-398-400 (e.g. 8897P); 404-406-408-412-414-416 (e.g. 8899P); and 420-422-424-428-430-432 (e.g. 8900P).

In a related embodiment, the present invention includes anti-KLB/FGFR1c antibodies, or FGF21R agonists, comprising a KLB-binding domain and/or an FGFR1c-binding domain, wherein the antibody or fragment comprises the heavy and light chain CDR domains contained within heavy and light chain variable region (HCVR/LCVR) sequences selected from the group consisting of SEQ ID NO: 82/90, 98/106, 114/122, 130/138, 146/154, 162/170, 178/186, 194/202, 210/218, 226/234, 242/250, 258/266, 274/282, 290/298, 306/314, 322/330, 338/346, 354/362, 370/378, 386/394, 402/410, and 418/426. Methods and techniques for identifying CDRs within HCVR and LCVR amino acid sequences are well known in the art and can be used to identify CDRs within the specified HCVR and/or LCVR amino acid sequences disclosed herein. Exemplary conventions that can be used to identify the boundaries of CDRs include, e.g., the Kabat definition, the Chothia definition, and the AbM definition. In general terms, the Kabat definition is based on sequence variability, the Chothia definition is based on the location of the structural loop regions, and the AbM definition is a compromise between the Kabat and Chothia approaches. See, e.g., Kabat, "Sequences of Proteins of Immunological Interest," National Institutes of Health, Bethesda, Md. (1991); Al-Lazikani et al., *J. Mol. Biol.* 273:927-948 (1997); and Martin et al., *Proc. Natl. Acad. Sci. USA* 86:9268-9272 (1989). Public databases are also available for identifying CDR sequences within an antibody.

In another aspect, the invention provides nucleic acid molecules encoding anti-KLB/FGFR1c antibodies or antigen-binding fragments thereof. Recombinant expression vectors carrying the nucleic acids of the invention, and host cells into which such vectors have been introduced, are also encompassed by the invention, as are methods of producing the antibodies by culturing the host cells under conditions permitting production of the antibodies, and recovering the antibodies produced.

In one embodiment, the invention provides anti-KLB/FGFR1c antibodies, or FGF21R agonists, comprising a KLB-binding domain and/or an FGFR1c-binding domain comprising a HCVR encoded by a nucleic acid sequence selected from the group consisting of SEQ ID NO: 81, 97, 113, 129, 145, 161, 177, 193, 209, 225, 241, 257, 273, 289, 305, 321, 337, 353, 369, 385, 401, and 417, or a substantially identical sequence having at least 90%, at least 95%, at least 98%, or at least 99% homology thereof.

The present invention also provides anti-KLB/FGFR1c antibodies, or FGF21R agonists, comprising a KLB-binding domain and/or an FGFR1c-binding domain comprising a LCVR encoded by a nucleic acid sequence selected from the group consisting of SEQ ID NO: 89, 105, 121, 137, 153, 169, 185, 201, 217, 233, 249, 265, 281, 297, 313, 329, 345, 361, 377, 393, 409, and 425, or a substantially identical sequence having at least 90%, at least 95%, at least 98%, or at least 99% homology thereof.

The present invention also provides anti-KLB/FGFR1c antibodies, or FGF21R agonists, comprising a KLB-binding domain and/or an FGFR1c-binding domain comprising a HCDR3 domain encoded by a nucleotide sequence selected from the group consisting of SEQ ID NO: 87, 103, 119, 135, 151, 167, 183, 199, 215, 231, 247, 263, 279, 295, 311, 327, 343, 359, 375, 391, 407, and 423, or a substantially identical sequence having at least 90%, at least 95%, at least 98%, or at least 99% homology thereof; and a LCDR3 domain encoded by a nucleotide sequence selected from the group consisting of SEQ ID NO: 95, 111, 127, 143, 159, 175, 191, 207, 223, 239, 255, 271, 287, 303, 319, 335, 351, 367, 383, 399, 415, and 431, or a substantially identical sequence having at least 90%, at least 95%, at least 98%, or at least 99% homology thereof.

The present invention also provides anti-KLB/FGFR1c antibodies, or FGF21R agonists, comprising a KLB-binding domain and/or an FGFR1c-binding domain further comprising a HCDR1 domain encoded by a nucleotide sequence selected from the group consisting of SEQ ID NO: 83, 99, 115, 131, 147, 163, 179, 195, 211, 227, 243, 259, 275, 291, 307, 323, 339, 355, 371, 389, 403, and 419, or a substantially identical sequence having at least 90%, at least 95%, at least 98%, or at least 99% homology thereof; a HCDR2 domain encoded by a nucleotide sequence selected from the group consisting of SEQ ID NO: 85, 101, 117, 133, 149, 165, 181, 197, 213, 229, 245, 261, 277, 293, 309, 325, 341, 357, 373, 389, 405, and 421, or a substantially identical sequence having at least 90%, at least 95%, at least 98%, or at least 99% homology thereof; a LCDR1 domain encoded by a nucleotide sequence selected from the group consisting of SEQ ID NO: 91, 107, 123, 139, 155, 171, 187, 203, 219, 235, 251, 267, 283, 299, 315, 331, 347, 363, 379, 395, 411, and 429, or a substantially identical sequence having at least 90%, at least 95%, at least 98%, or at least 99% homology thereof; and a LCDR2 domain encoded by a nucleotide sequence selected from the group consisting of SEQ ID NO: 93, 109, 125, 141, 157, 173, 189, 205, 221, 237, 253, 269, 285, 301, 317, 333, 349, 365, 381, 397, 413, and 429, or a substantially identical sequence having at least 90%, at least 95%, at least 98%, or at least 99% homology thereof.

According to certain embodiments, the antibody or fragment thereof comprises the heavy and light chain CDR sequences encoded by the nucleic acid sequence pairs of SEQ ID NOs: 81/89 (e.g. 8898P); 97/105 (e.g. 8115N); 113/121 (e.g. 8091N); 129/137 (e.g. 8092N); 145/153 (e.g. 8093N); 161/169 (e.g. 8096N); 177/185 (e.g. 8098N); 193/201 (e.g. 8109N); 209/217 (e.g. 8832N); 225/233 (e.g. 8833N); 241/249 (e.g. 8837P); 257/265 (e.g. 8852P); 273/281 (e.g. 8856P); 289/297 (e.g. 8859P); 305/313 (e.g. 8870P); 321/329 (e.g. 8871P); 337/345 (e.g. 8878P); 353/361 (e.g. 8880P); 369/377 (e.g. 8881P); 385/393 (e.g. 8897P); 401/409 (e.g. 8899P); and 417/425 (e.g. 8900P).

The invention provides bispecific FGF21R antibodies comprising a first antigen-binding domain that binds human KLB or a KLB-interacting domain of FGF21, a second antigen-binding domain that binds human FGFR1c or a FGFR1c-interacting domain of FGF21, and a multimerizing domain tethered to each of the first and second antigen-binding domains. Tables 2 and 7A describe the amino acid sequence identifiers for the anti-FGF21, anti-KLB and anti-FGFR1c examples of the invention. The bispecific antibody comprises a first HCVR/LCVR pair comprising a HCDR1, HCDR2, HCDR3, LCDR1, LCDR2 and LCDR3 of Tables 2 or 7A paired with a multimerizing domain M1 of the invention. The bispecific antibody comprises a second HCVR/LCVR pair comprising a HCDR1, HCDR2, HCDR3, LCDR1, LCDR2 and LCDR3 of Tables 2 or 7A paired with a multimerizing domain M2 of the invention. The first or second antigen binding-domain comprises a HCVR/LCVR pair selected from the group consisting of (i) Fab fragments; (ii) F(ab')2 fragments; (iii) Fd fragments; (iv) Fv fragments; and (v) single-chain Fv (scFv) polypeptides. The first antigen binding-domain comprises a first HCVR/LCVR pair in an arrangement consisting essentially of Fab or scFv. The second antigen binding-domain comprises a second HCVR/LCVR pair in an arrangement consisting essentially of Fab or scFv.

Alternatively, the invention provides bispecific antibodies comprising a first antigen-binding scFV that binds human KLB attached at the N-terminus of a multimerizing domain, and b) a second antigen-binding scFV that binds human FGFR1c attached at the C-terminus of the same multimerizing domain. In other embodiments, the invention provides bispecific antibodies comprising a first antigen-binding scFV that binds human FGFR1c attached at the N-terminus of a multimerizing domain, and b) a second antigen-binding scFV that binds human KLB attached at the C-terminus of the same multimerizing domain.

In any of the arrangements described herein, the bispecific molecule comprises a homodimer or heterodimer of the constituent polypeptide chains. In some embodiments, the multimerizing domain M1 and/or M2 is a constant fragment (Fc) domain of an immunoglobulin. In other embodiments, the multimerizing domain M1 and/or M2 is mutated or modified Fc domain. In other embodiments, M1 or M2 comprises a modified CH3 domain comprising at least one amino acid substitution, deletion or addition that reduces the binding of the M1 or M2 component to Protein A as compared to an M1 or M2 component with an unmodified CH3 domain. In other embodiments, antigen-binding domain is attached to M1 and/or M2 via a linker component (L).

In certain embodiments, an antigen-binding fragment of an antibody may contain at least one variable domain covalently linked to at least one constant fragment (Fc) domain, or otherwise tethered to an Fc domain. The term "tethered to" refers to a direct linkage via covalent bond, or a linker polypeptide sequence (L), to bring together two components such as a variable domain tethered to a constant domain. Thus, in certain examples, variable domains comprising a first and second antigen-binding domain, such as those that bind KLB and FGF1Rc to form a bispecific antibody, are each directly linked (or tethered) via a covalent bond or a linker amino acid sequence to, e.g. (from N-terminus to C-terminus) full or partial CH1, full or partial hinge, CH2 and CH3 domains. Non-limiting, exemplary configurations of variable and constant domains that may be found within an antigen-binding fragment of an antibody of the present invention include, but are not limited to: (i) VH-CH1-hinge-CH2-CH3; (ii) VH-hinge-CH2-CH3; (iii) VH-CL; (iv) VL-CH1-CH2-CH3; (v) VL-CH2-CH3; (vi) VL-CL; (vii) VH-VL-CH1-hinge-CH2-CH3; (viii) VH-VL-hinge-CH2-CH3; (ix) VH-VL-CL; (x) VH-VL-CH1-CH2-CH3; (xi) VH-VL-CH2-CH3; and (xii) VH-VL-CL. In any of these configurations, a hinge region may consist of at least upper and lower hinge amino acids which result in a flexible or semi-flexible linkage between adjacent variable and/or constant domains in a single polypeptide molecule. Moreover, an antigen-binding fragment of an antibody of the present invention may comprise a homo-dimer or heterodimer (or other multimer) of any of the variable and constant domain configurations listed above in non-covalent association with one another and/or with one or more monomeric VH or VL domain (e.g., by disulfide bond(s)). In still other embodiments, multispecific formats may include a variable region covalently linked to the C-terminus of a constant domain, e.g. VH-VL-CH1-hinge-CH2-CH3-VH-VL (see FIG. 2).

A multispecific antibody format of the invention, including the exemplary bispecific antibody formats disclosed herein, typically comprises at least two different variable domains, wherein each variable domain is capable of specifically binding to a separate antigen. Other multispecific formats of the invention, including the exemplary bispecific formats disclosed herein, comprise at least two different antigen-binding fragments, including one or two receptor-binding fragments of FGF21. In this context, an antigen-binding domain that binds KLB or FGFR1c includes fragments of FGF21 protein, and variants thereof. Multispecific formats may be adapted for use in the context of an antigen-binding fragment of an antibody or a receptor-binding fragment of FGF21 of the present invention using routine techniques available in the art.

The invention provides an FGF21R agonist comprising a bispecific antigen-binding molecule, wherein the bispecific antigen-binding molecule comprises a first antigen-binding domain that binds KLB or KLB/FGFR1c, and a second antigen-binding domain that binds FGFR1c or KLB/FGFR1c. The invention further provides a first antigen-binding domain comprising a heavy chain variable region (HCVR) amino acid sequence selected from the group consisting of SEQ ID NO: 98, 130, 146, 162, 178, 194, 242, 338, 354, and 370, and (ii) the light chain variable region (LCVR) amino acid sequence selected from the group consisting of SEQ ID NO: 106, 138, 154, 170, 186, 202, 250, 346, 362, and 378. The invention also provides a second antigen-binding domain comprises a heavy chain variable region (HCVR) amino acid sequence selected from the group consisting of SEQ ID NO: 290, 306, and 418, and (ii) the light chain variable region (LCVR) amino acid sequence selected from the group consisting of SEQ ID NO: 298, 314, and 426.

pH-Dependent Binding

The present invention provides FGF21R agonists comprising a KLB-interacting domain (K1) and an FGFR1c-interacting domain (F1), wherein one or both of the domains (K1 and/or F2) binds its antigen (e.g., KLB or FGFR1c) in a pH-dependent manner. For example, a KLB-interacting domain may exhibit reduced binding to KLB at acidic pH as compared to neutral pH. Likewise, an FGFR1c-interacting domain may exhibit reduced binding to FGFR1c at acidic pH as compared to neutral pH. Alternatively, one or both interacting domains may exhibit enhanced binding to its antigen at acidic pH as compared to neutral pH. The present invention also includes anti-FGF21 antibodies with pH-dependent binding characteristics.

Antigen-binding domains with pH-dependent binding characteristics for use in the context of the FGF21R agonists (or anti-FGF21 antibodies) of the present invention may be obtained, e.g., by screening a population of antibodies for reduced (or enhanced) binding to a particular antigen at acidic pH as compared to neutral pH. Additionally, modifications of the antigen-binding domain at the amino acid level may yield antigen-binding domains with pH-dependent characteristics. For example, by substituting one or more amino acid of an antigen-binding domain (e.g., within a CDR) with a histidine residue, an antigen-binding domain with reduced antigen-binding at acidic pH relative to neutral pH may be obtained. As used herein, the expression "acidic pH" means a pH of 6.0 or less. The expression "acidic pH" includes pH values of about 6.0, 5.95, 5.8, 5.75, 5.7, 5.65, 5.6, 5.55, 5.5, 5.45, 5.4, 5.35, 5.3, 5.25, 5.2, 5.15, 5.1, 5.05, 5.0, or less. As used herein, the expression "neutral pH" means a pH of about 7.0 to about 7.4. The expression "neutral pH" includes pH values of about 7.0, 7.05, 7.1, 7.15, 7.2, 7.25, 7.3, 7.35, and 7.4.

Therapeutic Formulation and Administration

The present invention provides pharmaceutical compositions comprising any of the FGF21R agonists, anti-KLB/FGFR1c antibodies or anti-FGF21 antibodies described herein. The pharmaceutical compositions of the invention are formulated with suitable carriers, excipients, and other agents that provide improved transfer, delivery, tolerance, and the like. A multitude of appropriate formulations can be found in the formulary known to all pharmaceutical chemists: Remington's Pharmaceutical Sciences, Mack Publishing Company, Easton, Pa. These formulations include, for example, powders, pastes, ointments, jellies, waxes, oils, lipids, lipid (cationic or anionic) containing vesicles (such as LIPOFECTIN™, Life Technologies, Carlsbad, Calif.), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) *J Pharm Sci Technol* 52:238-311.

The dose of FGF21R agonist, anti-KLB/FGFR1c antibody or anti-FGF21 antibody administered to a patient may vary depending upon the age and the size of the patient, target disease, conditions, route of administration, and the like. The preferred dose is typically calculated according to body weight or body surface area. Pharmaceutical compositions comprising FGF21R agonists, anti-KLB/FGFR1c antibodies or anti-FGF21 antibodies of the present invention may be administered to a subject in a single dose of about 0.01 to about 20 mg/kg body weight, more preferably about 0.02 to about 7, about 0.03 to about 5, or about 0.05 to about 3 mg/kg body weight. Depending on the severity of the condition, the frequency and the duration of the treatment can be adjusted. Effective dosages and schedules for administering the pharmaceutical compositions of the present invention may be determined empirically; for example, patient progress can be monitored by periodic assessment, and the dose adjusted accordingly. Moreover, interspecies scaling of dosages can be performed using well-known methods in the art (e.g., Mordenti et al., 1991, *Pharmaceul. Res.* 8:1351).

Various delivery systems are known and can be used to administer the pharmaceutical compositions of the invention, e.g., encapsulation in liposomes, microparticles, microcapsules, recombinant cells capable of expressing the mutant viruses, receptor mediated endocytosis (see, e.g., Wu et al., 1987, *J. Biol. Chem.* 262:4429-4432). Methods of introduction include, but are not limited to, intradermal, intramuscular, intraperitoneal, intravenous, subcutaneous, intranasal, epidural, and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

The pharmaceutical compositions of the present invention can be delivered subcutaneously or intravenously with a standard needle and syringe. In addition, with respect to subcutaneous delivery, a pen delivery device readily has applications in delivering a pharmaceutical composition of the present invention. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

Numerous reusable pen and autoinjector delivery devices have applications in the subcutaneous delivery of a pharmaceutical composition of the present invention. Examples include, but are not limited to AUTOPEN™ (Owen Mumford, Inc., Woodstock, UK), DISETRONIC™ pen (Disetronic Medical Systems, Bergdorf, Switzerland), HUMALOG MIX 75/25™ pen, HUMALOG™ pen, HUMALIN 70/30™ pen (Eli Lilly and Co., Indianapolis, Ind.), NOVOPEN™ I, II and III (Novo Nordisk, Copenhagen, Denmark), NOVOPEN JUNIOR™ (Novo Nordisk, Copenhagen, Denmark), BD™ pen (Becton Dickinson, Franklin Lakes, N.J.), OPTIPEN™, OPTIPEN PRO™, OPTIPEN STARLET™, and OPTICLIK™ (Sanofi-Aventis, Frankfurt, Germany), to name only a few. Examples of disposable pen delivery devices having applications in subcutaneous delivery of a pharmaceutical composition of the present invention include, but are not limited to the SOLOSTAR™ pen (Sanofi-Aventis), the FLEXPEN™ (Novo Nordisk), and the KWIKPEN™ (Eli Lilly), the SURECLICK™ Autoinjector (Amgen, Thousand Oaks, Calif.), the PENLET™ (Haselmeier, Stuttgart, Germany), the EPIPEN (Dey, L. P.), and the HUMIRA™ Pen (Abbott Labs, Abbott Park Ill.), to name only a few.

In certain situations, the pharmaceutical composition can be delivered in a controlled release system. In one embodiment, a pump may be used (see Langer, supra; Sefton, 1987, CRC Crit. Ref. Biomed. Eng. 14:201). In another embodiment, polymeric materials can be used; see, Medical Applications of Controlled Release, Langer and Wise (eds.), 1974, CRC Pres., Boca Raton, Fla. In yet another embodiment, a controlled release system can be placed in proximity of the composition's target, thus requiring only a fraction of the systemic dose (see, e.g., Goodson, 1984, in Medical Applications of Controlled Release, supra, vol. 2, pp. 115-138). Other controlled release systems are discussed in the review by Langer, 1990, Science 249:1527-1533.

The injectable preparations may include dosage forms for intravenous, subcutaneous, intracutaneous and intramuscular injections, drip infusions, etc. These injectable preparations may be prepared by methods publicly known. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc. The amount of active ingredient contained in such dosage forms is generally about 5 to about 500 mg per dosage form in a unit dose; especially in the form of injection, it is preferred that the aforesaid antibody is contained in about 5 to about 100 mg and in about 10 to about 250 mg for the other dosage forms.

Therapeutic Uses of the FGF21R Agonists

The FGF21R agonists, anti-KLB/FGFR1c antibodies and anti-FGF21 antibodies of the present invention are useful, inter alia, for the treatment or prevention of any disease or condition that may be improved or ameliorated by stimulating, mimicking and/or promoting FGF21 signaling. The FGF21R agonists, anti-KLB/FGFR1c antibodies and anti-FGF21 antibodies of the present invention are useful, inter alia, for the treatment or prevention of any disease or condition that may be improved by lowering blood glucose levels, activating glucose uptake in the subject, or increasing insulin sensitivity. For example, the present invention provides methods for treating a metabolic disease or disorder by administering an FGF21R agonist, anti-KLB/FGFR1c antibody or anti-FGF21 antibody (or pharmaceutical composition thereof) as described herein to a patient in need of such treatment. In the context of the methods of treatment described herein, the FGF21R agonist, anti-KLB/FGFR1c antibody or anti-FGF21 antibody may be administered as a monotherapy (i.e., as the only therapeutic agent) or in combination with one or more additional therapeutic agents (e.g. insulin, and other examples described elsewhere herein).

Exemplary diseases and disorders that are treatable by administering an FGF21R agonist, anti-KLB/FGFR1c antibody or anti-FGF21 antibody of the invention include, e.g., metabolic syndrome, obesity, hypertension, diabetes (e.g., type-2 diabetes, non-type-2 diabetes, type-1 diabetes, latent autoimmune diabetes, maturity onset diabetes of the young, etc.), dyslipidemia, hypercholesterolemia, hyperglycemia, non-alcoholic steatohepatitis (NASH), non-alcoholic fatty liver disease (NAFLD), and polycystic ovary syndrome (PCOS).

The present invention provides methods for decreasing body weight (e.g., total body mass), decreasing body mass index (BMI), increasing insulin sensitivity, reducing elevated blood glucose levels, reducing elevated triglycerides, and/or reducing cholesterol levels, by administering an FGF21R agonist, anti-KLB/FGFR1c antibody or anti-FGF21 antibody (or pharmaceutical composition thereof) as described herein to a patient in need of such treatment.

Combination Therapies and Formulations

The present invention includes compositions and therapeutic formulations comprising any of the FGF21R agonists, anti-KLB/FGFR1c antibodies or anti-FGF21 antibodies described herein in combination with one or more additional therapeutically active components, and methods of treatment comprising administering such combinations to subjects in need thereof.

The FGF21R agonists, anti-KLB/FGFR1c antibodies or anti-FGF21 antibodies of the present invention may be co-formulated with and/or administered in combination with additional therapeutically active components such as, e.g., biguanide (metformin); sulfonylureas (e.g., glyburide, glipizide); PPAR gamma agonists (e.g., pioglitazone, rosiglitazone); glinides (e.g., meglitinide, repaglinide, nateglinide); DPP-4 inhibitors (e.g., Januvia®, Onglyza®); alpha-glucosidase inhibitors (e.g., acarbose, voglibose); insulin; incretin mimetics (e.g., Byetta®, Exenatide®); GLP-1 analogs (e.g., liraglutide); GLP-1R agonists; glucagon receptor antagonist (e.g., anti-GCGR antibodies); leptin; and other agonists of the FGF21 signaling pathway (e.g., R1MAbs [Wu et al. (2011), Sci. Transl. Med. 3(111):113ra126; WO2012/158704]; mimAbs [Foltz et al. (2012), Sci. Transl. Med. 4(162):162ra153]).

The additional therapeutically active component(s) may be administered to a subject prior to administration of an FGF21R agonist, anti-KLB/FGFR1c antibody or anti-FGF21 antibody of the present invention. For example, a first component may be deemed to be administered "prior to" a second component if the first component is administered 1 week before, 72 hours before, 60 hours before, 48 hours before, 36 hours before, 24 hours before, 12 hours before, 6 hours before, 5 hours before, 4 hours before, 3 hours before, 2 hours before, 1 hour before, 30 minutes before, 15 minutes before, 10 minutes before, 5 minutes before, or less than 1 minute before administration of the second component. In other embodiments, the additional therapeutically active component(s) may be administered to a subject after administration of an FGF21R agonist of the present invention. For example, a first component may be deemed to be administered "after" a second component if the first component is administered 1 minute after, 5 minutes after, 10 minutes after, 15 minutes after, 30 minutes after, 1 hour after, 2 hours after, 3 hours after, 4 hours after, 5 hours after, 6 hours after, 12 hours after, 24 hours after, 36 hours after, 48 hours after, 60 hours after, 72 hours after administration of the second component. In yet other embodiments, the additional therapeutically active component(s) may be administered to a subject concurrent with administration of an FGF21R agonist of the present invention. "Concurrent" administration, for purposes of the present invention, includes, e.g., administration of an FGF21R agonist and an additional therapeutically active component to a subject in a single dosage form, or in separate dosage forms administered to the subject within about 30 minutes or less of each other. If administered in separate dosage forms, each dosage form may be administered via the same route (e.g., both the FGF21R agonist and the additional therapeutically active component may be administered intravenously, subcutaneously, etc.); alternatively, each dosage form may be administered via a different route (e.g., the FGF21R agonist may be administered subcutaneously, and the additional therapeutically active component may be administered intravenously or orally, etc.). In any event, administering the components in a single dosage from, in separate dosage forms by the same route, or in separate dosage forms by different routes are all considered "concurrent administration," for purposes of the present disclosure. Moreover, for purposes of the present disclosure, administration of an FGF21R agonist "prior to", "concurrent with," or "after" (as those terms are defined herein above) administration of an additional therapeutically active component is considered administration of an FGF21R agonist "in combination with" an additional therapeutically active component).

The present invention includes pharmaceutical compositions in which an FGF21R agonist of the present invention is co-formulated with one or more of the additional therapeutically active component(s) as described elsewhere herein.

Administration Regimens

According to certain embodiments of the present invention, multiple doses of an FGF21R agonist or anti-KLB/FGFR1c antibody or anti-FGF21 antibody (or a pharmaceutical composition thereof) may be administered to a subject over a defined time course. The methods according to this aspect of the invention comprise sequentially administering to a subject multiple doses of an FGF21R agonist, anti-KLB/FGFR1c antibody or anti-FGF21 antibody of the invention. As used herein, "sequentially administering" means that each dose of FGF21R agonist, anti-KLB/FGFR1c antibody or anti-FGF21 antibody is administered to the subject at a different point in time, e.g., on different days separated by a predetermined interval (e.g., hours, days, weeks or months). The present invention includes methods which comprise sequentially administering to the patient a single initial dose of an FGF21R agonist, anti-KLB/FGFR1c antibody or anti-FGF21 antibody, followed by one or more secondary doses of the FGF21R agonist, anti-KLB/FGFR1c antibody or anti-FGF21 antibody, and optionally followed by one or more tertiary doses of the FGF21R agonist, anti-KLB/FGFR1c antibody or anti-FGF21 antibody.

The terms "initial dose," "secondary doses," and "tertiary doses," refer to the temporal sequence of administration of the FGF21R agonist, anti-KLB/FGFR1c antibody or anti-FGF21 antibody of the invention. Thus, the "initial dose" is the dose which is administered at the beginning of the treatment regimen (also referred to as the "baseline dose"); the "secondary doses" are the doses which are administered after the initial dose; and the "tertiary doses" are the doses which are administered after the secondary doses. The initial, secondary, and tertiary doses may all contain the same amount of FGF21R agonist, anti-KLB/FGFR1c antibody or anti-FGF21 antibody, but generally may differ from one another in terms of frequency of administration. In certain embodiments, however, the amount of FGF21R agonist, anti-KLB/FGFR1c antibody or anti-FGF21 antibody contained in the initial, secondary and/or tertiary doses varies from one another (e.g., adjusted up or down as appropriate) during the course of treatment. In certain embodiments, two or more (e.g., 2, 3, 4, or 5) doses are administered at the beginning of the treatment regimen as "loading doses" followed by subsequent doses that are administered on a less frequent basis (e.g., "maintenance doses").

In certain exemplary embodiments of the present invention, each secondary and/or tertiary dose is administered 1 to 26 (e.g., 1, 1½%, 2, 2½%, 3, 3½%, 4, 4½%, 5, 5½%, 6, 6½%, 7, 7½%, 8, 8½%, 9, 9½%, 10, 10½%, 11, 11½%, 12, 12½%, 13, 13½%, 14, 14½%, 15, 15½%, 16, 16½%, 17, 17½%, 18, 18½%, 19, 19½%, 20, 20½%, 21, 21½%, 22, 22½%, 23, 23½%, 24, 24½%, 25, 25½%, 26, 26½%, or more) weeks after the immediately preceding dose. The phrase "the immediately preceding dose," as used herein, means, in a sequence of multiple administrations, the dose of FGF21R agonist, anti-KLB/FGFR1c antibody or anti-FGF21 antibody which is administered to a patient prior to the administration of the very next dose in the sequence with no intervening doses.

The methods according to this aspect of the invention may comprise administering to a patient any number of secondary and/or tertiary doses of an FGF21R agonist, anti-KLB/FGFR1c antibody or anti-FGF21 antibody. For example, in certain embodiments, only a single secondary dose is administered to the patient. In other embodiments, two or more (e.g., 2, 3, 4, 5, 6, 7, 8, or more) secondary doses are administered to the patient. Likewise, in certain embodiments, only a single tertiary dose is administered to the patient. In other embodiments, two or more (e.g., 2, 3, 4, 5, 6, 7, 8, or more) tertiary doses are administered to the patient.

In embodiments involving multiple secondary doses, each secondary dose may be administered at the same frequency as the other secondary doses. For example, each secondary dose may be administered to the patient 1 to 2 weeks or 1 to 2 months after the immediately preceding dose. Similarly, in embodiments involving multiple tertiary doses, each tertiary dose may be administered at the same frequency as the other tertiary doses. For example, each tertiary dose may be administered to the patient 2 to 12 weeks after the immediately preceding dose. In certain embodiments of the invention, the frequency at which the secondary and/or tertiary doses are administered to a patient can vary over the course of the treatment regimen. The frequency of administration may also be adjusted during the course of treatment by a physician depending on the needs of the individual patient following clinical examination.

The present invention includes administration regimens in which 2 to 6 loading doses are administered to a patient a first frequency (e.g., once a week, once every two weeks, once every three weeks, once a month, once every two months, etc.), followed by administration of two or more maintenance doses to the patient on a less frequent basis. For example, according to this aspect of the invention, if the loading doses are administered at a frequency of once a month, then the maintenance doses may be administered to the patient once every six weeks, once every two months, once every three months, etc.).

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1. Generation of Human Monoclonal Antibodies to FGF21

An immunogen comprising recombinantly expressed human FGF21 protein produced with a C-terminal epitope tag was administered directly, with an adjuvant to stimulate the immune response, to a VELOCIMMUNE® mouse comprising DNA encoding human Immunoglobulin heavy and kappa light chain variable regions. The antibody immune response was monitored by a FGF21-specific immunoassay. When a desired immune response was achieved splenocytes were harvested and fused with mouse myeloma cells to preserve their viability and form hybridoma cell lines. The hybridoma cell lines were screened and selected to identify cell lines that produce FGF21-specific antibodies. Using this technique several anti-FGF21 chimeric antibodies (i.e., antibodies possessing human variable domains and mouse constant domains) were obtained; exemplary antibodies generated in this manner were designated as follows: H2M6499N, H2M6504N and H2M6509N. The human variable domains from the chimeric antibodies were subsequently cloned onto human constant domains to make fully human anti-FGF21 antibodies as described herein.

Anti-FGF21 antibodies were also isolated directly from antigen-positive B cells without fusion to myeloma cells, as described in US 200710280945A1. Using this method, fully human anti-FGF21 antibodies (i.e., antibodies possessing human variable domains and human constant domains) were obtained; exemplary antibodies generated in this manner were designated as follows: H4H6879P and H4H6915P.

Certain biological properties of the exemplary anti-FGF21 antibodies generated in accordance with the methods of this Example are described in detail in the Examples set forth below.

Example 2. Heavy and Light Chain Variable Region Amino Acid Sequences

Table 2 sets forth the heavy and light chain variable region amino acid sequence pairs of selected anti-FGF21 antibodies and their corresponding antibody identifiers.

Antibodies are typically referred to herein according to the following nomenclature: Fc prefix (e.g. "H2M," "H4H," etc.), followed by a numerical identifier (e.g. "6499," "6504," or "6879" as shown in Table 2), followed by a "P" or "N" suffix. Thus, according to this nomenclature, an antibody may be referred to herein as, e.g., "H2M6499N," "H2M6504N," "H2M6509N," "H4H6879P," "H4H6915P," etc. The H2M and H4H prefixes on the antibody designations used herein indicate the particular Fc region isotype of the antibody. For example, an "H2M" antibody has a mouse IgG2 Fc, whereas an "H4H" antibody has a human IgG4 Fc. As will be appreciated by a person of ordinary skill in the art, an antibody having a particular Fc isotype can be converted to an antibody with a different Fc isotype (e.g., an antibody with a mouse IgG2 Fc can be converted to an antibody with a human IgG4, etc.), but in any event, the variable domains (including the CDRs)—which are indicated by the numerical identifiers shown in Table 2—will remain the same, and the binding properties are expected to be identical or substantially similar regardless of the nature of the Fc domain.

Example 3. Antibody Binding to Human FGF21 as Determined by Surface Plasmon Resonance Binding associative and dissociative rate constants ($k_a$ and $k_d$, respectively) and calculated equilibrium dissociation constants and dissociative half-lives ($K_D$ and $t_{1/2}$, respectively) for antigen binding to anti-FGF21 antibodies were determined using a real-time surface plasmon resonance biosensor (Biacore 4000, GE Healthcare Life Sciences, Piscataway, N.J.) assay performed at 25° C. and 37° C. Antibodies were captured on a goat anti-mouse IgG polyclonal antibody (GE Healthcare, BR-1008-38) surface created through direct amine coupling of the anti-IgG antibodies to a Biacore CM5 sensor chip. Kinetic experiments were carried out using HBS-EP (10 mM HEPES, 150 mM NaCl, 3 mM EDTA, 0.05% Surfactant P20, pH 7.4) as both the running buffer and the sample buffer. Antigen-antibody association rates were measured by injecting various concentrations (ranging from 200 to 12.5 nM, 4-fold dilutions) of recombinant human FGF21 expressed with an N-terminal hexahistidine tag (His6-hFGF21; SEQ ID NO: 436) or recombinant cynomolgus monkey FGF21 with an N-terminal hexhistidine tag (His6-MfFGF21; SEQ ID NO: 437) over the captured antibody surface at a flow rate of 30 µL/min. Antibody-antigen association was monitored for 180 seconds while dissociation in buffer was monitored for 300 seconds. Kinetic association ($k_a$) and dissociation ($k_d$) rate constants were determined by processing and fitting the data using Scrubber software version 2.0c. Binding dissociation equilibrium constants ($K_D$) and dissociative half-lives ($t_{1/2}$) were calculated from the kinetic rate constants as: $K_D=k_d/k_a$ and $t1/2=\ln(2)/k_d$. Kinetic binding parameters for different anti-FGF21 monoclonal antibodies are shown in Tables 3 (25° C.) and 4 (37° C.).

TABLE 2

| Antibody Designation | SEQ ID NOs: | | | | | | | |
|---|---|---|---|---|---|---|---|---|
| | HCVR | HCDR1 | HCDR2 | HCDR3 | LCVR | LCDR1 | LCDR2 | LCDR3 |
| 6499N | 2 | 4 | 6 | 8 | 10 | 12 | 14 | 16 |
| 6504N | 18 | 20 | 22 | 24 | 26 | 28 | 30 | 32 |
| 6509N | 34 | 36 | 38 | 40 | 42 | 44 | 46 | 48 |
| 6879P | 50 | 52 | 54 | 56 | 58 | 60 | 62 | 64 |
| 6915P | 66 | 68 | 70 | 72 | 74 | 76 | 78 | 80 |

TABLE 3

Binding Characteristics of Anti-FGF21 Antibodies to FGF21 constructs at 25° C.

| Antibody | Analyte | ka (Ms$^{-1}$) | kd (s$^{-1}$) | K$_D$ (Molar) | t$_{1/2}$ (min) |
|---|---|---|---|---|---|
| H2M6504N | His6-hFGF21 | 8.60E+05 | 1.97E-03 | 2.30E-09 | 5.9 |
|  | His6-MfFGF21 | 6.40E+05 | 2.37E-02 | 3.72E-08 | 0.5 |
| H2M6509N | His6-hFGF21 | 1.11E+05 | 2.97E-03 | 2.66E-08 | 3.9 |
|  | His6-MfFGF21 | 6.60E+04 | 3.16E-03 | 4.76E-08 | 3.7 |
| H2M6499N | His6-hFGF21 | 3.49E+05 | 6.69E-03 | 1.92E-08 | 1.7 |
|  | His6-MfFGF21 | 2.50E+05 | 5.78E-03 | 2.32E-08 | 2.0 |

TABLE 4

Binding Characteristics of Anti-FGF21 Antibodies to FGF21 constructs at 37° C.

| Antibody | Analyte | ka (Ms$^{-1}$) | kd (s$^{-1}$) | K$_D$ (Molar) | t$_{1/2}$ (min) |
|---|---|---|---|---|---|
| H2M6504N | His6-hFGF21 | 1.25E+06 | 5.49E-03 | 4.40E-09 | 2.1 |
|  | His6-MfFGF21 | 8.20E+05 | 5.30E-02 | 6.40E-08 | 0.2 |
| H2M6509N | His6-hFGF21 | 2.36E+05 | 1.39E-02 | 5.89E-08 | 0.8 |
|  | His6-MfFGF21 | 1.30E+05 | 1.42E-02 | 1.09E-07 | 0.8 |
| H2M6499N | His6-hFGF21 | 5.16E+05 | 2.12E-02 | 4.11E-08 | 0.5 |
|  | His6-MfFGF21 | 3.23E+05 | 1.50E-02 | 4.65E-08 | 0.8 |

As shown in Tables 3 and 4, all three of the exemplary anti-FGF21 antibodies tested bound His6-hFGF21 at 25° C. with K$_D$ values ranging from 2.3 nM to 26.6 nM and at 37° C. with K$_D$ values ranging from 4.4 nM to 58.9 nM. Moreover, all three of the exemplary anti-FGF21 antibodies tested also bound His6-MfFGF21 at 25° C. with K$_D$ values ranging from 23.2 nM to 47.6 nM and at 37° C. with K$_D$ values ranging from 46.5 nM to 109 nM.

Example 4A. Anti-FGF21 Antibodies Block FGF21-Mediated Signaling In Vitro

Fibroblast growth factor-21 (FGF21) is a 209 amino acid protein expressed in liver that potently activates glucose uptake on adipocytes. FGF21 activates the FGF21R, a single-pass transmembrane protein composed of beta-klotho (KLB) and tyrosine kinase fibroblast growth factor receptor 1 isoform IIIc (FGFR1c) coreceptor, hereinafter referred to as KLB/FGFR1c. Stimulation of KLB/FGFR1c by FGF21 leads to activation of the mitogen-activated protein kinase (MAPK) pathway.

In this Example, a bioassay was used to detect the activation of the MAPK pathway by FGF21 ligand. HEK293 cell lines were generated that stably express full-length human FGFR1c (amino acids 1-733 of GenBank accession number NP_075593, SEQ ID NO: 433), full-length human KLB (amino acids 1-1044 of GenBank accession number NP_783864.1, SEQ ID NO: 434), along with a luciferase reporter (SRE response element-luciferase, SA Bioscience, Valencia, Calif., Cat. #CLS-010L). The stable cell line containing these components (referred to as 293/hKLB/FGFR1c/SRE-Luc cell line) was maintained in DMEM supplemented with 10% FBS, NEAA, penicillin/streptomycin, 1 µg/mL puromycin, 500 µg/mL G418, and 100 µg/mL hygromycin B.

For the bioassay, 293/hKLB/FGFR1c/SRE-Luc cells were seeded into 96-well assay plates at 20,000 cells/well in OPTIMEM (Invitrogen, Carlsbad, Calif., Cat #31985-070) supplemented with 0.1% FBS, penicillin/streptomycin and L-glutamine, and then incubated at 37° C. and 5% $CO_2$ overnight. The next morning, recombinant human FGF21 expressed with an N-terminal hexahistidine tag (His6-hFGF21; SEQ ID NO: 436) was serially diluted (1:3) from 300 nM to 0.005 nM (plus a sample containing buffer alone without FGF21) to determine the FGF-21 dose response. Antibodies were also serially diluted (1:3), from 100 nM to 0.002 nM (plus a sample containing buffer alone without antibody), and then incubated with a fixed concentration (1 nM) of FGF21 for 1 hour at room temperature. After 1 hour, the FGF-21 dose response samples and the antibody/FGF21 mixtures were added to cells and allowed to incubate for 5.5 hours at 37° C. in the presence of 5% $CO_2$ The luciferase activity was detected after this incubation by the addition of OneGlo reagent (Promega, Madison, Wis., Cat #E6051) and measurement of luminescence using a Victor X instrument (Perkin Elmer, Waltham, Mass.). IC$_{50}$ values for the anti-FGF21 antibodies and isotype controls are shown in Table 5A. (Isotype Control 1=a mouse isotype negative control; Isotype Control 2=a human isotype negative control).

TABLE 5A

Inhibition of FGF21 Activation of 293/KLB/FGFR1c/SRE-Luc Cells by Anti-FGF21 Antibodies

| Antibody | IC$_{50}$ (M) |
|---|---|
| H2aM6499N | 1.1E-08 |
| H2aM6504N | 1.0E-09 |
| H2aM6509N | 9.1E-09 |
| H4H6879P | 1.3E-09 |
| H4H6915P | 5.0E-10 |
| Isotype Control 1 | Not Blocking |
| Isotype Control 2 | Not Blocking |

As shown in Table 5A, all 5 anti-FGF21 antibodies tested in the 293/hKLB/FGFR1c/SRE-Luc bioassay blocked activation induced by 1 nM FGF21 with IC$_{50}$ values ranging from 500 pM to 11 nM. The two isotype control antibodies displayed no blocking of FGF21 activation. Human FGF21 activated the 293/hKLB/FGFR1cSRE-Luc cells with an EC$_{50}$ value of 1.9 nM in this assay.

Example 4B. Anti-FGF21 Antibodies Block FGF21 Binding to KLB as Detected by ELISA The ability of anti-FGF21 antibodies to block human FGF21 binding to a cognate binding partner human klotho beta was evaluated with an ELISA-based immunoassay. Briefly, human klotho beta (hKLB-10his; R&D systems, #5889-KB-050) was coated at 2 µg/mL on a 96-well plate in PBS buffer overnight at 4° C. Nonspecific binding sites were subsequently blocked using a 0.5% (w/v) solution of BSA in PBS. This plate was used to measure free biotinylated human FGF21 expressed with a N-terminal hexahistidine tag (biotin-6His-hFGF21) in a 6His-hFGF21 (SEQ ID: 436) solution pre-equilibrated with varying concentrations of anti-FGF21 antibodies. A constant concentration of 300pM of human FGF21 expressed with a N-terminal hexahistidine tag (biotin-6His-hFGF21) was pre-mixed with varied amounts of anti-FGF21 antibodies, ranging from 0 to −200 nM in serial dilutions, followed by an 1 hour incubation at room temperature (RT) to allow antibody-antigen binding to reach equilibrium. The equilibrated sample solutions were then transferred to hKLB-10his-coated plates. After 1 hour of binding at RT, the plates were washed and bound biotin 6His-hFGF21 was detected using HRP conjugated streptavidin (Thermo Scientific, #N200). Samples were developed with a TMB solution to produce a colorimetric reaction and then neutralized with 1M sulfuric acid before measuring absorbance at 450 nm on a Victor plate reader. Data analysis was performed using a sigmoidal dose-response model within Prism™ software (GraphPad).

The calculated $IC_{50}$ values (represented in M) for the antibodies tested were defined as the amount of antibody required to achieve 50% reduction of biotin 6His-hFGF21 bound to the plate-coated receptor. The absorbance measured for the constant concentration of biotin 6His-hFGF21 alone is defined as 0% blocking and the absorbance measured for no added biotin 6His-hFGF21 is defined as 100% blocking. Percent blockade was calculated as the ratio of the reduction in signal observed in the presence of antibody relative to the difference between the signal with biotin 6His-hFGF21 alone and background (signal from HRP conjugated streptavidin alone) subtracted from 100% blocking as defined previously. The absorbance values of the wells containing the highest concentration for each antibody were used to determine the percent maximum blockade. The results, shown in Table 5B, indicate that one antibody, H2aM6499N, blocked the biotin 6His-hFGF21 from binding the hKLB-10his with a subnanomolar $IC_{50}$ value and the other four anti-FGF21 antibodies tested are weak or non-blockers of the biotin 6His-hFGF21/hKLB-10his interaction.

TABLE 5B

Anti-FGF21 antibody blocking of biotin 6His-Human FGF21 binding to hKLB-10his

| Antibody | Blocking of biotin 6His-Human FGF21 binding to hKLB $IC_{50}$ (M) | % Blocking at 100 nM Antibody Concentration |
| --- | --- | --- |
| H2aM6499N | 7.6E−11 | 98 |
| H2aM6504N | IC | 64 |
| H2aM6509N | >1.0E−07 | 31 |
| H4H6879P | >1.0E−07 | 34 |
| H4H6915P | Non-blocker | 8 |

IC = inconclusive; sample has enhancement of signal before blocking at high concentrations

Example 5. Anti-FGF21 Antibodies Stabilize Exogenous Human FGF21 In Vivo

To evaluate the ability of anti-FGF21 monoclonal antibodies to stabilize circulating FGF21 in vivo, a type 2 diabetic ob/ob mouse model was used. The experiment was performed on ob/ob mice purchased from Harlan Laboratories, Indianapolis, Ind. (Strain B6.V-Lepob/J: #000632) that were 9 weeks old. Since all antibodies tested do not bind to mouse or rat FGF21, the ob/ob study was designed to measure circulating human FGF21 levels after an injection of exogenous human FGF21.

Mice were fed an ad lib diet and administered a single subcutaneous injection of an anti-FGF21 antibody or an isotype control antibody at a dose of 3 mg/kg. On day 1 after antibody administration, mice were then intraperitoneally injected with recombinant human FGF21 expressed with a N-terminal hexahistidine tag (6His-hFGF21; SEQ ID NO: 436) at a dose of 1 mg/kg. Plasma samples were collected from all mice after 4 hours of fasting on day 2 and day 7. Circulating FGF21 levels were determined from mouse plasma samples using a sandwich ELISA (human FGF21 ELISA kit, R&D Systems, # DF2100). The ELISA also detects mouse FGF21 (approximately 21% cross-reactivity, based on vendor specifications), so the values obtained from the ob/ob mice reflect both endogenous mouse FGF21 and the exogenous 6His-hFGF21. Average plasma FGF21 levels (ng/mL) for each treatment group at Day 2 and Day 7 are shown in Table 6. (All values are plotted as mean+/− standard error of the mean (SEM). Statistical analysis was performed utilizing GraphPad software Prism 5.0.)

TABLE 6

Effect of Anti-FGF21 Antibodies on Exogenous FGF21 in ob/ob Mice

| | FGF21 Levels in circulation (ng/mL) | |
| --- | --- | --- |
| Antibody | Day 2 | Day 7 |
| Isotype control (n = 6) | 5.736 ± 5.590 | 21.18 ± 10.20 |
| H4H6879P (n = 6) | 1748 ± 564.0 | 184.4 ± 170.7 |
| H4H6915P (n = 6) | 5659 ± 949.0*** | 443.7 ± 146.3 |
| H4H6504N (n = 6) | 3291 ± 289.4** | 108.7 ± 38.6 |

***P < 0.001 compared with Isotype control in each time point
**P < 0.01 compared with Isotype control in each time point Statistical significance of treatment groups compared to the isotype control group was determined by one-way ANOVA with Tukey post-test. As shown in Table 6, two of the tested antibodies showed a statistically significant increase in circulating FGF21 levels compared to isotype control antibody group on day 2. The anti-FGF21 antibodies stabilized exogenously injected human FGF21 up to day 7, although the levels at day 7 were not statistically significant given the wide variation of FGF21 levels observed between mice in each group.

Example 6. Generation of Human Monoclonal Antibodies to FGF21 Receptor

An immunogen comprising recombinantly expressed human KLB/FGFR1c coreceptor protein produced with a C-terminal epitope tag was administered directly, with an adjuvant to stimulate the immune response, to a VELOCIMMUNE® mouse comprising DNA encoding human Immunoglobulin heavy and kappa light chain variable regions. The antibody immune response was monitored by a KLB/FGFR1c-specific immunoassay. When a desired immune response was achieved splenocytes were harvested and fused with mouse myeloma cells to preserve their viability and form hybridoma cell lines. The hybridoma cell lines were screened and selected to identify cell lines that produce KLB/FGFR1c-specific antibodies. Using this technique several anti-KLB/FGFR1c chimeric antibodies (i.e., antibodies possessing human variable domains and mouse constant domains) were obtained. The human variable domains from the chimeric antibodies were subsequently cloned onto human constant domains to make fully human anti-KLB/FGFR1c antibodies as described herein.

Anti-KLB/FGFR1c antibodies were also isolated directly from antigen-positive B cells without fusion to myeloma cells, as described in US 200710280945A1.

Certain biological properties of the exemplary anti-KLB/FGFR1c antibodies generated in accordance with the methods of this Example are described in detail in subsequent Examples.

Example 7. Heavy and Light Chain Variable Region Amino Acid Sequences

Table 7A sets forth the heavy and light chain variable region amino acid sequence pairs of selected anti-KLB/FGFR1c antibodies and their corresponding antibody identifiers.

TABLE 7A

| | Amino acid sequence identifiers | | | | | | | |
|---|---|---|---|---|---|---|---|---|
| Antibody | SEQ ID NOs: | | | | | | | |
| Designation | HCVR | HCDR1 | HCDR2 | HCDR3 | LCVR | LCDR1 | LCDR2 | LCDR3 |
| 8898P | 82 | 84 | 86 | 88 | 90 | 92 | 94 | 96 |
| 8115N | 98 | 100 | 102 | 104 | 106 | 108 | 110 | 112 |
| 8091N | 114 | 116 | 118 | 120 | 122 | 124 | 126 | 128 |
| 8092N | 130 | 132 | 134 | 136 | 138 | 140 | 142 | 144 |
| 8093N | 146 | 148 | 150 | 152 | 154 | 156 | 158 | 160 |
| 8096N | 162 | 164 | 166 | 168 | 170 | 172 | 174 | 176 |
| 8098N | 178 | 180 | 182 | 184 | 186 | 188 | 190 | 192 |
| 8109N | 194 | 196 | 198 | 200 | 202 | 204 | 206 | 208 |
| 8832N | 210 | 212 | 214 | 216 | 218 | 220 | 222 | 224 |
| 8833N | 226 | 228 | 230 | 232 | 234 | 236 | 238 | 240 |
| 8837P | 242 | 244 | 246 | 248 | 250 | 252 | 254 | 256 |
| 8852P | 258 | 260 | 262 | 264 | 266 | 268 | 270 | 272 |
| 8856P | 274 | 276 | 278 | 280 | 282 | 284 | 286 | 288 |
| 8859P | 290 | 292 | 294 | 296 | 298 | 300 | 302 | 304 |
| 8870P | 306 | 308 | 310 | 312 | 314 | 316 | 318 | 320 |
| 8871P | 322 | 324 | 326 | 328 | 330 | 332 | 334 | 336 |
| 8878P | 338 | 340 | 342 | 344 | 346 | 348 | 350 | 352 |
| 8880P | 354 | 356 | 358 | 360 | 362 | 364 | 366 | 368 |
| 8881P | 370 | 372 | 374 | 376 | 378 | 380 | 382 | 384 |
| 8897P | 386 | 388 | 390 | 392 | 394 | 396 | 398 | 400 |
| 8899P | 402 | 404 | 406 | 408 | 410 | 412 | 414 | 416 |
| 8900P | 418 | 420 | 422 | 424 | 426 | 428 | 430 | 432 |

Anti-KLB/FGFR1c antibodies are typically referred to herein according to the following nomenclature, as explained supra: Fc prefix (e.g. "H1M," "H2M," "H4H," etc.), followed by a numerical identifier (e.g. "8115," "8837," or "8852" as shown in Tables 7A and 7B), followed by a "P" or "N" suffix. Thus, according to this nomenclature, an antibody may be referred to herein as, e.g., "H1M8115N," "H2M8091N," "H2M8092N," "H4H8837P," "H4H8852P," etc.

Table 7B sets forth the heavy and light chain variable region nucleic acid sequence pairs of selected anti-KLB/FGFR1c antibodies and their corresponding antibody identifiers.

TABLE 7B

| | Nucleic acid sequence identifiers | | | | | | | |
|---|---|---|---|---|---|---|---|---|
| Antibody | SEQ ID NOs: | | | | | | | |
| Designation | HCVR | HCDR1 | HCDR2 | HCDR3 | LCVR | LCDR1 | LCDR2 | LCDR3 |
| 8898P | 81 | 83 | 85 | 87 | 89 | 91 | 93 | 95 |
| 8115N | 97 | 99 | 101 | 103 | 105 | 107 | 109 | 111 |
| 8091N | 113 | 115 | 117 | 119 | 121 | 123 | 125 | 127 |
| 8092N | 129 | 131 | 133 | 135 | 137 | 139 | 141 | 143 |
| 8093N | 145 | 147 | 149 | 151 | 153 | 155 | 157 | 159 |
| 8096N | 161 | 163 | 165 | 167 | 169 | 171 | 173 | 175 |
| 8098N | 177 | 179 | 181 | 183 | 185 | 187 | 189 | 191 |
| 8109N | 193 | 195 | 197 | 199 | 201 | 203 | 205 | 207 |
| 8832N | 209 | 211 | 213 | 215 | 217 | 219 | 221 | 223 |
| 8833N | 225 | 227 | 229 | 231 | 233 | 235 | 237 | 239 |
| 8837P | 241 | 243 | 245 | 247 | 249 | 251 | 253 | 255 |
| 8852P | 257 | 259 | 261 | 263 | 265 | 267 | 269 | 271 |
| 8856P | 273 | 275 | 277 | 279 | 281 | 283 | 285 | 287 |
| 8859P | 289 | 291 | 293 | 295 | 297 | 299 | 301 | 303 |
| 8870P | 305 | 307 | 309 | 311 | 313 | 315 | 317 | 319 |
| 8871P | 321 | 323 | 325 | 327 | 329 | 331 | 333 | 335 |
| 8878P | 337 | 339 | 341 | 343 | 345 | 347 | 349 | 351 |
| 8880P | 353 | 355 | 357 | 359 | 361 | 363 | 365 | 367 |
| 8881P | 369 | 371 | 373 | 375 | 377 | 379 | 381 | 383 |
| 8897P | 385 | 387 | 389 | 391 | 393 | 395 | 397 | 399 |
| 8899P | 401 | 403 | 405 | 407 | 409 | 411 | 413 | 415 |
| 8900P | 417 | 419 | 421 | 423 | 425 | 427 | 429 | 431 |

Example 8. Binding to Cells Expressing hFGF1c, hKLB, or Both hFGF1c and hKLB as Determined by FACS Analysis To determine binding specificity of the monoclonal anti-KLB/FGFR1c antibodies, the antibodies were tested in a fluorescence-activated cell sorting (FACS) binding assay to cell lines expressing human FGFR1c, human KLB, and both human FGFR1c and human KLB. HEK293 cell lines were generated that stably express full-length human FGFR1c (hFGFR1c; SEQ ID NO:433) or full-length human KLB (hKLB; SEQ ID NO:434) or both human FGFR1c and human KLB, along with a luciferase reporter [SRE (serum response element)-luciferase, SA Bioscience, #CLS-010L]. The resulting cell lines, referred to as HEK293/hFGFR1c/SRE-luc, HEK293/hKLB/SRE-luc, and HEK293/hKLB/hFGFR1c/SRE-luc, respectively, were maintained in DMEM supplemented with 10% FBS, NEAA, penicillin/streptomycin, 1 μg/mL puromycin and 100 μg/mL hygromycin B, 1 μg/mL puromycin and 500 μg/mL G418, or all three antibiotics.

For the FACS analysis, HEK293 parental, HEK293/hFGFR1c/SRE-luc, HEK293/hKLB/SRE-luc, and HEK293/hKLB/hFGFR1c/SRE-luc cells were dissociated and plated onto 96-well v-bottom plates at $5\times10^5$ cells/well in PBS containing 1% FBS. Cells were then incubated with either 10 μg/mL of anti-KLB/FGFR1c antibodies or irrelevant IgG control antibodies for 30 minutes at 4° C., followed by washing and incubation with 4 μg/mL of either an anti-mouse IgG or anti-human IgG secondary antibody conjugated with Alexa488 (Jackson ImmunoResearch, #115-547-003 or #109-547-003, respectively) for 30 minutes at 4° C. Cells were filtered and subsequently analyzed on a Hypercyte Flow Cytometer (Intellicyt Corp.). Unstained and secondary antibody alone controls were also tested for binding to all cell lines. The results were analyzed using FlowJo version 9.52 software and geometric mean (Geom. Mean) of fluorescence for viable cells was determined. Geom. mean of fluorescence for each antibody was then normalized to Geom. mean of unstained cells to obtain relative binding of antibody (binding ratios) per each cell type.

TABLE 8

Binding of anti-KLB/FGFR1c antibodies to HEK293, HEK293/hFGFR1c/SRE-luc, HEK293/hKLB/SRE-luc, and HEK293/hKLB/hFGFR1c/SRE-luc cells.

| | | Normalized by Unstained Cells | | |
| --- | --- | --- | --- | --- |
| Antibody | HEK293 Parental | HEK293/ hFGFR1c/ SRE-luc cells | HEK293/ hKLB/ SRE-luc cells | HEK293/ hKLB/ hFGFR1c/ SRE-luc cells |
| H2aM8091N | 1 | 1 | 8 | 37 |
| H2aM8092N | 1 | 1 | 15 | 46 |
| H2aM8093N | 1 | 1 | 15 | 41 |
| H2bM8096N | 2 | 2 | 17 | 40 |
| H2aM8098N | 1 | 1 | 11 | 23 |
| H2aM8109N | 5 | 7 | 21 | 58 |
| H2aM8832N | 2 | 6 | 2 | 7 |
| H2bM8833N | 3 | 9 | 3 | 11 |
| H1M8115N | 1 | 2 | 13 | 33 |
| H4H8837P | 1 | 2 | 13 | 33 |
| H4H8852P | 1 | 1 | 7 | 33 |
| H4H8856P | 1 | 1 | 5 | 30 |
| H4H8859P | 5 | 5 | 5 | 4 |
| H4H8870P | 4 | 5 | 4 | 4 |
| H4H8871P | 1 | 1 | 7 | 33 |
| H4H8878P | 1 | 2 | 11 | 35 |
| H4H8880P | 2 | 2 | 14 | 32 |
| H4H8881P | 1 | 2 | 15 | 35 |
| H1H8897P | 1 | 1 | 1 | 8 |
| H1H8898P | 1 | 1 | 1 | 8 |
| H1H8899P | 3 | 5 | 3 | 4 |
| H1H8900P | 1 | 5 | 1 | 6 |
| Unstained Cells | 1 | 1 | 1 | 1 |
| Anti-Mouse IgG Secondary Antibody | 1 | 1 | 1 | 1 |
| Anti-Human IgG Secondary Antibody | 1 | 1 | 2 | 1 |
| Irrelevant IgG control 1* | 1 | 1 | 1 | 2 |
| Irrelevant IgG control 2* | 1 | 2 | 2 | 2 |
| Comparator 2## | 2 | 39 | 1 | 16 |
| Comparator 3### | 2 | 27 | 2 | 33 |
| Comparator 1# | 1 | 1 | 10 | 22 |

Comparator 1 was obtained using the methods described in WO2011/071783A1 for Ab "16H7".
Comparator 2 was obtained using the methods described in EP1680140B1 for Ab "FR1-A1"
Comparator 3 was obtained using the methods described in EP1680140B1 for Ab "FR1-H7"
*IgG Control Antibody 1 and 2 are non-specific antibodies having binding specificity irrelevant to the target antigen As shown in Table 8, 22 anti-KLB/FGFR1c antibodies of the invention demonstrated binding ratios ranging from 1 to 5 fold on HEK293 cells, from 1 to 9 fold on HEK293/hFGFR1c/SRE-luc cells, from 1 to 21 fold on HEK293/hKLB/SRE-luc cells, and from 4 to 58 fold on HEK293/hKLB/hFGFR1c/SRE-luc cells. Three antibodies, H2aM8832N, H2bM8833N, and H1H8900P showed greater binding to HEK293/hFGFR1c/SRE-luc cells (with ratios of 6, 9 and 5, respectively) than to HEK293/hKLB/SRE-luc cells (with ratios of 2, 3 and 1, respectively). These antibodies also bound to HEK293/hKLB/hFGFR1c/SRE-luc cells (ratios of 7, 11, and 6). Accordingly, H2aM8832N, H2bM8833N, and H1H8900P display preferential binding to FGFR1c, in this assy.

Two antibodies tested, H1H8897P and H1H8898P, bound only to HEK293/hKLB/hFGFR1c/SRE-luc cells. Accordingly, H1H8897P and H1H8898P display preferential binding to the KLB/FGFR1c coreceptor complex, in this particular assay.

Three antibodies, H4H8859P, H4H8870P and H1H8899P, showed weak binding to all cell lines including the HEK293 cells (with binding ratios ranging from 3 to 5 on all cell lines).

Fourteen antibodies of the invention showed greater binding to HEK293/hKLB/SRE-luc cells (with binding ratios ranging from 5 to 21) than to HEK293/hFGFR1c/SRE-luc cells and in addition bound to HEK293/hKLB/hFGFR1c/SRE-luc cells with ratios ranging from 23 to 58. Accordingly, H2aM8091N, H2aM8092N, H2aM8093N, H2bM8096N, H2aM8098N, H2aM8109N, H1M8115N, H4H8837P, H4H8852P, H4H8856P, H4H8871P, H4H8878P, H4H8880P, and H4H8881P display preferential binding to KLB, in this particular assay.

Comparator 1 demonstrated binding ratios of 1 fold on HEK293 cells, 1 fold on HEK293/hFGFR1c/SRE-luc cells, 10 fold on HEK293/hKLB/SRE-luc cells, and 22 fold on HEK293/hKLB/hFGFR1c/SRE-luc cells. Comparator 2 demonstrated binding ratios of 2 fold on HEK293 cells, 39 fold on HEK293/hFGFR1c/SRE-luc cells, 1 fold on HEK293/hKLB/SRE-luc cells, and 16 fold on HEK293/hKLB/hFGFR1c/SRE-luc cells. Comparator 3 demonstrated binding ratios of 2 fold on HEK293 cells, 27 fold on HEK293/hFGFR1c/SRE-luc cells, 2 fold on HEK293/hKLB/SRE-luc cells, and 33 fold on HEK293/hKLB/hFGFR1c/SRE-luc cells.

The anti-mouse or human IgG secondary antibodies as well as the irrelevant IgG control antibodies bound to all cell lines tested with binding ratios ranging from 1 to 2 fold.

Example 9: MAPK-Signaling of Anti-FGF21R Antibodies in hKLB/hFGFR1c-Expressing Cells Stimulation of KLB/FGFR1c, i.e. FGF21R, by FGF21 leads to activation of the mitogen-activated protein kinase (MAPK) pathway (Ogawa et al., 2007, supra). The bioassay to detect MAPK signaling, was developed similarly as before (see Example 4), whereas an HEK293 cell line stably expressing full-length human FGFR1c (amino acids 1-733 of accession number NP_075593, SEQ ID NO:433), full-length human KLB (amino acids 1-1044 of accession number NP_783864.1, SEQ ID NO:434) along with a luciferase reporter [SRE (serum response element)-luciferase; SA Bioscience, #CLS-010L] was generated. The stable cell line is designated HEK293/hKLB/hFGFR1c/SRE-Luc in this Example.

Other stable cell lines were made in essentially the same manner for subsequent testing (for example, HEK293/MfKLB/hFGFR1c/SRE-Luc, and HEK293/mKLB/mFGFR1c/SRE-Luc, HEK293/hFGFR1c/SRE-Luc in Examples 10, 11, and 12, respectively).

All stable cell lines were maintained in DMEM supplemented with 10% FBS, NEAA, penicillin/streptomycin, 1 μg/mL puromycin, 500 μg/mL G418, and 100 μg/mL hygromycin B (except HEK293/hFGFR1c/SRE-luc cell line was maintained without G418 selection).

For this bioassay, cells were seeded into 96-well assay plates at 20,000 cells/well in OPTIMEM (Invitrogen, #31985-070) supplemented with 0.1% FBS, penicillin/streptomycin and L-glutamine, and then incubated at 37° C. in 5% CO2 overnight. The next morning, ligand [human FGF21 expressed with a N-terminal hexahistidine tag (His6-hFGF21; SEQ ID: 436) in this Example, was serially diluted (1:3) from 300 nM to 0.005 nM (plus a sample containing buffer alone without ligand) to determine the activation dose response of the ligands.

Antibodies alone were also tested for activation in the bioassays through an antibody concentration range of 0.002 nM to 100 nM (through a 1:3 serial dilution; plus a sample containing buffer alone without antibody). To test for inhibition, antibodies were serially diluted (1:3), from 100 nM to 0.002 nM (plus a sample containing buffer alone without antibody), added to cells, and allowed to incubate for 60 minutes at room temperature followed by addition of fixed concentrations (close to the observed $EC_{50}$ values) of ligand (1 nM His6-hFGF21, in this Example).

Cells were subsequently incubated for 5.5 hours at 37° C. in 5% CO2 and after this incubation OneGlo reagent (Promega, #E6051) was added to the cells. The luciferase activity was then detected using a Victor X instrument (Perkin Elmer). The results were analyzed using nonlinear regression (4-parameter logistics) with Prism 5 software (GraphPad) to obtain $EC_{50}$ and $IC_{50}$ values. Maximum Activation of antibodies was calculated such that 0-100% activation is the range of activation from 0 to 300 nM ligand. Inhibition of antibodies was calculated such that 0-100% inhibition is the range of inhibition from the fixed concentration of ligand.

The collection of 22 antibodies (Table 9A) was tested for direct activation of HEK293/hKLB/hFGFR1c/SRE-Luc cells in the absence of ligand in three separate assay runs (run on different days), and in each assay separate dose response curves were generated for the His6-hFGF21 ligand as a reference. As shown in Table 9A, 19 out of 22 antibodies stimulated these cells at levels that were from 0.5% to 11% of the maximum stimulation levels observed when 300 nM His6-hFGF21 alone was added. The $EC_{50}$ values for these activating antibodies ranged from 53 pM to 23 nM. In these three separate assay runs, His6-hFGF21 activated the coreceptor-expressing cells with $EC_{50}$ values of 1.4 nM, 0.73 nM and 1.4 nM.

TABLE 9A

Activation of HEK293/hKLB/hFGFR1c/SRE-Luc cells by anti-FGF21R antibodies

| | $EC_{50}$ value of His6-hFGF21 alone [M] Activation by ligand alone (His6-hFGF21) in three separate assays | | | | | |
|---|---|---|---|---|---|---|
| | 1.4E−09 | | 7.3E−10 | | 1.4E−09 | |
| | Activation by antibodies in the absence of ligand | | | | | |
| Antibody | Maximum Activation (%) | $EC_{50}$ [M] | Maximum Activation (%) | $EC_{50}$ [M] | Maximum Activation (%) | $EC_{50}$ [M] |
| H2aM8091N | 1% | 3.6E−09 | Not tested | | Not tested | |
| H2aM8092N | 1% | 2.0E−10 | Not tested | | Not tested | |
| H2aM8093N | 1% | 6.8E−11 | Not tested | | Not tested | |
| H2bM8096N | 11% | 2.0E−08 | Not tested | | Not tested | |
| H2aM8098N | 1% | 2.3E−08 | Not tested | | Not tested | |
| H2aM8109N | 0.5% | 3.3E−09 | Not tested | | Not tested | |
| H1M8115N | 1% | 5.3E−11 | Not tested | | Not tested | |
| H2aM8832N | Not tested | | 4% | 7.5E−10 | Not tested | |
| H2bM8833N | Not tested | | 4% | 3.0E−09 | Not tested | |
| H4H8837P | Not tested | | Not tested | | 1% | 1.2E−10 |
| H4H8852P | Not tested | | Not tested | | 5% | 2.1E−10 |
| H4H8856P | Not tested | | Not tested | | 6% | 3.0E−10 |
| H4H8859P | Not tested | | Not tested | | No Activation | |
| H4H8870P | Not tested | | Not tested | | No Activation | |
| H4H8871P | Not tested | | Not tested | | 5% | 1.8E−10 |

TABLE 9A-continued

Activation of HEK293/hKLB/hFGFR1c/SRE-Luc cells by anti-FGF21R antibodies

EC$_{50}$ value of His6-hFGF21 alone [M]
Activation by ligand alone (His6-hFGF21) in three separate assays

| 1.4E−09 | 7.3E−10 | 1.4E−09 |

Activation by antibodies in the absence of ligand

| Antibody | Maximum Activation (%) | EC$_{50}$ [M] | Maximum Activation (%) | EC$_{50}$ [M] | Maximum Activation (%) | EC$_{50}$ [M] |
|---|---|---|---|---|---|---|
| H4H8878P | Not tested | | Not tested | | 1% | 4.1E−10 |
| H4H8880P | Not tested | | Not tested | | 1% | 5.4E−11 |
| H4H8881P | Not tested | | Not tested | | 7% | 7.2E−11 |
| H1H8897P | Not tested | | Not tested | | 1% | 1.9E−08 |
| H1H8898P | Not tested | | Not tested | | 3% | 8.9E−09 |
| H1H8899P | Not tested | | Not tested | | No Activation | |
| H1H8900P | Not tested | | Not tested | | 2% | 1.7E−08 |
| mouse IgG control 1 | No Activation | | No Activation | | Not tested | |
| human IgG control 2 | Not tested | | Not tested | | No Activation | |

The antibodies were also tested in three separate assay runs (run on different days) for inhibition in the presence of constant concentrations of ligand.

TABLE 9B

Inhibition of 1 nM hFGF21 in HEK293/hKLB/hFGFR1c/SRE-Luc cells by Anti-FGF21R Antibodies EC$_{50}$ value of His6-hFGF21 [M]
Activation by ligand alone (His6-hFGF21) in the separate assays

| 2.2E−09 | 7.3E−10 | 1.4E−09 |

Inhibition of 1 nM hFGF21

| Antibody | Maximum Inhibition (%) | IC$_{50}$ [M] | Maximum Inhibition (%) | IC$_{50}$ [M] | Maximum Inhibition (%) | IC$_{50}$ [M] |
|---|---|---|---|---|---|---|
| H2aM8091N | 106% | 1.5E−09 | Not tested | | Not tested | |
| H2aM8092N | 50% | 1.2E−10 | Not tested | | Not tested | |
| H2aM8093N | 65% | 6.7E−11 | Not tested | | Not tested | |
| H2bM8096N | 75% | 6.5E−10 | Not tested | | Not tested | |
| H2aM8098N | 62% | 1.5E−08 | Not tested | | Not tested | |
| H2aM8109N | 23% | 3.3E−11 | Not tested | | Not tested | |
| H1M8115N | 65% | 9.0E−11 | Not tested | | Not tested | |
| H2aM8832N | Not tested | | No Inhibition | | Not tested | |
| H2bM8833N | Not tested | | No Inhibition | | Not tested | |
| H4H8837P | Not tested | | Not tested | | 51% | 8.0E−11 |
| H4H8852P | Not tested | | Not tested | | 101% | 3.8E−10 |
| H4H8856P | Not tested | | Not tested | | 91% | 6.5E−10 |
| H4H8859P | Not tested | | Not tested | | No Inhibition | |
| H4H8870P | Not tested | | Not tested | | No Inhibition | |
| H4H8871P | Not tested | | Not tested | | 92% | 3.8E−10 |
| H4H8878P | Not tested | | Not tested | | 38% | 2.3E−10 |
| H4H8880P | Not tested | | Not tested | | 39% | 1.5E−10 |
| H4H8881P | Not tested | | Not tested | | 77% | 6.7E−11 |
| H1H8897P | Not tested | | Not tested | | 101% | 9.7E−10 |
| H1H8898P | Not tested | | Not tested | | 97% | 2.0E−09 |
| H1H8899P | Not tested | | Not tested | | 20% | 4.0E−11 |
| H1H8900P | Not tested | | Not tested | | 41% | 4.5E−09 |
| mouse IgG control 1 | No Inhibition | | No Inhibition | | Not tested | |
| Isotype human IgG control 2 | Not tested | | Not tested | | No Inhibition | |

As shown in Table 9B, 18 of the 22 antibodies inhibited HEK293/hKLB/hFGFR1c/SRE-Luc cells stimulated by 1 nM hFGF21 with maximum percent inhibition values ranging from 20 to 106% and IC$_{50}$ values ranging from 33 pM to 15 nM. In these three assays, His6-hFGF21 activated with EC$_{50}$ values of 2.2 nM, 0.73 nM, and 1.4 nM. Irrelevant IgG control antibodies displayed no activation or inhibition in either assay.

Example 10: MAPK-Signaling of Anti-FGF21R Antibodies in MfKLB/hFGFR1c-Expressing Cells To test anti-KLB/FGFR1c antibodies for species cross-reactivity, the stable cell line designated HEK293/MfKLB/hFGFR1c/SRE-Luc was developed. In this Example, the cell line stably expresses full-length M. fascicularis KLB (amino acids 1-1044) with full-length human FGFR1c (the ectodomain shares identical amino acid sequence with *M. fascicularis* FGFR1c). The bioassay is performed as described for Example 9, with or without His6-tagged M. fascicularis FGF21 ligand (His6-MfFGF21; SEQ ID: 437).

TABLE 10

Activation and/or inhibition of MAPK signal in HEK293/MfKLB/hFGFR1c/SRE-Luc cells by anti-FGF21R antibodies

| | $EC_{50}$ value of His6-MfFGF21 [M] | | | |
|---|---|---|---|---|
| | Activation by ligand alone (His6-MfFGF21) in the separate assays | | | |
| | 5.2E−09 | 1.4E−09 | 2.2E−09 | 1.4E−09 |
| | Activation by antibodies alone | | Inhibition of 10 nM mfFGF21 | |
| Antibody | Maximum Activation (%) | $EC_{50}$ [M] | Maximum Activation (%) | $EC_{50}$ [M] | Maximum Inhibition (%) | $IC_{50}$ [M] | Maximum Inhibition (%) | $IC_{50}$ [M] |
| H2aM8091N | No Activation | Not tested | 104% | 2.3E−09 | Not tested | | | |
| H2aM8092N | No Activation | Not tested | 18% | 2.2E−10 | Not tested | | | |
| H2aM8093N | No Activation | Not tested | 46% | 2.6E−11 | Not tested | | | |
| H2bM8096N | No Activation | Not tested | 55% | 1.1E−10 | Not tested | | | |
| H2aM8109N | No Activation | Not tested | 32% | 1.9E−10 | Not tested | | | |
| H1M8115N | No Activation | Not tested | 47% | 3.0E−11 | Not tested | | | |
| H2aM8832N | No Activation | Not tested | 15% | 1.1E−10 | Not tested | | | |
| H2bM8833N | No Activation | Not tested | 16% | 9.9E−11 | Not tested | | | |
| H4H8837P | Not tested | No Activation | Not tested | 51% | 8.9E−11 | | | |
| H4H8852P | Not tested | 5% | 4.6E−11 | Not tested | 101% | 4.7E−10 | | |
| H4H8856P | Not tested | 5% | 1.8E−10 | Not tested | 91% | 7.9E−10 | | |
| H4H8859P | Not tested | No Activation | Not tested | No Inhibition | | | | |
| H4H8870P | Not tested | No Activation | Not tested | No Inhibition | | | | |
| H4H8871P | Not tested | 4% | 1.3E−10 | Not tested | 92% | 3.9E−10 | | |
| H4H8878P | Not tested | No Activation | Not tested | 38% | 1.2E−10 | | | |
| H4H8880P | Not tested | No Activation | Not tested | 39% | 1.2E−10 | | | |
| H4H8881P | Not tested | 3% | 2.0E−11 | Not tested | 77% | 4.6E−11 | | |
| H1H8897P | Not tested | No Activation | Not tested | 101% | 5.2E−09 | | | |
| H1H8898P | Not tested | No Activation | Not tested | 97% | 1.2E−08 | | | |
| H1H8899P | Not tested | No Activation | Not tested | No Inhibition | | | | |
| H1H8900P | Not tested | No Activation | Not tested | No Inhibition | | | | |
| mouse IgG control 1 | No Activation | Not tested | No Inhibition | Not tested | | | | |
| Isotype human IgG control 2 | Not tested | No Activation | Not tested | No Inhibition | | | | |

As shown in Table 10, 4 of the 21 tested antibodies activated HEK293/MfKLB/hFGFR1c/SRE-Luc cells in the absence of FGF21 at levels that were 3% to 5% of the maximum stimulation observed with 300 nM His6-MfFGF21, with $EC_{50}$ values ranging from 20 pM to 180 pM.

In addition, 17 of the 21 tested antibodies inhibited the activation of HEK293/MfKLB/hFGFR1c/SRE-Luc cells by 10 nM His6-MfFGF21 with maximum percent inhibition values ranging from 15 to 104% and $IC_{50}$ values ranging from 26 pM to 12 nM. His6-MfFGF21 alone activated with $EC_{50}$ values ranging from 1.4 nM to 5.2 nM in separate assays. Irrelevant IgG control antibodies displayed no activation or inhibition in either the direct activation or ligand inhibition assays.

Example 11: MAPK-Signaling of Anti-FGF21R Antibodies in mKLB/mFGFR1c-Expressing Cells Anti-KLB/FGFR1c antibodies were further tested for species cross-reactivity using the stable cell line designated HEK293/mKLB/mFGFR1c/SRE-Luc. This cell line stably expresses full-length mouse FGFR1c (amino acids 1-731; SEQ ID NO:440) and full-length mouse KLB (amino acids 1-1043; SEQ ID NO:441). The MAPK SRE-Luc bioassay is performed essentially as described above, with or without mouse FGF21 ligand (mFGF21; Prospec, # CYT-339).

TABLE 11

Activation and inhibition of 0.8 nM mFGF21 in HEK293/m FGFR1c/mKLB/SRE-Luc cells by anti-FGF21R antibodies

| | EC$_{50}$ value of mFGF21 [M] Activation by ligand alone (mFGF21) in the separate assays | | | |
|---|---|---|---|---|
| | 3.3E-10 | 3.7E-10 | 3.3E-10 | 3.7E-10 |
| | Activation by antibodies alone | | Inhibition of 0.8 nM mFGF21 | |
| Antibody | Maximum Activation (%) | Maximum Activation (%) | Maximum Inhibition (%) | Maximum Inhibition (%) |
| H2aM8091N | No Activation | Not tested | 90% | Not tested |
| H2bM8096N | Not tested | No Activation | Not tested | Not tested |
| H1M8115N | No Activation | Not tested | No Inhibition | Not tested |
| H2aM8832N | No Activation | Not tested | No Inhibition | Not tested |
| H2bM8833N | No Activation | Not tested | No Inhibition | Not tested |
| H4H8837P | Not tested | No Activation | Not tested | No Inhibition |
| H4H8852P | Not tested | No Activation | Not tested | No Inhibition |
| H4H8856P | Not tested | No Activation | Not tested | No Inhibition |
| H4H8859P | Not tested | No Activation | Not tested | No Inhibition |
| H4H8870P | Not tested | No Activation | Not tested | No Inhibition |
| H4H8871P | Not tested | No Activation | Not tested | No Inhibition |
| H4H8878P | Not tested | No Activation | Not tested | No Inhibition |
| H4H8880P | Not tested | 2% | Not tested | 16% |
| H4H8881P | Not tested | No Activation | Not tested | Non-Inhibitor |
| H1H8897P | Not tested | 3% | Not tested | 50% |
| H1H8898P | Not tested | 2% | Not tested | 29% |
| H1H8899P | Not tested | No Activation | Not tested | No Inhibition |
| H1H8900P | Not tested | No Activation | Not tested | No Inhibition |
| mouse IgG control 1 | No Activation | Not tested | No Inhibition | Not tested |
| Isotype human IgG control 2 | Not tested | No Activation | Not tested | No Inhibition |

As shown in Table 11, 3 of the 18 tested antibodies activated HEK293/mKLB/mFGFR1c/SRE-Luc cells in the absence of mFGF21 at levels that were from 2% to 3% of the maximum stimulation observed with 300 nM mFGF21.

In addition, 4 of the 18 tested antibodies inhibited the activation of HEK293/mKLB/mFGFR1c/SRE-Luc cells stimulated by 0.8 nM of mFGF21, with maximum percent inhibition values ranging from 16 to 90%. Mouse FGF21 activated with EC$_{50}$ values ranging from 0.33 to 0.37 nM in the separate assays. Irrelevant IgG control antibodies displayed no activation or inhibition in either assay.

Example 12: MAPK-Signaling of Anti-FGF21R Antibodies in hFGFR1c-Expressing Cells An HEK293 cell line stably expressing full length human FGFR1c along with the SRE-luciferase reporter (HEK293/hFGFR1c/SRE-Luc) was developed to test for FGF2 activation or blockade. The MAPK SRE-luc bioassay is performed essentially as described above (see Example 9), except in the presence of human FGF2 (hFGF2; R&D Systems, #233-FB/CF).

TABLE 12

Inhibition of 0.2 nM hFGF2 in HEK293/hFGFR1c/SRE-Luc cells by anti-FGF21R antibodies

| | EC$_{50}$ value of hFGF2 [M] Activation by ligand alone (hFGF2) | |
|---|---|---|
| | 4.0E-10 | 8.0E-10 |
| | Inhibition of 0.4 nM hFGF2 | |
| Antibody | Inhibition | Inhibition |
| H2aM8091N | No Inhibition | Not tested |
| H2bM8096N | Not tested | No Inhibition |
| H2aM8832N | No Inhibition | Not tested |
| H2bM8833N | No Inhibition | Not tested |
| H4H8837P | Not tested | No Inhibition |
| H4H8852P | Not tested | No Inhibition |
| H4H8856P | Not tested | No Inhibition |
| H4H8859P | Not tested | No Inhibition |
| H4H8870P | Not tested | No Inhibition |
| H4H8871P | Not tested | No Inhibition |
| H4H8878P | Not tested | No Inhibition |
| H4H8880P | Not tested | No Inhibition |
| H4H8881P | Not tested | No Inhibition |
| H1H8897P | Not tested | No Inhibition |
| H1H8898P | Not tested | No Inhibition |
| H1H8899P | Not tested | No Inhibition |
| H1H8900P | Not tested | No Inhibition |
| mouse IgG control 1 | No Inhibition | Not tested |
| Isotype human IgG control 2 | Not tested | No Inhibition |

As shown in Table 12, human FGF2 activated hFGFR1c in each of two separate assays, with EC$_{50}$ values ranging from 0.4 to 0.8 nM. None of the tested antibodies, including irrelevant IgG controls, demonstrated inhibition of 0.4 nM hFGF2 in either bioassay. Thus, none of the antibodies tested confer cellular MAPK activity in cells expressing FGFR1c, but not expressing KLB.

Example 13: Generation of FGF21R Bispecific Antibodies

Bispecific antibodies were generated using well-known methods to engineer two binding arms having specificity to different targets. As such, exemplary bispecific antibodies were made consisting of heterodimeric chains, where (from N- to C-terminus) one chain is composed of segments scFv1-hinge-$C_H2$-$C_H3$, a second chain is composed of segments scFv2-hinge-$C_H2$-$C_H3$, and the two chains are linked through interchain disulfides joining the two hinge regions, as for a human IgG1 antibody. Each chain of a bispecific antibody as described above is referred to here as scFv-Fc. In constructing each Fv region, the C-terminus of a particular HCVR is joined to the N-terminus of a distinct LCVR through the flexible linker (Gly-Gly-Gly-Ser)$_4$ (SEQ ID NO:446). The HCVR and LCVR sequences for each scFv-Fc chain can be derived from a particular antibody of Table 7A or 7B.

For example, 8870P ScFv-Fc* was constructed using well-known molecular biology cloning techniques to express a recombinant polypeptide comprising (from 5'- to -3') the HCVR of antibody 8870P, a (Gly-Gly-Gly-Ser)4 linker (SEQ ID NO: 446), the LCVR of 8870P and IgG4 Fc* fragment (amino acid residues 6 to 229 of SEQ ID NO: 443). Fc* refers to a modified IgG Fc fragment having a modification in the CH3 domain for ease of purification (e.g. H95R/Y96F by IMGT numbering; see US20100331527A1, published Dec. 30, 2010). The HCVR/LCVR amino acid sequence pair sequence identifiers for antibody 8870P are SEQ ID NOs: 306/314.

8092N ScFv-Fc comprises (from 5'- to -3') the HCVR of antibody 8092N, a (Gly-Gly-Gly-Ser)$_4$(SEQ ID NO: 446) linker, the LCVR of 8092N and IgG4 Fc fragment (amino acid residues 6 to 229 of SEQ ID NO: 442). The HCVR/LCVR amino acid sequence pair sequence identifiers for antibody 8092N are SEQ ID NOs: 130/138.

Both the 8870P ScFv-Fc* and 8092N ScFv-Fc polypeptides were co-expressed in CHO cells and the bispecific antibody isolated by Protein A purification using well-known methods. The bispecific 8900P ScFv-Fc*/8092N ScFv-Fc was prepared analogously.

Example 14: MAPK-Signaling of Bispecific Antibodies in hKLB/hFGFR1c-Expressing Cells The stable cell line, HEK293/hKLB/hFGFR1c/SRE-Luc, was utilized in a bioassay as described above to detect the activation of the MAPK pathway by FGF21. Briefly, For the bioassay, cells were seeded into 96-well assay plates at 20,000 cells/well in OPTIMEM (Invitrogen, #31985-070) supplemented with 0.1% FBS, penicillin/streptomycin and L-glutamine, and then incubated at 37° C. in 5% $CO_2$ overnight. The next morning, human FGF21 expressed with an N-terminal hexahistidine tag (His6-hFGF21; SEQ ID: 436) was added to the cells at concentrations ranging from 300 nM to 0.005 nM (plus a sample containing buffer alone without 6His-hFGF21) to determine the dose response curves for the ligand.

To test activation by either antibody combinations (i.e. two full antibodies), single antibodies, or bispecific antibodies, the test antibodies were serially diluted (1:3), from 50 nM to 0.0008 nM, or 100 nM to 0.002 nM (plus a sample containing buffer alone without antibody), and added to cells in the absence of His6-hFGF21 (SEQ ID NO: 436).

To test their ability to inhibit 6His-hFGF21-induced signaling, antibodies were serially diluted (1:3), from 50 nM to 0.0008 nM or 100 nM to 0.002 nM (plus a sample containing buffer alone without antibody) and added to cells for 60 minutes at room temperature followed by addition of a fixed concentration of 1 nM His6-hFGF21. Cells were incubated for 5.5 hours at 37° C. in the presence of 5% CO2 After this incubation, OneGlo reagent (Promega, #E6051) was added to the cells and luminescence was measured using a Victor X instrument (Perkin Elmer). The results were analyzed using nonlinear regression (4-parameter logistics) with Prism 5 software (GraphPad) to obtain $EC_{50}$ and $IC_{50}$ values. Activation of antibodies was calculated such that 0 to 100% activation is the range of activation from 0 to 300 nM 6His-hFGF21. Inhibition of antibodies was calculated such that 0 to 100% inhibition is the range of inhibition from the fixed concentration of 6His-hFGF21 to 0 nM of FGF21.

TABLE 13

FGF21R Bispecific Constructs

Figure 3:
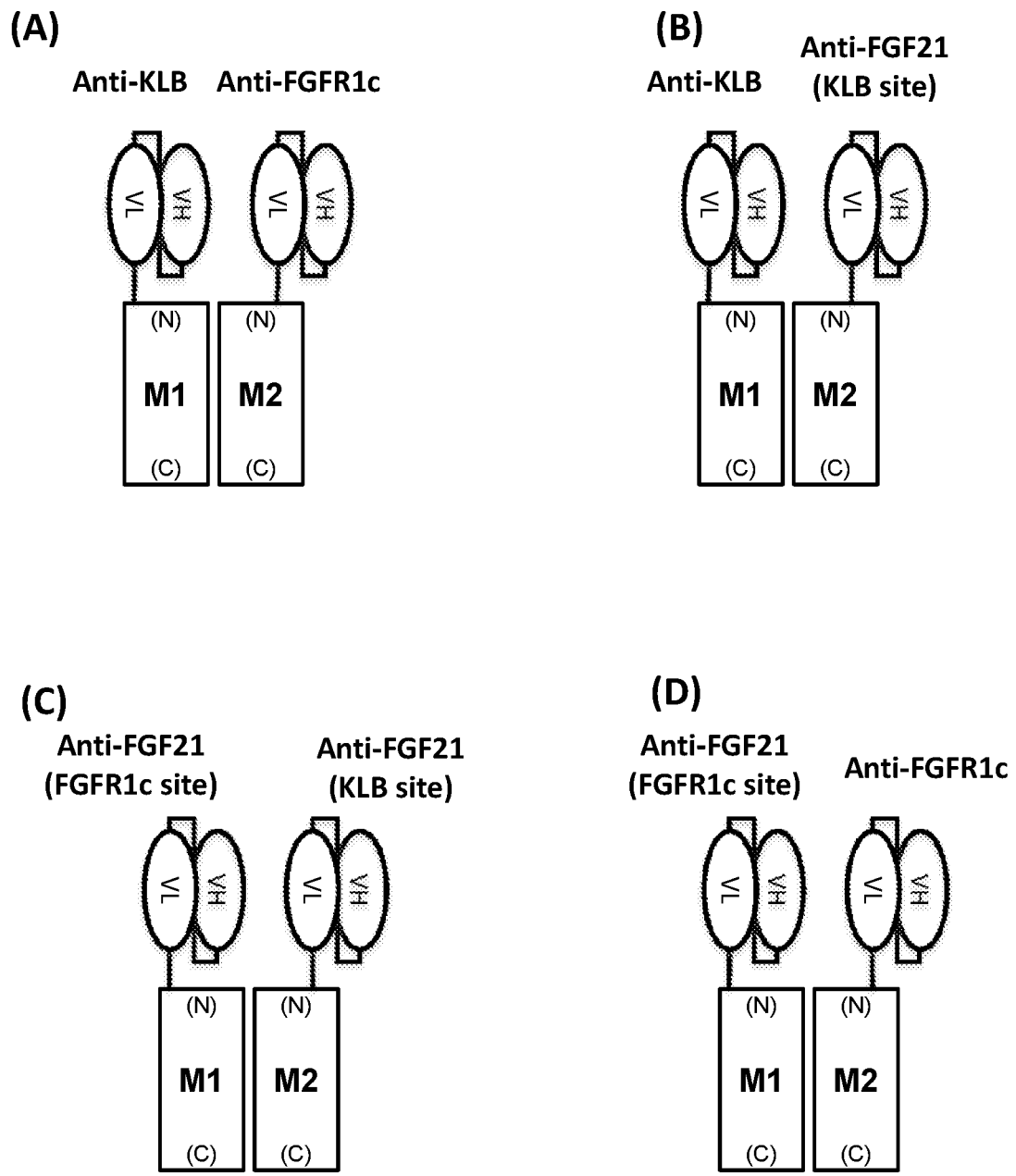
FIG. 3 illustrates four specific exemplary FGF21R agonists, each comprising a single KLB-interacting domain (K1) and a single FGFR1c-interacting domain (F1). In Panel A, an anti-KLB scFv is attached to the N-terminus of M1 and an anti-FGFR1c scFv is attached to the N-terminus of M2. In Panel B, an anti-KLB scFv is attached to the N-terminus of M1, and an anti-FGF21 scFv which specifically binds the KLB-binding site of FGF21 is attached to the N-terminus of M2. In Panel C, an anti-FGF21 scFv which specifically binds the FGFR1c-binding site of FGF21 is attached to the N-terminus of M1, and an anti-FGF21 scFv which specifically binds the KLB-binding site of FGF21 is attached to the N-terminus of M2. In Panel D, an anti-FGF21 scFv which specifically binds the FGFR1c-binding site of FGF21 is attached to the N-terminus of M1, and an anti-FGFR1c scFv is attached to the N-terminus of M2.

| Designation | Specificity | IgG (Fc) | SEQ ID NO: | Figure Reference |
|---|---|---|---|---|
| scFv8092N-IgG4mutFc × scFv8870P-IgG4mutFc* Heterodimer | Anti-KLB (scFv8092N) | hIgG4mutFc* | 456 | FIG. 1, Panel A or |
| | Anti-FGFR1c (scFv8870P) | hIgG4mutFc | 457 | FIG. 3, Panel A |
| scFv8092N-IgG4mutFc × scFv8900P-IgG4mutFc* Heterodimer | Anti-KLB (scFv8092N) | hIgG4mutFc* | 456 | FIG. 1, Panel A or |
| | Anti-FGFR1c (scFv8900P) | hIgG4mutFc* | 458 | FIG. 3, Panel A |
| scFv8870-IgG-scFv8092 Homodimer | Anti-FGF21Rc (N-term scFv8870) and Anti-KLB (C-term scFv8092) | hIgG4mutFc | 459 | FIG. 2, Panel A |
| scFv8900-IgG-scFv8092 Homodimer | Anti-FGF21Rc (N-term scFv8900) and Anti-KLB (C-term scFv8092) | hIgG4mutFc | 460 | FIG. 2, Panel A |

TABLE 14

Activation and inhibition in HEK293/hFGFR1c/hKLB/SRE-
Luc cell based assay by anti-FGF21R single antibodies,
antibody combinations and bispecific antibodies

| | 6His-hFGF21 EC$_{50}$ [M] | | | |
|---|---|---|---|---|
| | 2.4E−09 Activation | | 2.2E−09 Inhibition of 1 nM 6His-hFGF21 | |
| Antibodies | EC$_{50}$ [M] | Maximum Activation (%) | IC$_{50}$ [M] | Maximum Inhibition (%) |
| 8870P ScFv-Fc*/ 8092N ScFv-Fc | 1.2E−09 | 2.2 | 7.2E−10 | 58 |
| 8900P ScFv-Fc*/ 8092N ScFv-Fc | 2.8E−10 | 0.5 | 3.9E−10 | 90 |
| H1H8900P | Weak/No Activation | | 2.2E−09 | 36 |
| H4H8870P | No Activation | | Weak Inhibition | 10 |
| H2aM8092N | 2.9E−10 | 0.6 | 1.9E−10 | 74 |
| H2aM8092N + H4H8870P | 4.4E−10 | 0.6 | 1.9E−10 | 76 |
| H2aM8092N + H4H8900P | 2.9E−09 | 1.3 | 3.1E−10 | 58 |
| Comparator 1[#] | 1.5E−10 | 4.5 | 1.1E−10 | 72 |
| IgG Control Antibody* | No Activation | | No Inhibition | |

[#]Comparator 1 was obtained using the methods described in WO 2011/071783 A1 for Ab "16H7".
*IgG Control Antibody is a non-specific antibody having binding specificity irrelevant to the target antigen As shown in Table 14, H2aM8092N, the combination of H2aM8092N and H4H8870P, the combination of H2aM8092N and H4H8900P, the bispecific 8870P ScFv-Fc*/8092N ScFv-Fc, and the bispecific 8900P ScFv-Fc*/8092N ScFv-Fc stimulated HEK293/hFGFR1c/hKLB/SRE-Luc cells at levels that were from 0.5% to 2.2% of the maximum stimulation levels observed when 300 nM His6-hFGF21 alone was added. The EC$_{50}$ values for these activating antibodies ranged from 280 pM to 2.9 nM. Comparator 1 demonstrated maximal activation of 4.5% with an EC$_{50}$ of 0.15 nM. However, both 8900P ScFv-Fc*/8092N ScFv-Fc bispecific and Comparator 1 showed decreased activation at high concentrations after reaching a maximal activation at approximately 3 nM.

Further shown in Table 14, H2aM8092N, H1H8900P, H4H8870P, the combination of H2aM8092N and H4H8870P, the combination of H2aM8092N and H4H8900P, the bispecific 8870P ScFv-Fc*/8092N ScFv-Fc, and the bispecific 8900P ScFv-Fc*/8092N ScFv-Fc all demonstrated inhibition of 1 nM His6-hFGF21 stimulation of HEK293/hFGFR1c/hKLB/SRE-Luc cells at levels that were from 10% to 90%. The IC$_{50}$ values for these antibodies, antibody combinations and bispecifics ranged from 190 pM to 2.2 nM, however no IC$_{50}$ value could be determined for H4H8870P. Comparator 1 demonstrated maximal inhibition of 72% with an IC$_{50}$ of 110 pM. An irrelevant IgG control antibody was also tested and displayed no activation or inhibition. 6His-hFGF21 activated with EC$_{50}$ values of 2.4 and 2.2 nM.

Thus, the FGF21R agonists of the invention, such as the antibody combinations and bispecific constructs, provide greater avidity through their multiple binding interactions with the receptor.

Example 15: Binding Kinetics Cells of Anti-KLB/FGFR1c Antibodies to hKLB or hFGF1c as Determined by Biacore Equilibrium dissociation constants (K$_D$ values) for human KLB or human FGFR1c binding to purified anti-KLB/FGFR1c monoclonal antibodies were determined using a real-time surface plasmon resonance biosensor using a Biacore T-200 or 4000 instrument. The Biacore sensor surface was derivatized by amine coupling with either a polyclonal rabbit anti-mouse antibody (GE, # BR-1008-38) or with a monoclonal mouse anti-human Fc antibody (GE, # BR-1008-39) to capture anti-KLB/FGFR1c monoclonal antibodies expressed with either a mouse Fc or a human Fc, respectively. All Biacore binding studies were performed in a buffer composed of 0.01M HEPES pH 7.4, 0.15M NaCl, 3 mM EDTA, 0.05% v/v Surfactant P20 (HBST running buffer). Different concentrations of the extracellular domain of human KLB expressed with C-terminal HA and hexahistidine tags (hKLB-HA-6His; SEQ ID NO: 438) prepared in HBST running buffer (ranging from 60 to 0.74 nM, 3-fold dilutions) or the extracellular domain of human FGFR1c expressed with C-terminal V5 and hexahistidine tags (hFGFR1c-V5-6His; SEQ ID NO: 439) (ranging from 180 to 2.22 nM, 3-fold dilutions) were injected over the anti-KLB/FGFR1c monoclonal antibody captured surface at a flow rate of 50 µL/minute. Association of hKLB-HA-6His or hFGFR1c-V5-6His to the captured monoclonal antibody was monitored for 3.5 to 4 minutes and the dissociation of hKLB-HA-6His or hFGFR1c-V5-6His in HBST running buffer was monitored for 8-12 minutes. All the binding kinetics experiments were performed at 25° C. or 37° C. Kinetic association (k$_a$) and dissociation (k$_d$) rate constants were determined by fitting the real-time sensorgrams to a 1:1 binding model using Scrubber 2.0c curve fitting software. Binding dissociation equilibrium constants (K$_D$) and dissociative half-lives (t½) were calculated from the kinetic rate constants as:

$$K_D(M) = \frac{kd}{ka}, \text{ and } t\frac{1}{2}(\min) = \frac{\ln(z)}{60*kd}$$

Binding kinetic parameters for hKLB-HA-6His and hFGFR1c-V5-6His binding to different anti-KLB/FGFR1c monoclonal antibodies at 25° C. and 37° C. are shown in Tables 15A through 15D.

TABLE 15A

Binding Kinetics parameters of anti-KLB/FGFR1c
antibodies binding to hKLB-HA-6His at 25° C.

| Antibody | mAb Capture (RU) | 20 nM hKLB-HA-6His Bind (RU) | k$_a$ (1/Ms) | k$_d$ (1/s) | K$_D$ (M) | t$_{1/2}$ (min) |
|---|---|---|---|---|---|---|
| H2aM8091N | 165.9 ± 0.7 | −2.0 | NB | NB | NB | NB |
| H2aM8092N | 218.1 ± 0.8 | 64.1 | 1.45E+05 | 5.56E−05 | 3.83E−10 | 207.8 |
| H2aM8093N | 169.6 ± 1.4 | 146.9 | 4.49E+05 | 9.80E−05 | 2.18E−10 | 117.8 |

TABLE 15A-continued

Binding Kinetics parameters of anti-KLB/FGFR1c antibodies binding to hKLB-HA-6His at 25° C.

| Antibody | mAb Capture (RU) | 20 nM hKLB-HA-6His Bind (RU) | $k_a$ (1/Ms) | $k_d$ (1/s) | $K_D$ (M) | $t_{1/2}$ (min) |
|---|---|---|---|---|---|---|
| H2bM8096N | 148 ± 3.5 | 44.1 | 1.33E+05 | 9.25E−04 | 6.95E−09 | 12.5 |
| H2aM8098N | 104.7 ± 0.4 | 2.7 | IC | IC | IC | IC |
| H2aM8109N | 91.3 ± 4.2 | 21.3 | 1.01E+05 | 4.49E−04 | 4.44E−09 | 25.7 |
| H2aM8832N | 150.2 ± 0.1 | −0.2 | NB | NB | NB | NB |
| H2bM8833N | 124 ± 1.4 | −2.1 | NB | NB | NB | NB |
| H1M8115N | 84.3 ± 1.1 | 77.6 | 4.55E+05 | 5.02E−05 | 1.10E−10 | 230.1 |
| H4H8837P | 78 ± 0.7 | 63.0 | 3.50E+05 | 1.28E−04 | 3.67E−10 | 89.95 |
| H4H8852P | 44.9 ± 0.2 | −0.2 | NB | NB | NB | NB |
| H4H8856P | 58.5 ± 0.2 | −0.4 | NB | NB | NB | NB |
| H4H8859P | 78.3 ± 0.4 | −0.8 | NB | NB | NB | NB |
| H4H8870P | 62.4 ± 0.3 | −0.6 | NB | NB | NB | NB |
| H4H8871P | 68.8 ± 0.3 | −0.7 | NB | NB | NB | NB |
| H4H8878P | 48 ± 0.2 | 28.4 | 1.70E+05 | 2.13E−04 | 1.25E−09 | 54.33 |
| H4H8880P | 69 ± 0.2 | 68.1 | 4.48E+05 | 2.87E−04 | 6.40E−10 | 40.30 |
| H4H8881P | 61.6 ± 0.4 | 92.7 | 1.44E+06 | 1.78E−04 | 1.24E−10 | 64.96 |
| H1H8897P | 70.6 ± 0.3 | −0.4 | NB | NB | NB | NB |
| H1H8898P | 92.3 ± 0.4 | −0.2 | NB | NB | NB | NB |
| H1H8899P | 85.3 ± 0.3 | 0.5 | NB | NB | NB | NB |
| H1H8900P | 88.2 ± 0.3 | 0.3 | NB | NB | NB | NB |
| Comparator 2[##] | 110.9 ± 0.3 | 0.0 | NB | NB | NB | NB |
| Comparator 3[###] | 34.4 ± 0.3 | −1.1 | NB | NB | NB | NB |
| Comparator 1[#] | 62.2 ± 0.1 | 75.3 | 4.89E+05 | 1.49E−04 | 3.05E−10 | 77.52 |
| H4H8870P ScFv-Fc*/H4H8092N ScFv-Fc | 63 ± 0.3 | 12.8 | 1.23E+05 | 8.92E−05 | 7.25E−10 | 129.48 |
| H4H8900P ScFv-Fc*/H4H8092N ScFv-Fc | 111.4 ± 1.3 | 27.3 | 1.24E+05 | 3.94E−05 | 3.18E−10 | 293.45 |

TABLE 15B

Binding Kinetics parameters of anti-KLB/FGFR1c antibodies binding to hKLB-HA-6His at 37° C.

| Antibody | mAb Capture (RU) | 20 nM hKLB-HA-6His Bind (RU) | $k_a$ (1/Ms) | $k_d$ (1/s) | $K_D$ (M) | $t_{1/2}$ (min) |
|---|---|---|---|---|---|---|
| H2aM8091N | 170.5 ± 1 | −2.3 | NB | NB | NB | NB |
| H2aM8092N | 218.7 ± 1.8 | 93.6 | 1.94E+05 | 8.00E−05 | 4.12E−10 | 144.4 |
| H2aM8093N | 191.9 ± 1.8 | 211.3 | 8.12E+05 | 1.80E−04 | 2.22E−10 | 64.1 |
| H2bM8096N | 163.4 ± 1.7 | 69.6 | 2.42E+05 | 2.64E−03 | 1.09E−08 | 4.4 |
| H2aM8098N | 124.5 ± 0.5 | 3.9 | IC | IC | IC | IC |
| H2aM8109N | 95.4 ± 4.1 | 36.8 | 2.11E+05 | 1.31E−03 | 6.20E−09 | 8.8 |
| H2aM8832N | 171 ± 0.4 | −0.7 | NB | NB | NB | NB |
| H2bM8833N | 132.3 ± 0.9 | −3.3 | NB | NB | NB | NB |
| H1M8115N | 91.9 ± 1.5 | 117.5 | 6.99E+05 | 1.44E−04 | 2.06E−10 | 80.3 |
| H4H8837P | 462.6 ± 7.6 | 371.8 | 3.20E+05 | 1.28E−04 | 4.01E−10 | 90.1 |
| H4H8852P | 178.8 ± 4.5 | 5.1 | NB | NB | NB | NB |
| H4H8856P | 196 ± 2.5 | −0.5 | NB | NB | NB | NB |
| H4H8859P | 214.6 ± 3.3 | 0.8 | NB | NB | NB | NB |
| H4H8870P | 271.4 ± 8.8 | −0.8 | NB | NB | NB | NB |
| H4H8871P | 142.1 ± 2.3 | −0.9 | NB | NB | NB | NB |
| H4H8878P | 160.8 ± 5 | 101.3 | 7.90E+05 | 2.41E−04 | 3.05E−10 | 48.0 |
| H4H8880P | 143.4 ± 4.8 | 148.5 | 5.56E+05 | 5.26E−04 | 9.45E−10 | 22.0 |
| H4H8881P | 52.9 ± 1.3 | 100.9 | 1.45E+06 | 4.63E−04 | 3.20E−10 | 24.9 |
| H1H8897P | 129.5 ± 1.5 | 1.9 | NB | NB | NB | NB |
| H1H8898P | 297.4 ± 1.5 | −1.9 | NB | NB | NB | NB |
| H1H8899P | 172.3 ± 2.0 | −0.1 | NB | NB | NB | NB |
| H1H8900P | 220.6 ± 2.5 | 2.6 | NB | NB | NB | NB |
| Comparator 2[##] | 453.2 ± 6.5 | 10.4 | NB | NB | NB | NB |
| Comparators 3[###] | 269 ± 8.3 | −1.0 | NB | NB | NB | NB |
| Comparator 1[#] | 161 ± 1.2 | 189.2 | 5.23E+05 | 3.21E−04 | 6.14E−10 | 36.0 |
| H4H8870P ScFv-Fc*/H4H8092N ScFv-Fc | 208.6 ± 5.7 | 45.4 | 9.16E+04 | 2.65E−04 | 2.89E−09 | 43.7 |

TABLE 15B-continued

Binding Kinetics parameters of anti-KLB/FGFR1c antibodies binding to hKLB-HA-6His at 37° C.

| Antibody | mAb Capture (RU) | 20 nM hKLB-HA-6His Bind (RU) | $k_a$ (1/Ms) | $k_d$ (1/s) | $K_D$ (M) | $t_{1/2}$ (min) |
|---|---|---|---|---|---|---|
| H4H8900P ScFv-Fc*/H4H8092N ScFv-Fc | 415.2 ± 2.9 | 86.7 | 1.37E+05 | 1.78E−04 | 1.30E−09 | 65.0 |

TABLE 15C

Binding Kinetics parameters of anti-KLB/FGFR1c antibodies binding to hFGFR1c-V5-6His at 25° C.

| Antibody | mAb Capture (RU) | 180 nM hFGFR1c-V5-6His Bind (RU) | $k_a$ (1/Ms) | $k_d$ (1/s) | $K_D$ (M) | $t_{1/2}$ (min) |
|---|---|---|---|---|---|---|
| H2aM8091N | 165.7 ± 0.2 | −0.8 | NB | NB | NB | NB |
| H2aM8092N | 216.3 ± 0.5 | −1.3 | NB | NB | NB | NB |
| H2aM8093N | 170.1 ± 0.1 | −1.2 | NB | NB | NB | NB |
| H2bM8096N | 140.2 ± 1.5 | −0.7 | NB | NB | NB | NB |
| H2aM8098N | 105.2 ± 0.3 | −0.9 | NB | NB | NB | NB |
| H2aM8109N | 83.2 ± 1.4 | −0.7 | NB | NB | NB | NB |
| H2aM8832N | 149.9 ± 0.1 | 5.8 | IC | IC | IC | IC |
| H2bM8833N | 121.1 ± 0.8 | 1.9 | IC | IC | IC | IC |
| H1M8115N | 84.5 ± 0.2 | −1.8 | NB | NB | NB | NB |
| H4H8837P | 77.5 ± 0.5 | 0.2 | NB | NB | NB | NB |
| H4H8852P | 44.9 ± 0.2 | 0.0 | NB | NB | NB | NB |
| H4H8856P | 58.4 ± 0.2 | 0.1 | NB | NB | NB | NB |
| H4H8859P | 77.4 ± 0.4 | 4.9 | 1.52E+05 | 5.36E−02 | 3.52E−07 | 0.22 |
| H4H8870P | 62.1 ± 0.3 | 6.9 | 2.19E+05 | 4.32E−02 | 1.97E−07 | 0.27 |
| H4H8871P | 68.3 ± 0.2 | 0.4 | NB | NB | NB | NB |
| H4H8878P | 48.4 ± 0.2 | 0.4 | NB | NB | NB | NB |
| H4H8880P | 69 ± 0.4 | 0.4 | NB | NB | NB | NB |
| H4H8881P | 61.9 ± 0.2 | 0.3 | NB | NB | NB | NB |
| H1H8897P | 70.4 ± 0.2 | 0.9 | NB | NB | NB | NB |
| H1H8898P | 91.6 ± 0.3 | 2.9 | NB | NB | NB | NB |
| H1H8899P | 84.6 ± 0.1 | 2.4 | NB | NB | NB | NB |
| H1H8900P | 87.6 ± 0.1 | 1.3 | NB | NB | NB | NB |
| Comparator 2[##] | 109.6 ± 0.4 | 28.4 | 1.02E+05 | 6.81E−03 | 6.69E−08 | 1.70 |
| Comparator 3[###] | 34.4 ± 0.2 | 16.4 | 3.13E+06 | 1.29E−02 | 4.12E−09 | 0.90 |
| Comparator 1[#] | 62.1 ± 0.2 | 0.4 | NB | NB | NB | NB |
| H4H8870P ScFv-Fc*/H4H8092N ScFv-Fc | 62.7 ± 0.2 | 1.2 | NB | NB | NB | NB |
| H4H8900P ScFv-Fc*/H4H8092N ScFv-Fc | 110 ± 0.4 | 0.9 | NB | NB | NB | NB |

TABLE 15D

Binding Kinetics parameters of anti-KLB/FGFR1c antibodies binding to hFGFR1c-V5-6His at 37° C.

| Antibody | mAb Capture (RU) | 180 nM hFGFR1c-V5-6His Bind (RU) | $k_a$ (1/Ms) | $k_d$ (1/s) | $K_D$ (M) | $t_{1/2}$ (min) |
|---|---|---|---|---|---|---|
| H2aM8091N | 171.9 ± 0.3 | −1.3 | NB | NB | NB | NB |
| H2aM8092N | 219.1 ± 0.5 | 0.5 | NB | NB | NB | NB |
| H2aM8093N | 193.2 ± 0.2 | 0.6 | NB | NB | NB | NB |
| H2bM8096N | 158.1 ± 1.3 | −1.2 | NB | NB | NB | NB |
| H2aM8098N | 125.1 ± 0.4 | −1.4 | NB | NB | NB | NB |
| H2aM8109N | 85.6 ± 1.6 | 0.7 | NB | NB | NB | NB |
| H2aM8832N | 169.3 ± 0.3 | 2.3 | IC | IC | IC | IC |
| H2bM8833N | 129 ± 0.6 | 1.4 | IC | IC | IC | IC |
| H1M8115N | 92.7 ± 0.3 | 0.4 | NB | NB | NB | NB |
| H4H8837P | 438.9 ± 5.7 | 0.1 | NB | NB | NB | NB |
| H4H8852P | 169 ± 5 | 1.0 | NB | NB | NB | NB |

TABLE 15D-continued

Binding Kinetics parameters of anti-KLB/FGFR1c
antibodies binding to hFGFR1c-V5-6His at 37° C.

| Antibody | mAb Capture (RU) | 180 nM hFGFR1c-V5-6His Bind (RU) | $k_a$ (1/Ms) | $k_d$ (1/s) | $K_D$ (M) | $t_{1/2}$ (min) |
|---|---|---|---|---|---|---|
| H4H8856P | 185.4 ± 4.6 | 0.3 | NB | NB | NB | NB |
| H4H8859P | 202.1 ± 6.3 | 6.8 | 7.68E+04 | 3.82E−02 | 4.97E−07 | 0.3 |
| H4H8870P | 266.2 ± 7.7 | 10.6 | 2.64E+05 | 7.95E−02 | 3.01E−07 | 0.1 |
| H4H8871P | 133.3 ± 2.6 | −1.4 | NB | NB | NB | NB |
| H4H8878P | 147.3 ± 7.4 | 0.8 | NB | NB | NB | NB |
| H4H8880P | 142 ± 1.4 | 0.1 | NB | NB | NB | NB |
| H4H8881P | 47.3 ± 1.5 | 0.0 | NB | NB | NB | NB |
| H1H8897P | 123.5 ± 3.1 | 0.7 | NB | NB | NB | NB |
| H1H8898P | 285.8 ± 2.7 | 0.4 | NB | NB | NB | NB |
| H1H8899P | 167.3 ± 2.1 | 2.8 | NB | NB | NB | NB |
| H1H8900P | 213.9 ± 1.6 | 1.6 | NB | NB | NB | NB |
| Comparator 2## | 429.8 ± 5.6 | 69.8 | 1.75E+05 | 2.86E−02 | 1.64E−07 | 0.4 |
| Comparator 3### | 251.7 ± 8.3 | 88.8 | 2.37E+06 | 2.08E−02 | 8.76E−09 | 0.6 |
| Comparator 1# | 153.6 ± 2.5 | 0.0 | NB | NB | NB | NB |
| H4H8870P ScFv-Fc*/H4H8092N ScFv-Fc | 187.8 ± 4.7 | 1.2 | NB | NB | NB | NB |
| H4H8900P ScFv-Fc*/H4H8092N ScFv-Fc | 404 ± 4.7 | 0.4 | NB | NB | NB | NB |

In each of the above Tables 15A-D, IC means inconclusive since very weak binding was observed under the experimental conditions and the real-time binding data could not be reliably fit into the 1:1 binding model; NB means non-binding under experimental conditions; #: Comparator 1 was obtained using the methods described in WO2011/071783A1 for Ab "16H7"; ##: Comparator 2 was obtained using the methods described in EP1680140B1 for Ab "FR1-A1"; and ###: Comparator 3 was obtained using the methods described in EP1680140B1 for Ab "FR1-H7".

Anti-KLB/FGFR1c Antibody Binding to hKLB-HA-6His at 25° C. and 37° C.

At 25° C., hKLB-HA-6His bound to 9 of the 22 anti-KLB/FGFR1c antibodies of the invention with $K_D$ values ranging from 110 pM to 6.95 nM, as shown in Table 15A, while hKLB-HA-6His bound Comparator 1 with a $K_D$ value 305 pM.

Thirteen of the 22 anti-KLB/FGFR1c antibodies of the invention as well as Comparator 2 and 3 did not demonstrate any measurable binding to hKLB-HA-6His at 25° C.

In contrast, hKLB-HA-6His bound to the bispecific H4H8870P ScFv-Fe/H4H8092N ScFv-Fc, and the bispecific H4H8900P ScFv-Fe/H4H8092N ScFv-Fc with $K_D$ values of 725pM and 318pM, respectively, at 25° C.

At 37° C., hKLB-HA-6His bound to 9 of the 22 anti-KLB/FGFR1c antibodies of the invention with $K_D$ values ranging from 206 pM to 10.9 nM, as shown in Table 15B, while hKLB-HA-6His bound Comparator 1 with a $K_D$ value of 614 pM.

Thirteen of the 22 anti-KLB/FGFR1c antibodies of the invention as well as Comparator 2 and 3 did not demonstrate any measurable binding to hKLB-HA-6His at 37° C.

In contrast, hKLB-HA-6His bound to the bispecific H4H8870P ScFv-Fe/H4H8092N ScFv-Fc, and the bispecific H4H8900P ScFv-Fe/H4H8092N ScFv-Fc with $K_D$ values of 2.89 nM and 1.30 nM, respectively.

anti-KLB/FGFR1c antibody binding to hFGFR1c-V5-6His at 25° C. and 37° C.

At 25° C., hFGFR1c-V5-6His bound to 2 of the 22 anti-KLB/FGFR1c antibodies with $K_D$ values of 197 nM and 352 nM, respectively, as shown in Table 15C, while Comparator 2 and Comparator 3 bound to hFGFR1c-V5-6His with $K_D$ values of 66.9 nM and 4.12 nM, respectively.

Twenty of the 22 anti-KLB/FGFR1c antibodies of the invention as well as Comparator 1, the bispecific H4H8870P ScFv-Fe/H4H8092N ScFv-Fc, and the bispecific H4H8900P ScFv-Fc*/H4H8092N ScFv-Fc did not demonstrate any measurable binding to hFGFR1c-V5-6His at 25° C.

At 37° C., hFGFR1c-V5-6His bound to 2 of the 22 anti-KLB/FGFR1c antibodies of the invention with $K_D$ values ranging from 301 nM to 497 nM, as shown in Table 15D, while Comparator 2 and Comparator 3 bound to hFGFR1c-V5-6His with $K_D$ values of 164 nM and 8.76 nM, respectively.

Twenty of the 22 anti-KLB/FGFR1c antibodies of the invention as well as Comparator 1, the bispecific H4H8870P ScFv-Fe/H4H8092N ScFv-Fc, and the bispecific H4H8900P ScFv-Fc*/H4H8092N ScFv-Fc did not demonstrate any measurable binding to hFGFR1c-V5-6His at 37° C.

Example 16: Octet Cross-Competition Between Different Anti-KLB/FGFR1c Monoclonal Antibodies Binding competition between anti-KLB/FGFR1c monoclonal antibodies that had been previously determined to bind to human KLB (see Example 15) was determined using a real time, label-free bio-layer interferometry (BLI) assay on an Octet HTX biosensor 8aq (ForteBio Corp., A Division of Pall Life Sciences). The entire experiment was performed at 25° C. in buffer comprised of 0.01M HEPES pH7.4, 0.15M NaCl, 3 mM EDTA, 0.05% v/v Surfactant P20, 0.1 mg/mL BSA (Octet HBST buffer) with the plate shaking at a speed of 1000 rpm. To assess whether two antibodies are able to compete with one another for binding to their respective epitopes on the recombinant human KLB expressed with C-terminal HA and hexahistidine tags (hKLB-HA-6his; SEQ ID NO: 438), approximately 0.55 nm of hKLB-HA-6his was first captured onto anti-penta-His antibody coated Octet biosensors (Fortebio Inc, #18-5079)

by submerging the biosensors for 5 minutes into wells containing a 15 µg/mL solution of hKLB-HA-6his. The antigen-captured biosensors were then saturated with the first anti-KLB/FGFR1c monoclonal antibody (subsequently referred to as mAb-1, see Table 16) by immersion into wells containing a 50 µg/mL solution of mAb-1 for 5 minutes. The biosensors were then subsequently submerged into wells containing a 50 µg/mL solution of a second anti-KLB/FGFR1c monoclonal antibody (subsequently referred to as mAb-2, for example, see Table 16) for 3 minutes. All the biosensors were washed in Octet HBST buffer in between each step of the experiment. The real-time binding response was monitored during the course of the experiment and the binding response at the end of every step was recorded as shown in Table 16. The response of mAb-2 binding to hKLB-HA-6his pre-complexed with mAb-1 was compared and competitive/non-competitive behavior of different anti-KLB/FGFR1c monoclonal antibodies was determined. Each exemplary anti-KLB/FGFR1c monoclonal antibody (mAb-1, -2, -3, -4, etc.) was compared to one another as indicated in Table 16.

Panel B, and FIG. 5, Panels A-B. One exemplary fusion (SEQ ID NO: 463) was engineered comprising an anti-FGFR1c scFv (8900P ScFv) attached to the N-terminus of an Fc fragment and a FGF21 polypeptide fragment comprising the KLB-interacting domain, i.e., C-terminal portion of FGF21 (such as L37-5209 ΔN-FGF21; SEQ ID NO: 448) is attached to the C-terminus of the Fc fragment.

As such, exemplary fusion constructs may consist of homodimeric chains, where (from N- to C-terminus) each chain is composed of segments scFv-hinge-CH2-CH3-ΔFGF21, and two chains are linked through interchain disulfides joining the two hinge regions, similarly to a human IgG4 antibody. In constructing the single chain Fv region, the C-terminus of a particular antibody HCVR was joined to the N-terminus of a distinct LCVR through the flexible linker (Gly-Gly-Gly-Ser)$_3$ (SEQ ID NO: 476). The HCVR and LCVR sequences for each scFv-Fc chain can be derived from any antibody of Table 2, Table 7A or 7B. ΔFGF21, i.e. FGF21 fragments, may be derived from N-terminal truncation (ΔN-FGF21) or C-terminal truncation (ΔC-

TABLE 16

Cross-competition of anti-KLB/FGFR1c antibodies for binding to hKLB-HA-6his.

| Antibody | hKLB-HA-6his Binding (nm) | First mAb Binding (nm) | mAb # | Response of 50 ug/mL Second mAb Competing with First mAb Bound to hKLB-HA-6his (nm) | | | | | | | | | | | | | |
|---|---|---|---|---|---|---|---|---|---|---|---|---|---|---|---|---|---|
| | | | | 1 | 2 | 3 | 4 | 5 | 6 | 7 | 8 | 9 | 10 | 11 | 12 | 13 | 14 |
| H2bM8096N | 0.57 ± 0.01 | 0.34 ± 0.01 | 1 | <u>0.08</u> | *0.03* | 0.30 | 0.24 | 0.21 | 0.23 | 0.20 | 0.20 | 0.32 | 0.28 | 029 | 0.03 | 0.04 | 0.03 |
| H2aM8109N | 0.56 ± 0.01 | 0.29 ± 0.01 | 2 | *0.07* | <u>0.04</u> | 0.29 | 0.25 | 0.27 | 0.29 | 0.26 | 0.26 | 0.32 | 0.28 | 0.29 | 0.04 | 0.04 | 0.03 |
| H2aM8098N | 0.56 ± 0.01 | 0.37 ± 0.01 | 3 | 0.29 | 0.24 | <u>0.10</u> | *0.08* | 0.24 | 0.26 | 0.25 | 0.24 | 0.21 | 0.21 | 0.22 | 0.02 | 0.02 | 0.01 |
| H2aM8092N | 0.56 ± 0.01 | 0.30 ± 0.01 | 4 | 0.26 | 0.24 | *0.10* | <u>0.04</u> | 0.26 | 0.28 | 0.26 | 0.26 | 0.31 | 0.28 | 0.28 | 0.03 | 0.04 | 0.03 |
| H2aM8093N | 0.56 ± 0.01 | 0.28 ± 0.01 | 5 | 0.26 | 0.26 | 0.29 | 0.29 | <u>0.04</u> | *0.04* | *0.05* | *0.03* | 0.32 | 0.28 | 0.28 | 0.03 | 0.04 | 0.03 |
| H4H8881P | 0.49 ± 0.15 | 0.28 ± 0.06 | 6 | 0.24 | 0.25 | 0.26 | 0.26 | *0.04* | <u>0.02</u> | *0.03* | *0.03* | 0.30 | 0.27 | 0.27 | 0.03 | 0.02 | 0.02 |
| Comparator 1 | 0.55 ± 0.02 | 0.26 ± 0.01 | 7 | 0.25 | 0.25 | 0.28 | 0.28 | *0.05* | *0.05* | <u>0.03</u> | 0.16 | 0.31 | 0.28 | 0.27 | 0.03 | 0.03 | 0.02 |
| H1M8115N | 0.56 ± 0.01 | 0.28 ± 0.01 | 8 | 0.26 | 0.25 | 0.28 | 0.28 | *0.04* | *0.04* | 0.17 | <u>0.03</u> | 0.33 | 0.28 | 0.28 | 0.02 | 0.03 | 0.03 |
| H4H8837P | 0.55 ± 0.02 | 0.32 ± 0.01 | 9 | 0.28 | 0.26 | 0.24 | 0.29 | 0.27 | 0.28 | 0.25 | 0.26 | <u>0.03</u> | *0.03* | *0.04* | 0.03 | 0.03 | 0.03 |
| H4H8878P | 0.52 ± 0.10 | 0.30 ± 0.04 | 10 | 0.26 | 0.25 | 0.26 | 0.29 | 0.27 | | 0.24 | 0.26 | *0.05* | <u>0.03</u> | 0.25 | 0.03 | 0.04 | 0.02 |
| H4H8880P | 0.50 ± 0.12 | 0.31 ± 0.04 | 11 | 0.26 | 0.25 | 0.25 | 0.27 | 0.26 | | 0.24 | 0.26 | *0.03* | 0.24 | <u>0.03</u> | 0.03 | 0.03 | 0.02 |
| mIgG2a Isotype Control | 0.56 ± 0.01 | 0.03 ± 0.01 | 12 | 0.27 | 0.25 | 0.28 | 0.26 | 0.25 | 0.26 | 0.25 | 0.24 | 0.30 | 0.27 | 0.27 | <u>0.04</u> | 0.03 | 0.02 |
| hIgG4 Isotype Control | 0.55 ± 0.02 | 0.02 ± 0.01 | 13 | 0.25 | 0.24 | 0.26 | 0.25 | 0.25 | 0.25 | 0.23 | 0.24 | 0.29 | 0.26 | 0.26 | 0.03 | <u>0.03</u> | 0.02 |
| hIgG1 Isotype Control | 0.53 ± 0.08 | 0.02 ± 0.01 | 14 | 0.25 | 0.25 | 0.27 | 0.26 | 0.25 | | 0.23 | 0.24 | 0.29 | 0.26 | 0.25 | 0.03 | 0.03 | <u>0.02</u> |

As shown in Table 16, boxes with underlined text (along a diagonal) represent self-competition (where mAb-1=mAb-2). Antibodies competing in both directions, independent of the order of binding, are represented by boxes with dashed underlined, bold and italic text, thereby indicating competition for the same epitope on hKLB. Boxes without underlining represent no competition between antibodies, which suggests each antibody has a distinct binding epitope. Finally, inconclusive data is represented by empty boxes. Several antibodies have been identified as competing for the same epitope.

Example 17: Generation of FGF21R Antibody-FGF21 Fusion Constructs Example 17: Generation of FGF21R Antibody-FGF21 Fusion Constructs Fusion constructs were generated using well-known methods to engineer a multimerizing ScFv-Fc to a FGF21 fragment, therefore having multiple coreceptor interactions. See, e.g., FIG. 1, Panels B-C, FIG. 2, Panels A-D, FIG. 4, FGF21) of native mammalian FGF21, depending on whether KLB-interacting or FGFR1c-interacting fragments, respectively, are desirable.

For example, 8900P ScFv-Fc fusion ("Fusion 3") was constructed using well-known molecular biology cloning techniques to express a recombinant polypeptide comprising (from 5'- to -3') the HCVR of antibody 8900P (SEQ ID NO: 418), a (Gly-Gly-Gly-Ser)3 (SEQ ID NO: 476) linker, the LCVR of 8900P (SEQ ID NO: 426), mutated IgG4 Fc fragment (SEQ ID NO: 454), and L37-5209 (C-terminal) fragment of FGF21 (SEQ ID NO: 448). The amino acid sequence of a full-length 8900P fusion monomer is identified herein as SEQ ID NO:463.

Other ScFv-Fc fusion constructs were prepared analogously, for example comprising the HCVR/LCVR amino acid sequence pairs for antibody 8870P (SEQ ID NOs: 306/314) ("Fusion 2").

Still other antibody-FGF21 fusion proteins, as exemplified in Table 17, were made using standard molecular biology techniques.

TABLE 17

Antibody-FGF21 Fusion Constructs

Figure 4:
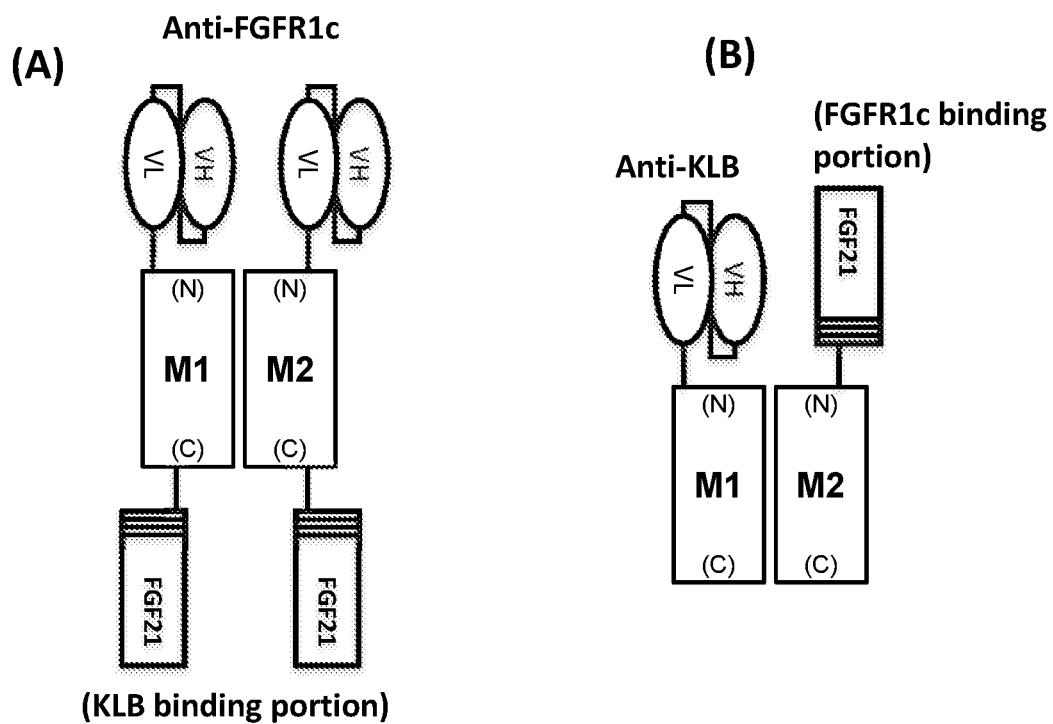
FIG. 4 illustrates two specific exemplary FGF21R agonists wherein portions of the FGF21 polypeptide function as either the KLB-binding domain (Panel A) or the FGFR1c-binding domain (Panel B). In Panel A, a first anti-FGFR1c scFv is attached to the N-terminus of M1, a second (identical) anti-FGFR1c scFv is attached to the N-terminus of M2, a first FGF21 polypeptide fragments comprising the KLB-interacting domain (i.e., C-terminal portion of FGF21, also referred to as N-terminally truncated FGF21 (ΔN-FGF21)) is attached to the C-terminus of M1, and a second (identical) FGF21 polypeptide fragment is attached to the C-terminus of M2. In Panel B, an anti-KLB scFv is attached to the N-terminus of M1 and a portion of FGF21 comprising the FGFR1c-interacting domain (i.e., N-terminal portion of FGF21, also referred to as C-terminally truncated FGF21 (ΔC-FGF21)) is attached to the N-terminus of M2.

| Designation | N-terminus | Multimerizing domain | C-terminus | SEQ ID NO: | Figure Reference No. |
|---|---|---|---|---|---|
| Fusion 1 (Heterodimer) | Anti-KLB (scFv8092N) | hIgG4mutFc | n/a | 456 | FIG. 1, Panel A or FIG. 4, Panel B |
|  | ΔC FGF21 (H29-S195/L174P) | hIgG4mutFc* | n/a | 461 |  |
| Fusion 2 (Homodimer) | Anti-FGFR1c (ScFv8870P) | hIgG4mutFc | ΔN FGF21 (L37-S209) | 462 | FIG. 1, Panel C or FIG. 4, Panel A |
| Fusion 3 (Homodimer) | Anti-FGFR1c (ScFv8900P) | hIgG4mutFc | ΔN FGF21 (L37-S209) | 463 | FIG. 1, Panel C or FIG. 4, Panel A |
| Fusion 4 (Homodimer) | ΔC FGF21 (H29-P36) | hIgG1Fc | ΔN FGF21 (L37-S209) | 464 | FIG. 1, Panel C |
| Fusion 5 (Homodimer) | ΔC FGF21 (H29-P45) | hIgG1Fc | ΔN FGF21 (L37-S209) | 465 | FIG. 1, Panel C |

Example 18: Binding of FGF21 Fusion Construct to Cells Expressing hFGF1c, hKLB, or Both hFGF1c and hKLB as Determined by FACS Analysis Cell lines were developed and tested with Fusion 3, which is an 8900P fusion construct (i.e. SEQ ID NO:463, see Table 17) to determine the specificity of binding to cells expressing human and mouse FGFR1c and KLB. HEK293 cell lines were generated that stably express full-length human FGFR1c (hFGFR1c), both human FGFR1c and human KLB (hFGFR1c/hKLB), or both full-length mouse FGFR1c (SEQ ID NO:440) and mouse KLB (SEQ ID NO:441) (mFGFR1c/mKLB) along with a luciferase reporter (SRE response element-luciferase, SA Bioscience, #CLS-010L). The stable cell lines, HEK293/hFGFR1c/hKLB/SRE-Luc (HEK293/hFGFR1c/hKLB), HEK293/mFGFR1c/mKLB/SRE-Luc (HEK293/mFGFR1c/mKLB), and HEK293/hFGFR1c/SRE-Luc (HEK293/hFGFR1c), were maintained in DMEM supplemented with 10% FBS, NEAA, penicillin/streptomycin, 1 µg/mL puromycin, and 100 µg/mL hygromycin B. Media for cell lines containing hKLB or mKLB also contained 500 µL G418.

For the FACS analysis, HEK293 parental, HEK293/hFGFR1c, HEK293/hFGFR1c/hKLB, and HEK293/mFGFR1c/mKLB cells were dissociated and plated onto 96-well v-bottom plates at 0.5×10⁶ cells/well in 2% FBS/PBS. Cells were incubated with 67 nM of Fusion 3, 965 nM and 33 nM of H1H8900, and 33 nM of all other proteins for 30 minutes at 4° C. Control mAb2 was tested at a concentration of 965 nM. After primary protein incubation cells were washed and incubated with 3.75 µg/mL fluorescently conjugated secondary antibodies for 30 minutes at 4° C. Cells were filtered and analyzed on Accuri™ 6 Flow Cytometer. Unstained and secondary antibody alone controls were also tested for all cell lines. The results were analyzed using FlowJo version 9.52 software and geometric mean (Geom. Mean) of fluorescence for viable cells were determined. Geom. mean of fluorescence for each antibody was then normalized to Geom. mean of unstained cells to obtain relative binding of antibody (binding ratios) per each cell type.

As shown in Table 18, Fusion 3 bound to HEK293/hFGFR1c cells with a ratio of 4, to HEK293/hFGFR1c/hKLB cells with a ratio of 12, and to HEK293/mFGFR1c/mKLB cells with a ratio of 9. H1H8900P, the parental antibody from which ScFv for Fusion 3 was derived, bound to cell lines, with ratios of 2-5 when tested at two different concentrations. Control mAb3, a positive control for FGFR1c binding, shows binding ratios of 21, 23 and 7, to HEK293/hFGFR1c, HEK293/hFGFR1c/hKLB, and HEK293/mFGFR1c cells, respectively. Control mAb2, a positive control for KLB binding, shows binding to HEK293/hFGFR1c/hKLB cells. All antibodies and Fusion 3 showed no significant binding to HEK293 parental cells (ratios of 1-2). The anti-human IgG secondary antibody alone, Control mAb2, an irrelevant human IgG control antibody, showed little to no binding to cells with binding ratios of 2 for all lines.

TABLE 18

Binding of hFGFR1c/hKLB binding proteins to HEK293, HEK293/hFGFR1c/SRE-luc, HEK293/hFGFR1c/hKLB/SRE-luc, and, HEK293/mFGFR1c/mKLB/SRE-luc cells.

| Protein Tested | Description | MFI Ratio to unstained cells | | | |
|---|---|---|---|---|---|
| | | 293 (HZ) | 293/ hFGFR1c | 293/ hFGFR1c/ hKLB | 293/ mFGFR1c/ mKLB |
| Fusion 3 (67 nM) | H4H8900/ ΔN-hFGF21 | 1 | 4 | 12 | 9 |
| H1H8900P (965 nM) | hFGFR1c binder | 1 | 5 | 5 | 2 |
| H1H8900P (33 nM) | hFGFR1c binder | 1 | 2 | 2 | 1 |
| Control mAb3 (33 nM) | hFGFR1c binder | 1 | 21 | 23 | 7 |
| Control mAb1 (33 nM) | KLB Binder | 1 | 1 | 15 | 1 |
| Control mAb 2 (965 nM) | Irrelevant Control mAb | 2 | 2 | 2 | 2 |
| 2" Alone | | 1 | 1 | 1 | 1 |
| Unstained | | 1 | 1 | 1 | 1 |

Example 19: Bioassay to Detect the Activation of MAPK Pathway by FGF21 Fusion Constructs Since stimulation of FGFR1c/KLB by FGF21 leads to activation of the mitogen-activated protein kinase (MAPK) pathway (Ogawa et al., 2007, supra), a bioassay was developed to detect the activation of the MAPK pathway by FGF21. HEK293 cell lines were generated that stably express cell-surface human FGFR1c (hFGFR1c, amino acids 1-731 of accession number NP_075594) with cell-surface human KLB (hKLB, amino acids 1-1044 of accession number NP_783864.1), cell-surface mouse FGFR1c (mFGFR1c, SEQ ID NO:440) with cell-surface mouse KLB (mKLB, SEQ ID NO:441), and cell-surface hFGFR1c alone. All cell lines also had a luciferase reporter (SRE response element-luciferase, SRE-luc, SA Bioscience, #CLS-010L). The stable cell lines, HEK293/hFGFR1c/hKLB/SRE-Luc, HEK293/mFGFR1c/mKLB/SRE-Luc, and HEK293/hFGFR1c/SRE-Luc, respectively, were maintained in DMEM supplemented with 10% FBS, NEAA, penicillin/streptomycin, 1 µg/mL puromycin, and 100 µg/mL hygromycin B. Media for cell lines containing hKLB or mKLB also contained 500 µg/mL G418.

For the bioassay, cells were seeded into 96-well assay plates at 20,000 cells/well in OPTIMEM (Invitrogen, #31985-070) supplemented with 0.1% FBS, penicillin/streptomycin and L-glutamine, and then incubated at 37° C. in 5% $CO_2$ overnight. The next morning, human FGF21 with an N-terminal hexahistidine tag (His6-hFGF21; SEQ 436) or human FGF2 (R&D Systems, #233-FB) were titrated from 300 nM to 0.005 nM (plus a sample containing buffer alone without ligand) and added to the FGFR1c/KLB containing cell line (FGF21) or the FGFR1c-alone containing cell line (FGF2). These titrations were used to determine the ligand dose response titration curves for each cell line. To test activation by the various molecules containing antibody single chain variable fragments (scFv) and/or truncated versions of hFGF21, these molecules were serially diluted (1:3), from either 300 nM to 0.005 nM, 100 nM to 0.002 nM or 51.1 nM to 0.0009 nM (plus a sample containing buffer alone without test molecule), and added to cells without FGF ligands. After addition of either ligand or test molecules, the cells were then incubated for 5.5 hours at 37° C. in the presence of 5% $CO_2$ Luciferase activity was detected after this incubation by the addition of OneGlo reagent (Promega, #E6051) and measurement of luminescence using a Victor X instrument (Perkin Elmer). The results were analyzed using nonlinear regression (4-parameter logistics) with Prism 5 software (GraphPad) to obtain $EC_{50}$ and $IC_{50}$ values. Activation of antibodies was calculated such that 0 to 100% activation is defined as the range of activation achieved from doses of His6-hFGF21 ranging from 0 to 300 nM.

The activation of HEK293/hFGFR1c/hKLB/SRE-luc cells with bivalent molecules is shown in Tables 19A and 19B. Bivalent molecules showed maximal activation ranging from 1.3 to 22.6% relative to activation by His6-hFGF21 with $EC_{50}$ values ranging from 0.21 to 22 nM, with some molecules where the $EC_{50}$ value could not be determined using the conditions tested. The parental antibodies, H1H8900P, H4H8700P and H2aM8092N showed little to no activation with maximal activation of 0 to 1.4%.

Fusion 3 was the strongest activator among the bivalent molecules tested (22.6% and 20.2% relative to maximal His6-hFGF21 activation), along with having significantly greater sensitivity than the other activators with comparable amounts of activation (EC50 values of 1.0 nM and 1.1 nM; Tables 19 and 19B; Fusion 3 (SEQ ID NO:463; Anti-hFGFR1c(H4H8900P ScFv)-Fc-[ΔN hFGF21(L37-S209)]) is a molecule composed of a single-chain Fv fragment (ScFv) from anti-hFGFR1c antibody H1H8900P fused at its C-terminus to the hinge-CH2-CH3 fragment of the human IgG4 constant region followed at its C-terminus by an N-terminally-truncated human FGF21 designed as a KLB-binding component. This bispecific format is produced as a homodimer (disulfide-linked through the hinge region) and therefore provides bivalent-binding entities for FGFR1c and for KLB at its N- and C-termini, respectively. The bispecific molecule Fusion 2 (SEQ ID NO:462; anti-hFGFR1c (H4H8870P ScFv)-Fc-[ΔN hFGF21(L37-S209)] shares an analogous design as Fusion 3, but replaces the ScFv component with one that binds FGFR1c more weakly based on cell binding data (see example 18). It is noted that Fusion 2 requires higher concentrations to reach similar activation levels as Fusion 3 (maximum activation of 21.4% relative to maximal His6-hFGF21 activation), consistent with the weaker binding of the FGFR1c-binding component.

Two control molecules were tested to examine the nature of activation seen by Fusion 3. Control scFv8900-hIgG4mutFc (SEQ ID NO:466), having the same anti-FGFR1c antibody fragment used in Fusion 3 fused to the Fc portion of IgG4, gave 2.4% activation (relative to maximal His6-hFGF21 stimulation) with an EC50 value of 58 nM. Control hIgG4mutFc-hFGF21 (L37-S209) (SEQ ID NO:467), a Fc of IgG4 fused to the N-terminally-truncated human FGF21 used in Fusion 3, gave 22.8% activation (relative to maximal His6-hFGF21 stimulation) with an EC50 value of 16 nM (Table 19B). These Control molecules did not exhibit comparable activation and sensitivity of Fusion 3 suggesting that the activation of Fusion 3 can be attributed to the bispecific targeting and hence functional avidity of both hFGFR1c-interacting (through the H4H8900P ScFv) and KLB-interacting (through the N-terminally-truncated human FGF21) components.

Control mAb1, a positive control antibody (obtain using methods described in WO2011/071783A1 for Ab "16H7") showed maximal activation of 6.1% and 7.5%, with EC50 values of 0.17 nM and 0.24 nM (Tables 19A and 19B). Control mAb2 and Control mAb3, both irrelevant IgG controls, were also tested and displayed no activation. Human FGF21 activated with EC50 values of 1.1 nM and 1.4 nM (Tables 19A and 19B).

The bispecific scFv8900-IgG-scFv8092 [anti-hFGFR1c (H4H8900P ScFv)-Fc-Anti-hKLB(H4H8092N ScFv); SEQ ID NO:460] showed activation levels (7.7% activation relative to His6-hFGF21; EC50 value of 0.21 nM) comparable to the control mAb1 (6.1% activation relative to His6-hFGF21; EC50 value of 0.17 nM).

Fusion 3 also activated HEK293/mFGFR1c/mKLB/SRE-luc cells, with an observed maximum activation of 44% relative to His6-hFGF21 and an EC50 value of 0.87 nM. His6-hFGF21 activated HEK293/mFGFR1c/mKLB/SRE-luc cells with an EC50 value of 0.41 nM. Fusion 3 showed no significant activation of HEK293/hFGFR1c cells, indicating that its activation is dependent on the presence of KLB, while human FGF2 activated these cells with an EC50 value of 1.6 nM.

TABLE 19A

Activation in HEK293/hFGFR1c/hKLB/SRE-Luc cells by anti-hFGFRh1c/hKLB antibodies and associated controls- Run 1

| Antibodies/Molecules | $EC_{50}$ [M] | % Activation |
|---|---|---|
| His6-hFGF21 | 1.1E−09 | 100.0 |
| scFv8092N -IgG4mutFc × scFv8870P-IgG4mutFc* (SEQ ID NO: 456/457) | 1.3E−09 | 2.2 |
| scFv8092N -IgG4mutFc × scFv8900P-IgG4mutFc* (SEQ ID NO: 456/458) | >5.0E−09 | 1.6 |
| scFv8870 -IgG-scFv8092 (SEQ ID NO: 459) | 3.8E−08 | 5.3 |
| scFv8900 -IgG-scFv8092 (SEQ ID NO: 460) | 2.1E−10 | 7.7 |
| Fusion 1 (SEQ ID NO: 456/461) | 1.2E−09 | 5.2 |
| Fusion 2 (SEQ ID NO: 462) | >1.0E−08 | 21.4 |
| Fusion 3 (SEQ ID NO: 463) | 1.0E−09 | 22.6 |
| Fusion 4 (SEQ ID NO: 464) | 2.2E−08 | 1.3 |
| Fusion 5 SEQ ID NO: 465) | 1.5E−08 | 1.4 |
| H1H8900 | >1.0E−08 | 1.4 |
| H4H8870P | | No Activation |
| H2aM8092N | 1.5E−10 | 0.8 |
| Control mAb 1** | 1.7E−10 | 6.1 |
| Control mAb 2 | | No Activation |

TABLE 19B

Activation of HEK293/hFGFR1c/hKLB/SRE-Luc cells by hFGFR1c/hKLB binding bow-body molecule Fusion 3 and associated controls- Run 2

| Antibodies/Molecules | $EC_{50}$ [M] | % Activation |
|---|---|---|
| His6-hFGF21 | 1.4E−09 | 100.0 |
| Fusion 3 (SEQ ID NO: 463) | 1.1E−09 | 20.2 |
| Control scFv8900-hIgG4mutFc (SEQ ID NO: 466) | 5.8E−08 | 2.4 |
| Control hIgG4mutFc-hFGF21(L37-S209) (SEQ ID NO: 467) | 1.6E−08 | 22.8 |
| H1H8900 | 4.7E−08 | 0.7 |
| Control mAb 1** | 2.4E−10 | 7.5 |
| Control mAb 3 | | No Activation |

**Control mAb1 1 was obtained using the methods described in WO2011/071783A1 for Ab "16H7".

Example 20: the In Vivo Effect of Chronic Administration of an Anti-FGFR1c/KLB Fusion in a Diabetic Mice Model The chronic effects of an FGF21R agonist of the invention, 8900P ScFv-Fc fusion ("Fusion 3"), on blood glucose levels and oral glucose tolerance were determined in the obese mutant mouse strain ob/ob in a C57BL/6J background. These mice are homozygous for a spontaneous mutation of the leptin gene and exhibit obesity, hyperphagia, and a diabetes-like syndrome of hyperglycemia, glucose intolerance, and elevated plasma insulin levels even when maintained on a normal diet. At four months of age, 14 male ob/ob mice (Jackson Laboratories) were divided into two groups of 7 animals based on similar average baseline blood glucose levels. Baseline plasma was collected and blood glucose and body weights were determined five days prior to and on the day of the experiment (day 0). Each group received subcutaneous injections on day 0, day 2, and day 5 of either 10 mg/kg Fusion 3 or 10 mg/kg of an isotype control antibody that does not bind to any known mouse protein. Two, five, and seven days after the initial dosing, immediately prior to any subsequent dosing, body weights were measured and tail bleeds were collected. On day 6, after overnight fasting, an oral glucose tolerance test was performed by oral gavage of 1.0 g/kg glucose with tail vein blood collection at 0, 15, 30, 60, and 120 minutes after treatment.

Blood glucose levels from tail bleed samples were determined using ACCU-CHEK® Compact Plus (Roche Diagnostics). For determination of drug levels, anti-human IgG sandwich ELISAs were carried out on serum samples collected on days 2 and 7. Briefly, samples were diluted in 10% diluent buffer, incubated in 96-well plates coated with goat anti-human IgG (Jackson ImmunoResearch Laboratories), washed, and bound material detected with HRP-conjugated goat anti-human IgG (Jackson), followed by TMB reaction; purified antibodies were used to derive standard curves for relevant serum samples.

Figure 6:
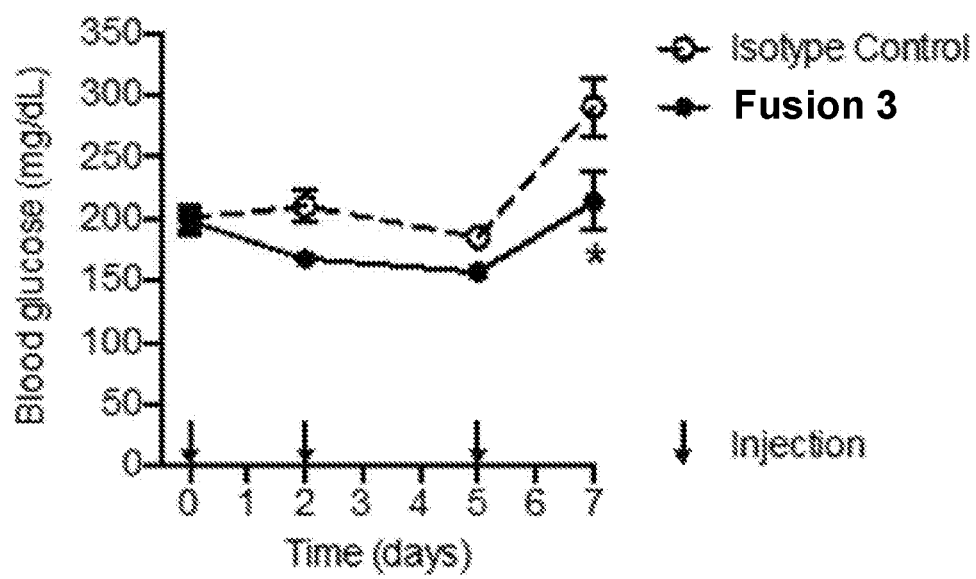
FIG. 6 shows blood glucose levels in ob/ob mice during administration of Fusion 3 or isotype control antibody; arrows indicate injections on days 0, 2, and 5 (*$p<0.05$ by two-way ANOVA with Bonferroni's multiple comparison test).

Over the course of multiple antibody injections, blood glucose levels were measured for each treatment group and the reduction in blood glucose from the mean blood glucose levels of the control group was calculated for each 8900P fusion-treated animal at each time point. Table 20 summarizes the mean blood glucose levels of each treatment group and mean percent blood glucose reduction in animals treated with Fusion 3; these results are also shown in FIG. 6. As can be seen, mice treated with Fusion 3 exhibited significant reduction in blood glucose levels at day 7 compared to mice injected with isotype control antibody; Fusion 3 injected mice showed a trend towards lower glucose on all previous days but these levels did not reach significance.

Figure 7:
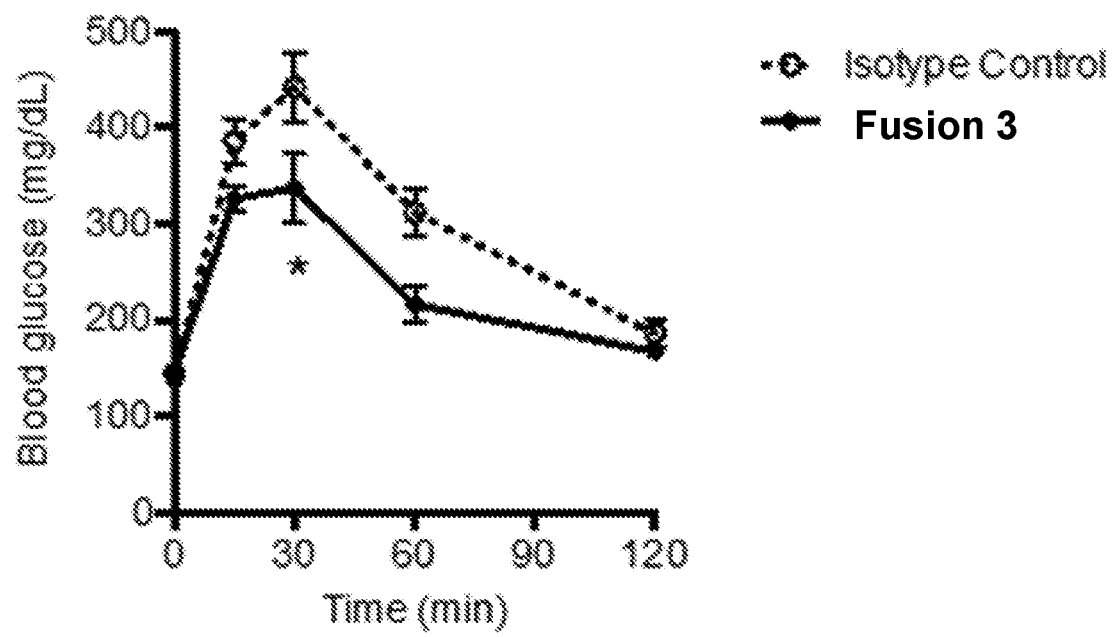
FIG. 7 shows blood glucose levels during oral glucose tolerance test in ob/ob mice after repeated administration of Fusion 3 or control antibody (*$p<0.05$ by two-way ANOVA with Bonferroni's multiple comparison test).

The ability of Fusion 3 to improve glycemic control in this diabetic model as determined by an oral glucose tolerance test conducted after three successive antibody injections; results are summarized in Table 21 and FIG. 7. After a glucose bolus, the circulating glucose levels in the Fusion 3-treated animals remained lower than those in the control animals, with the 30 minute time point showing a statistically significance decrease.

Figure 8:
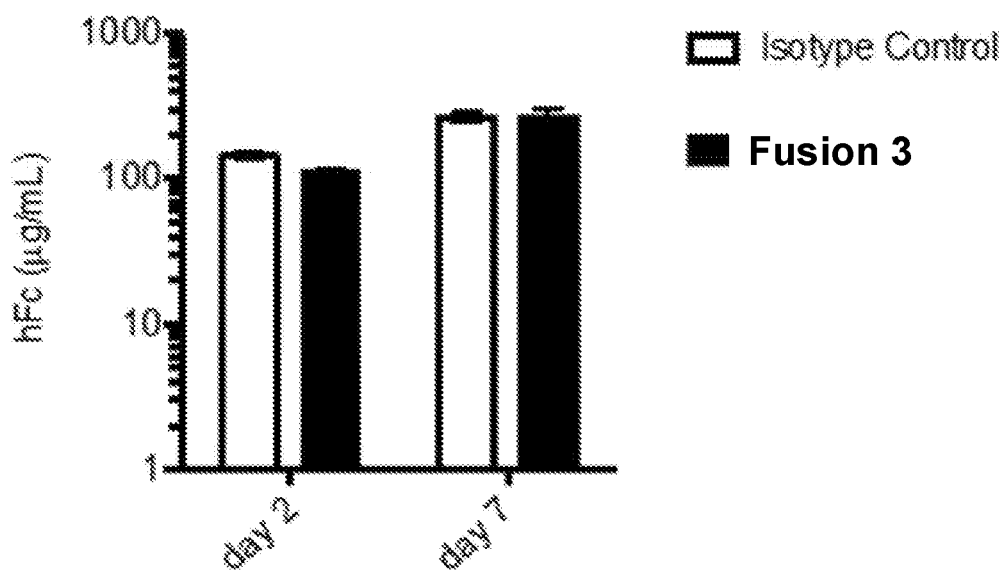
FIG. 8 depicts serum antibody levels of Fusion 3 or isotype control at day 2 (48 hours after first injection) and day 7 (48 hours after last injection).

The serum levels of antibodies over the course of the experiment were determined by ELISA at days 2 and 7 and the results are summarized in FIG. 8. There was no significant difference between the levels of the isotype control antibody or Fusion 3 at either time point.

There were no significant changes in body weight for each mouse in either treatment over the course of the experiment (data not shown).

TABLE 20

Blood glucose levels (mg/dL) and percent reduction in blood glucose levels as compared to isotype control treatment.

| Time (days) | Blood glucose level (mg/dL) ± SEM | | Percent reduction vs. control ± SEM |
|---|---|---|---|
| | Control | Fusion 3 | |
| 0 | 200 ± 9 | 198 ± 11 | 1 ± 5 |
| 2 | 210 ± 13 | 167 ± 7 | 20 ± 3 |
| 5 | 185 ± 6 | 156 ± 6 | 15 ± 3 |
| 7 | 290 ± 24 | 213 ± 24* | 26 ± 8 |

*$p < 0.05$ by two-way ANOVA with Bonferroni's multiple comparison test

TABLE 21

Blood glucose levels (mg/dL) during an oral glucose tolerance test administered after three antibody injections.

| Time (minutes) | Blood glucose (mg/dL) ± SEM | |
|---|---|---|
| | Control | Fusion 3 |
| 0 | 143 ± 8 | 146 ± 9 |
| 15 | 387 ± 23 | 326 ± 13 |
| 30 | 442 ± 36 | 337 ± 36 * |
| 60 | 312 ± 26 | 216 ± 20 |
| 120 | 186 ± 14 | 167 ± 6 |

* $p < 0.05$ by two-way ANOVA with Bonferroni's multiple comparison test

In conclusion, repeated administration of Fusion 3 to diabetic ob/ob mice for seven (7) days significantly reduced blood glucose and lead to an improvement in glycemic control upon challenge with exogenous glucose. Fusion 3 appeared to have reasonable serum stability as the circulating levels did not differ significantly from those of an isotype control antibody that does not bind mouse antigens.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

What is claimed is:

1. An FGF21 receptor (FGF21R) agonist that is capable of simultaneously binding βKlotho (KLB) and FGFR1c, wherein the FGF21R agonist comprises:
   - a first KLB-interacting domain (K1) and a second KLB-interacting domain (K2), wherein each of K1 and K2 comprise an N-terminally truncated FGF21 fragment (ΔN-FGF21) comprising the amino acid sequence of SEQ ID NO: 448;
   - a first FGFR1c-interacting domain (F1) and a second FGFR1-c-interacting domain (F2), wherein each of F1 and F2 comprise an antigen-binding portion of an anti-FGFR1c antibody, wherein the antigen-binding portion comprises three complementarity determining regions (CDRs) of a heavy chain variable region (HCVR) comprising the amino acid sequence of SEQ ID NO: 306 and three CDRs of a light chain variable region (LCVR) comprising the amino acid sequence of SEQ ID NO: 314; and
   - a first multimerizing domain (M1), and a second multimerizing domain, wherein each of M1 and M2 is selected from an immunoglobulin $C_H2$ domain, an immunoglobulin $C_H3$ domain, and an Fc domain of an immunoglobulin;
   - wherein K1 is attached to the C-terminus of M1, K2 is attached to the C-terminus of M2, F1 is attached to the N-terminus of M1, and F2 is attached to the N-terminus of M2.

2. A pharmaceutical composition comprising an FGF21R agonist of claim 1, and a pharmaceutically acceptable carrier or diluent.

3. The FGF21R agonist of claim 1, wherein the antigen-binding portion of the anti-FGFR1c antibody is a Fab.

4. The FGF21R agonist of claim 1, wherein the antigen-binding portion of the anti-FGFR1c antibody is an scFv.

5. The FGF21R agonist of claim 1, wherein the antigen-binding portion of the anti-FGFR1c antibody comprises an HCVR/LCVR amino acid sequence pair of SEQ ID NOs: 306/314.

6. The FGF21R agonist of claim 1, wherein M1 and M2 are each an Fc domain of an immunoglobulin.

7. The FGF21R agonist of claim 1, wherein K1, K2, F1 and/or F2 are attached to M1 and/or M2 via a linker component (L).

8. The FGF21R agonist of claim 7, wherein L is an amino acid sequence having the formula $(G_4S)_n$, wherein n is an integer from 1 to 10.

9. The FGF21R agonist of claim 1 that is a homodimer, wherein each monomer of the homodimer comprises the amino acid sequence of SEQ ID NO: 462.

10. A pharmaceutical composition comprising an FGF21R agonist of claim 9, and a pharmaceutically acceptable carrier or diluent.

* * * * *

SEQUENCE LISTING

```
<160> NUMBER OF SEQ ID NOS: 476

<210> SEQ ID NO 1
<211> LENGTH: 345
<212> TYPE: DNA
<213> ORGANISM: Artificial Sequence
<220> FEATURE:
<223> OTHER INFORMATION: synthetic

<400> SEQUENCE: 1
caggtacatc tggtgcagtc tggggctgag gtgaagaagc ctggggcctc agtgaaggtc     60
tcctgcaagg cttctggcta ctccttcacc gactactatg ttcactgggt gcgacaggcc    120
cctggacagg gccttgagtg gatgggatgg ttcaacccta aaagtggtga cacaaattct    180
gtacagaagt tcagggcag agtctccatg accggggaca cgtccatcac cacagcctac     240
ctggacctga aagactgac atctgacgac acggccgtat attactgtgg gagaagtggg     300
tattttgact tctgggccca gggaaccctg gtcaccgttt cttca                    345

<210> SEQ ID NO 2
<211> LENGTH: 115
<212> TYPE: PRT
<213> ORGANISM: Artificial Sequence
<220> FEATURE:
<223> OTHER INFORMATION: synthetic

<400> SEQUENCE: 2

Gln Val His Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Asp Tyr
                20                  25                  30

Tyr Val His Trp Val Arg Gln Ala Pro Gly Gln Gly Leu Glu Trp Met
            35                  40                  45

Gly Trp Phe Asn Pro Lys Ser Gly Asp Thr Asn Ser Val Gln Lys Phe
        50                  55                  60

Gln Gly Arg Val Ser Met Thr Gly Asp Thr Ser Ile Thr Thr Ala Tyr
65                  70                  75                  80

Leu Asp Leu Arg Arg Leu Thr Ser Asp Asp Thr Ala Val Tyr Tyr Cys
                85                  90                  95

Gly Arg Ser Gly Tyr Phe Asp Phe Trp Gly Gln Gly Thr Leu Val Thr
            100                 105                 110

Val Ser Ser
        115
```

```
<210> SEQ ID NO 3
<211> LENGTH: 24
<212> TYPE: DNA
<213> ORGANISM: Artificial Sequence
<220> FEATURE:
<223> OTHER INFORMATION: synthetic

<400> SEQUENCE: 3
ggctactcct tcaccgacta ctat                                              24

<210> SEQ ID NO 4
<211> LENGTH: 8
<212> TYPE: PRT
<213> ORGANISM: Artificial Sequence
<220> FEATURE:
<223> OTHER INFORMATION: synthetic

<400> SEQUENCE: 4

Gly Tyr Ser Phe Thr Asp Tyr Tyr
1               5

<210> SEQ ID NO 5
<211> LENGTH: 24
<212> TYPE: DNA
<213> ORGANISM: Artificial Sequence
<220> FEATURE:
<223> OTHER INFORMATION: synthetic

<400> SEQUENCE: 5
ttcaacccta aaagtggtga caca                                              24

<210> SEQ ID NO 6
<211> LENGTH: 8
<212> TYPE: PRT
<213> ORGANISM: Artificial Sequence
<220> FEATURE:
<223> OTHER INFORMATION: synthetic

<400> SEQUENCE: 6

Phe Asn Pro Lys Ser Gly Asp Thr
1               5

<210> SEQ ID NO 7
<211> LENGTH: 24
<212> TYPE: DNA
<213> ORGANISM: Artificial Sequence
<220> FEATURE:
<223> OTHER INFORMATION: synthetic

<400> SEQUENCE: 7
gggagaagtg ggtatttttga cttc                                             24

<210> SEQ ID NO 8
<211> LENGTH: 8
<212> TYPE: PRT
<213> ORGANISM: Artificial Sequence
<220> FEATURE:
<223> OTHER INFORMATION: synthetic

<400> SEQUENCE: 8

Gly Arg Ser Gly Tyr Phe Asp Phe
1               5

<210> SEQ ID NO 9
<211> LENGTH: 336
<212> TYPE: DNA
<213> ORGANISM: Artificial Sequence
```

<220> FEATURE:
<223> OTHER INFORMATION: synthetic

<400> SEQUENCE: 9

```
gatgttgtga tgactcagtc tccactctcc ctgtccgtca cccttggaca gccggcctcc    60
atctcctgca ggtctagtca aagcctcgta ttcagtgatg gaaataccct cttgaattgg   120
tttcagcaga ggccaggcca atctccaagg cgcctaattt ataatctttc taaccgggac   180
tctggggtcc cagacagatt cagcggcagt gggtcaggca ctgatttcac actgaagatc   240
agcggggtgg aggctgagga tgttggggtt tattactgca tgcaaggtac acactggcct   300
ctcactttcg gcggagggac caaggtggag atcaaa                            336
```

<210> SEQ ID NO 10
<211> LENGTH: 112
<212> TYPE: PRT
<213> ORGANISM: Artificial Sequence
<220> FEATURE:
<223> OTHER INFORMATION: synthetic

<400> SEQUENCE: 10

```
Asp Val Val Met Thr Gln Ser Pro Leu Ser Leu Ser Val Thr Leu Gly
1               5                   10                  15
Gln Pro Ala Ser Ile Ser Cys Arg Ser Ser Gln Ser Leu Val Phe Ser
            20                  25                  30
Asp Gly Asn Thr Phe Leu Asn Trp Phe Gln Gln Arg Pro Gly Gln Ser
        35                  40                  45
Pro Arg Arg Leu Ile Tyr Asn Leu Ser Asn Arg Asp Ser Gly Val Pro
    50                  55                  60
Asp Arg Phe Ser Gly Ser Gly Ser Gly Thr Asp Phe Thr Leu Lys Ile
65                  70                  75                  80
Ser Gly Val Glu Ala Glu Asp Val Gly Val Tyr Tyr Cys Met Gln Gly
                85                  90                  95
Thr His Trp Pro Leu Thr Phe Gly Gly Gly Thr Lys Val Glu Ile Lys
            100                 105                 110
```

<210> SEQ ID NO 11
<211> LENGTH: 33
<212> TYPE: DNA
<213> ORGANISM: Artificial Sequence
<220> FEATURE:
<223> OTHER INFORMATION: synthetic

<400> SEQUENCE: 11

```
caaagcctcg tattcagtga tggaaatacc ttc                                33
```

<210> SEQ ID NO 12
<211> LENGTH: 11
<212> TYPE: PRT
<213> ORGANISM: Artificial Sequence
<220> FEATURE:
<223> OTHER INFORMATION: synthetic

<400> SEQUENCE: 12

```
Gln Ser Leu Val Phe Ser Asp Gly Asn Thr Phe
1               5                   10
```

<210> SEQ ID NO 13
<211> LENGTH: 9
<212> TYPE: DNA
<213> ORGANISM: Artificial Sequence
<220> FEATURE:

```
<223> OTHER INFORMATION: synthetic

<400> SEQUENCE: 13 aatctttct                                                                9

<210> SEQ ID NO 14
<211> LENGTH: 3
<212> TYPE: PRT
<213> ORGANISM: Artificial Sequence
<220> FEATURE:
<223> OTHER INFORMATION: synthetic

<400> SEQUENCE: 14

Asn Leu Ser
1

<210> SEQ ID NO 15
<211> LENGTH: 27
<212> TYPE: DNA
<213> ORGANISM: Artificial Sequence
<220> FEATURE:
<223> OTHER INFORMATION: synthetic

<400> SEQUENCE: 15
atgcaaggta cacactggcc tctcact                                           27

<210> SEQ ID NO 16
<211> LENGTH: 9
<212> TYPE: PRT
<213> ORGANISM: Artificial Sequence
<220> FEATURE:
<223> OTHER INFORMATION: synthetic

<400> SEQUENCE: 16

Met Gln Gly Thr His Trp Pro Leu Thr
1               5

<210> SEQ ID NO 17
<211> LENGTH: 360
<212> TYPE: DNA
<213> ORGANISM: Artificial Sequence
<220> FEATURE:
<223> OTHER INFORMATION: synthetic

<400> SEQUENCE: 17
gaagtacatc tggtggagtc tgggggaggc ttggtacagc ctggcaggtc cctgagactc       60
tcctgtgtag cctctggatt caccttttgat gattatgcca tgcactgggt ccggcaagtt     120
ccagggaagg gcctggagtg ggtctcagtt attacttgga atagtggtag cataggctat     180
gcggactctg tgaagggccg cttcaccatc tccagagaca cgccaagaa ctccctgttt      240 ctgcaagtga gcagtctgag agctgaggac acggccttgt attactgtgc aaaaggtata     300
tccccaactg gaacgacgcc tgactactgg ggccagggga ccctggtcac cgtctcctca     360

<210> SEQ ID NO 18
<211> LENGTH: 120
<212> TYPE: PRT
<213> ORGANISM: Artificial Sequence
<220> FEATURE:
<223> OTHER INFORMATION: synthetic

<400> SEQUENCE: 18

Glu Val His Leu Val Glu Ser Gly Gly Gly Leu Val Gln Pro Gly Arg
1               5                   10                  15
```

```
Ser Leu Arg Leu Ser Cys Val Ala Ser Gly Phe Thr Phe Asp Asp Tyr
            20                  25                  30

Ala Met His Trp Val Arg Gln Val Pro Gly Lys Gly Leu Glu Trp Val
        35                  40                  45

Ser Val Ile Thr Trp Asn Ser Gly Ser Ile Gly Tyr Ala Asp Ser Val
 50                  55                  60

Lys Gly Arg Phe Thr Ile Ser Arg Asp Asn Ala Lys Asn Ser Leu Phe
 65                  70                  75                  80

Leu Gln Val Ser Ser Leu Arg Ala Glu Asp Thr Ala Leu Tyr Tyr Cys
                85                  90                  95

Ala Lys Gly Ile Ser Pro Thr Gly Thr Thr Pro Asp Tyr Trp Gly Gln
            100                 105                 110

Gly Thr Leu Val Thr Val Ser Ser
        115                 120
```

<210> SEQ ID NO 19
<211> LENGTH: 24
<212> TYPE: DNA
<213> ORGANISM: Artificial Sequence
<220> FEATURE:
<223> OTHER INFORMATION: synthetic

<400> SEQUENCE: 19
ggattcacct ttgatgatta tgcc                                        24

<210> SEQ ID NO 20
<211> LENGTH: 8
<212> TYPE: PRT
<213> ORGANISM: Artificial Sequence
<220> FEATURE:
<223> OTHER INFORMATION: synthetic

<400> SEQUENCE: 20

Gly Phe Thr Phe Asp Asp Tyr Ala
1               5

<210> SEQ ID NO 21
<211> LENGTH: 24
<212> TYPE: DNA
<213> ORGANISM: Artificial Sequence
<220> FEATURE:
<223> OTHER INFORMATION: synthetic

<400> SEQUENCE: 21
attacttgga atagtggtag cata                                        24

<210> SEQ ID NO 22
<211> LENGTH: 8
<212> TYPE: PRT
<213> ORGANISM: Artificial Sequence
<220> FEATURE:
<223> OTHER INFORMATION: synthetic

<400> SEQUENCE: 22

Ile Thr Trp Asn Ser Gly Ser Ile
1               5

<210> SEQ ID NO 23
<211> LENGTH: 39
<212> TYPE: DNA
<213> ORGANISM: Artificial Sequence
<220> FEATURE:
<223> OTHER INFORMATION: synthetic

<400> SEQUENCE: 23
gcaaaaggta tatccccaac tggaacgacg cctgactac        39

<210> SEQ ID NO 24
<211> LENGTH: 13
<212> TYPE: PRT
<213> ORGANISM: Artificial Sequence
<220> FEATURE:
<223> OTHER INFORMATION: synthetic

<400> SEQUENCE: 24

Ala Lys Gly Ile Ser Pro Thr Gly Thr Thr Pro Asp Tyr
1               5                   10

<210> SEQ ID NO 25
<211> LENGTH: 336
<212> TYPE: DNA
<213> ORGANISM: Artificial Sequence
<220> FEATURE:
<223> OTHER INFORMATION: synthetic

<400> SEQUENCE: 25
gatattgtga tgactcagtc tccactctcc ctgcccgtca cccctggaga gccggcctcc        60
atctcctgca ggtctagtca gagcctcctg catagtaatg gatacaacta tttggattgg       120
tacctgcaga agccagggca gtctccacag ctcctgatct atttgggttc tactcgggcc       180
tccggggtcc ctgacaggtt cagtggcagt ggatcaggca cagattttac actgaaaatc       240
agcagagtgg aggctgagga tgttggggtt tattactgca tgcaagctct acaaactcct       300
cccactttcg gcggagggac caaggtggag atcaaa                                 336

<210> SEQ ID NO 26
<211> LENGTH: 112
<212> TYPE: PRT
<213> ORGANISM: Artificial Sequence
<220> FEATURE:
<223> OTHER INFORMATION: synthetic

<400> SEQUENCE: 26

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
                20                  25                  30

Asn Gly Tyr Asn Tyr Leu Asp Trp Tyr Leu Gln Lys Pro Gly Gln Ser
            35                  40                  45

Pro Gln Leu Leu Ile Tyr Leu Gly Ser Thr Arg Ala Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Pro Thr Phe Gly Gly Gly Thr Lys Val Glu Ile Lys
            100                 105                 110

<210> SEQ ID NO 27
<211> LENGTH: 33
<212> TYPE: DNA
<213> ORGANISM: Artificial Sequence
<220> FEATURE:
<223> OTHER INFORMATION: synthetic

<400> SEQUENCE: 27
cagagcctcc tgcatagtaa tggatacaac tat                                33

<210> SEQ ID NO 28
<211> LENGTH: 11
<212> TYPE: PRT
<213> ORGANISM: Artificial Sequence
<220> FEATURE:
<223> OTHER INFORMATION: synthetic

<400> SEQUENCE: 28

Gln Ser Leu Leu His Ser Asn Gly Tyr Asn Tyr
1               5                   10

<210> SEQ ID NO 29
<211> LENGTH: 9
<212> TYPE: DNA
<213> ORGANISM: Artificial Sequence
<220> FEATURE:
<223> OTHER INFORMATION: synthetic

<400> SEQUENCE: 29 ttgggttct                                                            9

<210> SEQ ID NO 30
<211> LENGTH: 3
<212> TYPE: PRT
<213> ORGANISM: Artificial Sequence
<220> FEATURE:
<223> OTHER INFORMATION: synthetic

<400> SEQUENCE: 30

Leu Gly Ser
1

<210> SEQ ID NO 31
<211> LENGTH: 27
<212> TYPE: DNA
<213> ORGANISM: Artificial Sequence
<220> FEATURE:
<223> OTHER INFORMATION: synthetic

<400> SEQUENCE: 31
atgcaagctc tacaaactcc tcccact                                       27

<210> SEQ ID NO 32
<211> LENGTH: 9
<212> TYPE: PRT
<213> ORGANISM: Artificial Sequence
<220> FEATURE:
<223> OTHER INFORMATION: synthetic

<400> SEQUENCE: 32

Met Gln Ala Leu Gln Thr Pro Pro Thr
1               5

<210> SEQ ID NO 33
<211> LENGTH: 369
<212> TYPE: DNA
<213> ORGANISM: Artificial Sequence
<220> FEATURE:
<223> OTHER INFORMATION: synthetic

<400> SEQUENCE: 33
gaggtgcaat tggtggagtc tgggggaggc ttggtaaagc ctgggggtc ccttagactc      60 tcctgtgcag cctctggatt cactttcagt aacgcctgga tgagctgggt ccgccaggct   120

```
ccagggaagg ggctggactg ggttggccgt attaaaaata aacttgatgg tgggacaaca    180
gactacgctg cacccgtgaa aggcagattc accatctcaa gagatgattc aaaaaacacg    240
ctgtatctgc aaatgaatag cctgaaaacc gaggacacag ccgtgtatta ctgtaccaca    300
gatcacggct ggaactacta ctacggtatg gacgtctggg gccaagggac cacggtcacc    360
gtctcctca                                                           369
```

<210> SEQ ID NO 34
<211> LENGTH: 123
<212> TYPE: PRT
<213> ORGANISM: Artificial Sequence
<220> FEATURE:
<223> OTHER INFORMATION: synthetic

<400> SEQUENCE: 34

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Asp Trp Val
        35                  40                  45

Gly Arg Ile Lys Asn Lys Leu Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr Asp His Gly Trp Asn Tyr Tyr Tyr Gly Met Asp Val
            100                 105                 110

Trp Gly Gln Gly Thr Thr Val Thr Val Ser Ser
        115                 120

<210> SEQ ID NO 35
<211> LENGTH: 24
<212> TYPE: DNA
<213> ORGANISM: Artificial Sequence
<220> FEATURE:
<223> OTHER INFORMATION: synthetic

<400> SEQUENCE: 35
ggattcactt tcagtaacgc ctgg                                           24

<210> SEQ ID NO 36
<211> LENGTH: 8
<212> TYPE: PRT
<213> ORGANISM: Artificial Sequence
<220> FEATURE:
<223> OTHER INFORMATION: synthetic

<400> SEQUENCE: 36

Gly Phe Thr Phe Ser Asn Ala Trp
1               5

<210> SEQ ID NO 37
<211> LENGTH: 30
<212> TYPE: DNA
<213> ORGANISM: Artificial Sequence
<220> FEATURE:
<223> OTHER INFORMATION: synthetic

<400> SEQUENCE: 37

```
attaaaaata aacttgatgg tgggacaaca                                    30

<210> SEQ ID NO 38
<211> LENGTH: 10
<212> TYPE: PRT
<213> ORGANISM: Artificial Sequence
<220> FEATURE:
<223> OTHER INFORMATION: synthetic

<400> SEQUENCE: 38

Ile Lys Asn Lys Leu Asp Gly Gly Thr Thr
1               5                   10

<210> SEQ ID NO 39
<211> LENGTH: 42
<212> TYPE: DNA
<213> ORGANISM: Artificial Sequence
<220> FEATURE:
<223> OTHER INFORMATION: synthetic

<400> SEQUENCE: 39
accacagatc acggctggaa ctactactac ggtatggacg tc                     42

<210> SEQ ID NO 40
<211> LENGTH: 14
<212> TYPE: PRT
<213> ORGANISM: Artificial Sequence
<220> FEATURE:
<223> OTHER INFORMATION: synthetic

<400> SEQUENCE: 40

Thr Thr Asp His Gly Trp Asn Tyr Tyr Tyr Gly Met Asp Val
1               5                   10

<210> SEQ ID NO 41
<211> LENGTH: 321
<212> TYPE: DNA
<213> ORGANISM: Artificial Sequence
<220> FEATURE:
<223> OTHER INFORMATION: synthetic

<400> SEQUENCE: 41
gacatccaga tgacccagtc tccatcctca ctgtctgcat ctgtaggaga cagagtcacc    60
atcacttgtc gggcgagtca ggacattagc aattatttag cctggtttca gcacaaacca   120
gggaaagccc ctaagtccct gatctatgct gcatccagtt tgcaaggtgg ggtcccatca   180
aagttcagcg gcagtggatc tgggacagat ttcactctca ccatcagcag cctgcagcct   240
gaagattttg caacttatta ttgccaacaa tataatactt accctcccac tttcggcgca   300
gggaccaagg tggagatcaa a                                            321

<210> SEQ ID NO 42
<211> LENGTH: 107
<212> TYPE: PRT
<213> ORGANISM: Artificial Sequence
<220> FEATURE:
<223> OTHER INFORMATION: synthetic

<400> SEQUENCE: 42

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30
```

-continued

```
Leu Ala Trp Phe Gln His Lys Pro Gly Lys Ala Pro Lys Ser Leu Ile
            35                  40                  45

Tyr Ala Ala Ser Ser Leu Gln Gly Gly Val Pro Ser Lys Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Asn Thr Tyr Pro Pro
                 85                  90                  95

Thr Phe Gly Ala Gly Thr Lys Val Glu Ile Lys
            100                 105

<210> SEQ ID NO 43
<211> LENGTH: 18
<212> TYPE: DNA
<213> ORGANISM: Artificial Sequence
<220> FEATURE:
<223> OTHER INFORMATION: synthetic

<400> SEQUENCE: 43
caggacatta gcaattat                                                 18

<210> SEQ ID NO 44
<211> LENGTH: 6
<212> TYPE: PRT
<213> ORGANISM: Artificial Sequence
<220> FEATURE:
<223> OTHER INFORMATION: synthetic

<400> SEQUENCE: 44

Gln Asp Ile Ser Asn Tyr
1               5

<210> SEQ ID NO 45
<211> LENGTH: 9
<212> TYPE: DNA
<213> ORGANISM: Artificial Sequence
<220> FEATURE:
<223> OTHER INFORMATION: synthetic

<400> SEQUENCE: 45 gctgcatcc                                                            9

<210> SEQ ID NO 46
<211> LENGTH: 3
<212> TYPE: PRT
<213> ORGANISM: Artificial Sequence
<220> FEATURE:
<223> OTHER INFORMATION: synthetic

<400> SEQUENCE: 46

Ala Ala Ser
1

<210> SEQ ID NO 47
<211> LENGTH: 27
<212> TYPE: DNA
<213> ORGANISM: Artificial Sequence
<220> FEATURE:
<223> OTHER INFORMATION: synthetic

<400> SEQUENCE: 47
caacaatata atacttaccc tcccact                                       27

<210> SEQ ID NO 48
```

<210> SEQ ID NO 48
<211> LENGTH: 9
<212> TYPE: PRT
<213> ORGANISM: Artificial Sequence
<220> FEATURE:
<223> OTHER INFORMATION: synthetic

<400> SEQUENCE: 48

Gln Gln Tyr Asn Thr Tyr Pro Pro Thr
1               5

<210> SEQ ID NO 49
<211> LENGTH: 351
<212> TYPE: DNA
<213> ORGANISM: Artificial Sequence
<220> FEATURE:
<223> OTHER INFORMATION: synthetic

<400> SEQUENCE: 49

```
caggtgcagc tgcaggagtc gggcccaggt ctggtgaagc cttcggagac cctgtccctc      60
acctgcactg tctctggtgg ctccatcagt ggttactact ggagctggat ccggcagccc     120
ccagggaagg gactggagtg gattgggtat ttctataaca gtgggagcac caactacaac     180
ccctccctca agagtcgagt caccatgtca gtagacacgt ccaagaacca attctccctg     240
aggctgacct ctgtgaccgc tgcggacacg gccgtatatt actgtacgag agagagggag     300
ctactgtact ttgactactg gggccaggga accctggtca ccgtctcctc a             351
```

<210> SEQ ID NO 50
<211> LENGTH: 117
<212> TYPE: PRT
<213> ORGANISM: Artificial Sequence
<220> FEATURE:
<223> OTHER INFORMATION: synthetic

<400> SEQUENCE: 50

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Gly Tyr
            20                  25                  30

Tyr Trp Ser Trp Ile Arg Gln Pro Pro Gly Lys Gly Leu Glu Trp Ile
        35                  40                  45

Gly Tyr Phe Tyr Asn Ser Gly Ser Thr Asn Tyr Asn Pro Ser Leu Lys
    50                  55                  60

Ser Arg Val Thr Met Ser Val Asp Thr Ser Lys Asn Gln Phe Ser Leu
65                  70                  75                  80

Arg Leu Thr Ser Val Thr Ala Ala Asp Thr Ala Val Tyr Tyr Cys Thr
                85                  90                  95

Arg Glu Arg Glu Leu Leu Tyr Phe Asp Tyr Trp Gly Gln Gly Thr Leu
            100                 105                 110

Val Thr Val Ser Ser
        115

<210> SEQ ID NO 51
<211> LENGTH: 24
<212> TYPE: DNA
<213> ORGANISM: Artificial Sequence
<220> FEATURE:
<223> OTHER INFORMATION: synthetic

<400> SEQUENCE: 51
ggtggctcca tcagtggtta ctac      24

<210> SEQ ID NO 52
<211> LENGTH: 8
<212> TYPE: PRT
<213> ORGANISM: Artificial Sequence
<220> FEATURE:
<223> OTHER INFORMATION: synthetic

<400> SEQUENCE: 52

Gly Gly Ser Ile Ser Gly Tyr Tyr
1               5

<210> SEQ ID NO 53
<211> LENGTH: 21
<212> TYPE: DNA
<213> ORGANISM: Artificial Sequence
<220> FEATURE:
<223> OTHER INFORMATION: synthetic

<400> SEQUENCE: 53
ttctataaca gtgggagcac c                                          21

<210> SEQ ID NO 54
<211> LENGTH: 7
<212> TYPE: PRT
<213> ORGANISM: Artificial Sequence
<220> FEATURE:
<223> OTHER INFORMATION: synthetic

<400> SEQUENCE: 54

Phe Tyr Asn Ser Gly Ser Thr
1               5

<210> SEQ ID NO 55
<211> LENGTH: 33
<212> TYPE: DNA
<213> ORGANISM: Artificial Sequence
<220> FEATURE:
<223> OTHER INFORMATION: synthetic

<400> SEQUENCE: 55
acgagagaga gggagctact gtactttgac tac                             33

<210> SEQ ID NO 56
<211> LENGTH: 11
<212> TYPE: PRT
<213> ORGANISM: Artificial Sequence
<220> FEATURE:
<223> OTHER INFORMATION: synthetic

<400> SEQUENCE: 56

Thr Arg Glu Arg Glu Leu Leu Tyr Phe Asp Tyr
1               5                   10

<210> SEQ ID NO 57
<211> LENGTH: 339
<212> TYPE: DNA
<213> ORGANISM: Artificial Sequence
<220> FEATURE:
<223> OTHER INFORMATION: synthetic

<400> SEQUENCE: 57
gacatcgtga tgacccagtc tccagactcc ctggctgtgt ctctgggcga gagggccacc    60
atcaactgca gtccagcca gagtgtttta tacagctccg acaataagaa ctacttagct   120
tggtaccagc agaaaccagg acagcctcct agcctgctca tttactgggc atctacccgg   180

```
gaatccgggg tccctgaccg attcagtggc agcgggtctg ggacagattt cactctcacc    240
atcagaagcc tgcgggctga agatgtggca gtttattact gtcagcaata ttatagtact    300
ccgctcactt tcggcggagg gaccaaggtg gagatcaaa                            339
```

<210> SEQ ID NO 58
<211> LENGTH: 113
<212> TYPE: PRT
<213> ORGANISM: Artificial Sequence
<220> FEATURE:
<223> OTHER INFORMATION: synthetic

<400> SEQUENCE: 58

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asp Asn Lys Asn Tyr Leu Ala Trp Tyr Gln Gln Lys Pro Gly Gln
        35                  40                  45

Pro Pro Ser Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Arg Ser Leu Arg Ala Glu Asp Val Ala Val Tyr Tyr Cys Gln Gln
                85                  90                  95

Tyr Tyr Ser Thr Pro Leu Thr Phe Gly Gly Gly Thr Lys Val Glu Ile
            100                 105                 110

Lys
```

<210> SEQ ID NO 59
<211> LENGTH: 36
<212> TYPE: DNA
<213> ORGANISM: Artificial Sequence
<220> FEATURE:
<223> OTHER INFORMATION: synthetic

<400> SEQUENCE: 59

```
cagagtgttt tatacagctc cgacaataag aactac                               36
```

<210> SEQ ID NO 60
<211> LENGTH: 12
<212> TYPE: PRT
<213> ORGANISM: Artificial Sequence
<220> FEATURE:
<223> OTHER INFORMATION: synthetic

<400> SEQUENCE: 60

```
Gln Ser Val Leu Tyr Ser Ser Asp Asn Lys Asn Tyr
1               5                   10
```

<210> SEQ ID NO 61
<211> LENGTH: 9
<212> TYPE: DNA
<213> ORGANISM: Artificial Sequence
<220> FEATURE:
<223> OTHER INFORMATION: synthetic

<400> SEQUENCE: 61

```
tgggcatct                                                             9
```

<210> SEQ ID NO 62
<211> LENGTH: 3

```
<212> TYPE: PRT
<213> ORGANISM: Artificial Sequence
<220> FEATURE:
<223> OTHER INFORMATION: synthetic

<400> SEQUENCE: 62

Trp Ala Ser
1

<210> SEQ ID NO 63
<211> LENGTH: 27
<212> TYPE: DNA
<213> ORGANISM: Artificial Sequence
<220> FEATURE:
<223> OTHER INFORMATION: synthetic

<400> SEQUENCE: 63
cagcaatatt atagtactcc gctcact                                            27

<210> SEQ ID NO 64
<211> LENGTH: 9
<212> TYPE: PRT
<213> ORGANISM: Artificial Sequence
<220> FEATURE:
<223> OTHER INFORMATION: synthetic

<400> SEQUENCE: 64

Gln Gln Tyr Tyr Ser Thr Pro Leu Thr
1               5

<210> SEQ ID NO 65
<211> LENGTH: 363
<212> TYPE: DNA
<213> ORGANISM: Artificial Sequence
<220> FEATURE:
<223> OTHER INFORMATION: synthetic

<400> SEQUENCE: 65
caggtgcagc tggtggagtc tgggggaggc gtggtccagc ctgggaggtc cctgagactc         60
tcctgtgcag cctctggatt caccttcagt agttatgtca tgcactgggt ccgccaggct        120
ccaggcaagg ggctggagtg ggtgtcagtt atatcatatg atggaggtaa taaatactat        180
gcagactccg tgaagggccg attcaccatc tccagagaca attccaagaa cacgctggat        240
ctgcaaatga acagcctgag agctgaagac acggctgtgt attactgtgc gaaagaggat        300
gattacattt ggggggggtt cttcgatctc tggggccgtg gcaccctggt caccgtctcc        360
tca                                                                     363

<210> SEQ ID NO 66
<211> LENGTH: 121
<212> TYPE: PRT
<213> ORGANISM: Artificial Sequence
<220> FEATURE:
<223> OTHER INFORMATION: synthetic

<400> SEQUENCE: 66

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Val Met His Trp Val Arg Gln Ala Pro Gly Lys Gly Leu Glu Trp Val
        35                  40                  45

Ser Val Ile Ser Tyr Asp Gly Gly Asn Lys Tyr Tyr Ala Asp Ser Val
```

```
                50                  55                  60
Lys Gly Arg Phe Thr Ile Ser Arg Asp Asn Ser Lys Asn Thr Leu Asp
 65                  70                  75                  80

Leu Gln Met Asn Ser Leu Arg Ala Glu Asp Thr Ala Val Tyr Tyr Cys
                 85                  90                  95

Ala Lys Glu Asp Asp Tyr Ile Trp Gly Phe Phe Asp Leu Trp Gly
            100                 105                 110

Arg Gly Thr Leu Val Thr Val Ser Ser
        115                 120
```

<210> SEQ ID NO 67
<211> LENGTH: 24
<212> TYPE: DNA
<213> ORGANISM: Artificial Sequence
<220> FEATURE:
<223> OTHER INFORMATION: synthetic

<400> SEQUENCE: 67
ggattcacct tcagtagtta tgtc                                    24

<210> SEQ ID NO 68
<211> LENGTH: 8
<212> TYPE: PRT
<213> ORGANISM: Artificial Sequence
<220> FEATURE:
<223> OTHER INFORMATION: synthetic

<400> SEQUENCE: 68

```
Gly Phe Thr Phe Ser Ser Tyr Val
 1               5
```

<210> SEQ ID NO 69
<211> LENGTH: 24
<212> TYPE: DNA
<213> ORGANISM: Artificial Sequence
<220> FEATURE:
<223> OTHER INFORMATION: synthetic

<400> SEQUENCE: 69
atatcatatg atggaggtaa taaa                                    24

<210> SEQ ID NO 70
<211> LENGTH: 8
<212> TYPE: PRT
<213> ORGANISM: Artificial Sequence
<220> FEATURE:
<223> OTHER INFORMATION: synthetic

<400> SEQUENCE: 70

```
Ile Ser Tyr Asp Gly Gly Asn Lys
 1               5
```

<210> SEQ ID NO 71
<211> LENGTH: 42
<212> TYPE: DNA
<213> ORGANISM: Artificial Sequence
<220> FEATURE:
<223> OTHER INFORMATION: synthetic

<400> SEQUENCE: 71
gcgaaagagg atgattacat ttggggggggg ttcttcgatc tc                42

<210> SEQ ID NO 72
<211> LENGTH: 14

```
<212> TYPE: PRT
<213> ORGANISM: Artificial Sequence
<220> FEATURE:
<223> OTHER INFORMATION: synthetic

<400> SEQUENCE: 72

Ala Lys Glu Asp Asp Tyr Ile Trp Gly Gly Phe Phe Asp Leu
1               5                   10

<210> SEQ ID NO 73
<211> LENGTH: 321
<212> TYPE: DNA
<213> ORGANISM: Artificial Sequence
<220> FEATURE:
<223> OTHER INFORMATION: synthetic

<400> SEQUENCE: 73
gacatccaga tgacccagtc tccatcctcc ctgtctgcat ctgtaggaga cagagtcacc      60
atcacttgcc gggcaagtca gggcattaga aatgatttag gctggtatca agaaaaccca    120
gggaaagccc ctaagcgcct gatctctgct gcatacagtt tgcaaagtgg ggtcacttca    180
aggttcagcg gcagtggatc tgggacagaa ttcactctca caatcagcag cctgcagcct    240
gaagattttg caacttatta ctgtctacag cataatagtt acccgtggac gttcggccaa    300
gggaccaagg tggaaatcaa a                                              321

<210> SEQ ID NO 74
<211> LENGTH: 107
<212> TYPE: PRT
<213> ORGANISM: Artificial Sequence
<220> FEATURE:
<223> OTHER INFORMATION: synthetic

<400> SEQUENCE: 74

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Lys Lys Pro Gly Lys Ala Pro Lys Arg Leu Ile
        35                  40                  45

Ser Ala Ala Tyr Ser Leu Gln Ser Gly Val Thr Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Trp
                85                  90                  95

Thr Phe Gly Gln Gly Thr Lys Val Glu Ile Lys
            100                 105

<210> SEQ ID NO 75
<211> LENGTH: 18
<212> TYPE: DNA
<213> ORGANISM: Artificial Sequence
<220> FEATURE:
<223> OTHER INFORMATION: synthetic

<400> SEQUENCE: 75
cagggcatta gaaatgat                                                   18

<210> SEQ ID NO 76
<211> LENGTH: 6
<212> TYPE: PRT
```

```
<213> ORGANISM: Artificial Sequence
<220> FEATURE:
<223> OTHER INFORMATION: synthetic

<400> SEQUENCE: 76

Gln Gly Ile Arg Asn Asp
1               5

<210> SEQ ID NO 77
<211> LENGTH: 9
<212> TYPE: DNA
<213> ORGANISM: Artificial Sequence
<220> FEATURE:
<223> OTHER INFORMATION: synthetic

<400> SEQUENCE: 77 gctgcatac                                                            9

<210> SEQ ID NO 78
<211> LENGTH: 3
<212> TYPE: PRT
<213> ORGANISM: Artificial Sequence
<220> FEATURE:
<223> OTHER INFORMATION: synthetic

<400> SEQUENCE: 78

Ala Ala Tyr
1

<210> SEQ ID NO 79
<211> LENGTH: 27
<212> TYPE: DNA
<213> ORGANISM: Artificial Sequence
<220> FEATURE:
<223> OTHER INFORMATION: synthetic

<400> SEQUENCE: 79
ctacagcata atagttaccc gtggacg                                       27

<210> SEQ ID NO 80
<211> LENGTH: 9
<212> TYPE: PRT
<213> ORGANISM: Artificial Sequence
<220> FEATURE:
<223> OTHER INFORMATION: synthetic

<400> SEQUENCE: 80

Leu Gln His Asn Ser Tyr Pro Trp Thr
1               5

<210> SEQ ID NO 81
<211> LENGTH: 363
<212> TYPE: DNA
<213> ORGANISM: Artificial Sequence
<220> FEATURE:
<223> OTHER INFORMATION: synthetic

<400> SEQUENCE: 81
caggtgcagc tggtggagtc tgggggaggc ttggtcaagc ctggagggtc cctgagactc    60
tcctgtgcag cctctggatt catcttcagt gactactaca tgagctggat ccgccaggct   120
ccagggaagg ggctggactg gatttcatac attagtccta gtggtagtac catatactac   180
gcagactctg tgaagggccg attcaccatc tccagggaca cgccaagaa ctcactgtat    240 ctgcaaatga acagcctgag agccgacgac acggccgtgt attactgtgc gagaacagga   300
```

-continued

```
atacagttat ggtccgtcta ctttgactac tggggccagg gaaccctggt caccgtctcc    360
tca                                                                  363
```

<210> SEQ ID NO 82
<211> LENGTH: 121
<212> TYPE: PRT
<213> ORGANISM: Artificial Sequence
<220> FEATURE:
<223> OTHER INFORMATION: synthetic

<400> SEQUENCE: 82

```
Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Ile Phe Ser Asp Tyr
            20                  25                  30

Tyr Met Ser Trp Ile Arg Gln Ala Pro Gly Lys Gly Leu Asp Trp Ile
        35                  40                  45

Ser Tyr Ile Ser Pro Ser Gly Ser Thr Ile Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Asp Asp Thr Ala Val Tyr Tyr Cys
                85                  90                  95

Ala Arg Thr Gly Ile Gln Leu Trp Ser Val Tyr Phe Asp Tyr Trp Gly
            100                 105                 110

Gln Gly Thr Leu Val Thr Val Ser Ser
        115                 120
```

<210> SEQ ID NO 83
<211> LENGTH: 24
<212> TYPE: DNA
<213> ORGANISM: Artificial Sequence
<220> FEATURE:
<223> OTHER INFORMATION: synthetic

<400> SEQUENCE: 83

```
ggattcatct tcagtgacta ctac                                           24
```

<210> SEQ ID NO 84
<211> LENGTH: 8
<212> TYPE: PRT
<213> ORGANISM: Artificial Sequence
<220> FEATURE:
<223> OTHER INFORMATION: synthetic

<400> SEQUENCE: 84

```
Gly Phe Ile Phe Ser Asp Tyr Tyr
1               5
```

<210> SEQ ID NO 85
<211> LENGTH: 24
<212> TYPE: DNA
<213> ORGANISM: Artificial Sequence
<220> FEATURE:
<223> OTHER INFORMATION: synthetic

<400> SEQUENCE: 85

```
attagtccta gtggtagtac cata                                           24
```

<210> SEQ ID NO 86
<211> LENGTH: 8
<212> TYPE: PRT

<213> ORGANISM: Artificial Sequence
<220> FEATURE:
<223> OTHER INFORMATION: synthetic

<400> SEQUENCE: 86

Ile Ser Pro Ser Gly Ser Thr Ile
1               5

<210> SEQ ID NO 87
<211> LENGTH: 42
<212> TYPE: DNA
<213> ORGANISM: Artificial Sequence
<220> FEATURE:
<223> OTHER INFORMATION: synthetic

<400> SEQUENCE: 87
gcgagaacag gaatacagtt atggtccgtc tactttgact ac            42

<210> SEQ ID NO 88
<211> LENGTH: 14
<212> TYPE: PRT
<213> ORGANISM: Artificial Sequence
<220> FEATURE:
<223> OTHER INFORMATION: synthetic

<400> SEQUENCE: 88

Ala Arg Thr Gly Ile Gln Leu Trp Ser Val Tyr Phe Asp Tyr
1               5                   10

<210> SEQ ID NO 89
<211> LENGTH: 318
<212> TYPE: DNA
<213> ORGANISM: Artificial Sequence
<220> FEATURE:
<223> OTHER INFORMATION: synthetic

<400> SEQUENCE: 89
gaaatagtga tgacgcagtc tccagccacc ctgtctgtgt ctccagggga aagagccacc    60
ctctcctgca gggccagtca gagtgttgga agcaacttag cctggtacca gcagaaacct   120
ggccaggctc ccaggctcct catctatggt gcatccacca gggccaatgg catcccagcc   180
aggttcagtg gcagtgggtc tgggacagag ttcactctca ccatcagcgg cctgcagtct   240
gaagattttg cagtttatta ctgtcagcag tataataact ggcctacttt tggccagggg   300
accaagctgg agatcaaa                                                  318

<210> SEQ ID NO 90
<211> LENGTH: 106
<212> TYPE: PRT
<213> ORGANISM: Artificial Sequence
<220> FEATURE:
<223> OTHER INFORMATION: synthetic

<400> SEQUENCE: 90

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Gly Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Asn Gly Ile Pro Ala Arg Phe Ser Gly
    50                  55                  60

Ser Gly Ser Gly Thr Glu Phe Thr Leu Thr Ile Ser Gly Leu Gln Ser

```
                65                  70                  75                  80
Glu Asp Phe Ala Val Tyr Tyr Cys Gln Gln Tyr Asn Asn Trp Pro Thr
                    85                  90                  95
Phe Gly Gln Gly Thr Lys Leu Glu Ile Lys
            100                 105
```

<210> SEQ ID NO 91
<211> LENGTH: 18
<212> TYPE: DNA
<213> ORGANISM: Artificial Sequence
<220> FEATURE:
<223> OTHER INFORMATION: synthetic

<400> SEQUENCE: 91
cagagtgttg gaagcaac                                                  18

<210> SEQ ID NO 92
<211> LENGTH: 6
<212> TYPE: PRT
<213> ORGANISM: Artificial Sequence
<220> FEATURE:
<223> OTHER INFORMATION: synthetic

<400> SEQUENCE: 92

```
Gln Ser Val Gly Ser Asn
1               5
```

<210> SEQ ID NO 93
<211> LENGTH: 9
<212> TYPE: DNA
<213> ORGANISM: Artificial Sequence
<220> FEATURE:
<223> OTHER INFORMATION: synthetic

<400> SEQUENCE: 93 ggtgcatcc                                                             9

<210> SEQ ID NO 94
<211> LENGTH: 3
<212> TYPE: PRT
<213> ORGANISM: Artificial Sequence
<220> FEATURE:
<223> OTHER INFORMATION: synthetic

<400> SEQUENCE: 94

```
Gly Ala Ser
1
```

<210> SEQ ID NO 95
<211> LENGTH: 24
<212> TYPE: DNA
<213> ORGANISM: Artificial Sequence
<220> FEATURE:
<223> OTHER INFORMATION: synthetic

<400> SEQUENCE: 95
cagcagtata ataactggcc tact                                           24

<210> SEQ ID NO 96
<211> LENGTH: 8
<212> TYPE: PRT
<213> ORGANISM: Artificial Sequence
<220> FEATURE:
<223> OTHER INFORMATION: synthetic

<400> SEQUENCE: 96

Gln Gln Tyr Asn Asn Trp Pro Thr
1               5

<210> SEQ ID NO 97
<211> LENGTH: 348
<212> TYPE: DNA
<213> ORGANISM: Artificial Sequence
<220> FEATURE:
<223> OTHER INFORMATION: synthetic

<400> SEQUENCE: 97

```
caggtccagc tggtgcagtc tggggctgag gtgaagaagc ctgggtcctc ggtgaaggtc      60
tcctgcaagg cttctggagg caccttcagc acctatgaga tcagctgggt gcgacaggcc     120
cctggacaag gcttgagtg gatgggaggg atcatccctg tctttggtac aacacactac     180
gcacagaagt tccaagacag cgtcacgatt accacggacg aatccacggg cacagccttc     240
atggaactga gcagcctgaa atctgaggac acggccgtat attactgtgc gagaggtgga     300
gcgggcgggg caactgggg ccagggaacc ctggtcaccg tctcctca                   348
```

<210> SEQ ID NO 98
<211> LENGTH: 116
<212> TYPE: PRT
<213> ORGANISM: Artificial Sequence
<220> FEATURE:
<223> OTHER INFORMATION: synthetic

<400> SEQUENCE: 98

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Thr Tyr
            20                  25                  30

Glu Ile Ser Trp Val Arg Gln Ala Pro Gly Gln Gly Leu Glu Trp Met
        35                  40                  45

Gly Gly Ile Ile Pro Val Phe Gly Thr Thr His Tyr Ala Gln Lys Phe
    50                  55                  60

Gln Asp Ser Val Thr Ile Thr Thr Asp Glu Ser Thr Gly Thr Ala Phe
65                  70                  75                  80

Met Glu Leu Ser Ser Leu Lys Ser Glu Asp Thr Ala Val Tyr Tyr Cys
                85                  90                  95

Ala Arg Gly Gly Ala Gly Gly Asp Asn Trp Gly Gln Gly Thr Leu Val
            100                 105                 110

Thr Val Ser Ser
        115

<210> SEQ ID NO 99
<211> LENGTH: 24
<212> TYPE: DNA
<213> ORGANISM: Artificial Sequence
<220> FEATURE:
<223> OTHER INFORMATION: synthetic

<400> SEQUENCE: 99
ggaggcacct tcagcaccta tgag                                             24

<210> SEQ ID NO 100
<211> LENGTH: 8
<212> TYPE: PRT
<213> ORGANISM: Artificial Sequence
<220> FEATURE:
<223> OTHER INFORMATION: synthetic

<400> SEQUENCE: 100

Gly Gly Thr Phe Ser Thr Tyr Glu
1               5

<210> SEQ ID NO 101
<211> LENGTH: 24
<212> TYPE: DNA
<213> ORGANISM: Artificial Sequence
<220> FEATURE:
<223> OTHER INFORMATION: synthetic

<400> SEQUENCE: 101
atcatccctg tctttggtac aaca                                          24

<210> SEQ ID NO 102
<211> LENGTH: 8
<212> TYPE: PRT
<213> ORGANISM: Artificial Sequence
<220> FEATURE:
<223> OTHER INFORMATION: synthetic

<400> SEQUENCE: 102

Ile Ile Pro Val Phe Gly Thr Thr
1               5

<210> SEQ ID NO 103
<211> LENGTH: 27
<212> TYPE: DNA
<213> ORGANISM: Artificial Sequence
<220> FEATURE:
<223> OTHER INFORMATION: synthetic

<400> SEQUENCE: 103
gcgagaggtg gagcgggcgg ggacaac                                       27

<210> SEQ ID NO 104
<211> LENGTH: 9
<212> TYPE: PRT
<213> ORGANISM: Artificial Sequence
<220> FEATURE:
<223> OTHER INFORMATION: synthetic

<400> SEQUENCE: 104

Ala Arg Gly Gly Ala Gly Gly Asp Asn
1               5

<210> SEQ ID NO 105
<211> LENGTH: 321
<212> TYPE: DNA
<213> ORGANISM: Artificial Sequence
<220> FEATURE:
<223> OTHER INFORMATION: synthetic

<400> SEQUENCE: 105
gacatccaga tgacccagtc tccttccacc ctgtctgcat ctgtaggaga cagagtcacc     60
atcacttgcc gggccagtca gagtgttagt aactggttgg cctggtatca gcagaaacca    120
gggaaagccc ctaagctcct gatctataag gcgtctagtt tagaaagtgg ggtcccatca    180
aggttcagcg gcagtggatc tgggacagaa ttcactctca ccatcagcag cctgcagcct    240
gatgattttg caacttatta ctgtcaacag tataatagtt attcgtacac ttttggccag    300
gggaccaaac tggagatcaa a                                              321

<210> SEQ ID NO 106
<211> LENGTH: 107
<212> TYPE: PRT
<213> ORGANISM: Artificial Sequence
<220> FEATURE:
<223> OTHER INFORMATION: synthetic

<400> SEQUENCE: 106

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Val Ser Asn Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Ser Tyr
                85                  90                  95

Thr Phe Gly Gln Gly Thr Lys Leu Glu Ile Lys
            100                 105
```

<210> SEQ ID NO 107
<211> LENGTH: 18
<212> TYPE: DNA
<213> ORGANISM: Artificial Sequence
<220> FEATURE:
<223> OTHER INFORMATION: synthetic

<400> SEQUENCE: 107
cagagtgtta gtaactgg                                                 18

<210> SEQ ID NO 108
<211> LENGTH: 6
<212> TYPE: PRT
<213> ORGANISM: Artificial Sequence
<220> FEATURE:
<223> OTHER INFORMATION: synthetic

<400> SEQUENCE: 108

```
Gln Ser Val Ser Asn Trp
1               5
```

<210> SEQ ID NO 109
<211> LENGTH: 9
<212> TYPE: DNA
<213> ORGANISM: Artificial Sequence
<220> FEATURE:
<223> OTHER INFORMATION: synthetic

<400> SEQUENCE: 109 aaggcgtct                                                            9

<210> SEQ ID NO 110
<211> LENGTH: 3
<212> TYPE: PRT
<213> ORGANISM: Artificial Sequence
<220> FEATURE:
<223> OTHER INFORMATION: synthetic

<400> SEQUENCE: 110

```
Lys Ala Ser
1
```

<210> SEQ ID NO 111
<211> LENGTH: 27
<212> TYPE: DNA
<213> ORGANISM: Artificial Sequence
<220> FEATURE:
<223> OTHER INFORMATION: synthetic

<400> SEQUENCE: 111
caacagtata atagttattc gtacact    27

<210> SEQ ID NO 112
<211> LENGTH: 9
<212> TYPE: PRT
<213> ORGANISM: Artificial Sequence
<220> FEATURE:
<223> OTHER INFORMATION: synthetic

<400> SEQUENCE: 112

Gln Gln Tyr Asn Ser Tyr Ser Tyr Thr
1               5

<210> SEQ ID NO 113
<211> LENGTH: 366
<212> TYPE: DNA
<213> ORGANISM: Artificial Sequence
<220> FEATURE:
<223> OTHER INFORMATION: synthetic

<400> SEQUENCE: 113
caggttcaac tggtgcagtc tggagctgat atgaagaagc ctggggcctc agtgaaggtc    60
tcctgcaagg cttctggtta cacctttacc acctatggta tcaactgggt gcgacaggcc   120
cctggacaag gcttgagtg gatgggatgg atcagcgctt acagtggtat cacaaactat   180
gcacagagct tccagggcag agtcaccatg accacagaca catccacgag cacggcctac   240
atggagctga ggagcctgag atctgacgac acggccgtgt attactgtgc gagagggga    300
tataactggg ctacggggga ctactttgat tactggggcc agggaaccct ggtcaccgtc   360
tcctca                                                              366

<210> SEQ ID NO 114
<211> LENGTH: 122
<212> TYPE: PRT
<213> ORGANISM: Artificial Sequence
<220> FEATURE:
<223> OTHER INFORMATION: synthetic

<400> SEQUENCE: 114

Gln Val Gln Leu Val Gln Ser Gly Ala Asp Met Lys Lys Pro Gly Ala
1               5                   10                  15

Ser Val Lys Val Ser Cys Lys Ala Ser Gly Tyr Thr Phe Thr Thr Tyr
            20                  25                  30

Gly Ile Asn Trp Val Arg Gln Ala Pro Gly Gln Gly Leu Glu Trp Met
        35                  40                  45

Gly Trp Ile Ser Ala Tyr Ser Gly Ile Thr Asn Tyr Ala Gln Ser Phe
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Gly Tyr Asn Trp Ala Thr Gly Asp Tyr Phe Asp Tyr Trp

Gly Gln Gly Thr Leu Val Thr Val Ser Ser
    100             105             110
        115             120

<210> SEQ ID NO 115
<211> LENGTH: 24
<212> TYPE: DNA
<213> ORGANISM: Artificial Sequence
<220> FEATURE:
<223> OTHER INFORMATION: synthetic

<400> SEQUENCE: 115
ggttacacct ttaccaccta tggt                                          24

<210> SEQ ID NO 116
<211> LENGTH: 8
<212> TYPE: PRT
<213> ORGANISM: Artificial Sequence
<220> FEATURE:
<223> OTHER INFORMATION: synthetic

<400> SEQUENCE: 116

Gly Tyr Thr Phe Thr Thr Tyr Gly
1               5

<210> SEQ ID NO 117
<211> LENGTH: 24
<212> TYPE: DNA
<213> ORGANISM: Artificial Sequence
<220> FEATURE:
<223> OTHER INFORMATION: synthetic

<400> SEQUENCE: 117
atcagcgctt acagtggtat caca                                          24

<210> SEQ ID NO 118
<211> LENGTH: 8
<212> TYPE: PRT
<213> ORGANISM: Artificial Sequence
<220> FEATURE:
<223> OTHER INFORMATION: synthetic

<400> SEQUENCE: 118

Ile Ser Ala Tyr Ser Gly Ile Thr
1               5

<210> SEQ ID NO 119
<211> LENGTH: 45
<212> TYPE: DNA
<213> ORGANISM: Artificial Sequence
<220> FEATURE:
<223> OTHER INFORMATION: synthetic

<400> SEQUENCE: 119
gcgagagggg gatataactg ggctacgggg gactactttg attac                   45

<210> SEQ ID NO 120
<211> LENGTH: 15
<212> TYPE: PRT
<213> ORGANISM: Artificial Sequence
<220> FEATURE:
<223> OTHER INFORMATION: synthetic

<400> SEQUENCE: 120

Ala Arg Gly Gly Tyr Asn Trp Ala Thr Gly Asp Tyr Phe Asp Tyr
1               5                   10                  15

<210> SEQ ID NO 121
<211> LENGTH: 324
<212> TYPE: DNA
<213> ORGANISM: Artificial Sequence
<220> FEATURE:
<223> OTHER INFORMATION: synthetic

<400> SEQUENCE: 121

```
gacatccaga tgacccagtc tccttccacc ctgtctgcat ctataggaga cagagtcacc      60
atcacttgcc gggccagtca gagtattagt agctggttgg cctggtatca gcagaaaccg     120
gggaaagccc ctaagttcct gatctataag gcgtctagtt tagcaagtgg ggtcccatca     180
aggttcagcg gcagtggatc tgggacagaa ttcactctca ccatcagcag cctgcagcct     240
gatgattttg caacttatta ctgccaacag tatgatagtt attctccgta tactttggc     300
caggggacca aggtggagat caaa                                            324
```

<210> SEQ ID NO 122
<211> LENGTH: 108
<212> TYPE: PRT
<213> ORGANISM: Artificial Sequence
<220> FEATURE:
<223> OTHER INFORMATION: synthetic

<400> SEQUENCE: 122

```
Asp Ile Gln Met Thr Gln Ser Pro Ser Thr Leu Ser Ala Ser Ile Gly
1               5                   10                  15
Asp Arg Val Thr Ile Thr Cys Arg Ala Ser Gln Ser Ile Ser Ser Trp
            20                  25                  30
Leu Ala Trp Tyr Gln Gln Lys Pro Gly Lys Ala Pro Lys Phe Leu Ile
        35                  40                  45
Tyr Lys Ala Ser Ser Leu Ala Ser Gly Val Pro Ser Arg Phe Ser Gly
    50                  55                  60
Ser Gly Ser Gly Thr Glu Phe Thr Leu Thr Ile Ser Ser Leu Gln Pro
65                  70                  75                  80
Asp Asp Phe Ala Thr Tyr Tyr Cys Gln Gln Tyr Asp Ser Tyr Ser Pro
                85                  90                  95
Tyr Thr Phe Gly Gln Gly Thr Lys Val Glu Ile Lys
            100                 105
```

<210> SEQ ID NO 123
<211> LENGTH: 18
<212> TYPE: DNA
<213> ORGANISM: Artificial Sequence
<220> FEATURE:
<223> OTHER INFORMATION: synthetic

<400> SEQUENCE: 123

```
cagagtatta gtagctgg                                                    18
```

<210> SEQ ID NO 124
<211> LENGTH: 6
<212> TYPE: PRT
<213> ORGANISM: Artificial Sequence
<220> FEATURE:
<223> OTHER INFORMATION: synthetic

<400> SEQUENCE: 124

```
Gln Ser Ile Ser Ser Trp
1               5
```

<210> SEQ ID NO 125
<211> LENGTH: 9
<212> TYPE: DNA
<213> ORGANISM: Artificial Sequence
<220> FEATURE:
<223> OTHER INFORMATION: synthetic

<400> SEQUENCE: 125 aaggcgtct                                                                  9

<210> SEQ ID NO 126
<211> LENGTH: 3
<212> TYPE: PRT
<213> ORGANISM: Artificial Sequence
<220> FEATURE:
<223> OTHER INFORMATION: synthetic

<400> SEQUENCE: 126

Lys Ala Ser
1

<210> SEQ ID NO 127
<211> LENGTH: 30
<212> TYPE: DNA
<213> ORGANISM: Artificial Sequence
<220> FEATURE:
<223> OTHER INFORMATION: synthetic

<400> SEQUENCE: 127
caacagtatg atagttattc tccgtatact                                          30

<210> SEQ ID NO 128
<211> LENGTH: 10
<212> TYPE: PRT
<213> ORGANISM: Artificial Sequence
<220> FEATURE:
<223> OTHER INFORMATION: synthetic

<400> SEQUENCE: 128

Gln Gln Tyr Asp Ser Tyr Ser Pro Tyr Thr
1               5                   10

<210> SEQ ID NO 129
<211> LENGTH: 363
<212> TYPE: DNA
<213> ORGANISM: Artificial Sequence
<220> FEATURE:
<223> OTHER INFORMATION: synthetic

<400> SEQUENCE: 129
caggtgcagc tccaggagtc gggcccagga ctggtgaagc cttcggagac cctgtccctc          60
acctgcactg tctctggtgg ctccatcagt agttactact ggagctggat acgacagccc         120
ccagggaagg gactggactg gattggccat atctattaca gtgggaccac ctactacaac         180
ccctccctca gagtcgagt cagcatatca ttagacacgt ccaagaatca gttctccctg          240
aagctgagct ctgtgaccgc cgcagacacg gccgtctatt actgtgcgag acacttacgt         300
ggatacagct ctgggaggga gtttgactac tggggccagg gaaccctggt caccgtctcc         360
tca                                                                      363

<210> SEQ ID NO 130
<211> LENGTH: 121
<212> TYPE: PRT
<213> ORGANISM: Artificial Sequence
<220> FEATURE:
<223> OTHER INFORMATION: synthetic

<400> SEQUENCE: 130

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Asp Trp Ile
        35                  40                  45

Gly His Ile Tyr Tyr Ser Gly Thr Thr Tyr Tyr Asn Pro Ser Leu Lys
    50                  55                  60

Ser Arg Val Ser Ile Ser Leu Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg His Leu Arg Gly Tyr Ser Ser Gly Arg Glu Phe Asp Tyr Trp Gly
            100                 105                 110

Gln Gly Thr Leu Val Thr Val Ser Ser
        115                 120

<210> SEQ ID NO 131
<211> LENGTH: 24
<212> TYPE: DNA
<213> ORGANISM: Artificial Sequence
<220> FEATURE:
<223> OTHER INFORMATION: synthetic

<400> SEQUENCE: 131
ggtggctcca tcagtagtta ctac                                          24

<210> SEQ ID NO 132
<211> LENGTH: 8
<212> TYPE: PRT
<213> ORGANISM: Artificial Sequence
<220> FEATURE:
<223> OTHER INFORMATION: synthetic

<400> SEQUENCE: 132

Gly Gly Ser Ile Ser Ser Tyr Tyr
1               5

<210> SEQ ID NO 133
<211> LENGTH: 21
<212> TYPE: DNA
<213> ORGANISM: Artificial Sequence
<220> FEATURE:
<223> OTHER INFORMATION: synthetic

<400> SEQUENCE: 133
atctattaca gtgggaccac c                                             21

<210> SEQ ID NO 134
<211> LENGTH: 7
<212> TYPE: PRT
<213> ORGANISM: Artificial Sequence
<220> FEATURE:
<223> OTHER INFORMATION: synthetic

<400> SEQUENCE: 134

Ile Tyr Tyr Ser Gly Thr Thr
1               5

<210> SEQ ID NO 135
<211> LENGTH: 45
<212> TYPE: DNA
<213> ORGANISM: Artificial Sequence
<220> FEATURE:
<223> OTHER INFORMATION: synthetic

<400> SEQUENCE: 135
gcgagacact tacgtggata cagctctggg agggagtttg actac                45

<210> SEQ ID NO 136
<211> LENGTH: 15
<212> TYPE: PRT
<213> ORGANISM: Artificial Sequence
<220> FEATURE:
<223> OTHER INFORMATION: synthetic

<400> SEQUENCE: 136

Ala Arg His Leu Arg Gly Tyr Ser Ser Gly Arg Glu Phe Asp Tyr
1               5                   10                  15

<210> SEQ ID NO 137
<211> LENGTH: 321
<212> TYPE: DNA
<213> ORGANISM: Artificial Sequence
<220> FEATURE:
<223> OTHER INFORMATION: synthetic

<400> SEQUENCE: 137
gacatccaga tgacccagtc tccatcctcc ctgtctgctt ctgtaggagg cagagtctcc    60
cttacttgcc gggcaagtca gagcattttt agctatttaa attggtatca acagaaacca   120
gggaaagccc ctaaactcct gatctatgct gcatccaatt tgcaaagtgg ggtcccatca   180
aggttcagtg gcagtggatc tgggacagat ttcactctca ccatcagcag tctgcaacct   240
gaagattttg caacttattc atgtcaacag agttacaata tcccgtacac ttttggccag   300
gggaccaagc tggagatcaa a                                            321

<210> SEQ ID NO 138
<211> LENGTH: 107
<212> TYPE: PRT
<213> ORGANISM: Artificial Sequence
<220> FEATURE:
<223> OTHER INFORMATION: synthetic

<400> SEQUENCE: 138

Asp Ile Gln Met Thr Gln Ser Pro Ser Ser Leu Ser Ala Ser Val Gly
1               5                   10                  15

Gly Arg Val Ser Leu Thr Cys Arg Ala Ser Gln Ser Ile Phe Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Ser Cys Gln Gln Ser Tyr Asn Ile Pro Tyr
                85                  90                  95

Thr Phe Gly Gln Gly Thr Lys Leu Glu Ile Lys
            100                 105

<210> SEQ ID NO 139
<211> LENGTH: 18
<212> TYPE: DNA
<213> ORGANISM: Artificial Sequence
<220> FEATURE:
<223> OTHER INFORMATION: synthetic

<400> SEQUENCE: 139
cagagcattt tcagctat                                                 18

<210> SEQ ID NO 140
<211> LENGTH: 6
<212> TYPE: PRT
<213> ORGANISM: Artificial Sequence
<220> FEATURE:
<223> OTHER INFORMATION: synthetic

<400> SEQUENCE: 140

Gln Ser Ile Phe Ser Tyr
1               5

<210> SEQ ID NO 141
<211> LENGTH: 9
<212> TYPE: DNA
<213> ORGANISM: Artificial Sequence
<220> FEATURE:
<223> OTHER INFORMATION: synthetic

<400> SEQUENCE: 141 gctgcatcc                                                            9

<210> SEQ ID NO 142
<211> LENGTH: 3
<212> TYPE: PRT
<213> ORGANISM: Artificial Sequence
<220> FEATURE:
<223> OTHER INFORMATION: synthetic

<400> SEQUENCE: 142

Ala Ala Ser
1

<210> SEQ ID NO 143
<211> LENGTH: 27
<212> TYPE: DNA
<213> ORGANISM: Artificial Sequence
<220> FEATURE:
<223> OTHER INFORMATION: synthetic

<400> SEQUENCE: 143
caacagagtt acaatatccc gtacact                                        27

<210> SEQ ID NO 144
<211> LENGTH: 9
<212> TYPE: PRT
<213> ORGANISM: Artificial Sequence
<220> FEATURE:
<223> OTHER INFORMATION: synthetic

<400> SEQUENCE: 144

Gln Gln Ser Tyr Asn Ile Pro Tyr Thr
1               5

<210> SEQ ID NO 145
<211> LENGTH: 345
<212> TYPE: DNA
<213> ORGANISM: Artificial Sequence
<220> FEATURE:
<223> OTHER INFORMATION: synthetic

<400> SEQUENCE: 145

```
caggtccagt tggtgcagtc tggggctgag gtgaagaggc ctgggtcctc ggtgaaggtc      60
tcctgcaagg cttctggaga caccttcagc acctatgcta tcagttgggt gcgacaggcc     120
cctggacaag gacttgagtg gatgggaggg atcatccctg tctttggtac aacaaactac    180
gcacagaagt tccaggacag agtcacgatc accacggacg aatccacgcg cacagcctac    240
atggagctga gcagcctgag atctgaggac acggccgtgt attactgtgc gggtatagca    300
ggtccggact actggggcca gggaaccctg gtcaccgtct cctca                    345
```

<210> SEQ ID NO 146
<211> LENGTH: 115
<212> TYPE: PRT
<213> ORGANISM: Artificial Sequence
<220> FEATURE:
<223> OTHER INFORMATION: synthetic

<400> SEQUENCE: 146

```
Gln Val Gln Leu Val Gln Ser Gly Ala Glu Val Lys Arg Pro Gly Ser
1               5                   10                  15
Ser Val Lys Val Ser Cys Lys Ala Ser Gly Asp Thr Phe Ser Thr Tyr
            20                  25                  30
Ala Ile Ser Trp Val Arg Gln Ala Pro Gly Gln Gly Leu Glu Trp Met
        35                  40                  45
Gly Gly Ile Ile Pro Val Phe Gly Thr Thr Asn Tyr Ala Gln Lys Phe
    50                  55                  60
Gln Asp Arg Val Thr Ile Thr Thr Asp Glu Ser Thr Arg Thr Ala Tyr
65                  70                  75                  80
Met Glu Leu Ser Ser Leu Arg Ser Glu Asp Thr Ala Val Tyr Tyr Cys
                85                  90                  95
Ala Gly Ile Ala Gly Pro Asp Tyr Trp Gly Gln Gly Thr Leu Val Thr
            100                 105                 110
Val Ser Ser
        115
```

<210> SEQ ID NO 147
<211> LENGTH: 24
<212> TYPE: DNA
<213> ORGANISM: Artificial Sequence
<220> FEATURE:
<223> OTHER INFORMATION: synthetic

<400> SEQUENCE: 147

```
ggagacacct tcagcaccta tgct                                            24
```

<210> SEQ ID NO 148
<211> LENGTH: 8
<212> TYPE: PRT
<213> ORGANISM: Artificial Sequence
<220> FEATURE:
<223> OTHER INFORMATION: synthetic

<400> SEQUENCE: 148

```
Gly Asp Thr Phe Ser Thr Tyr Ala
1               5
```

<210> SEQ ID NO 149
<211> LENGTH: 24

<210> SEQ ID NO 149
<211> LENGTH: 24
<212> TYPE: DNA
<213> ORGANISM: Artificial Sequence
<220> FEATURE:
<223> OTHER INFORMATION: synthetic

<400> SEQUENCE: 149
atcatccctg tctttggtac aaca                                         24

<210> SEQ ID NO 150
<211> LENGTH: 8
<212> TYPE: PRT
<213> ORGANISM: Artificial Sequence
<220> FEATURE:
<223> OTHER INFORMATION: synthetic

<400> SEQUENCE: 150

Ile Ile Pro Val Phe Gly Thr Thr
1               5

<210> SEQ ID NO 151
<211> LENGTH: 24
<212> TYPE: DNA
<213> ORGANISM: Artificial Sequence
<220> FEATURE:
<223> OTHER INFORMATION: synthetic

<400> SEQUENCE: 151
gcgggtatag caggtccgga ctac                                         24

<210> SEQ ID NO 152
<211> LENGTH: 8
<212> TYPE: PRT
<213> ORGANISM: Artificial Sequence
<220> FEATURE:
<223> OTHER INFORMATION: synthetic

<400> SEQUENCE: 152

Ala Gly Ile Ala Gly Pro Asp Tyr
1               5

<210> SEQ ID NO 153
<211> LENGTH: 321
<212> TYPE: DNA
<213> ORGANISM: Artificial Sequence
<220> FEATURE:
<223> OTHER INFORMATION: synthetic

<400> SEQUENCE: 153
gacatccaga tgacccagtc tccatcctca ctgtctgcat ctgttggaga cagagtcacc    60
atcacttgtc gggcgagtca gggcattagg aattatttag cctggtttca gcagaaacca   120
gggaaagccc ctaagtccct gatctatctt gcaaccagtt tgcaaagtgg ggtcccatca   180
aagttcagcg gcagtggatc tgggacagat ttcactctca ccatcagcag cctgcagcct   240
gaagattttg caacttatta ctgccaacag tattatagtt acccgtggac gttcggccaa   300
gggaccaagg tggaaatcaa a                                            321

<210> SEQ ID NO 154
<211> LENGTH: 107
<212> TYPE: PRT
<213> ORGANISM: Artificial Sequence
<220> FEATURE:
<223> OTHER INFORMATION: synthetic

<400> SEQUENCE: 154

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Tyr
            20                  25                  30

Leu Ala Trp Phe Gln Gln Lys Pro Gly Lys Ala Pro Lys Ser Leu Ile
            35                  40                  45

Tyr Leu Ala Thr Ser Leu Gln Ser Gly Val Pro Ser Lys Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ser Tyr Pro Trp
                85                  90                  95

Thr Phe Gly Gln Gly Thr Lys Val Glu Ile Lys
            100                 105
```

<210> SEQ ID NO 155
<211> LENGTH: 18
<212> TYPE: DNA
<213> ORGANISM: Artificial Sequence
<220> FEATURE:
<223> OTHER INFORMATION: synthetic

<400> SEQUENCE: 155
cagggcatta ggaattat                                                 18

<210> SEQ ID NO 156
<211> LENGTH: 6
<212> TYPE: PRT
<213> ORGANISM: Artificial Sequence
<220> FEATURE:
<223> OTHER INFORMATION: synthetic

<400> SEQUENCE: 156

```
Gln Gly Ile Arg Asn Tyr
1               5
```

<210> SEQ ID NO 157
<211> LENGTH: 9
<212> TYPE: DNA
<213> ORGANISM: Artificial Sequence
<220> FEATURE:
<223> OTHER INFORMATION: synthetic

<400> SEQUENCE: 157 cttgcaacc                                                            9

<210> SEQ ID NO 158
<211> LENGTH: 3
<212> TYPE: PRT
<213> ORGANISM: Artificial Sequence
<220> FEATURE:
<223> OTHER INFORMATION: synthetic

<400> SEQUENCE: 158

```
Leu Ala Thr
1
```

<210> SEQ ID NO 159
<211> LENGTH: 27
<212> TYPE: DNA
<213> ORGANISM: Artificial Sequence
<220> FEATURE:
<223> OTHER INFORMATION: synthetic

<400> SEQUENCE: 159
caacagtatt atagttaccc gtggacg    27

<210> SEQ ID NO 160
<211> LENGTH: 9
<212> TYPE: PRT
<213> ORGANISM: Artificial Sequence
<220> FEATURE:
<223> OTHER INFORMATION: synthetic

<400> SEQUENCE: 160

Gln Gln Tyr Tyr Ser Tyr Pro Trp Thr
1               5

<210> SEQ ID NO 161
<211> LENGTH: 375
<212> TYPE: DNA
<213> ORGANISM: Artificial Sequence
<220> FEATURE:
<223> OTHER INFORMATION: synthetic

<400> SEQUENCE: 161
caggtacaac tggtggagtc tgggggaggc gtggtccagc ctgggaggtc cctgagactc    60
tcctgtgcag cgtctggatt caccttcagt agctatggct tgcactgggt ccgccaggct   120
ccaggcaagg ggctggagtg ggtggcagtt atttggcatg atggaagtca taaatactat   180
gcagactccg tgaagggccg attcaccatc tccagagaca attccaagaa cacggtgtat   240
ctgcaaatga acagcctgag agccgaggac acggctgtgt attactgtgc gagagatgga   300
ataccagtgg ctgaggacta ctacttgtac ggtatggacg tctggggcca agggaccacg   360
gtcaccgtct cctca    375

<210> SEQ ID NO 162
<211> LENGTH: 125
<212> TYPE: PRT
<213> ORGANISM: Artificial Sequence
<220> FEATURE:
<223> OTHER INFORMATION: synthetic

<400> SEQUENCE: 162

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Leu His Trp Val Arg Gln Ala Pro Gly Lys Gly Leu Glu Trp Val
        35                  40                  45

Ala Val Ile Trp His Asp Gly Ser His Lys Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Ala Glu Asp Thr Ala Val Tyr Tyr Cys
                85                  90                  95

Ala Arg Asp Gly Ile Pro Val Ala Glu Asp Tyr Tyr Leu Tyr Gly Met
            100                 105                 110

Asp Val Trp Gly Gln Gly Thr Thr Val Thr Val Ser Ser
        115                 120                 125

<210> SEQ ID NO 163
<211> LENGTH: 24
<212> TYPE: DNA

```
<213> ORGANISM: Artificial Sequence
<220> FEATURE:
<223> OTHER INFORMATION: synthetic

<400> SEQUENCE: 163
ggattcacct tcagtagcta tggc                                         24

<210> SEQ ID NO 164
<211> LENGTH: 8
<212> TYPE: PRT
<213> ORGANISM: Artificial Sequence
<220> FEATURE:
<223> OTHER INFORMATION: synthetic

<400> SEQUENCE: 164

Gly Phe Thr Phe Ser Ser Tyr Gly
1               5

<210> SEQ ID NO 165
<211> LENGTH: 24
<212> TYPE: DNA
<213> ORGANISM: Artificial Sequence
<220> FEATURE:
<223> OTHER INFORMATION: synthetic

<400> SEQUENCE: 165
atttggcatg atggaagtca taaa                                         24

<210> SEQ ID NO 166
<211> LENGTH: 8
<212> TYPE: PRT
<213> ORGANISM: Artificial Sequence
<220> FEATURE:
<223> OTHER INFORMATION: synthetic

<400> SEQUENCE: 166

Ile Trp His Asp Gly Ser His Lys
1               5

<210> SEQ ID NO 167
<211> LENGTH: 54
<212> TYPE: DNA
<213> ORGANISM: Artificial Sequence
<220> FEATURE:
<223> OTHER INFORMATION: synthetic

<400> SEQUENCE: 167
gcgagagatg gaataccagt ggctgaggac tactacttgt acggtatgga cgtc         54

<210> SEQ ID NO 168
<211> LENGTH: 18
<212> TYPE: PRT
<213> ORGANISM: Artificial Sequence
<220> FEATURE:
<223> OTHER INFORMATION: synthetic

<400> SEQUENCE: 168

Ala Arg Asp Gly Ile Pro Val Ala Glu Asp Tyr Tyr Leu Tyr Gly Met
1               5                   10                  15
Asp Val

<210> SEQ ID NO 169
<211> LENGTH: 321
<212> TYPE: DNA
<213> ORGANISM: Artificial Sequence
<220> FEATURE:
```

<223> OTHER INFORMATION: synthetic

<400> SEQUENCE: 169
gaaattgtgt tgacgcagtc tccaggcacc ctgtctttgt ctccagggga aagagccacc 60
ctctcctgca gggccagtca gagtgttgac agcagctact tagcctggta ccaccagaaa 120
cctggccagg ctcccaggct cctcatctat ggtgcatcca gcagggccac tggcatccca 180
gacaggttca gtggcagtgg gtctgggaca gacttcactc tcaccatcag cagactggag 240
cctgaagatt ttgcagtgta ttactgtcag cagtatggta gctcacggac gttcggccaa 300
gggaccaagg tggaaatcaa a 321

<210> SEQ ID NO 170
<211> LENGTH: 107
<212> TYPE: PRT
<213> ORGANISM: Artificial Sequence
<220> FEATURE:
<223> OTHER INFORMATION: synthetic

<400> SEQUENCE: 170

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Asp Ser Ser
            20                  25                  30

Tyr Leu Ala Trp Tyr His Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Arg
                85                  90                  95

Thr Phe Gly Gln Gly Thr Lys Val Glu Ile Lys
            100                 105

<210> SEQ ID NO 171
<211> LENGTH: 21
<212> TYPE: DNA
<213> ORGANISM: Artificial Sequence
<220> FEATURE:
<223> OTHER INFORMATION: synthetic

<400> SEQUENCE: 171
cagagtgttg acagcagcta c 21

<210> SEQ ID NO 172
<211> LENGTH: 7
<212> TYPE: PRT
<213> ORGANISM: Artificial Sequence
<220> FEATURE:
<223> OTHER INFORMATION: synthetic

<400> SEQUENCE: 172

Gln Ser Val Asp Ser Ser Tyr
1               5

<210> SEQ ID NO 173
<211> LENGTH: 9
<212> TYPE: DNA
<213> ORGANISM: Artificial Sequence
<220> FEATURE:
<223> OTHER INFORMATION: synthetic

<400> SEQUENCE: 173 ggtgcatcc                                                                                    9

<210> SEQ ID NO 174
<211> LENGTH: 3
<212> TYPE: PRT
<213> ORGANISM: Artificial Sequence
<220> FEATURE:
<223> OTHER INFORMATION: synthetic

<400> SEQUENCE: 174

Gly Ala Ser
1

<210> SEQ ID NO 175
<211> LENGTH: 24
<212> TYPE: DNA
<213> ORGANISM: Artificial Sequence
<220> FEATURE:
<223> OTHER INFORMATION: synthetic

<400> SEQUENCE: 175
cagcagtatg gtagctcacg gacg                                                                  24

<210> SEQ ID NO 176
<211> LENGTH: 8
<212> TYPE: PRT
<213> ORGANISM: Artificial Sequence
<220> FEATURE:
<223> OTHER INFORMATION: synthetic

<400> SEQUENCE: 176

Gln Gln Tyr Gly Ser Ser Arg Thr
1               5

<210> SEQ ID NO 177
<211> LENGTH: 360
<212> TYPE: DNA
<213> ORGANISM: Artificial Sequence
<220> FEATURE:
<223> OTHER INFORMATION: synthetic

<400> SEQUENCE: 177
cagctgcagc tgcaggagtc gggcccagga ctggtgaagc cttcggagac cctgtccctc        60
acctgcactg tctctggtgg ctccatcagc agtagtaatt actactggga ctggatccgc       120
cagaccccag agaaggggct ggagtggatt gggagtatcc attatagtgg gacctcctac       180
tacaacccgt ccctcaagag tcgagtcacc atatccgttg acacgtccaa gaaccaattc       240
tccctgaaac tgaggtctgt gaccgccgca gacgcggctg tgtattattg cgcgagacag       300
accagcgtct actggtattt cgatatctgg ggccatggca ccctggtcac tgtctccaca       360

<210> SEQ ID NO 178
<211> LENGTH: 120
<212> TYPE: PRT
<213> ORGANISM: Artificial Sequence
<220> FEATURE:
<223> OTHER INFORMATION: synthetic

<400> SEQUENCE: 178

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser

```
                    20                  25                  30
Asn Tyr Tyr Trp Asp Trp Ile Arg Gln Thr Pro Glu Lys Gly Leu Glu
            35                  40                  45

Trp Ile Gly Ser Ile His Tyr Ser Gly Thr Ser Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Arg Ser Val Thr Ala Ala Asp Ala Ala Val Tyr Tyr
                85                  90                  95

Cys Ala Arg Gln Thr Ser Val Tyr Trp Tyr Phe Asp Ile Trp Gly His
            100                 105                 110

Gly Thr Leu Val Thr Val Ser Thr
            115                 120

<210> SEQ ID NO 179
<211> LENGTH: 30
<212> TYPE: DNA
<213> ORGANISM: Artificial Sequence
<220> FEATURE:
<223> OTHER INFORMATION: synthetic

<400> SEQUENCE: 179
ggtggctcca tcagcagtag taattactac                                          30

<210> SEQ ID NO 180
<211> LENGTH: 10
<212> TYPE: PRT
<213> ORGANISM: Artificial Sequence
<220> FEATURE:
<223> OTHER INFORMATION: synthetic

<400> SEQUENCE: 180

Gly Gly Ser Ile Ser Ser Ser Asn Tyr Tyr
1               5                   10

<210> SEQ ID NO 181
<211> LENGTH: 21
<212> TYPE: DNA
<213> ORGANISM: Artificial Sequence
<220> FEATURE:
<223> OTHER INFORMATION: synthetic

<400> SEQUENCE: 181
atccattata gtgggacctc c                                                   21

<210> SEQ ID NO 182
<211> LENGTH: 7
<212> TYPE: PRT
<213> ORGANISM: Artificial Sequence
<220> FEATURE:
<223> OTHER INFORMATION: synthetic

<400> SEQUENCE: 182

Ile His Tyr Ser Gly Thr Ser
1               5

<210> SEQ ID NO 183
<211> LENGTH: 36
<212> TYPE: DNA
<213> ORGANISM: Artificial Sequence
<220> FEATURE:
<223> OTHER INFORMATION: synthetic

<400> SEQUENCE: 183
```

```
gcgagacaga ccagcgtcta ctggtatttc gatatc                                36
```

<210> SEQ ID NO 184
<211> LENGTH: 12
<212> TYPE: PRT
<213> ORGANISM: Artificial Sequence
<220> FEATURE:
<223> OTHER INFORMATION: synthetic

<400> SEQUENCE: 184

```
Ala Arg Gln Thr Ser Val Tyr Trp Tyr Phe Asp Ile
1               5                   10
```

<210> SEQ ID NO 185
<211> LENGTH: 324
<212> TYPE: DNA
<213> ORGANISM: Artificial Sequence
<220> FEATURE:
<223> OTHER INFORMATION: synthetic

<400> SEQUENCE: 185

```
gaaattgtgt tgacgcagtc tccaggcacc ctatcattgt ctccagggga aggagccacc     60
ctctcctgca gggccagtca gagtgttcgt aacaactact tagcctggta ccagcagaaa    120
cctggccagg ctcccaggct cctcatctat ggtgcttcca gcagggccat tggcatccca    180
gacaggttca gtggcagtgg gtctgggaca gacttcactc tcaccatcag cagactggag    240
cctaaagatt ttgtagttta ttactgtcag cagtatggtg ctcactgtt cactttcggc    300 cctgggacca aagtggatat caaa                                          324
```

<210> SEQ ID NO 186
<211> LENGTH: 108
<212> TYPE: PRT
<213> ORGANISM: Artificial Sequence
<220> FEATURE:
<223> OTHER INFORMATION: synthetic

<400> SEQUENCE: 186

```
Glu Ile Val Leu Thr Gln Ser Pro Gly Thr Leu Ser Leu Ser Pro Gly
1               5                   10                  15

Glu Gly Ala Thr Leu Ser Cys Arg Ala Ser Gln Ser Val Arg Asn Asn
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Ile Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Lys Asp Phe Val Val Tyr Tyr Cys Gln Gln Tyr Gly Gly Ser Leu
                85                  90                  95

Phe Thr Phe Gly Pro Gly Thr Lys Val Asp Ile Lys
            100                 105
```

<210> SEQ ID NO 187
<211> LENGTH: 21
<212> TYPE: DNA
<213> ORGANISM: Artificial Sequence
<220> FEATURE:
<223> OTHER INFORMATION: synthetic

<400> SEQUENCE: 187

```
cagagtgttc gtaacaacta c                                              21
```

<210> SEQ ID NO 188
<211> LENGTH: 7
<212> TYPE: PRT
<213> ORGANISM: Artificial Sequence
<220> FEATURE:
<223> OTHER INFORMATION: synthetic

<400> SEQUENCE: 188

Gln Ser Val Arg Asn Asn Tyr
1               5

<210> SEQ ID NO 189
<211> LENGTH: 9
<212> TYPE: DNA
<213> ORGANISM: Artificial Sequence
<220> FEATURE:
<223> OTHER INFORMATION: synthetic

<400> SEQUENCE: 189

```
ggtgcttcc                                                             9
```

<210> SEQ ID NO 190
<211> LENGTH: 3
<212> TYPE: PRT
<213> ORGANISM: Artificial Sequence
<220> FEATURE:
<223> OTHER INFORMATION: synthetic

<400> SEQUENCE: 190

Gly Ala Ser
1

<210> SEQ ID NO 191
<211> LENGTH: 27
<212> TYPE: DNA
<213> ORGANISM: Artificial Sequence
<220> FEATURE:
<223> OTHER INFORMATION: synthetic

<400> SEQUENCE: 191

```
cagcagtatg gtggctcact gttcact                                        27
```

<210> SEQ ID NO 192
<211> LENGTH: 9
<212> TYPE: PRT
<213> ORGANISM: Artificial Sequence
<220> FEATURE:
<223> OTHER INFORMATION: synthetic

<400> SEQUENCE: 192

Gln Gln Tyr Gly Gly Ser Leu Phe Thr
1               5

<210> SEQ ID NO 193
<211> LENGTH: 375
<212> TYPE: DNA
<213> ORGANISM: Artificial Sequence
<220> FEATURE:
<223> OTHER INFORMATION: synthetic

<400> SEQUENCE: 193

```
caggtgcaag tggtggagtc tgggggaggc gtggtccagc ctgggaggtc cctgagactc     60
tcctgtgcag cgtctggatt caccttcagt agctatggct tgcactgggt ccgccaggct    120
```

```
ccaggcaagg ggctggagtg ggtggcagtt atatggcatg atggaagtca taaatactat    180
gcagactccg tgaagggccg attcaccatc tccagagaca attccaagaa cacgctgtat    240
ctgcaaatga acagcctgag agccgaggac acggctgtgt attactgtgc gagagatggt    300
ataccagtgg ctgaggacta ctacttctac ggtatggacg tctggggcca agggaccacg    360
gtcaccgtct cctca                                                    375
```

```
<210> SEQ ID NO 194
<211> LENGTH: 125
<212> TYPE: PRT
<213> ORGANISM: Artificial Sequence
<220> FEATURE:
<223> OTHER INFORMATION: synthetic

<400> SEQUENCE: 194
```

Gln Val Gln Val Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Leu His Trp Val Arg Gln Ala Pro Gly Lys Gly Leu Glu Trp Val
        35                  40                  45

Ala Val Ile Trp His Asp Gly Ser His Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Ile Pro Val Ala Glu Asp Tyr Tyr Phe Tyr Gly Met
            100                 105                 110

Asp Val Trp Gly Gln Gly Thr Thr Val Thr Val Ser Ser
        115                 120                 125

```
<210> SEQ ID NO 195
<211> LENGTH: 24
<212> TYPE: DNA
<213> ORGANISM: Artificial Sequence
<220> FEATURE:
<223> OTHER INFORMATION: synthetic

<400> SEQUENCE: 195
ggattcacct tcagtagcta tggc                                           24

<210> SEQ ID NO 196
<211> LENGTH: 8
<212> TYPE: PRT
<213> ORGANISM: Artificial Sequence
<220> FEATURE:
<223> OTHER INFORMATION: synthetic

<400> SEQUENCE: 196
```

Gly Phe Thr Phe Ser Ser Tyr Gly
1               5

```
<210> SEQ ID NO 197
<211> LENGTH: 24
<212> TYPE: DNA
<213> ORGANISM: Artificial Sequence
<220> FEATURE:
<223> OTHER INFORMATION: synthetic

<400> SEQUENCE: 197
```

```
atatggcatg atggaagtca taaa                                           24
```

<210> SEQ ID NO 198
<211> LENGTH: 8
<212> TYPE: PRT
<213> ORGANISM: Artificial Sequence
<220> FEATURE:
<223> OTHER INFORMATION: synthetic

<400> SEQUENCE: 198

```
Ile Trp His Asp Gly Ser His Lys
1               5
```

<210> SEQ ID NO 199
<211> LENGTH: 54
<212> TYPE: DNA
<213> ORGANISM: Artificial Sequence
<220> FEATURE:
<223> OTHER INFORMATION: synthetic

<400> SEQUENCE: 199

```
gcgagagatg gtataccagt ggctgaggac tactacttct acggtatgga cgtc          54
```

<210> SEQ ID NO 200
<211> LENGTH: 18
<212> TYPE: PRT
<213> ORGANISM: Artificial Sequence
<220> FEATURE:
<223> OTHER INFORMATION: synthetic

<400> SEQUENCE: 200

```
Ala Arg Asp Gly Ile Pro Val Ala Glu Asp Tyr Tyr Phe Tyr Gly Met
1               5                   10                  15

Asp Val
```

<210> SEQ ID NO 201
<211> LENGTH: 315
<212> TYPE: DNA
<213> ORGANISM: Artificial Sequence
<220> FEATURE:
<223> OTHER INFORMATION: synthetic

<400> SEQUENCE: 201

```
gacatccaga tgacccagtc tccatcctcc ctgtctgcat ctgtaggaga cagagtcacc    60
atcacttgcc gggcaagtca gggcattaga aatgatttag gctggtatca gcagaaacca   120
gggaaagccc ctaagcgcct gatctatgct gcatccagtt tgcaaagtgg ggtcccatca   180
aggttcagcg gcagtggatc tgggacagaa ttcactctca caatcagcag cctgcagcct   240
gaagattttg caattttata ctgtctacag cataatagtc tcactttcgg cggagggacc   300
aaggtggaga tcaaa                                                   315
```

<210> SEQ ID NO 202
<211> LENGTH: 105
<212> TYPE: PRT
<213> ORGANISM: Artificial Sequence
<220> FEATURE:
<223> OTHER INFORMATION: synthetic

<400> SEQUENCE: 202

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30
```

Leu Gly Trp Tyr Gln Gln Lys Pro Gly Lys Ala Pro Lys Arg Leu Ile
            35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Ile Tyr Tyr Cys Leu Gln His Asn Ser Leu Thr Phe
                85                  90                  95

Gly Gly Gly Thr Lys Val Glu Ile Lys
            100                 105

<210> SEQ ID NO 203
<211> LENGTH: 18
<212> TYPE: DNA
<213> ORGANISM: Artificial Sequence
<220> FEATURE:
<223> OTHER INFORMATION: synthetic

<400> SEQUENCE: 203
cagggcatta gaaatgat                                                   18

<210> SEQ ID NO 204
<211> LENGTH: 6
<212> TYPE: PRT
<213> ORGANISM: Artificial Sequence
<220> FEATURE:
<223> OTHER INFORMATION: synthetic

<400> SEQUENCE: 204

Gln Gly Ile Arg Asn Asp
1               5

<210> SEQ ID NO 205
<211> LENGTH: 9
<212> TYPE: DNA
<213> ORGANISM: Artificial Sequence
<220> FEATURE:
<223> OTHER INFORMATION: synthetic

<400> SEQUENCE: 205 gctgcatcc                                                              9

<210> SEQ ID NO 206
<211> LENGTH: 3
<212> TYPE: PRT
<213> ORGANISM: Artificial Sequence
<220> FEATURE:
<223> OTHER INFORMATION: synthetic

<400> SEQUENCE: 206

Ala Ala Ser
1

<210> SEQ ID NO 207
<211> LENGTH: 21
<212> TYPE: DNA
<213> ORGANISM: Artificial Sequence
<220> FEATURE:
<223> OTHER INFORMATION: synthetic

<400> SEQUENCE: 207
ctacagcata atagtctcac t                                               21

<210> SEQ ID NO 208
<211> LENGTH: 7
<212> TYPE: PRT
<213> ORGANISM: Artificial Sequence
<220> FEATURE:
<223> OTHER INFORMATION: synthetic

<400> SEQUENCE: 208

Leu Gln His Asn Ser Leu Thr
1               5

<210> SEQ ID NO 209
<211> LENGTH: 351
<212> TYPE: DNA
<213> ORGANISM: Artificial Sequence
<220> FEATURE:
<223> OTHER INFORMATION: synthetic

<400> SEQUENCE: 209

```
caggtgcagc tggtggagtc tgggggaggc gtggtccagc ctggagggtc cctgagactc      60
tcctgtgcag cgtctggatt caccttcagt cgctatggca tgcactgggt ccgccaggct     120
ccaggcaagg ggctggagtg ggtggcagtt atatggtatg atggaactaa taaatactat     180
gaagactccc tgaagggccg attcaccatc tccagagaca attccaagaa cacgctgtat     240
ctgcaaatga acagcctgag agccgaggac tcggctgtgt attactgtgc gagagatcag     300
gggaaataca ttgactactg gggccaggga accctggtca ccgtctcctc a              351
```

<210> SEQ ID NO 210
<211> LENGTH: 117
<212> TYPE: PRT
<213> ORGANISM: Artificial Sequence
<220> FEATURE:
<223> OTHER INFORMATION: synthetic

<400> SEQUENCE: 210

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Arg Tyr
            20                  25                  30

Gly Met His Trp Val Arg Gln Ala Pro Gly Lys Gly Leu Glu Trp Val
        35                  40                  45

Ala Val Ile Trp Tyr Asp Gly Thr Asn Lys Tyr Tyr Glu Asp Ser Leu
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Ser Ala Val Tyr Tyr Cys
                85                  90                  95

Ala Arg Asp Gln Gly Lys Tyr Ile Asp Tyr Trp Gly Gln Gly Thr Leu
            100                 105                 110

Val Thr Val Ser Ser
        115

<210> SEQ ID NO 211
<211> LENGTH: 24
<212> TYPE: DNA
<213> ORGANISM: Artificial Sequence
<220> FEATURE:
<223> OTHER INFORMATION: synthetic

<400> SEQUENCE: 211
ggattcacct tcagtcgcta tggc                                              24

<210> SEQ ID NO 212
<211> LENGTH: 8
<212> TYPE: PRT
<213> ORGANISM: Artificial Sequence
<220> FEATURE:
<223> OTHER INFORMATION: synthetic

<400> SEQUENCE: 212

Gly Phe Thr Phe Ser Arg Tyr Gly
1               5

<210> SEQ ID NO 213
<211> LENGTH: 24
<212> TYPE: DNA
<213> ORGANISM: Artificial Sequence
<220> FEATURE:
<223> OTHER INFORMATION: synthetic

<400> SEQUENCE: 213
atatggtatg atggaactaa taaa                                          24

<210> SEQ ID NO 214
<211> LENGTH: 8
<212> TYPE: PRT
<213> ORGANISM: Artificial Sequence
<220> FEATURE:
<223> OTHER INFORMATION: synthetic

<400> SEQUENCE: 214

Ile Trp Tyr Asp Gly Thr Asn Lys
1               5

<210> SEQ ID NO 215
<211> LENGTH: 30
<212> TYPE: DNA
<213> ORGANISM: Artificial Sequence
<220> FEATURE:
<223> OTHER INFORMATION: synthetic

<400> SEQUENCE: 215
gcgagagatc agggggaaata cattgactac                                    30

<210> SEQ ID NO 216
<211> LENGTH: 10
<212> TYPE: PRT
<213> ORGANISM: Artificial Sequence
<220> FEATURE:
<223> OTHER INFORMATION: synthetic

<400> SEQUENCE: 216

Ala Arg Asp Gln Gly Lys Tyr Ile Asp Tyr
1               5                   10

<210> SEQ ID NO 217
<211> LENGTH: 321
<212> TYPE: DNA
<213> ORGANISM: Artificial Sequence
<220> FEATURE:
<223> OTHER INFORMATION: synthetic

<400> SEQUENCE: 217
gccatccaga tgacccagtc tccatcctcc ctgtctgcat ctgtaggaga cagagtcacc    60
atcacttgcc ggacaagtca ggacattaga aatgatttag ctggtatca gcagaaacca   120 gggaaagtcc ctaatctcct gatctatgct gcatccactt tacaaagtgg ggtcccatca   180

```
aggttcagcg gcagtggatc tggcacagat ttcactctca ccatcagcag cctgcagcct    240
gaagattttg caacttatta ctgtctacag gattacaatt acccattcac tttcggccct    300
gggaccaaag tggatatcaa a                                              321
```

<210> SEQ ID NO 218
<211> LENGTH: 107
<212> TYPE: PRT
<213> ORGANISM: Artificial Sequence
<220> FEATURE:
<223> OTHER INFORMATION: synthetic

<400> SEQUENCE: 218

```
Ala Ile Gln Met Thr Gln Ser Pro Ser Ser Leu Ser Ala Ser Val Gly
1               5                   10                  15

Asp Arg Val Thr Ile Thr Cys Arg Thr Ser Gln Asp Ile Arg Asn Asp
            20                  25                  30

Leu Gly Trp Tyr Gln Gln Lys Pro Gly Lys Val Pro Asn Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Asp Tyr Asn Tyr Pro Phe
                85                  90                  95

Thr Phe Gly Pro Gly Thr Lys Val Asp Ile Lys
            100                 105
```

<210> SEQ ID NO 219
<211> LENGTH: 18
<212> TYPE: DNA
<213> ORGANISM: Artificial Sequence
<220> FEATURE:
<223> OTHER INFORMATION: synthetic

<400> SEQUENCE: 219

```
caggacatta gaaatgat                                                   18
```

<210> SEQ ID NO 220
<211> LENGTH: 6
<212> TYPE: PRT
<213> ORGANISM: Artificial Sequence
<220> FEATURE:
<223> OTHER INFORMATION: synthetic

<400> SEQUENCE: 220

```
Gln Asp Ile Arg Asn Asp
1               5
```

<210> SEQ ID NO 221
<211> LENGTH: 9
<212> TYPE: DNA
<213> ORGANISM: Artificial Sequence
<220> FEATURE:
<223> OTHER INFORMATION: synthetic

<400> SEQUENCE: 221

```
gctgcatcc                                                              9
```

<210> SEQ ID NO 222
<211> LENGTH: 3
<212> TYPE: PRT

<213> ORGANISM: Artificial Sequence
<220> FEATURE:
<223> OTHER INFORMATION: synthetic

<400> SEQUENCE: 222

Ala Ala Ser
1

<210> SEQ ID NO 223
<211> LENGTH: 27
<212> TYPE: DNA
<213> ORGANISM: Artificial Sequence
<220> FEATURE:
<223> OTHER INFORMATION: synthetic

<400> SEQUENCE: 223
ctacaggatt acaattaccc attcact                                          27

<210> SEQ ID NO 224
<211> LENGTH: 9
<212> TYPE: PRT
<213> ORGANISM: Artificial Sequence
<220> FEATURE:
<223> OTHER INFORMATION: synthetic

<400> SEQUENCE: 224

Leu Gln Asp Tyr Asn Tyr Pro Phe Thr
1               5

<210> SEQ ID NO 225
<211> LENGTH: 351
<212> TYPE: DNA
<213> ORGANISM: Artificial Sequence
<220> FEATURE:
<223> OTHER INFORMATION: synthetic

<400> SEQUENCE: 225
caggtgcagc tggtggagtc tgggggaggc gtggtccagc ctggggaggtc cctgagactc      60 tcctgtgcag cgtctggatt caccttcagt cgctatggca tacactgggt ccgccaggct     120
ccaggcaagg ggctggagtg gtggcagtt atatggtatg atggaagtaa taaatactat      180
gcagactccc tgaagggccg attcaccatc tccagagaca attccaagaa cacgctgtat     240
ctgcaaatga acagcctgag agccgaggac acggctgtgt attactgtgc gagagatcaa     300
gggaactaca ttgactactg gggccaggga accctggtca ccgtctcctc a              351

<210> SEQ ID NO 226
<211> LENGTH: 117
<212> TYPE: PRT
<213> ORGANISM: Artificial Sequence
<220> FEATURE:
<223> OTHER INFORMATION: synthetic

<400> SEQUENCE: 226

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Arg Tyr
            20                  25                  30

Gly Ile His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Leu
    50                  55                  60

Lys Gly Arg Phe Thr Ile Ser Arg Asp Asn Ser Lys Asn Thr Leu Tyr

```
            65                  70                  75                  80
Leu Gln Met Asn Ser Leu Arg Ala Glu Asp Thr Ala Val Tyr Tyr Cys
                85                  90                  95

Ala Arg Asp Gln Gly Asn Tyr Ile Asp Tyr Trp Gly Gln Gly Thr Leu
            100                 105                 110

Val Thr Val Ser Ser
        115
```

<210> SEQ ID NO 227
<211> LENGTH: 24
<212> TYPE: DNA
<213> ORGANISM: Artificial Sequence
<220> FEATURE:
<223> OTHER INFORMATION: synthetic

<400> SEQUENCE: 227
ggattcacct tcagtcgcta tggc                                          24

<210> SEQ ID NO 228
<211> LENGTH: 8
<212> TYPE: PRT
<213> ORGANISM: Artificial Sequence
<220> FEATURE:
<223> OTHER INFORMATION: synthetic

<400> SEQUENCE: 228

```
Gly Phe Thr Phe Ser Arg Tyr Gly
1               5
```

<210> SEQ ID NO 229
<211> LENGTH: 24
<212> TYPE: DNA
<213> ORGANISM: Artificial Sequence
<220> FEATURE:
<223> OTHER INFORMATION: synthetic

<400> SEQUENCE: 229
atatggtatg atggaagtaa taaa                                          24

<210> SEQ ID NO 230
<211> LENGTH: 8
<212> TYPE: PRT
<213> ORGANISM: Artificial Sequence
<220> FEATURE:
<223> OTHER INFORMATION: synthetic

<400> SEQUENCE: 230

```
Ile Trp Tyr Asp Gly Ser Asn Lys
1               5
```

<210> SEQ ID NO 231
<211> LENGTH: 30
<212> TYPE: DNA
<213> ORGANISM: Artificial Sequence
<220> FEATURE:
<223> OTHER INFORMATION: synthetic

<400> SEQUENCE: 231
gcgagagatc aagggaacta cattgactac                                    30

<210> SEQ ID NO 232
<211> LENGTH: 10
<212> TYPE: PRT
<213> ORGANISM: Artificial Sequence
<220> FEATURE:

```
<223> OTHER INFORMATION: synthetic

<400> SEQUENCE: 232

Ala Arg Asp Gln Gly Asn Tyr Ile Asp Tyr
1               5                   10

<210> SEQ ID NO 233
<211> LENGTH: 321
<212> TYPE: DNA
<213> ORGANISM: Artificial Sequence
<220> FEATURE:
<223> OTHER INFORMATION: synthetic

<400> SEQUENCE: 233
gccatccaga tgacccagtc tccatcctcc ctgtctgcat ctgtaggaga cagagtcacc      60
atcacttgcc ggacaagtca gggcattaga aatgatttag ctggtatca gcagaaacca     120 gggaaagtcc ctaagctcct gatctatgct gcatccagtt tacaaagtgg ggtcccatca    180
aggttcagcg gcagtggatc tggcacagat ttcactctca ccatcagcag cctgcagcct    240
gaagattttg caacttatta ctgtctacaa gattacaatt acccattcac tttcggccct    300
gggaccaaag tggatatcaa a                                               321

<210> SEQ ID NO 234
<211> LENGTH: 107
<212> TYPE: PRT
<213> ORGANISM: Artificial Sequence
<220> FEATURE:
<223> OTHER INFORMATION: synthetic

<400> SEQUENCE: 234

Ala Ile Gln Met Thr Gln Ser Pro Ser Leu Ser Ala Ser Val Gly
1               5                   10                  15

Asp Arg Val Thr Ile Thr Cys Arg Thr Ser Gln Gly Ile Arg Asn Asp
            20                  25                  30

Leu Gly Trp Tyr Gln Gln Lys Pro Gly Lys Val Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Asp Tyr Asn Tyr Pro Phe
                85                  90                  95

Thr Phe Gly Pro Gly Thr Lys Val Asp Ile Lys
            100                 105

<210> SEQ ID NO 235
<211> LENGTH: 18
<212> TYPE: DNA
<213> ORGANISM: Artificial Sequence
<220> FEATURE:
<223> OTHER INFORMATION: synthetic

<400> SEQUENCE: 235
cagggcatta gaaatgat                                                    18

<210> SEQ ID NO 236
<211> LENGTH: 6
<212> TYPE: PRT
<213> ORGANISM: Artificial Sequence
<220> FEATURE:
<223> OTHER INFORMATION: synthetic
```

-continued

<400> SEQUENCE: 236

Gln Gly Ile Arg Asn Asp
1               5

<210> SEQ ID NO 237
<211> LENGTH: 9
<212> TYPE: DNA
<213> ORGANISM: Artificial Sequence
<220> FEATURE:
<223> OTHER INFORMATION: synthetic

<400> SEQUENCE: 237 gctgcatcc                                                                  9

<210> SEQ ID NO 238
<211> LENGTH: 3
<212> TYPE: PRT
<213> ORGANISM: Artificial Sequence
<220> FEATURE:
<223> OTHER INFORMATION: synthetic

<400> SEQUENCE: 238

Ala Ala Ser
1

<210> SEQ ID NO 239
<211> LENGTH: 27
<212> TYPE: DNA
<213> ORGANISM: Artificial Sequence
<220> FEATURE:
<223> OTHER INFORMATION: synthetic

<400> SEQUENCE: 239
ctacaagatt acaattaccc attcact                                             27

<210> SEQ ID NO 240
<211> LENGTH: 9
<212> TYPE: PRT
<213> ORGANISM: Artificial Sequence
<220> FEATURE:
<223> OTHER INFORMATION: synthetic

<400> SEQUENCE: 240

Leu Gln Asp Tyr Asn Tyr Pro Phe Thr
1               5

<210> SEQ ID NO 241
<211> LENGTH: 372
<212> TYPE: DNA
<213> ORGANISM: Artificial Sequence
<220> FEATURE:
<223> OTHER INFORMATION: synthetic

<400> SEQUENCE: 241
caggtgcagc tggtggagtc tgggggaggc gtggtccagc ctggggaggtc cctgagactc        60 tcctgtgcag cctctggatt caccttcaat agctatgcca tgcactgggt ccgccaggct       120
ccaggcatgg ggctggagtg ggtggcagtt atatcgtctg atggaagtaa taaatattat       180
gcagactccg tgaggggccg attcaccgtc tccagagaca attccaagaa cacgctatat       240
ctacaaatga acagcttgag atctgaggac acggctgtat attactgtgc gaaagacgga       300
cgtggataca gctccttctc ccacttcggt atggacgtct ggggccaagg gaccacggtc       360
accgtctcct ca                                                           372

<210> SEQ ID NO 242
<211> LENGTH: 124
<212> TYPE: PRT
<213> ORGANISM: Artificial Sequence
<220> FEATURE:
<223> OTHER INFORMATION: synthetic

<400> SEQUENCE: 242

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Asn Ser Tyr
                20                  25                  30

Ala Met His Trp Val Arg Gln Ala Pro Gly Met Gly Leu Glu Trp Val
            35                  40                  45

Ala Val Ile Ser Ser Asp Gly Ser Asn Lys Tyr Tyr Ala Asp Ser Val
        50                  55                  60

Arg Gly Arg Phe Thr Val Ser Arg Asp Asn Ser Lys Asn Thr Leu Tyr
65                  70                  75                  80

Leu Gln Met Asn Ser Leu Arg Ser Glu Asp Thr Ala Val Tyr Tyr Cys
                85                  90                  95

Ala Lys Asp Gly Arg Gly Tyr Ser Ser Phe Ser His Phe Gly Met Asp
            100                 105                 110

Val Trp Gly Gln Gly Thr Thr Val Thr Val Ser Ser
        115                 120

<210> SEQ ID NO 243
<211> LENGTH: 24
<212> TYPE: DNA
<213> ORGANISM: Artificial Sequence
<220> FEATURE:
<223> OTHER INFORMATION: synthetic

<400> SEQUENCE: 243
ggattcacct tcaatagcta tgcc                                          24

<210> SEQ ID NO 244
<211> LENGTH: 8
<212> TYPE: PRT
<213> ORGANISM: Artificial Sequence
<220> FEATURE:
<223> OTHER INFORMATION: synthetic

<400> SEQUENCE: 244

Gly Phe Thr Phe Asn Ser Tyr Ala
1               5

<210> SEQ ID NO 245
<211> LENGTH: 24
<212> TYPE: DNA
<213> ORGANISM: Artificial Sequence
<220> FEATURE:
<223> OTHER INFORMATION: synthetic

<400> SEQUENCE: 245
atatcgtctg atggaagtaa taaa                                          24

<210> SEQ ID NO 246
<211> LENGTH: 8
<212> TYPE: PRT
<213> ORGANISM: Artificial Sequence
<220> FEATURE:
<223> OTHER INFORMATION: synthetic

<400> SEQUENCE: 246

Ile Ser Ser Asp Gly Ser Asn Lys
1               5

<210> SEQ ID NO 247
<211> LENGTH: 51
<212> TYPE: DNA
<213> ORGANISM: Artificial Sequence
<220> FEATURE:
<223> OTHER INFORMATION: synthetic

<400> SEQUENCE: 247
gcgaaagacg gacgtggata cagctccttc tcccacttcg gtatggacgt c          51

<210> SEQ ID NO 248
<211> LENGTH: 17
<212> TYPE: PRT
<213> ORGANISM: Artificial Sequence
<220> FEATURE:
<223> OTHER INFORMATION: synthetic

<400> SEQUENCE: 248

Ala Lys Asp Gly Arg Gly Tyr Ser Ser Phe Ser His Phe Gly Met Asp
1               5                   10                  15

Val

<210> SEQ ID NO 249
<211> LENGTH: 315
<212> TYPE: DNA
<213> ORGANISM: Artificial Sequence
<220> FEATURE:
<223> OTHER INFORMATION: synthetic

<400> SEQUENCE: 249
gacatccaga tgacccagtc tccttccacc ctgtctgcat ctgtaggaga cagagtcacc     60
atcacttgcc gggccagtca gagtattggt agctggttgg cctggtatca gcagaaacca    120
gggaaagccc ctaagctcct gatctataag acgtctagtt tagaaagtgg ggtcccatca    180
aggttcagcg gcagtggatc tgggacagaa ttcactctca ccatcagcag cctgcagcct    240
gatgattttg caagttacta ctgccaacag tataatagtt attcgttcgg ccaagggacc    300
aaggtggaaa tcaaa                                                     315

<210> SEQ ID NO 250
<211> LENGTH: 105
<212> TYPE: PRT
<213> ORGANISM: Artificial Sequence
<220> FEATURE:
<223> OTHER INFORMATION: synthetic

<400> SEQUENCE: 250

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Gly Ser Trp
                20                  25                  30

Leu Ala Trp Tyr Gln Gln Lys Pro Gly Lys Ala Pro Lys Leu Leu Ile
        35                  40                  45

Tyr Lys Thr Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Ser Tyr Tyr Cys Gln Gln Tyr Asn Ser Tyr Ser Phe
            85                  90                  95

Gly Gln Gly Thr Lys Val Glu Ile Lys
        100                 105

<210> SEQ ID NO 251
<211> LENGTH: 18
<212> TYPE: DNA
<213> ORGANISM: Artificial Sequence
<220> FEATURE:
<223> OTHER INFORMATION: synthetic

<400> SEQUENCE: 251
cagagtattg gtagctgg                                                   18

<210> SEQ ID NO 252
<211> LENGTH: 6
<212> TYPE: PRT
<213> ORGANISM: Artificial Sequence
<220> FEATURE:
<223> OTHER INFORMATION: synthetic

<400> SEQUENCE: 252

Gln Ser Ile Gly Ser Trp
1               5

<210> SEQ ID NO 253
<211> LENGTH: 9
<212> TYPE: DNA
<213> ORGANISM: Artificial Sequence
<220> FEATURE:
<223> OTHER INFORMATION: synthetic

<400> SEQUENCE: 253 aagacgtct                                                              9

<210> SEQ ID NO 254
<211> LENGTH: 3
<212> TYPE: PRT
<213> ORGANISM: Artificial Sequence
<220> FEATURE:
<223> OTHER INFORMATION: synthetic

<400> SEQUENCE: 254

Lys Thr Ser
1

<210> SEQ ID NO 255
<211> LENGTH: 21
<212> TYPE: DNA
<213> ORGANISM: Artificial Sequence
<220> FEATURE:
<223> OTHER INFORMATION: synthetic

<400> SEQUENCE: 255
caacagtata atagttattc g                                               21

<210> SEQ ID NO 256
<211> LENGTH: 7
<212> TYPE: PRT
<213> ORGANISM: Artificial Sequence
<220> FEATURE:
<223> OTHER INFORMATION: synthetic

<400> SEQUENCE: 256

Gln Gln Tyr Asn Ser Tyr Ser
1               5

<210> SEQ ID NO 257
<211> LENGTH: 360
<212> TYPE: DNA
<213> ORGANISM: Artificial Sequence
<220> FEATURE:
<223> OTHER INFORMATION: synthetic

<400> SEQUENCE: 257

```
caggtgcagc tgcaggagtc gggcccagga ctggtgaagc cttcggagac cctgtccctc    60
acctgcactg tctctggtgg ctccatcagt agttactatt ggagctggat ccggcagccc   120
ccagggaagg gactggagtg gattggctat atctattcca gtgggatcat caagtacaac   180
ccctccctca gagtcgagt caccatatca gcagacacgt ccaagaacca gttctccctg   240
aagctgagct ctgtgaccgc cgcagacacg gccgtatatt actgtgcgag acacgggatt   300
tttggagtga tggaatactt ccaacgctgg ggccagggca ccctggtcac cgtctcctca   360
```

<210> SEQ ID NO 258
<211> LENGTH: 120
<212> TYPE: PRT
<213> ORGANISM: Artificial Sequence
<220> FEATURE:
<223> OTHER INFORMATION: synthetic

<400> SEQUENCE: 258

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Ser Ser Gly Ile Ile Lys Tyr Asn Pro Ser Leu Lys
    50                  55                  60

Ser Arg Val Thr Ile Ser Ala Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg His Gly Ile Phe Gly Val Met Glu Tyr Phe Gln Arg Trp Gly Gln
            100                 105                 110

Gly Thr Leu Val Thr Val Ser Ser
        115                 120

<210> SEQ ID NO 259
<211> LENGTH: 24
<212> TYPE: DNA
<213> ORGANISM: Artificial Sequence
<220> FEATURE:
<223> OTHER INFORMATION: synthetic

<400> SEQUENCE: 259

```
ggtggctcca tcagtagtta ctat                                           24
```

<210> SEQ ID NO 260
<211> LENGTH: 8
<212> TYPE: PRT
<213> ORGANISM: Artificial Sequence
<220> FEATURE:
<223> OTHER INFORMATION: synthetic

<400> SEQUENCE: 260

Gly Gly Ser Ile Ser Ser Tyr Tyr
1               5

<210> SEQ ID NO 261
<211> LENGTH: 21
<212> TYPE: DNA
<213> ORGANISM: Artificial Sequence
<220> FEATURE:
<223> OTHER INFORMATION: synthetic

<400> SEQUENCE: 261
atctattcca gtgggatcat c                                           21

<210> SEQ ID NO 262
<211> LENGTH: 7
<212> TYPE: PRT
<213> ORGANISM: Artificial Sequence
<220> FEATURE:
<223> OTHER INFORMATION: synthetic

<400> SEQUENCE: 262

Ile Tyr Ser Ser Gly Ile Ile
1               5

<210> SEQ ID NO 263
<211> LENGTH: 42
<212> TYPE: DNA
<213> ORGANISM: Artificial Sequence
<220> FEATURE:
<223> OTHER INFORMATION: synthetic

<400> SEQUENCE: 263
gcgagacacg ggattttggg agtgatggaa tacttccaac gc                    42

<210> SEQ ID NO 264
<211> LENGTH: 14
<212> TYPE: PRT
<213> ORGANISM: Artificial Sequence
<220> FEATURE:
<223> OTHER INFORMATION: synthetic

<400> SEQUENCE: 264

Ala Arg His Gly Ile Phe Gly Val Met Glu Tyr Phe Gln Arg
1               5                   10

<210> SEQ ID NO 265
<211> LENGTH: 321
<212> TYPE: DNA
<213> ORGANISM: Artificial Sequence
<220> FEATURE:
<223> OTHER INFORMATION: synthetic

<400> SEQUENCE: 265
gacatccaga tgacccagtc tccatcctcc ctgtctgcat ctataggaga cagagtcacc    60
atcacttgcc aggcgagtca ggacattggc aacttttaa attggtatca gcagaaacca   120
gggaaagccc ctacgctcct gatctacgat gcatccaata tggaaacagg gtcccatca   180 aggttcagtg aagtggatc tgggacatat tttactttca ccatcagcag cctgcagcct   240
gaagatgttg caacatatta ctgtcaacag tatgataatc tccctctcac tttcggcgga   300
gggaccaagg tggagatcaa a                                             321

<210> SEQ ID NO 266

```
<211> LENGTH: 107
<212> TYPE: PRT
<213> ORGANISM: Artificial Sequence
<220> FEATURE:
<223> OTHER INFORMATION: synthetic

<400> SEQUENCE: 266

Asp Ile Gln Met Thr Gln Ser Pro Ser Ser Leu Ser Ala Ser Ile Gly
1               5                   10                  15

Asp Arg Val Thr Ile Thr Cys Gln Ala Ser Gln Asp Ile Gly Asn Phe
            20                  25                  30

Leu Asn Trp Tyr Gln Gln Lys Pro Gly Lys Ala Pro Thr Leu Leu Ile
        35                  40                  45

Tyr Asp Ala Ser Asn Met Glu Thr Gly Val Pro Ser Arg Phe Ser Gly
    50                  55                  60

Ser Gly Ser Gly Thr Tyr Phe Thr Phe Thr Ile Ser Ser Leu Gln Pro
65                  70                  75                  80

Glu Asp Val Ala Thr Tyr Tyr Cys Gln Gln Tyr Asp Asn Leu Pro Leu
                85                  90                  95

Thr Phe Gly Gly Gly Thr Lys Val Glu Ile Lys
            100                 105

<210> SEQ ID NO 267
<211> LENGTH: 18
<212> TYPE: DNA
<213> ORGANISM: Artificial Sequence
<220> FEATURE:
<223> OTHER INFORMATION: synthetic

<400> SEQUENCE: 267
caggacattg gcaactttt                                              18

<210> SEQ ID NO 268
<211> LENGTH: 6
<212> TYPE: PRT
<213> ORGANISM: Artificial Sequence
<220> FEATURE:
<223> OTHER INFORMATION: synthetic

<400> SEQUENCE: 268

Gln Asp Ile Gly Asn Phe
1               5

<210> SEQ ID NO 269
<211> LENGTH: 9
<212> TYPE: DNA
<213> ORGANISM: Artificial Sequence
<220> FEATURE:
<223> OTHER INFORMATION: synthetic

<400> SEQUENCE: 269 gatgcatcc                                                          9

<210> SEQ ID NO 270
<211> LENGTH: 3
<212> TYPE: PRT
<213> ORGANISM: Artificial Sequence
<220> FEATURE:
<223> OTHER INFORMATION: synthetic

<400> SEQUENCE: 270

Asp Ala Ser
1
```

<210> SEQ ID NO 271
<211> LENGTH: 27
<212> TYPE: DNA
<213> ORGANISM: Artificial Sequence
<220> FEATURE:
<223> OTHER INFORMATION: synthetic

<400> SEQUENCE: 271
caacagtatg ataatctccc tctcact                                           27

<210> SEQ ID NO 272
<211> LENGTH: 9
<212> TYPE: PRT
<213> ORGANISM: Artificial Sequence
<220> FEATURE:
<223> OTHER INFORMATION: synthetic

<400> SEQUENCE: 272

Gln Gln Tyr Asp Asn Leu Pro Leu Thr
1               5

<210> SEQ ID NO 273
<211> LENGTH: 360
<212> TYPE: DNA
<213> ORGANISM: Artificial Sequence
<220> FEATURE:
<223> OTHER INFORMATION: synthetic

<400> SEQUENCE: 273
caggtgcagc tgcaggagtc gggcccagga ctggtgaagc cttcggagac cctgtccctc       60
acctgcactg tctctggtgg ctccatcagt agttactact ggagctggat ccggcagccc      120
ccagggaagg gactggagtg gattgcctat atctattaca gtgggattac caagtacaac      180
ccctccctca agagtcgagt caccatatca gcagacacgt ccaagaacca gttctccctg      240
aagctgagct ctgtgaccgc cgcagacacg gccgtgtatt actgtgcgag acacgggatt      300
tttggagtga tggaatactt ccagcgctgg ggccagggca ccctggtcac cgtctcctca      360

<210> SEQ ID NO 274
<211> LENGTH: 120
<212> TYPE: PRT
<213> ORGANISM: Artificial Sequence
<220> FEATURE:
<223> OTHER INFORMATION: synthetic

<400> SEQUENCE: 274

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Ala Tyr Ile Tyr Tyr Ser Gly Ile Thr Lys Tyr Asn Pro Ser Leu Lys
    50                  55                  60

Ser Arg Val Thr Ile Ser Ala Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg His Gly Ile Phe Gly Val Met Glu Tyr Phe Gln Arg Trp Gly Gln
            100                 105                 110

Gly Thr Leu Val Thr Val Ser Ser
        115                 120

<210> SEQ ID NO 275
<211> LENGTH: 24
<212> TYPE: DNA
<213> ORGANISM: Artificial Sequence
<220> FEATURE:
<223> OTHER INFORMATION: synthetic

<400> SEQUENCE: 275
ggtggctcca tcagtagtta ctac                                          24

<210> SEQ ID NO 276
<211> LENGTH: 8
<212> TYPE: PRT
<213> ORGANISM: Artificial Sequence
<220> FEATURE:
<223> OTHER INFORMATION: synthetic

<400> SEQUENCE: 276

Gly Gly Ser Ile Ser Ser Tyr Tyr
1               5

<210> SEQ ID NO 277
<211> LENGTH: 21
<212> TYPE: DNA
<213> ORGANISM: Artificial Sequence
<220> FEATURE:
<223> OTHER INFORMATION: synthetic

<400> SEQUENCE: 277
atctattaca gtgggattac c                                             21

<210> SEQ ID NO 278
<211> LENGTH: 7
<212> TYPE: PRT
<213> ORGANISM: Artificial Sequence
<220> FEATURE:
<223> OTHER INFORMATION: synthetic

<400> SEQUENCE: 278

Ile Tyr Tyr Ser Gly Ile Thr
1               5

<210> SEQ ID NO 279
<211> LENGTH: 42
<212> TYPE: DNA
<213> ORGANISM: Artificial Sequence
<220> FEATURE:
<223> OTHER INFORMATION: synthetic

<400> SEQUENCE: 279
gcgagacacg ggatttttgg agtgatggaa tacttccagc gc                      42

<210> SEQ ID NO 280
<211> LENGTH: 14
<212> TYPE: PRT
<213> ORGANISM: Artificial Sequence
<220> FEATURE:
<223> OTHER INFORMATION: synthetic

<400> SEQUENCE: 280

Ala Arg His Gly Ile Phe Gly Val Met Glu Tyr Phe Gln Arg
1               5                   10

<210> SEQ ID NO 281

<211> LENGTH: 321
<212> TYPE: DNA
<213> ORGANISM: Artificial Sequence
<220> FEATURE:
<223> OTHER INFORMATION: synthetic

<400> SEQUENCE: 281

```
gacatccaga tgacccagtc tccatcctcc ctgtctgcat ctataggaga cagagtcacc    60
atcacttgcc aggcgagtca ggacattagc aacttttaa attggtatca gcagaaacca   120
gggaaagccc caacgctcct gatctacgat gtatccaata tggaaacagg ggtcccatca   180
aggttcagtg aagtggata tgggacagat tttactttaa ccatcagcag cctgaagcct   240
gaagatattg caacatatta ctgtcaacag tatgataata tccctctcac tttcggcgga   300
gggaccaagg tggagatcaa a                                             321
```

<210> SEQ ID NO 282
<211> LENGTH: 107
<212> TYPE: PRT
<213> ORGANISM: Artificial Sequence
<220> FEATURE:
<223> OTHER INFORMATION: synthetic

<400> SEQUENCE: 282

```
Asp Ile Gln Met Thr Gln Ser Pro Ser Ser Leu Ser Ala Ser Ile Gly
1               5                   10                  15
Asp Arg Val Thr Ile Thr Cys Gln Ala Ser Gln Asp Ile Ser Asn Phe
            20                  25                  30
Leu Asn Trp Tyr Gln Gln Lys Pro Gly Lys Ala Pro Thr Leu Leu Ile
        35                  40                  45
Tyr Asp Val Ser Asn Met Glu Thr Gly Val Pro Ser Arg Phe Ser Gly
    50                  55                  60
Ser Gly Tyr Gly Thr Asp Phe Thr Leu Thr Ile Ser Ser Leu Lys Pro
65                  70                  75                  80
Glu Asp Ile Ala Thr Tyr Tyr Cys Gln Gln Tyr Asp Asn Ile Pro Leu
                85                  90                  95
Thr Phe Gly Gly Gly Thr Lys Val Glu Ile Lys
            100                 105
```

<210> SEQ ID NO 283
<211> LENGTH: 18
<212> TYPE: DNA
<213> ORGANISM: Artificial Sequence
<220> FEATURE:
<223> OTHER INFORMATION: synthetic

<400> SEQUENCE: 283

```
caggacatta gcaacttt                                                  18
```

<210> SEQ ID NO 284
<211> LENGTH: 6
<212> TYPE: PRT
<213> ORGANISM: Artificial Sequence
<220> FEATURE:
<223> OTHER INFORMATION: synthetic

<400> SEQUENCE: 284

```
Gln Asp Ile Ser Asn Phe
1               5
```

<210> SEQ ID NO 285
<211> LENGTH: 9

<212> TYPE: DNA
<213> ORGANISM: Artificial Sequence
<220> FEATURE:
<223> OTHER INFORMATION: synthetic

<400> SEQUENCE: 285 gatgtatcc                                                             9

<210> SEQ ID NO 286
<211> LENGTH: 3
<212> TYPE: PRT
<213> ORGANISM: Artificial Sequence
<220> FEATURE:
<223> OTHER INFORMATION: synthetic

<400> SEQUENCE: 286

Asp Val Ser
1

<210> SEQ ID NO 287
<211> LENGTH: 27
<212> TYPE: DNA
<213> ORGANISM: Artificial Sequence
<220> FEATURE:
<223> OTHER INFORMATION: synthetic

<400> SEQUENCE: 287
caacagtatg ataatatccc tctcact                                        27

<210> SEQ ID NO 288
<211> LENGTH: 9
<212> TYPE: PRT
<213> ORGANISM: Artificial Sequence
<220> FEATURE:
<223> OTHER INFORMATION: synthetic

<400> SEQUENCE: 288

Gln Gln Tyr Asp Asn Ile Pro Leu Thr
1               5

<210> SEQ ID NO 289
<211> LENGTH: 339
<212> TYPE: DNA
<213> ORGANISM: Artificial Sequence
<220> FEATURE:
<223> OTHER INFORMATION: synthetic

<400> SEQUENCE: 289
gaggtgcagc tggtggagtc tgggggaagt gtggtacggc ctgggggtc cctgagactc      60 tcctgtgcag cctctggatt cacctttgat gtttatggca tgagctgggt ccgccaagct    120
ccagggaagg gactgagtg ggtctctggt attaattgga ttggtggtag cactggttat     180
gcagactctg tgaagggccg attcaccatc tccagagaca acgccaagaa ttccctgtat    240
ctgcaaatga acagtctgag agccgaggac acggccttgt attattgtac gagagaggag    300
gactactggg gccagggaac cctggtcacc gtctcctca                            339

<210> SEQ ID NO 290
<211> LENGTH: 113
<212> TYPE: PRT
<213> ORGANISM: Artificial Sequence
<220> FEATURE:
<223> OTHER INFORMATION: synthetic

<400> SEQUENCE: 290

-continued

Glu Val Gln Leu Val Glu Ser Gly Gly Ser Val Val Arg Pro Gly Gly
1               5                   10                  15

Ser Leu Arg Leu Ser Cys Ala Ala Ser Gly Phe Thr Phe Asp Val Tyr
            20                  25                  30

Gly Met Ser Trp Val Arg Gln Ala Pro Gly Lys Gly Leu Glu Trp Val
        35                  40                  45

Ser Gly Ile Asn Trp Ile Gly Gly Ser Thr Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Thr Arg Glu Glu Asp Tyr Trp Gly Gln Gly Thr Leu Val Thr Val Ser
            100                 105                 110

Ser

<210> SEQ ID NO 291
<211> LENGTH: 24
<212> TYPE: DNA
<213> ORGANISM: Artificial Sequence
<220> FEATURE:
<223> OTHER INFORMATION: synthetic

<400> SEQUENCE: 291
ggattcacct ttgatgttta tggc                                          24

<210> SEQ ID NO 292
<211> LENGTH: 8
<212> TYPE: PRT
<213> ORGANISM: Artificial Sequence
<220> FEATURE:
<223> OTHER INFORMATION: synthetic

<400> SEQUENCE: 292

Gly Phe Thr Phe Asp Val Tyr Gly
1               5

<210> SEQ ID NO 293
<211> LENGTH: 24
<212> TYPE: DNA
<213> ORGANISM: Artificial Sequence
<220> FEATURE:
<223> OTHER INFORMATION: synthetic

<400> SEQUENCE: 293
attaattgga ttggtggtag cact                                          24

<210> SEQ ID NO 294
<211> LENGTH: 8
<212> TYPE: PRT
<213> ORGANISM: Artificial Sequence
<220> FEATURE:
<223> OTHER INFORMATION: synthetic

<400> SEQUENCE: 294

Ile Asn Trp Ile Gly Gly Ser Thr
1               5

<210> SEQ ID NO 295
<211> LENGTH: 18
<212> TYPE: DNA
<213> ORGANISM: Artificial Sequence
<220> FEATURE:

<223> OTHER INFORMATION: synthetic

<400> SEQUENCE: 295
acgagagagg aggactac                                                  18

<210> SEQ ID NO 296
<211> LENGTH: 6
<212> TYPE: PRT
<213> ORGANISM: Artificial Sequence
<220> FEATURE:
<223> OTHER INFORMATION: synthetic

<400> SEQUENCE: 296

Thr Arg Glu Glu Asp Tyr
1               5

<210> SEQ ID NO 297
<211> LENGTH: 336
<212> TYPE: DNA
<213> ORGANISM: Artificial Sequence
<220> FEATURE:
<223> OTHER INFORMATION: synthetic

<400> SEQUENCE: 297
gatgttgtga tgactcagtc tccactctct ctggccgtca cccttggaca gccggcctcc    60
atctcctgca ggtctagtca aagcctcgta tacagtgatg aaacacccta cttgaattgg   120
tttcagcaga ggccaggcca atctccaagg cgcctatttt ataaggtttc taaccgggac   180
tctggggtcc cagacagatt cagcggcagt gggtcaggca ctgatttcac actgaaaatc   240
agcagggtgg aggctgagga tgttgggatt tattactgca tgcaaggtat aaagtggcct   300
ctcactttcg gcggagggac caaggtggag atcaaa                             336

<210> SEQ ID NO 298
<211> LENGTH: 112
<212> TYPE: PRT
<213> ORGANISM: Artificial Sequence
<220> FEATURE:
<223> OTHER INFORMATION: synthetic

<400> SEQUENCE: 298

Asp Val Val Met Thr Gln Ser Pro Leu Ser Leu Ala Val Thr Leu Gly
1               5                   10                  15

Gln Pro Ala Ser Ile Ser Cys Arg Ser Ser Gln Ser Leu Val Tyr Ser
            20                  25                  30

Asp Gly Asn Thr Tyr Leu Asn Trp Phe Gln Gln Arg Pro Gly Gln Ser
        35                  40                  45

Pro Arg Arg Leu Phe Tyr Lys Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Ile Tyr Tyr Cys Met Gln Gly
                85                  90                  95

Ile Lys Trp Pro Leu Thr Phe Gly Gly Gly Thr Lys Val Glu Ile Lys
            100                 105                 110

<210> SEQ ID NO 299
<211> LENGTH: 33
<212> TYPE: DNA
<213> ORGANISM: Artificial Sequence
<220> FEATURE:
<223> OTHER INFORMATION: synthetic

<400> SEQUENCE: 299
caaagcctcg tatacagtga tggaaacacc tac                                    33

<210> SEQ ID NO 300
<211> LENGTH: 11
<212> TYPE: PRT
<213> ORGANISM: Artificial Sequence
<220> FEATURE:
<223> OTHER INFORMATION: synthetic

<400> SEQUENCE: 300

Gln Ser Leu Val Tyr Ser Asp Gly Asn Thr Tyr
1               5                   10

<210> SEQ ID NO 301
<211> LENGTH: 9
<212> TYPE: DNA
<213> ORGANISM: Artificial Sequence
<220> FEATURE:
<223> OTHER INFORMATION: synthetic

<400> SEQUENCE: 301 aaggtttct                                                               9

<210> SEQ ID NO 302
<211> LENGTH: 3
<212> TYPE: PRT
<213> ORGANISM: Artificial Sequence
<220> FEATURE:
<223> OTHER INFORMATION: synthetic

<400> SEQUENCE: 302

Lys Val Ser
1

<210> SEQ ID NO 303
<211> LENGTH: 27
<212> TYPE: DNA
<213> ORGANISM: Artificial Sequence
<220> FEATURE:
<223> OTHER INFORMATION: synthetic

<400> SEQUENCE: 303
atgcaaggta taaagtggcc tctcact                                           27

<210> SEQ ID NO 304
<211> LENGTH: 9
<212> TYPE: PRT
<213> ORGANISM: Artificial Sequence
<220> FEATURE:
<223> OTHER INFORMATION: synthetic

<400> SEQUENCE: 304

Met Gln Gly Ile Lys Trp Pro Leu Thr
1               5

<210> SEQ ID NO 305
<211> LENGTH: 339
<212> TYPE: DNA
<213> ORGANISM: Artificial Sequence
<220> FEATURE:
<223> OTHER INFORMATION: synthetic

<400> SEQUENCE: 305
gaggtgcagc tggtggagtc ggggggaggt gtggtacggc ctggggggtc cctgagactc        60

```
tcctgtgcag cctctggatt caagtttgat gtttatggca tgagttgggt ccgccaactt    120
ccagggaagg ggttggagtg ggtctctggt attagttgga ctggaggtag ttcaggttat    180
gcagactctg tgaagggccg attcaccatc tcccgagaca acggcaagaa gtccctgtat    240
ctgcaaatga acagtctgag agccgaggac acggccttgt attattgtac gagagaggag    300
gactactggg gccagggaac cctggtcacc gtctcctca                           339
```

```
<210> SEQ ID NO 306
<211> LENGTH: 113
<212> TYPE: PRT
<213> ORGANISM: Artificial Sequence
<220> FEATURE:
<223> OTHER INFORMATION: synthetic

<400> SEQUENCE: 306
```

Glu Val Gln Leu Val Glu Ser Gly Gly Gly Val Val Arg Pro Gly Gly
1               5                   10                  15

Ser Leu Arg Leu Ser Cys Ala Ala Ser Gly Phe Lys Phe Asp Val Tyr
            20                  25                  30

Gly Met Ser Trp Val Arg Gln Leu Pro Gly Lys Gly Leu Glu Trp Val
        35                  40                  45

Ser Gly Ile Ser Trp Thr Gly Ser Ser Gly Tyr Ala Asp Ser Val
    50                  55                  60

Lys Gly Arg Phe Thr Ile Ser Arg Asp Asn Gly Lys Lys Ser Leu Tyr
65                  70                  75                  80

Leu Gln Met Asn Ser Leu Arg Ala Glu Asp Thr Ala Leu Tyr Tyr Cys
            85                  90                  95

Thr Arg Glu Glu Asp Tyr Trp Gly Gln Gly Thr Leu Val Thr Val Ser
            100                 105                 110

Ser

```
<210> SEQ ID NO 307
<211> LENGTH: 24
<212> TYPE: DNA
<213> ORGANISM: Artificial Sequence
<220> FEATURE:
<223> OTHER INFORMATION: synthetic

<400> SEQUENCE: 307
ggattcaagt ttgatgttta tggc                                            24

<210> SEQ ID NO 308
<211> LENGTH: 8
<212> TYPE: PRT
<213> ORGANISM: Artificial Sequence
<220> FEATURE:
<223> OTHER INFORMATION: synthetic

<400> SEQUENCE: 308
```

Gly Phe Lys Phe Asp Val Tyr Gly
1               5

```
<210> SEQ ID NO 309
<211> LENGTH: 24
<212> TYPE: DNA
<213> ORGANISM: Artificial Sequence
<220> FEATURE:
<223> OTHER INFORMATION: synthetic

<400> SEQUENCE: 309
```

```
attagttgga ctggaggtag ttca                                              24

<210> SEQ ID NO 310
<211> LENGTH: 8
<212> TYPE: PRT
<213> ORGANISM: Artificial Sequence
<220> FEATURE:
<223> OTHER INFORMATION: synthetic

<400> SEQUENCE: 310

Ile Ser Trp Thr Gly Gly Ser Ser
1               5

<210> SEQ ID NO 311
<211> LENGTH: 18
<212> TYPE: DNA
<213> ORGANISM: Artificial Sequence
<220> FEATURE:
<223> OTHER INFORMATION: synthetic

<400> SEQUENCE: 311
acgagagagg aggactac                                                     18

<210> SEQ ID NO 312
<211> LENGTH: 6
<212> TYPE: PRT
<213> ORGANISM: Artificial Sequence
<220> FEATURE:
<223> OTHER INFORMATION: synthetic

<400> SEQUENCE: 312

Thr Arg Glu Glu Asp Tyr
1               5

<210> SEQ ID NO 313
<211> LENGTH: 336
<212> TYPE: DNA
<213> ORGANISM: Artificial Sequence
<220> FEATURE:
<223> OTHER INFORMATION: synthetic

<400> SEQUENCE: 313
gatgttgtga tgacccagtc tccactctcc ctgcccgtca cccttggaca gccggcctcc       60
atctcctgcc ggtctagtca aagcctcgta tacagtgatg gaaatacgta cttgaattgg      120
tttcagcaga ggccaggcca atctccaagg cgcctaattt ataaggtttc taaccgggac      180
tctggggtcc cagacagatt cagcggcagt gggtcaggca ctgatttcac actgaaaatc      240
agcagggtgg aggctgaaga tgttggtatt tattactgca tgcaaggaac acaatggcct      300
ctcactttcg gcggagggac caaggtggag atcaaa                                336

<210> SEQ ID NO 314
<211> LENGTH: 112
<212> TYPE: PRT
<213> ORGANISM: Artificial Sequence
<220> FEATURE:
<223> OTHER INFORMATION: synthetic

<400> SEQUENCE: 314

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val Tyr Ser
            20                  25                  30

Asp Gly Asn Thr Tyr Leu Asn Trp Phe Gln Gln Arg Pro Gly Gln Ser
```

```
                35                  40                  45
Pro Arg Arg Leu Ile Tyr Lys Val Ser Asn Arg Asp Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Ile Tyr Tyr Cys Met Gln Gly
                85                  90                  95

Thr Gln Trp Pro Leu Thr Phe Gly Gly Gly Thr Lys Val Glu Ile Lys
            100                 105                 110
```

<210> SEQ ID NO 315
<211> LENGTH: 33
<212> TYPE: DNA
<213> ORGANISM: Artificial Sequence
<220> FEATURE:
<223> OTHER INFORMATION: synthetic

<400> SEQUENCE: 315
caaagcctcg tatacagtga tggaaatacg tac                                    33

<210> SEQ ID NO 316
<211> LENGTH: 11
<212> TYPE: PRT
<213> ORGANISM: Artificial Sequence
<220> FEATURE:
<223> OTHER INFORMATION: synthetic

<400> SEQUENCE: 316

```
Gln Ser Leu Val Tyr Ser Asp Gly Asn Thr Tyr
1               5                   10
```

<210> SEQ ID NO 317
<211> LENGTH: 9
<212> TYPE: DNA
<213> ORGANISM: Artificial Sequence
<220> FEATURE:
<223> OTHER INFORMATION: synthetic

<400> SEQUENCE: 317 aaggtttct                                                                9

<210> SEQ ID NO 318
<211> LENGTH: 3
<212> TYPE: PRT
<213> ORGANISM: Artificial Sequence
<220> FEATURE:
<223> OTHER INFORMATION: synthetic

<400> SEQUENCE: 318

```
Lys Val Ser
1
```

<210> SEQ ID NO 319
<211> LENGTH: 27
<212> TYPE: DNA
<213> ORGANISM: Artificial Sequence
<220> FEATURE:
<223> OTHER INFORMATION: synthetic

<400> SEQUENCE: 319
atgcaaggaa cacaatggcc tctcact                                           27

<210> SEQ ID NO 320
<211> LENGTH: 9

```
<212> TYPE: PRT
<213> ORGANISM: Artificial Sequence
<220> FEATURE:
<223> OTHER INFORMATION: synthetic

<400> SEQUENCE: 320

Met Gln Gly Thr Gln Trp Pro Leu Thr
1               5

<210> SEQ ID NO 321
<211> LENGTH: 360
<212> TYPE: DNA
<213> ORGANISM: Artificial Sequence
<220> FEATURE:
<223> OTHER INFORMATION: synthetic

<400> SEQUENCE: 321
caggtgcagc tgcaggagtc gggcccagga ctggtgaagc cttcggagac cctgtccctc      60
acctgcactg tctctggtgc ctccatcagt agttactatt ggagctggat ccggcagccc     120
ccagggaagg gactggagtg gattggctat atctattcca gtgggatcat caagtacaac     180
ccctccctca gagtcgagt caccatttca gcagacacgt ccaagaacca gttctccctg     240
aagctgagtt ctgtgaccgc cgcagacacg gccgtatatt actgtgcgag acacgggatt     300
tttggagtga tggaatactt ccaacgttgg ggccagggca ccctggtcac cgtctcctca     360

<210> SEQ ID NO 322
<211> LENGTH: 120
<212> TYPE: PRT
<213> ORGANISM: Artificial Sequence
<220> FEATURE:
<223> OTHER INFORMATION: synthetic

<400> SEQUENCE: 322

Gln Val Gln Leu Gln Glu Ser Gly Pro Gly Leu Val Lys Pro Ser Glu
1               5                   10                  15

Thr Leu Ser Leu Thr Cys Thr Val Ser Gly Ala Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Ser Ser Gly Ile Ile Lys Tyr Asn Pro Ser Leu Lys
    50                  55                  60

Ser Arg Val Thr Ile Ser Ala Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg His Gly Ile Phe Gly Val Met Glu Tyr Phe Gln Arg Trp Gly Gln
            100                 105                 110

Gly Thr Leu Val Thr Val Ser Ser
        115                 120

<210> SEQ ID NO 323
<211> LENGTH: 24
<212> TYPE: DNA
<213> ORGANISM: Artificial Sequence
<220> FEATURE:
<223> OTHER INFORMATION: synthetic

<400> SEQUENCE: 323
ggtgcctcca tcagtagtta ctat                                             24
```

<210> SEQ ID NO 324
<211> LENGTH: 8
<212> TYPE: PRT
<213> ORGANISM: Artificial Sequence
<220> FEATURE:
<223> OTHER INFORMATION: synthetic

<400> SEQUENCE: 324

Gly Ala Ser Ile Ser Ser Tyr Tyr
1               5

<210> SEQ ID NO 325
<211> LENGTH: 21
<212> TYPE: DNA
<213> ORGANISM: Artificial Sequence
<220> FEATURE:
<223> OTHER INFORMATION: synthetic

<400> SEQUENCE: 325
atctattcca gtgggatcat c                                        21

<210> SEQ ID NO 326
<211> LENGTH: 7
<212> TYPE: PRT
<213> ORGANISM: Artificial Sequence
<220> FEATURE:
<223> OTHER INFORMATION: synthetic

<400> SEQUENCE: 326

Ile Tyr Ser Ser Gly Ile Ile
1               5

<210> SEQ ID NO 327
<211> LENGTH: 42
<212> TYPE: DNA
<213> ORGANISM: Artificial Sequence
<220> FEATURE:
<223> OTHER INFORMATION: synthetic

<400> SEQUENCE: 327
gcgagacacg ggatttttgg agtgatggaa tacttccaac gt                 42

<210> SEQ ID NO 328
<211> LENGTH: 14
<212> TYPE: PRT
<213> ORGANISM: Artificial Sequence
<220> FEATURE:
<223> OTHER INFORMATION: synthetic

<400> SEQUENCE: 328

Ala Arg His Gly Ile Phe Gly Val Met Glu Tyr Phe Gln Arg
1               5                   10

<210> SEQ ID NO 329
<211> LENGTH: 321
<212> TYPE: DNA
<213> ORGANISM: Artificial Sequence
<220> FEATURE:
<223> OTHER INFORMATION: synthetic

<400> SEQUENCE: 329
gacatccaga tgacccagtc tccatcctcc ctgtctgcat ctataggaga cagagtcacc     60
atcacttgcc aggcgagtca ggacattggc aacttttaa attggtatca tcaaaaacca    120
gggaaagccc ctacgctcct gatctacgat gcatccaata tggaaacagg ggtcccatca    180
agattcagag gaagtggatc tgggacatat tttactttca tcatcagtag cctgcagcct    240

```
gaagatgttg caacatatta ctgtcaacag tatgataatc tccctctcac tttcggcgga    300
gggaccaagg tggagatcaa a                                              321
```

<210> SEQ ID NO 330
<211> LENGTH: 107
<212> TYPE: PRT
<213> ORGANISM: Artificial Sequence
<220> FEATURE:
<223> OTHER INFORMATION: synthetic

<400> SEQUENCE: 330

```
Asp Ile Gln Met Thr Gln Ser Pro Ser Ser Leu Ser Ala Ser Ile Gly
1               5                   10                  15

Asp Arg Val Thr Ile Thr Cys Gln Ala Ser Gln Asp Ile Gly Asn Phe
            20                  25                  30

Leu Asn Trp Tyr His Gln Lys Pro Gly Lys Ala Pro Thr Leu Leu Ile
        35                  40                  45

Tyr Asp Ala Ser Asn Met Glu Thr Gly Val Pro Ser Arg Phe Arg Gly
    50                  55                  60

Ser Gly Ser Gly Thr Tyr Phe Thr Phe Ile Ile Ser Ser Leu Gln Pro
65                  70                  75                  80

Glu Asp Val Ala Thr Tyr Tyr Cys Gln Gln Tyr Asp Asn Leu Pro Leu
                85                  90                  95

Thr Phe Gly Gly Gly Thr Lys Val Glu Ile Lys
            100                 105
```

<210> SEQ ID NO 331
<211> LENGTH: 18
<212> TYPE: DNA
<213> ORGANISM: Artificial Sequence
<220> FEATURE:
<223> OTHER INFORMATION: synthetic

<400> SEQUENCE: 331

```
caggacattg gcaacttt                                                  18
```

<210> SEQ ID NO 332
<211> LENGTH: 6
<212> TYPE: PRT
<213> ORGANISM: Artificial Sequence
<220> FEATURE:
<223> OTHER INFORMATION: synthetic

<400> SEQUENCE: 332

```
Gln Asp Ile Gly Asn Phe
1               5
```

<210> SEQ ID NO 333
<211> LENGTH: 9
<212> TYPE: DNA
<213> ORGANISM: Artificial Sequence
<220> FEATURE:
<223> OTHER INFORMATION: synthetic

<400> SEQUENCE: 333

```
gatgcatcc                                                            9
```

<210> SEQ ID NO 334
<211> LENGTH: 3
<212> TYPE: PRT
<213> ORGANISM: Artificial Sequence
<220> FEATURE:

<223> OTHER INFORMATION: synthetic

<400> SEQUENCE: 334

Asp Ala Ser
1

<210> SEQ ID NO 335
<211> LENGTH: 27
<212> TYPE: DNA
<213> ORGANISM: Artificial Sequence
<220> FEATURE:
<223> OTHER INFORMATION: synthetic

<400> SEQUENCE: 335
caacagtatg ataatctccc tctcact                                          27

<210> SEQ ID NO 336
<211> LENGTH: 9
<212> TYPE: PRT
<213> ORGANISM: Artificial Sequence
<220> FEATURE:
<223> OTHER INFORMATION: synthetic

<400> SEQUENCE: 336

Gln Gln Tyr Asp Asn Leu Pro Leu Thr
1               5

<210> SEQ ID NO 337
<211> LENGTH: 369
<212> TYPE: DNA
<213> ORGANISM: Artificial Sequence
<220> FEATURE:
<223> OTHER INFORMATION: synthetic

<400> SEQUENCE: 337
caggtgcagc tggtggagtc tgggggaggc gtggtccagc ctggggaggtc cctgagactc     60
tcctgtgcag cctctggatt caccctcaat acctatggca tgcactggat ccgccagact    120
ccaggcaagg ggctggagtg ggtgtcactt atatcatatg atgaaactaa agaatactat    180
gtagactccg tgaagggccg attcaccatc tccagagaca attccaagaa cacgctgtat    240
ctccaaatga acagtgtgag agttgaggac acggctgtat attactgtgc gaaacccta    300
actggaagta cggactatta ttacggtttg gacgtctggg gccaagggac cacggtcacc    360
gtctcctca                                                            369

<210> SEQ ID NO 338
<211> LENGTH: 123
<212> TYPE: PRT
<213> ORGANISM: Artificial Sequence
<220> FEATURE:
<223> OTHER INFORMATION: synthetic

<400> SEQUENCE: 338

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Leu Asn Thr Tyr
            20                  25                  30

Gly Met His Trp Ile Arg Gln Thr Pro Gly Lys Gly Leu Glu Trp Val
        35                  40                  45

Ser Leu Ile Ser Tyr Asp Glu Thr Lys Glu Tyr Tyr Val Asp Ser Val
    50                  55                  60

Lys Gly Arg Phe Thr Ile Ser Arg Asp Asn Ser Lys Asn Thr Leu Tyr

```
            65                  70                  75                  80
Leu Gln Met Asn Ser Val Arg Val Glu Asp Thr Ala Val Tyr Tyr Cys
                    85                  90                  95

Ala Lys Pro Leu Thr Gly Ser Thr Asp Tyr Tyr Tyr Gly Leu Asp Val
            100                 105                 110

Trp Gly Gln Gly Thr Thr Val Thr Val Ser Ser
        115                 120
```

<210> SEQ ID NO 339
<211> LENGTH: 24
<212> TYPE: DNA
<213> ORGANISM: Artificial Sequence
<220> FEATURE:
<223> OTHER INFORMATION: synthetic

<400> SEQUENCE: 339
ggattcaccc tcaataccta tggc                                          24

<210> SEQ ID NO 340
<211> LENGTH: 8
<212> TYPE: PRT
<213> ORGANISM: Artificial Sequence
<220> FEATURE:
<223> OTHER INFORMATION: synthetic

<400> SEQUENCE: 340

```
Gly Phe Thr Leu Asn Thr Tyr Gly
1               5
```

<210> SEQ ID NO 341
<211> LENGTH: 24
<212> TYPE: DNA
<213> ORGANISM: Artificial Sequence
<220> FEATURE:
<223> OTHER INFORMATION: synthetic

<400> SEQUENCE: 341
atatcatatg atgaaactaa agaa                                          24

<210> SEQ ID NO 342
<211> LENGTH: 8
<212> TYPE: PRT
<213> ORGANISM: Artificial Sequence
<220> FEATURE:
<223> OTHER INFORMATION: synthetic

<400> SEQUENCE: 342

```
Ile Ser Tyr Asp Glu Thr Lys Glu
1               5
```

<210> SEQ ID NO 343
<211> LENGTH: 48
<212> TYPE: DNA
<213> ORGANISM: Artificial Sequence
<220> FEATURE:
<223> OTHER INFORMATION: synthetic

<400> SEQUENCE: 343
gcgaaaccct aactggaag tacggactat tattacggtt tggacgtc                 48

<210> SEQ ID NO 344
<211> LENGTH: 16
<212> TYPE: PRT
<213> ORGANISM: Artificial Sequence
<220> FEATURE:

<223> OTHER INFORMATION: synthetic

<400> SEQUENCE: 344

Ala Lys Pro Leu Thr Gly Ser Thr Asp Tyr Tyr Gly Leu Asp Val
1               5                   10                  15

<210> SEQ ID NO 345
<211> LENGTH: 321
<212> TYPE: DNA
<213> ORGANISM: Artificial Sequence
<220> FEATURE:
<223> OTHER INFORMATION: synthetic

<400> SEQUENCE: 345

```
gacatccaga tgacccagtc tccatcttac gtgtctgcat ctgtaggaga cagagtcatc    60
atcacttgtc gggcgagtca ggacatcagc agctggttag cctggtatca gcagaaacca   120
ggtaaagccc ctaaactcct gatctacgtt acatccagtt tggaaagtgg ggtcccatca   180
aggttcagcg gcagtggatc ggggacagat ttcactctca ccatcagcgg cctgcagcct   240
gaagattttg caacttacta ttgtcaacag gttaaaagtt tccctcccac tttcggccct   300
gggaccaaag tggatatcaa a                                             321
```

<210> SEQ ID NO 346
<211> LENGTH: 107
<212> TYPE: PRT
<213> ORGANISM: Artificial Sequence
<220> FEATURE:
<223> OTHER INFORMATION: synthetic

<400> SEQUENCE: 346

Asp Ile Gln Met Thr Gln Ser Pro Ser Tyr Val Ser Ala Ser Val Gly
1               5                   10                  15

Asp Arg Val Ile Ile Thr Cys Arg Ala Ser Gln Asp Ile Ser Ser Trp
            20                  25                  30

Leu Ala Trp Tyr Gln Gln Lys Pro Gly Lys Ala Pro Lys Leu Leu Ile
        35                  40                  45

Tyr Val Thr Ser Ser Leu Glu Ser Gly Val Pro Ser Arg Phe Ser Gly
50                  55                  60

Ser Gly Ser Gly Thr Asp Phe Thr Leu Thr Ile Ser Gly Leu Gln Pro
65                  70                  75                  80

Glu Asp Phe Ala Thr Tyr Tyr Cys Gln Gln Val Lys Ser Phe Pro Pro
                85                  90                  95

Thr Phe Gly Pro Gly Thr Lys Val Asp Ile Lys
            100                 105

<210> SEQ ID NO 347
<211> LENGTH: 18
<212> TYPE: DNA
<213> ORGANISM: Artificial Sequence
<220> FEATURE:
<223> OTHER INFORMATION: synthetic

<400> SEQUENCE: 347
caggacatca gcagctgg                                                  18

<210> SEQ ID NO 348
<211> LENGTH: 6
<212> TYPE: PRT
<213> ORGANISM: Artificial Sequence
<220> FEATURE:
<223> OTHER INFORMATION: synthetic

<400> SEQUENCE: 348

Gln Asp Ile Ser Ser Trp
1               5

<210> SEQ ID NO 349
<211> LENGTH: 9
<212> TYPE: DNA
<213> ORGANISM: Artificial Sequence
<220> FEATURE:
<223> OTHER INFORMATION: synthetic

<400> SEQUENCE: 349 gttacatcc                                                              9

<210> SEQ ID NO 350
<211> LENGTH: 3
<212> TYPE: PRT
<213> ORGANISM: Artificial Sequence
<220> FEATURE:
<223> OTHER INFORMATION: synthetic

<400> SEQUENCE: 350

Val Thr Ser
1

<210> SEQ ID NO 351
<211> LENGTH: 27
<212> TYPE: DNA
<213> ORGANISM: Artificial Sequence
<220> FEATURE:
<223> OTHER INFORMATION: synthetic

<400> SEQUENCE: 351
caacaggtta aaagtttccc tcccact                                         27

<210> SEQ ID NO 352
<211> LENGTH: 9
<212> TYPE: PRT
<213> ORGANISM: Artificial Sequence
<220> FEATURE:
<223> OTHER INFORMATION: synthetic

<400> SEQUENCE: 352

Gln Gln Val Lys Ser Phe Pro Pro Thr
1               5

<210> SEQ ID NO 353
<211> LENGTH: 363
<212> TYPE: DNA
<213> ORGANISM: Artificial Sequence
<220> FEATURE:
<223> OTHER INFORMATION: synthetic

<400> SEQUENCE: 353
gaggtgcagc tggtggagtc tgggggaggc gtggtacagc ctggggggtc cctgagactc      60
tcctgtgcag cctctggctt cacctttagc ctctatgcca tgagctgggt ccgccaggct     120
ccagggaagg ggctggagtg ggtctcagct attagtggta gtgctcatgg cgcatactac     180
gcagactccg tgaagggccg attcaccatc tcccgagaca attccaagaa ctcgctgtat     240
ctgcaaatga acagcctgag agccgaggac acggccatat attactgtgc gaaagatctt     300
gttatagcag tggctggtac ctttgactac tggggccagg gaaccctggt cactgtctcc     360
tca                                                                  363

<210> SEQ ID NO 354
<211> LENGTH: 121
<212> TYPE: PRT
<213> ORGANISM: Artificial Sequence
<220> FEATURE:
<223> OTHER INFORMATION: synthetic

<400> SEQUENCE: 354

```
Glu Val Gln Leu Val Glu Ser Gly Gly Val Val Gln Pro Gly Gly
1               5                   10                  15

Ser Leu Arg Leu Ser Cys Ala Ala Ser Gly Phe Thr Phe Ser Leu Tyr
            20                  25                  30

Ala Met Ser Trp Val Arg Gln Ala Pro Gly Lys Gly Leu Glu Trp Val
        35                  40                  45

Ser Ala Ile Ser Gly Ser Ala His Gly Ala Tyr Tyr Ala Asp Ser Val
    50                  55                  60

Lys Gly Arg Phe Thr Ile Ser Arg Asp Asn Ser Lys Asn Ser Leu Tyr
65                  70                  75                  80

Leu Gln Met Asn Ser Leu Arg Ala Glu Asp Thr Ala Ile Tyr Tyr Cys
                85                  90                  95

Ala Lys Asp Leu Val Ile Ala Val Ala Gly Thr Phe Asp Tyr Trp Gly
            100                 105                 110

Gln Gly Thr Leu Val Thr Val Ser Ser
        115                 120
```

<210> SEQ ID NO 355
<211> LENGTH: 24
<212> TYPE: DNA
<213> ORGANISM: Artificial Sequence
<220> FEATURE:
<223> OTHER INFORMATION: synthetic

<400> SEQUENCE: 355
ggcttcacct ttagcctcta tgcc                                    24

<210> SEQ ID NO 356
<211> LENGTH: 8
<212> TYPE: PRT
<213> ORGANISM: Artificial Sequence
<220> FEATURE:
<223> OTHER INFORMATION: synthetic

<400> SEQUENCE: 356

```
Gly Phe Thr Phe Ser Leu Tyr Ala
1               5
```

<210> SEQ ID NO 357
<211> LENGTH: 24
<212> TYPE: DNA
<213> ORGANISM: Artificial Sequence
<220> FEATURE:
<223> OTHER INFORMATION: synthetic

<400> SEQUENCE: 357
attagtggta gtgctcatgg cgca                                    24

<210> SEQ ID NO 358
<211> LENGTH: 8
<212> TYPE: PRT
<213> ORGANISM: Artificial Sequence
<220> FEATURE:
<223> OTHER INFORMATION: synthetic

<400> SEQUENCE: 358

Ile Ser Gly Ser Ala His Gly Ala
1               5

<210> SEQ ID NO 359
<211> LENGTH: 42
<212> TYPE: DNA
<213> ORGANISM: Artificial Sequence
<220> FEATURE:
<223> OTHER INFORMATION: synthetic

<400> SEQUENCE: 359
gcgaaagatc ttgttatagc agtggctggt acctttgact ac                              42

<210> SEQ ID NO 360
<211> LENGTH: 14
<212> TYPE: PRT
<213> ORGANISM: Artificial Sequence
<220> FEATURE:
<223> OTHER INFORMATION: synthetic

<400> SEQUENCE: 360

Ala Lys Asp Leu Val Ile Ala Val Ala Gly Thr Phe Asp Tyr
1               5                   10

<210> SEQ ID NO 361
<211> LENGTH: 324
<212> TYPE: DNA
<213> ORGANISM: Artificial Sequence
<220> FEATURE:
<223> OTHER INFORMATION: synthetic

<400> SEQUENCE: 361
gacatccaga tgacccagtc tccatcctcc ctgtctgcat ctgtaggaga cagagtcacc          60
atcacttgcc gggcaagtca gatcattagc acctatttaa attggtatca gcagaaacca         120
gggaaagccc ctaagatcct gatctatact gcatccagtt tgaaaagtgg ggtcccatca         180
aggttcagtg gcagtggttc tgggacagat ttcactctca ccatcagcag tctgcaacct         240
gaagattttg caacttacta ctgtcaacag acttacagtt cccccagatt cactttcggc         300
cctgggacca agtggatat caaa                                                 324

<210> SEQ ID NO 362
<211> LENGTH: 108
<212> TYPE: PRT
<213> ORGANISM: Artificial Sequence
<220> FEATURE:
<223> OTHER INFORMATION: synthetic

<400> SEQUENCE: 362

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ile Ile Ser Thr Tyr
            20                  25                  30

Leu Asn Trp Tyr Gln Gln Lys Pro Gly Lys Ala Pro Lys Ile Leu Ile
        35                  40                  45

Tyr Thr Ala Ser Ser Leu Lys Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Tyr Ser Ser Pro Arg

```
                    85                  90                  95

Phe Thr Phe Gly Pro Gly Thr Lys Val Asp Ile Lys
            100                 105

<210> SEQ ID NO 363
<211> LENGTH: 18
<212> TYPE: DNA
<213> ORGANISM: Artificial Sequence
<220> FEATURE:
<223> OTHER INFORMATION: synthetic

<400> SEQUENCE: 363
cagatcatta gcacctat                                                    18

<210> SEQ ID NO 364
<211> LENGTH: 6
<212> TYPE: PRT
<213> ORGANISM: Artificial Sequence
<220> FEATURE:
<223> OTHER INFORMATION: synthetic

<400> SEQUENCE: 364

Gln Ile Ile Ser Thr Tyr
1               5

<210> SEQ ID NO 365
<211> LENGTH: 9
<212> TYPE: DNA
<213> ORGANISM: Artificial Sequence
<220> FEATURE:
<223> OTHER INFORMATION: synthetic

<400> SEQUENCE: 365 actgcatcc                                                              9

<210> SEQ ID NO 366
<211> LENGTH: 3
<212> TYPE: PRT
<213> ORGANISM: Artificial Sequence
<220> FEATURE:
<223> OTHER INFORMATION: synthetic

<400> SEQUENCE: 366

Thr Ala Ser
1

<210> SEQ ID NO 367
<211> LENGTH: 30
<212> TYPE: DNA
<213> ORGANISM: Artificial Sequence
<220> FEATURE:
<223> OTHER INFORMATION: synthetic

<400> SEQUENCE: 367
caacagactt acagttcccc cagattcact                                       30

<210> SEQ ID NO 368
<211> LENGTH: 10
<212> TYPE: PRT
<213> ORGANISM: Artificial Sequence
<220> FEATURE:
<223> OTHER INFORMATION: synthetic

<400> SEQUENCE: 368

Gln Gln Thr Tyr Ser Ser Pro Arg Phe Thr
1               5                   10
```

<210> SEQ ID NO 369
<211> LENGTH: 357
<212> TYPE: DNA
<213> ORGANISM: Artificial Sequence
<220> FEATURE:
<223> OTHER INFORMATION: synthetic

<400> SEQUENCE: 369

```
caggttcagc tggtgcagtc tggggctgag gtgaagaagc ctggggcctc agtgaaggtt      60
tcctgcaagg cttctggata caccttcact agctatgtta ttcattgggt gcgccaggcc     120
cccggacaaa gacttgagtg gatgggatgg agcaacgctg ccaatggtga cacaaaatat     180
tcacaggagt tccaggacag agtcaccttt accagggaca catccgcgag cacagcctac     240
atggagctga gcagcctgag atctgaggac atggctgtgt attactgtgc gagatggaac     300
tggaactacg gggcttttga tatctggggc caagggacaa tggtcaccgt ctcttca       357
```

<210> SEQ ID NO 370
<211> LENGTH: 119
<212> TYPE: PRT
<213> ORGANISM: Artificial Sequence
<220> FEATURE:
<223> OTHER INFORMATION: synthetic

<400> SEQUENCE: 370

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Val Ile His Trp Val Arg Gln Ala Pro Gly Gln Arg Leu Glu Trp Met
        35                  40                  45

Gly Trp Ser Asn Ala Ala Asn Gly Asp Thr Lys Tyr Ser Gln Glu Phe
    50                  55                  60

Gln Asp Arg Val Thr Phe Thr Arg Asp Thr Ser Ala Ser Thr Ala Tyr
65                  70                  75                  80

Met Glu Leu Ser Ser Leu Arg Ser Glu Asp Met Ala Val Tyr Tyr Cys
                85                  90                  95

Ala Arg Trp Asn Trp Asn Tyr Gly Ala Phe Asp Ile Trp Gly Gln Gly
            100                 105                 110

Thr Met Val Thr Val Ser Ser
        115
```

<210> SEQ ID NO 371
<211> LENGTH: 24
<212> TYPE: DNA
<213> ORGANISM: Artificial Sequence
<220> FEATURE:
<223> OTHER INFORMATION: synthetic

<400> SEQUENCE: 371

```
ggatacacct tcactagcta tgtt                                              24
```

<210> SEQ ID NO 372
<211> LENGTH: 8
<212> TYPE: PRT
<213> ORGANISM: Artificial Sequence
<220> FEATURE:
<223> OTHER INFORMATION: synthetic

<400> SEQUENCE: 372

Gly Tyr Thr Phe Thr Ser Tyr Val
1               5

<210> SEQ ID NO 373
<211> LENGTH: 24
<212> TYPE: DNA
<213> ORGANISM: Artificial Sequence
<220> FEATURE:
<223> OTHER INFORMATION: synthetic

<400> SEQUENCE: 373
agcaacgctg ccaatggtga caca                                    24

<210> SEQ ID NO 374
<211> LENGTH: 8
<212> TYPE: PRT
<213> ORGANISM: Artificial Sequence
<220> FEATURE:
<223> OTHER INFORMATION: synthetic

<400> SEQUENCE: 374

Ser Asn Ala Ala Asn Gly Asp Thr
1               5

<210> SEQ ID NO 375
<211> LENGTH: 36
<212> TYPE: DNA
<213> ORGANISM: Artificial Sequence
<220> FEATURE:
<223> OTHER INFORMATION: synthetic

<400> SEQUENCE: 375
gcgagatgga actggaacta cggggctttt gatatc                       36

<210> SEQ ID NO 376
<211> LENGTH: 12
<212> TYPE: PRT
<213> ORGANISM: Artificial Sequence
<220> FEATURE:
<223> OTHER INFORMATION: synthetic

<400> SEQUENCE: 376

Ala Arg Trp Asn Trp Asn Tyr Gly Ala Phe Asp Ile
1               5                   10

<210> SEQ ID NO 377
<211> LENGTH: 321
<212> TYPE: DNA
<213> ORGANISM: Artificial Sequence
<220> FEATURE:
<223> OTHER INFORMATION: synthetic

<400> SEQUENCE: 377
gacatccaga tgacccagtc tccatcctcc ctgtctgcat ctgtaggaga cagagtcacc    60
atcacttgcc aggcgagtca ggacattaac aattatttac attggtatca gcagaaatca   120
gggaaagccc ctaatctcct gatctacgat gcatccattt tggaaacagg ggtcccatca   180
aggttcagtg aagtggatc tgggacagat tttactttca ccatcagcag cctgcagcct   240
gaagatattg caacatatta ctgtcaacaa tatgataatc tcccgtacac ttttggccag   300
gggaccaagc tggagatcaa a                                            321

<210> SEQ ID NO 378
<211> LENGTH: 107
<212> TYPE: PRT

<213> ORGANISM: Artificial Sequence
<220> FEATURE:
<223> OTHER INFORMATION: synthetic

<400> SEQUENCE: 378

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Asn Asn Tyr
            20                  25                  30

Leu His Trp Tyr Gln Gln Lys Ser Gly Lys Ala Pro Asn Leu Leu Ile
        35                  40                  45

Tyr Asp Ala Ser Ile Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asp Asn Leu Pro Tyr
                85                  90                  95

Thr Phe Gly Gln Gly Thr Lys Leu Glu Ile Lys
            100                 105

<210> SEQ ID NO 379
<211> LENGTH: 18
<212> TYPE: DNA
<213> ORGANISM: Artificial Sequence
<220> FEATURE:
<223> OTHER INFORMATION: synthetic

<400> SEQUENCE: 379
caggacatta acaattat                                            18

<210> SEQ ID NO 380
<211> LENGTH: 6
<212> TYPE: PRT
<213> ORGANISM: Artificial Sequence
<220> FEATURE:
<223> OTHER INFORMATION: synthetic

<400> SEQUENCE: 380

Gln Asp Ile Asn Asn Tyr
1               5

<210> SEQ ID NO 381
<211> LENGTH: 9
<212> TYPE: DNA
<213> ORGANISM: Artificial Sequence
<220> FEATURE:
<223> OTHER INFORMATION: synthetic

<400> SEQUENCE: 381 gatgcatcc                                                       9

<210> SEQ ID NO 382
<211> LENGTH: 3
<212> TYPE: PRT
<213> ORGANISM: Artificial Sequence
<220> FEATURE:
<223> OTHER INFORMATION: synthetic

<400> SEQUENCE: 382

Asp Ala Ser
1

<210> SEQ ID NO 383

<211> LENGTH: 27
<212> TYPE: DNA
<213> ORGANISM: Artificial Sequence
<220> FEATURE:
<223> OTHER INFORMATION: synthetic

<400> SEQUENCE: 383
caacaatatg ataatctccc gtacact    27

<210> SEQ ID NO 384
<211> LENGTH: 9
<212> TYPE: PRT
<213> ORGANISM: Artificial Sequence
<220> FEATURE:
<223> OTHER INFORMATION: synthetic

<400> SEQUENCE: 384

Gln Gln Tyr Asp Asn Leu Pro Tyr Thr
1               5

<210> SEQ ID NO 385
<211> LENGTH: 363
<212> TYPE: DNA
<213> ORGANISM: Artificial Sequence
<220> FEATURE:
<223> OTHER INFORMATION: synthetic

<400> SEQUENCE: 385
caggtgcagc tggtggagtc tgggggaggc ttggtcaagc ctggagggtc cctgagactc    60
tcctgtgcag ccgctggatt caccttcagt gactactaca tgagctggat ccgccaggct   120
ccagggcagg ggctggagtg ggtttcatac attagtccta gtggtagtac cacatactac   180
gcagactctg tgcagggccg attcaccatt tccagggaca cgccaagag ctcactctat   240 ctgcaaatga acagcctgag agccgaggac acggccgtat attactgtgc gagaacagga   300
atacagctat ggtccgtcta ctttgactac tggggccagg gaaccctggt caccgtctcc   360
tca   363

<210> SEQ ID NO 386
<211> LENGTH: 121
<212> TYPE: PRT
<213> ORGANISM: Artificial Sequence
<220> FEATURE:
<223> OTHER INFORMATION: synthetic

<400> SEQUENCE: 386

Gln Val Gln Leu Val Glu Ser Gly Gly Gly Leu Val Lys Pro Gly Gly
1               5                   10                  15

Ser Leu Arg Leu Ser Cys Ala Ala Ala Gly Phe Thr Phe Ser Asp Tyr
            20                  25                  30

Tyr Met Ser Trp Ile Arg Gln Ala Pro Gly Gln Gly Leu Glu Trp Val
        35                  40                  45

Ser Tyr Ile Ser Pro Ser Gly Ser Thr Thr Tyr Tyr Ala Asp Ser Val
    50                  55                  60

Gln Gly Arg Phe Thr Ile Ser Arg Asp Asn Ala Lys Ser Ser Leu Tyr
65                  70                  75                  80

Leu Gln Met Asn Ser Leu Arg Ala Glu Asp Thr Ala Val Tyr Tyr Cys
                85                  90                  95

Ala Arg Thr Gly Ile Gln Leu Trp Ser Val Tyr Phe Asp Tyr Trp Gly
            100                 105                 110

Gln Gly Thr Leu Val Thr Val Ser Ser
        115                 120

<210> SEQ ID NO 387
<211> LENGTH: 24
<212> TYPE: DNA
<213> ORGANISM: Artificial Sequence
<220> FEATURE:
<223> OTHER INFORMATION: synthetic

<400> SEQUENCE: 387
ggattcacct tcagtgacta ctac                                              24

<210> SEQ ID NO 388
<211> LENGTH: 8
<212> TYPE: PRT
<213> ORGANISM: Artificial Sequence
<220> FEATURE:
<223> OTHER INFORMATION: synthetic

<400> SEQUENCE: 388

Gly Phe Thr Phe Ser Asp Tyr Tyr
1               5

<210> SEQ ID NO 389
<211> LENGTH: 24
<212> TYPE: DNA
<213> ORGANISM: Artificial Sequence
<220> FEATURE:
<223> OTHER INFORMATION: synthetic

<400> SEQUENCE: 389
attagtccta gtggtagtac caca                                              24

<210> SEQ ID NO 390
<211> LENGTH: 8
<212> TYPE: PRT
<213> ORGANISM: Artificial Sequence
<220> FEATURE:
<223> OTHER INFORMATION: synthetic

<400> SEQUENCE: 390

Ile Ser Pro Ser Gly Ser Thr Thr
1               5

<210> SEQ ID NO 391
<211> LENGTH: 42
<212> TYPE: DNA
<213> ORGANISM: Artificial Sequence
<220> FEATURE:
<223> OTHER INFORMATION: synthetic

<400> SEQUENCE: 391
gcgagaacag gaatacagct atggtccgtc tactttgact ac                          42

<210> SEQ ID NO 392
<211> LENGTH: 14
<212> TYPE: PRT
<213> ORGANISM: Artificial Sequence
<220> FEATURE:
<223> OTHER INFORMATION: synthetic

<400> SEQUENCE: 392

Ala Arg Thr Gly Ile Gln Leu Trp Ser Val Tyr Phe Asp Tyr
1               5                   10

<210> SEQ ID NO 393

<211> LENGTH: 318
<212> TYPE: DNA
<213> ORGANISM: Artificial Sequence
<220> FEATURE:
<223> OTHER INFORMATION: synthetic

<400> SEQUENCE: 393

```
gaaattgtga tgacgcagtc tccagccacc ctgtctgtgt ctccagggga aagagccgcc      60
ctctcctgca gggccagtca gagtgttagc agcgacttag cctggtacca gcagaaacct     120
ggccaggctc ccaggctctt aatctatggt gcatccacca gggccactgg tatcccagcc     180
aggttcagtg gcagtgggtc tgggacagag ttcactctca ccatcagcag cctgcagtct     240
gaagattttg cagtttatta ctgtcagcag tataataact ggcctacttt tggccagggg     300
accaagctgg agatcaaa                                                   318
```

<210> SEQ ID NO 394
<211> LENGTH: 106
<212> TYPE: PRT
<213> ORGANISM: Artificial Sequence
<220> FEATURE:
<223> OTHER INFORMATION: synthetic

<400> SEQUENCE: 394

```
Glu Ile Val Met Thr Gln Ser Pro Ala Thr Leu Ser Val Ser Pro Gly
1               5                   10                  15

Glu Arg Ala Ala Leu Ser Cys Arg Ala Ser Gln Ser Val Ser Ser Asp
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Thr
                85                  90                  95

Phe Gly Gln Gly Thr Lys Leu Glu Ile Lys
            100                 105
```

<210> SEQ ID NO 395
<211> LENGTH: 18
<212> TYPE: DNA
<213> ORGANISM: Artificial Sequence
<220> FEATURE:
<223> OTHER INFORMATION: synthetic

<400> SEQUENCE: 395

```
cagagtgtta gcagcgac                                                    18
```

<210> SEQ ID NO 396
<211> LENGTH: 6
<212> TYPE: PRT
<213> ORGANISM: Artificial Sequence
<220> FEATURE:
<223> OTHER INFORMATION: synthetic

<400> SEQUENCE: 396

```
Gln Ser Val Ser Ser Asp
1               5
```

<210> SEQ ID NO 397
<211> LENGTH: 9

```
<212> TYPE: DNA
<213> ORGANISM: Artificial Sequence
<220> FEATURE:
<223> OTHER INFORMATION: synthetic

<400> SEQUENCE: 397 ggtgcatcc                                                                      9

<210> SEQ ID NO 398
<211> LENGTH: 3
<212> TYPE: PRT
<213> ORGANISM: Artificial Sequence
<220> FEATURE:
<223> OTHER INFORMATION: synthetic

<400> SEQUENCE: 398

Gly Ala Ser
1

<210> SEQ ID NO 399
<211> LENGTH: 24
<212> TYPE: DNA
<213> ORGANISM: Artificial Sequence
<220> FEATURE:
<223> OTHER INFORMATION: synthetic

<400> SEQUENCE: 399
cagcagtata ataactggcc tact                                                    24

<210> SEQ ID NO 400
<211> LENGTH: 8
<212> TYPE: PRT
<213> ORGANISM: Artificial Sequence
<220> FEATURE:
<223> OTHER INFORMATION: synthetic

<400> SEQUENCE: 400

Gln Gln Tyr Asn Asn Trp Pro Thr
1               5

<210> SEQ ID NO 401
<211> LENGTH: 351
<212> TYPE: DNA
<213> ORGANISM: Artificial Sequence
<220> FEATURE:
<223> OTHER INFORMATION: synthetic

<400> SEQUENCE: 401
gaggtgcagc tggtggagtc tgggggaggc ttggtccagc ctgggggtc cctgagactc              60 tcctgtgcag cctctggatt caccttagt agccattgga tgagctgggt ccgccaggct             120
ccagggaagg ggctggagtg ggtggccaac ataaagcaag atggaagtga aaatactat             180 gtggactctg tgaagggccg attcaccatc tccagagaca acgccaagaa ctcactgtat            240
ctgcaaataa gcagcctgag agccgaggac acggctgtgt attactgtgc gagtaactgg            300
aacttcctct ttgacttctg gggccaggga accctggtca ccgtctcctc a                     351

<210> SEQ ID NO 402
<211> LENGTH: 117
<212> TYPE: PRT
<213> ORGANISM: Artificial Sequence
<220> FEATURE:
<223> OTHER INFORMATION: synthetic

<400> SEQUENCE: 402
```

-continued

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser His
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
50                  55                  60

Lys Gly Arg Phe Thr Ile Ser Arg Asp Asn Ala Lys Asn Ser Leu Tyr
65                  70                  75                  80

Leu Gln Ile Ser Ser Leu Arg Ala Glu Asp Thr Ala Val Tyr Tyr Cys
                85                  90                  95

Ala Ser Asn Trp Asn Phe Leu Phe Asp Phe Trp Gly Gln Gly Thr Leu
            100                 105                 110

Val Thr Val Ser Ser
        115
```

<210> SEQ ID NO 403
<211> LENGTH: 24
<212> TYPE: DNA
<213> ORGANISM: Artificial Sequence
<220> FEATURE:
<223> OTHER INFORMATION: synthetic

<400> SEQUENCE: 403
ggattcacct ttagtagcca ttgg                                      24

<210> SEQ ID NO 404
<211> LENGTH: 8
<212> TYPE: PRT
<213> ORGANISM: Artificial Sequence
<220> FEATURE:
<223> OTHER INFORMATION: synthetic

<400> SEQUENCE: 404

```
Gly Phe Thr Phe Ser Ser His Trp
1               5
```

<210> SEQ ID NO 405
<211> LENGTH: 24
<212> TYPE: DNA
<213> ORGANISM: Artificial Sequence
<220> FEATURE:
<223> OTHER INFORMATION: synthetic

<400> SEQUENCE: 405
ataaagcaag atggaagtga gaaa                                      24

<210> SEQ ID NO 406
<211> LENGTH: 8
<212> TYPE: PRT
<213> ORGANISM: Artificial Sequence
<220> FEATURE:
<223> OTHER INFORMATION: synthetic

<400> SEQUENCE: 406

```
Ile Lys Gln Asp Gly Ser Glu Lys
1               5
```

<210> SEQ ID NO 407
<211> LENGTH: 30
<212> TYPE: DNA
<213> ORGANISM: Artificial Sequence
<220> FEATURE:
<223> OTHER INFORMATION: synthetic

<400> SEQUENCE: 407
gcgagtaact ggaacttcct ctttgacttc                                30

<210> SEQ ID NO 408
<211> LENGTH: 10
<212> TYPE: PRT
<213> ORGANISM: Artificial Sequence
<220> FEATURE:
<223> OTHER INFORMATION: synthetic

<400> SEQUENCE: 408

Ala Ser Asn Trp Asn Phe Leu Phe Asp Phe
1               5                   10

<210> SEQ ID NO 409
<211> LENGTH: 339
<212> TYPE: DNA
<213> ORGANISM: Artificial Sequence
<220> FEATURE:
<223> OTHER INFORMATION: synthetic

<400> SEQUENCE: 409
gacatcgtga tgacccagtc tccagactcc ctggctgtgt ctctgggcga gagggccacc     60
atcaactgca gtccagcca gagtgtttta tacagctcca acaataagaa ctacttagct    120
tggtaccagc agaaaccagg acagcctcct aagctgctca tttactgggc atcgacccgg    180
gaatccgggg tccctgaccg attcagtggc agcgggtctg ggacagattt cactctcacc    240
atcagcagcc tgcaggctga agatgtggca gtttattact gtcagcaata ttatagtact    300
ccgctcactt tcggcggagg gaccaaggtg gagatcaaa                           339

<210> SEQ ID NO 410
<211> LENGTH: 113
<212> TYPE: PRT
<213> ORGANISM: Artificial Sequence
<220> FEATURE:
<223> OTHER INFORMATION: synthetic

<400> SEQUENCE: 410

Asp Ile Val Met Thr Gln Ser Pro Asp Ser Leu Ala Val Ser Leu Gly
1               5                   10                  15

Glu Arg Ala Thr Ile Asn Cys Lys Ser Gln Ser Val Leu Tyr Ser
                20                  25                  30

Ser Asn Asn Lys Asn Tyr Leu Ala Trp Tyr Gln Gln Lys Pro Gly Gln
            35                  40                  45

Pro Pro Lys Leu Leu Ile Tyr Trp Ala Ser Thr Arg Glu Ser Gly Val
        50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Leu Thr Phe Gly Gly Gly Thr Lys Val Glu Ile
            100                 105                 110

Lys

<210> SEQ ID NO 411
<211> LENGTH: 36
<212> TYPE: DNA

```
<213> ORGANISM: Artificial Sequence
<220> FEATURE:
<223> OTHER INFORMATION: synthetic

<400> SEQUENCE: 411
cagagtgttt tatacagctc caacaataag aactac                     36

<210> SEQ ID NO 412
<211> LENGTH: 12
<212> TYPE: PRT
<213> ORGANISM: Artificial Sequence
<220> FEATURE:
<223> OTHER INFORMATION: synthetic

<400> SEQUENCE: 412

Gln Ser Val Leu Tyr Ser Ser Asn Asn Lys Asn Tyr
1               5                   10

<210> SEQ ID NO 413
<211> LENGTH: 9
<212> TYPE: DNA
<213> ORGANISM: Artificial Sequence
<220> FEATURE:
<223> OTHER INFORMATION: synthetic

<400> SEQUENCE: 413 tgggcatcg                                                    9

<210> SEQ ID NO 414
<211> LENGTH: 3
<212> TYPE: PRT
<213> ORGANISM: Artificial Sequence
<220> FEATURE:
<223> OTHER INFORMATION: synthetic

<400> SEQUENCE: 414

Trp Ala Ser
1

<210> SEQ ID NO 415
<211> LENGTH: 27
<212> TYPE: DNA
<213> ORGANISM: Artificial Sequence
<220> FEATURE:
<223> OTHER INFORMATION: synthetic

<400> SEQUENCE: 415
cagcaatatt atagtactcc gctcact                               27

<210> SEQ ID NO 416
<211> LENGTH: 9
<212> TYPE: PRT
<213> ORGANISM: Artificial Sequence
<220> FEATURE:
<223> OTHER INFORMATION: synthetic

<400> SEQUENCE: 416

Gln Gln Tyr Tyr Ser Thr Pro Leu Thr
1               5

<210> SEQ ID NO 417
<211> LENGTH: 363
<212> TYPE: DNA
<213> ORGANISM: Artificial Sequence
<220> FEATURE:
<223> OTHER INFORMATION: synthetic
```

<400> SEQUENCE: 417

```
caggtgcagc tggtggagtc tgggggaggc gtggtccagc ctggggaggtc cctgagactc    60 tcctgtgtag cctctggatt cacgttcagt agttatggca tgcactgggt ccgccaggct   120
ccaggcaagg gctggagtg gtggcagtt atatcatttg atggaagtaa taaatactat   180
gcagactccg tgaagggccg attcaccatc tccagagaca attccaagaa cacgctgtat   240
ctgcaaatga acagcctgag acctgcggac acggctgtgt attattgcgc gaaagatagg   300
agtaactact attatttcgg tatggacgtc tggggccaag ggaccacggt caccgtctcc   360
tca                                                                   363
```

<210> SEQ ID NO 418
<211> LENGTH: 121
<212> TYPE: PRT
<213> ORGANISM: Artificial Sequence
<220> FEATURE:
<223> OTHER INFORMATION: synthetic

<400> SEQUENCE: 418

```
Gln Val Gln Leu Val Glu Ser Gly Gly Gly Val Val Gln Pro Gly Arg
1               5                   10                  15

Ser Leu Arg Leu Ser Cys Val Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Phe Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Ala Asp Thr Ala Val Tyr Tyr Cys
                85                  90                  95

Ala Lys Asp Arg Ser Asn Tyr Tyr Tyr Phe Gly Met Asp Val Trp Gly
            100                 105                 110

Gln Gly Thr Thr Val Thr Val Ser Ser
        115                 120
```

<210> SEQ ID NO 419
<211> LENGTH: 24
<212> TYPE: DNA
<213> ORGANISM: Artificial Sequence
<220> FEATURE:
<223> OTHER INFORMATION: synthetic

<400> SEQUENCE: 419

```
ggattcacgt tcagtagtta tggc                                            24
```

<210> SEQ ID NO 420
<211> LENGTH: 8
<212> TYPE: PRT
<213> ORGANISM: Artificial Sequence
<220> FEATURE:
<223> OTHER INFORMATION: synthetic

<400> SEQUENCE: 420

```
Gly Phe Thr Phe Ser Ser Tyr Gly
1               5
```

<210> SEQ ID NO 421
<211> LENGTH: 24
<212> TYPE: DNA

```
<213> ORGANISM: Artificial Sequence
<220> FEATURE:
<223> OTHER INFORMATION: synthetic

<400> SEQUENCE: 421
atatcatttg atggaagtaa taaa                                              24

<210> SEQ ID NO 422
<211> LENGTH: 8
<212> TYPE: PRT
<213> ORGANISM: Artificial Sequence
<220> FEATURE:
<223> OTHER INFORMATION: synthetic

<400> SEQUENCE: 422

Ile Ser Phe Asp Gly Ser Asn Lys
1               5

<210> SEQ ID NO 423
<211> LENGTH: 42
<212> TYPE: DNA
<213> ORGANISM: Artificial Sequence
<220> FEATURE:
<223> OTHER INFORMATION: synthetic

<400> SEQUENCE: 423
gcgaaagata ggagtaacta ctattatttc ggtatggacg tc                          42

<210> SEQ ID NO 424
<211> LENGTH: 14
<212> TYPE: PRT
<213> ORGANISM: Artificial Sequence
<220> FEATURE:
<223> OTHER INFORMATION: synthetic

<400> SEQUENCE: 424

Ala Lys Asp Arg Ser Asn Tyr Tyr Tyr Phe Gly Met Asp Val
1               5                   10

<210> SEQ ID NO 425
<211> LENGTH: 339
<212> TYPE: DNA
<213> ORGANISM: Artificial Sequence
<220> FEATURE:
<223> OTHER INFORMATION: synthetic

<400> SEQUENCE: 425
gatattgtga tgacccagac tccactctcc ctgcccgtca cccctggaga gccggcctcc        60
atctcctgca ggtctagtca gagcctcttg gatagtgatg atggaaacac ctatttggac       120
tggtacctgc agaagccagg gcagtctcca cagctcctga tctatacgct ttcctatcgg       180
gcctctggag tcccagacag gttcagtggc agtgggtcag gcactgattt cacactgaaa       240
atcagcaggg tggaggctga ggatgttgga gtttattact gcatgcaacg tatagagttt       300
ccgctcactt tcggcggagg gaccaaggtg gagatcaaa                              339

<210> SEQ ID NO 426
<211> LENGTH: 113
<212> TYPE: PRT
<213> ORGANISM: Artificial Sequence
<220> FEATURE:
<223> OTHER INFORMATION: synthetic

<400> SEQUENCE: 426

Asp Ile Val Met Thr Gln Thr Pro Leu Ser Leu Pro Val Thr Pro Gly
```

```
                1               5                  10                 15
            Glu Pro Ala Ser Ile Ser Cys Arg Ser Ser Gln Ser Leu Leu Asp Ser
                            20                  25                  30

Asp Asp Gly Asn Thr Tyr Leu Asp Trp Tyr Leu Gln Lys Pro Gly Gln
                        35                  40                  45

Ser Pro Gln Leu Leu Ile Tyr Thr Leu Ser Tyr Arg Ala Ser Gly Val
                    50                  55                  60

Pro Asp Arg Phe Ser Gly Ser Gly Ser Gly Thr Asp Phe Thr Leu Lys
             65                  70                  75                  80

Ile Ser Arg Val Glu Ala Glu Asp Val Gly Val Tyr Tyr Cys Met Gln
                            85                  90                  95

Arg Ile Glu Phe Pro Leu Thr Phe Gly Gly Thr Lys Val Glu Ile
                        100                 105                 110
            Lys
```

<210> SEQ ID NO 427
<211> LENGTH: 36
<212> TYPE: DNA
<213> ORGANISM: Artificial Sequence
<220> FEATURE:
<223> OTHER INFORMATION: synthetic

<400> SEQUENCE: 427
cagagcctct tggatagtga tgatggaaac acctat                    36

<210> SEQ ID NO 428
<211> LENGTH: 12
<212> TYPE: PRT
<213> ORGANISM: Artificial Sequence
<220> FEATURE:
<223> OTHER INFORMATION: synthetic

<400> SEQUENCE: 428

```
Gln Ser Leu Leu Asp Ser Asp Asp Gly Asn Thr Tyr
1               5                   10
```

<210> SEQ ID NO 429
<211> LENGTH: 9
<212> TYPE: DNA
<213> ORGANISM: Artificial Sequence
<220> FEATURE:
<223> OTHER INFORMATION: synthetic

<400> SEQUENCE: 429 acgctttcc                                                   9

<210> SEQ ID NO 430
<211> LENGTH: 3
<212> TYPE: PRT
<213> ORGANISM: Artificial Sequence
<220> FEATURE:
<223> OTHER INFORMATION: synthetic

<400> SEQUENCE: 430

```
Thr Leu Ser
1
```

<210> SEQ ID NO 431
<211> LENGTH: 27
<212> TYPE: DNA
<213> ORGANISM: Artificial Sequence
<220> FEATURE:
<223> OTHER INFORMATION: synthetic

<400> SEQUENCE: 431
atgcaacgta tagagtttcc gctcact                                27

<210> SEQ ID NO 432
<211> LENGTH: 9
<212> TYPE: PRT
<213> ORGANISM: Artificial Sequence
<220> FEATURE:
<223> OTHER INFORMATION: synthetic

<400> SEQUENCE: 432

Met Gln Arg Ile Glu Phe Pro Leu Thr
1               5

<210> SEQ ID NO 433
<211> LENGTH: 733
<212> TYPE: PRT
<213> ORGANISM: Artificial Sequence
<220> FEATURE:
<223> OTHER INFORMATION: synthetic

<400> SEQUENCE: 433

Met Trp Ser Trp Lys Cys Leu Leu Phe Trp Ala Val Leu Val Thr Ala
1               5                   10                  15

Thr Leu Cys Thr Ala Arg Pro Ser Pro Thr Leu Pro Glu Gln Asp Ala
                20                  25                  30

Leu Pro Ser Ser Glu Asp Asp Asp Asp Asp Asp Ser Ser Ser Glu
            35                  40                  45

Glu Lys Glu Thr Asp Asn Thr Lys Pro Asn Arg Met Pro Val Ala Pro
    50                  55                  60

Tyr Trp Thr Ser Pro Glu Lys Met Glu Lys Lys Leu His Ala Val Pro
65                  70                  75                  80

Ala Ala Lys Thr Val Lys Phe Lys Cys Pro Ser Ser Gly Thr Pro Asn
                85                  90                  95

Pro Thr Leu Arg Trp Leu Lys Asn Gly Lys Glu Phe Lys Pro Asp His
            100                 105                 110

Arg Ile Gly Gly Tyr Lys Val Arg Tyr Ala Thr Trp Ser Ile Ile Met
        115                 120                 125

Asp Ser Val Val Pro Ser Asp Lys Gly Asn Tyr Thr Cys Ile Val Glu
    130                 135                 140

Asn Glu Tyr Gly Ser Ile Asn His Thr Tyr Gln Leu Asp Val Val Glu
145                 150                 155                 160

Arg Ser Pro His Arg Pro Ile Leu Gln Ala Gly Leu Pro Ala Asn Lys
                165                 170                 175

Thr Val Ala Leu Gly Ser Asn Val Glu Phe Met Cys Lys Val Tyr Ser
            180                 185                 190

Asp Pro Gln Pro His Ile Gln Trp Leu Lys His Ile Glu Val Asn Gly
        195                 200                 205

Ser Lys Ile Gly Pro Asp Asn Leu Pro Tyr Val Gln Ile Leu Lys Thr
    210                 215                 220

Ala Gly Val Asn Thr Thr Asp Lys Glu Met Glu Val Leu His Leu Arg
225                 230                 235                 240

Asn Val Ser Phe Glu Asp Ala Gly Glu Tyr Thr Cys Leu Ala Gly Asn
                245                 250                 255

Ser Ile Gly Leu Ser His His Ser Ala Trp Leu Thr Val Leu Glu Ala
            260                 265                 270

```
Leu Glu Glu Arg Pro Ala Val Met Thr Ser Pro Leu Tyr Leu Glu Ile
            275                 280                 285

Ile Ile Tyr Cys Thr Gly Ala Phe Leu Ile Ser Cys Met Val Gly Ser
        290                 295                 300

Val Ile Val Tyr Lys Met Lys Ser Gly Thr Lys Lys Ser Asp Phe His
305                 310                 315                 320

Ser Gln Met Ala Val His Lys Leu Ala Lys Ser Ile Pro Leu Arg Arg
                325                 330                 335

Gln Val Thr Val Ser Ala Asp Ser Ala Ser Met Asn Ser Gly Val
            340                 345                 350

Leu Leu Val Arg Pro Ser Arg Leu Ser Ser Ser Gly Thr Pro Met Leu
            355                 360                 365

Ala Gly Val Ser Glu Tyr Glu Leu Pro Glu Asp Pro Arg Trp Glu Leu
370                 375                 380

Pro Arg Asp Arg Leu Val Leu Gly Lys Pro Leu Gly Glu Gly Cys Phe
385                 390                 395                 400

Gly Gln Val Val Leu Ala Glu Ala Ile Gly Leu Asp Lys Asp Lys Pro
                405                 410                 415

Asn Arg Val Thr Lys Val Ala Val Lys Met Leu Lys Ser Asp Ala Thr
            420                 425                 430

Glu Lys Asp Leu Ser Asp Leu Ile Ser Glu Met Glu Met Met Lys Met
435                 440                 445

Ile Gly Lys His Lys Asn Ile Ile Asn Leu Leu Gly Ala Cys Thr Gln
        450                 455                 460

Asp Gly Pro Leu Tyr Val Ile Val Glu Tyr Ala Ser Lys Gly Asn Leu
465                 470                 475                 480

Arg Glu Tyr Leu Gln Ala Arg Arg Pro Pro Gly Leu Glu Tyr Cys Tyr
                485                 490                 495

Asn Pro Ser His Asn Pro Glu Glu Gln Leu Ser Ser Lys Asp Leu Val
            500                 505                 510

Ser Cys Ala Tyr Gln Val Ala Arg Gly Met Glu Tyr Leu Ala Ser Lys
        515                 520                 525

Lys Cys Ile His Arg Asp Leu Ala Ala Arg Asn Val Leu Val Thr Glu
    530                 535                 540

Asp Asn Val Met Lys Ile Ala Asp Phe Gly Leu Ala Arg Asp Ile His
545                 550                 555                 560

His Ile Asp Tyr Tyr Lys Lys Thr Thr Asn Gly Arg Leu Pro Val Lys
                565                 570                 575

Trp Met Ala Pro Glu Ala Leu Phe Asp Arg Ile Tyr Thr His Gln Ser
            580                 585                 590

Asp Val Trp Ser Phe Gly Val Leu Leu Trp Glu Ile Phe Thr Leu Gly
        595                 600                 605

Gly Ser Pro Tyr Pro Gly Val Pro Val Glu Glu Leu Phe Lys Leu Leu
    610                 615                 620

Lys Glu Gly His Arg Met Asp Lys Pro Ser Asn Cys Thr Asn Glu Leu
625                 630                 635                 640

Tyr Met Met Met Arg Asp Cys Trp His Ala Val Pro Ser Gln Arg Pro
                645                 650                 655

Thr Phe Lys Gln Leu Val Glu Asp Leu Asp Arg Ile Val Ala Leu Thr
            660                 665                 670

Ser Asn Gln Glu Tyr Leu Asp Leu Ser Met Pro Leu Asp Gln Tyr Ser
        675                 680                 685

Pro Ser Phe Pro Asp Thr Arg Ser Ser Thr Cys Ser Ser Gly Glu Asp
```

```
                690                 695                 700
Ser Val Phe Ser His Glu Pro Leu Pro Glu Pro Cys Leu Pro Arg
705                 710                 715                 720

His Pro Ala Gln Leu Ala Asn Gly Gly Leu Lys Arg Arg
                725                 730

<210> SEQ ID NO 434
<211> LENGTH: 1044
<212> TYPE: PRT
<213> ORGANISM: Artificial Sequence
<220> FEATURE:
<223> OTHER INFORMATION: synthetic

<400> SEQUENCE: 434

Met Lys Pro Gly Cys Ala Ala Gly Ser Pro Gly Asn Glu Trp Ile Phe
1               5                   10                  15

Phe Ser Thr Asp Glu Ile Thr Thr Arg Tyr Arg Asn Thr Met Ser Asn
                20                  25                  30

Gly Gly Leu Gln Arg Ser Val Ile Leu Ser Ala Leu Ile Leu Leu Arg
            35                  40                  45

Ala Val Thr Gly Phe Ser Gly Asp Gly Arg Ala Ile Trp Ser Lys Asn
50                  55                  60

Pro Asn Phe Thr Pro Val Asn Glu Ser Gln Leu Phe Leu Tyr Asp Thr
65                  70                  75                  80

Phe Pro Lys Asn Phe Phe Trp Gly Ile Gly Thr Gly Ala Leu Gln Val
                85                  90                  95

Glu Gly Ser Trp Lys Lys Asp Gly Lys Gly Pro Ser Ile Trp Asp His
            100                 105                 110

Phe Ile His Thr His Leu Lys Asn Val Ser Ser Thr Asn Gly Ser Ser
        115                 120                 125

Asp Ser Tyr Ile Phe Leu Glu Lys Asp Leu Ser Ala Leu Asp Phe Ile
    130                 135                 140

Gly Val Ser Phe Tyr Gln Phe Ser Ile Ser Trp Pro Arg Leu Phe Pro
145                 150                 155                 160

Asp Gly Ile Val Thr Val Ala Asn Ala Lys Gly Leu Gln Tyr Tyr Ser
                165                 170                 175

Thr Leu Leu Asp Ala Leu Val Leu Arg Asn Ile Glu Pro Ile Val Thr
            180                 185                 190

Leu Tyr His Trp Asp Leu Pro Leu Ala Leu Gln Glu Lys Tyr Gly Gly
        195                 200                 205

Trp Lys Asn Asp Thr Ile Ile Asp Ile Phe Asn Asp Tyr Ala Thr Tyr
    210                 215                 220

Cys Phe Gln Met Phe Gly Asp Arg Val Lys Tyr Trp Ile Thr Ile His
225                 230                 235                 240

Asn Pro Tyr Leu Val Ala Trp His Gly Tyr Gly Thr Gly Met His Ala
                245                 250                 255

Pro Gly Glu Lys Gly Asn Leu Ala Ala Val Tyr Thr Val Gly His Asn
            260                 265                 270

Leu Ile Lys Ala His Ser Lys Val Trp His Asn Tyr Asn Thr His Phe
        275                 280                 285

Arg Pro His Gln Lys Gly Trp Leu Ser Ile Thr Leu Gly Ser His Trp
    290                 295                 300

Ile Glu Pro Asn Arg Ser Glu Asn Thr Met Asp Ile Phe Lys Cys Gln
305                 310                 315                 320

Gln Ser Met Val Ser Val Leu Gly Trp Phe Ala Asn Pro Ile His Gly
```

```
                    325                 330                 335
Asp Gly Asp Tyr Pro Glu Gly Met Arg Lys Lys Leu Phe Ser Val Leu
                340                 345                 350

Pro Ile Phe Ser Glu Ala Glu Lys His Glu Met Arg Gly Thr Ala Asp
                355                 360                 365

Phe Phe Ala Phe Ser Phe Gly Pro Asn Asn Phe Lys Pro Leu Asn Thr
370                 375                 380

Met Ala Lys Met Gly Gln Asn Val Ser Leu Asn Leu Arg Glu Ala Leu
385                 390                 395                 400

Asn Trp Ile Lys Leu Glu Tyr Asn Asn Pro Arg Ile Leu Ile Ala Glu
                405                 410                 415

Asn Gly Trp Phe Thr Asp Ser Arg Val Lys Thr Glu Asp Thr Thr Ala
                420                 425                 430

Ile Tyr Met Met Lys Asn Phe Leu Ser Gln Val Leu Gln Ala Ile Arg
                435                 440                 445

Leu Asp Glu Ile Arg Val Phe Gly Tyr Thr Ala Trp Ser Leu Leu Asp
                450                 455                 460

Gly Phe Glu Trp Gln Asp Ala Tyr Thr Ile Arg Arg Gly Leu Phe Tyr
465                 470                 475                 480

Val Asp Phe Asn Ser Lys Gln Lys Glu Arg Lys Pro Lys Ser Ser Ala
                485                 490                 495

His Tyr Tyr Lys Gln Ile Ile Arg Glu Asn Gly Phe Ser Leu Lys Glu
                500                 505                 510

Ser Thr Pro Asp Val Gln Gly Gln Phe Pro Cys Asp Phe Ser Trp Gly
                515                 520                 525

Val Thr Glu Ser Val Leu Lys Pro Glu Ser Val Ala Ser Ser Pro Gln
                530                 535                 540

Phe Ser Asp Pro His Leu Tyr Val Trp Asn Ala Thr Gly Asn Arg Leu
545                 550                 555                 560

Leu His Arg Val Glu Gly Val Arg Leu Lys Thr Arg Pro Ala Gln Cys
                565                 570                 575

Thr Asp Phe Val Asn Ile Lys Lys Gln Leu Glu Met Leu Ala Arg Met
                580                 585                 590

Lys Val Thr His Tyr Arg Phe Ala Leu Asp Trp Ala Ser Val Leu Pro
                595                 600                 605

Thr Gly Asn Leu Ser Ala Val Asn Arg Gln Ala Leu Arg Tyr Tyr Arg
                610                 615                 620

Cys Val Val Ser Glu Gly Leu Lys Leu Gly Ile Ser Ala Met Val Thr
625                 630                 635                 640

Leu Tyr Tyr Pro Thr His Ala His Leu Gly Leu Pro Glu Pro Leu Leu
                645                 650                 655

His Ala Asp Gly Trp Leu Asn Pro Ser Thr Ala Glu Ala Phe Gln Ala
                660                 665                 670

Tyr Ala Gly Leu Cys Phe Gln Glu Leu Gly Asp Leu Val Lys Leu Trp
                675                 680                 685

Ile Thr Ile Asn Glu Pro Asn Arg Leu Ser Asp Ile Tyr Asn Arg Ser
                690                 695                 700

Gly Asn Asp Thr Tyr Gly Ala Ala His Asn Leu Leu Val Ala His Ala
705                 710                 715                 720

Leu Ala Trp Arg Leu Tyr Asp Arg Gln Phe Arg Pro Ser Gln Arg Gly
                725                 730                 735

Ala Val Ser Leu Ser Leu His Ala Asp Trp Ala Glu Pro Ala Asn Pro
                740                 745                 750
```

```
Tyr Ala Asp Ser His Trp Arg Ala Glu Arg Phe Leu Gln Phe Glu
        755                 760                 765
Ile Ala Trp Phe Ala Glu Pro Leu Phe Lys Thr Gly Asp Tyr Pro Ala
770                 775                 780
Ala Met Arg Glu Tyr Ile Ala Ser Lys His Arg Arg Gly Leu Ser Ser
785                 790                 795                 800
Ser Ala Leu Pro Arg Leu Thr Glu Ala Glu Arg Leu Leu Lys Gly
                805                 810                 815
Thr Val Asp Phe Cys Ala Leu Asn His Phe Thr Thr Arg Phe Val Met
            820                 825                 830
His Glu Gln Leu Ala Gly Ser Arg Tyr Asp Ser Asp Arg Asp Ile Gln
        835                 840                 845
Phe Leu Gln Asp Ile Thr Arg Leu Ser Ser Pro Thr Arg Leu Ala Val
        850                 855                 860
Ile Pro Trp Gly Val Arg Lys Leu Leu Arg Trp Val Arg Arg Asn Tyr
865                 870                 875                 880
Gly Asp Met Asp Ile Tyr Ile Thr Ala Ser Gly Ile Asp Asp Gln Ala
                885                 890                 895
Leu Glu Asp Asp Arg Leu Arg Lys Tyr Tyr Leu Gly Lys Tyr Leu Gln
            900                 905                 910
Glu Val Leu Lys Ala Tyr Leu Ile Asp Lys Val Arg Ile Lys Gly Tyr
        915                 920                 925
Tyr Ala Phe Lys Leu Ala Glu Glu Lys Ser Lys Pro Arg Phe Gly Phe
    930                 935                 940
Phe Thr Ser Asp Phe Lys Ala Lys Ser Ser Ile Gln Phe Tyr Asn Lys
945                 950                 955                 960
Val Ile Ser Ser Arg Gly Phe Pro Phe Glu Asn Ser Ser Arg Cys
                965                 970                 975
Ser Gln Thr Gln Glu Asn Thr Glu Cys Thr Val Cys Leu Phe Leu Val
            980                 985                 990
Gln Lys Lys Pro Leu Ile Phe Leu Gly Cys Cys Phe Phe Ser Thr Leu
        995                 1000                1005
Val Leu Leu Leu Ser Ile Ala Ile Phe Gln Arg Gln Lys Arg Arg Lys
    1010                1015                1020
Phe Trp Lys Ala Lys Asn Leu Gln His Ile Pro Leu Lys Lys Gly Lys
1025                1030                1035                1040
Arg Val Val Ser
```

<210> SEQ ID NO 435
<211> LENGTH: 209
<212> TYPE: PRT
<213> ORGANISM: Artificial Sequence
<220> FEATURE:
<223> OTHER INFORMATION: synthetic

<400> SEQUENCE: 435

```
Met Asp Ser Asp Glu Thr Gly Phe Glu His Ser Gly Leu Trp Val Ser
1               5                   10                  15
Val Leu Ala Gly Leu Leu Leu Gly Ala Cys Gln Ala His Pro Ile Pro
            20                  25                  30
Asp Ser Ser Pro Leu Leu Gln Phe Gly Gly Gln Val Arg Gln Arg Tyr
        35                  40                  45
Leu Tyr Thr Asp Asp Ala Gln Gln Thr Glu Ala His Leu Glu Ile Arg
    50                  55                  60
```

```
Glu Asp Gly Thr Val Gly Gly Ala Ala Asp Gln Ser Pro Glu Ser Leu
 65                  70                  75                  80

Leu Gln Leu Lys Ala Leu Lys Pro Gly Val Ile Gln Ile Leu Gly Val
                 85                  90                  95

Lys Thr Ser Arg Phe Leu Cys Gln Arg Pro Asp Gly Ala Leu Tyr Gly
            100                 105                 110

Ser Leu His Phe Asp Pro Glu Ala Cys Ser Phe Arg Glu Leu Leu Leu
        115                 120                 125

Glu Asp Gly Tyr Asn Val Tyr Gln Ser Glu Ala His Gly Leu Pro Leu
    130                 135                 140

His Leu Pro Gly Asn Lys Ser Pro His Arg Asp Pro Ala Pro Arg Gly
145                 150                 155                 160

Pro Ala Arg Phe Leu Pro Leu Pro Gly Leu Pro Pro Ala Leu Pro Glu
                165                 170                 175

Pro Pro Gly Ile Leu Ala Pro Gln Pro Pro Asp Val Gly Ser Ser Asp
            180                 185                 190

Pro Leu Ser Met Val Gly Pro Ser Gln Gly Arg Ser Pro Ser Tyr Ala
        195                 200                 205

Ser

<210> SEQ ID NO 436
<211> LENGTH: 187
<212> TYPE: PRT
<213> ORGANISM: Artificial Sequence
<220> FEATURE:
<223> OTHER INFORMATION: synthetic

<400> SEQUENCE: 436

His His His His His His Pro Ile Pro Asp Ser Ser Pro Leu Leu
1               5                   10                  15

Gln Phe Gly Gly Gln Val Arg Gln Arg Tyr Leu Tyr Thr Asp Asp Ala
                20                  25                  30

Gln Gln Thr Glu Ala His Leu Glu Ile Arg Glu Asp Gly Thr Val Gly
            35                  40                  45

Gly Ala Ala Asp Gln Ser Pro Glu Ser Leu Leu Gln Leu Lys Ala Leu
 50                  55                  60

Lys Pro Gly Val Ile Gln Ile Leu Gly Val Lys Thr Ser Arg Phe Leu
 65                  70                  75                  80

Cys Gln Arg Pro Asp Gly Ala Leu Tyr Gly Ser Leu His Phe Asp Pro
                 85                  90                  95

Glu Ala Cys Ser Phe Arg Glu Leu Leu Leu Glu Asp Gly Tyr Asn Val
            100                 105                 110

Tyr Gln Ser Glu Ala His Gly Leu Pro Leu His Leu Pro Gly Asn Lys
        115                 120                 125

Ser Pro His Arg Asp Pro Ala Pro Arg Gly Pro Ala Arg Phe Leu Pro
    130                 135                 140

Leu Pro Gly Leu Pro Pro Ala Leu Pro Glu Pro Pro Gly Ile Leu Ala
145                 150                 155                 160

Pro Gln Pro Pro Asp Val Gly Ser Ser Asp Pro Leu Ser Met Val Gly
                165                 170                 175

Pro Ser Gln Gly Arg Ser Pro Ser Tyr Ala Ser
                180                 185

<210> SEQ ID NO 437
<211> LENGTH: 187
<212> TYPE: PRT
```

<213> ORGANISM: Artificial Sequence
<220> FEATURE:
<223> OTHER INFORMATION: synthetic

<400> SEQUENCE: 437

```
His His His His His His Pro Ile Pro Asp Ser Ser Pro Leu Leu
1               5                   10                  15

Gln Phe Gly Gly Gln Val Arg Gln Arg Tyr Leu Tyr Thr Asp Asp Ala
                20                  25                  30

Gln Gln Thr Glu Ala His Leu Glu Ile Arg Glu Asp Gly Thr Val Gly
            35                  40                  45

Gly Ala Ala His Glu Ser Pro Glu Ser Leu Leu Glu Leu Lys Ala Leu
50                  55                  60

Lys Pro Gly Val Ile Glu Ile Leu Gly Val Lys Thr Ser Arg Phe Leu
65                  70                  75                  80

Cys Gln Lys Pro Asp Gly Ala Leu Tyr Gly Ser Leu His Phe Asp Pro
                85                  90                  95

Glu Ala Cys Ser Phe Arg Glu Leu Leu Leu Glu Asn Gly Tyr Asn Val
            100                 105                 110

Tyr Glu Ser Glu Ala His Gly Leu Pro Leu His Leu Pro Gly Asn Lys
        115                 120                 125

Ser Pro His Arg Asp Pro Ala Ser Glu Gly Pro Ala Arg Phe Leu Pro
130                 135                 140

Leu Pro Gly Leu Pro Pro Ala Pro Pro Glu Pro Pro Gly Ile Leu Ala
145                 150                 155                 160

Pro Glu Pro Pro Asp Val Gly Ser Ser Asp Pro Leu Ser Met Val Gly
                165                 170                 175

Pro Ser Glu Ala Arg Ser Pro Ser Tyr Ala Ser
            180                 185
```

<210> SEQ ID NO 438
<211> LENGTH: 1059
<212> TYPE: PRT
<213> ORGANISM: Artificial Sequence
<220> FEATURE:
<223> OTHER INFORMATION: synthetic

<400> SEQUENCE: 438

```
Met Lys Pro Gly Cys Ala Ala Gly Ser Pro Gly Asn Glu Trp Ile Phe
1               5                   10                  15

Phe Ser Thr Asp Glu Ile Thr Thr Arg Tyr Arg Asn Thr Met Ser Asn
                20                  25                  30

Gly Gly Leu Gln Arg Ser Val Ile Leu Ser Ala Leu Ile Leu Leu Arg
            35                  40                  45

Ala Val Thr Gly Phe Ser Gly Asp Gly Arg Ala Ile Trp Ser Lys Asn
50                  55                  60

Pro Asn Phe Thr Pro Val Asn Glu Ser Gln Leu Phe Leu Tyr Asp Thr
65                  70                  75                  80

Phe Pro Lys Asn Phe Phe Trp Gly Ile Gly Thr Gly Ala Leu Gln Val
                85                  90                  95

Glu Gly Ser Trp Lys Lys Asp Gly Lys Gly Pro Ser Ile Trp Asp His
            100                 105                 110

Phe Ile His Thr His Leu Lys Asn Val Ser Ser Thr Asn Gly Ser Ser
        115                 120                 125

Asp Ser Tyr Ile Phe Leu Glu Lys Asp Leu Ser Ala Leu Asp Phe Ile
        130                 135                 140
```

```
Gly Val Ser Phe Tyr Gln Phe Ser Ile Ser Trp Pro Arg Leu Phe Pro
145                 150                 155                 160

Asp Gly Ile Val Thr Val Ala Asn Ala Lys Gly Leu Gln Tyr Tyr Ser
            165                 170                 175

Thr Leu Leu Asp Ala Leu Val Leu Arg Asn Ile Glu Pro Ile Val Thr
                180                 185                 190

Leu Tyr His Trp Asp Leu Pro Leu Ala Leu Gln Glu Lys Tyr Gly Gly
        195                 200                 205

Trp Lys Asn Asp Thr Ile Ile Asp Ile Phe Asn Asp Tyr Ala Thr Tyr
    210                 215                 220

Cys Phe Gln Met Phe Gly Asp Arg Val Lys Tyr Trp Ile Thr Ile His
225                 230                 235                 240

Asn Pro Tyr Leu Val Ala Trp His Gly Tyr Gly Thr Gly Met His Ala
                245                 250                 255

Pro Gly Glu Lys Gly Asn Leu Ala Ala Val Tyr Thr Val Gly His Asn
                260                 265                 270

Leu Ile Lys Ala His Ser Lys Val Trp His Asn Tyr Asn Thr His Phe
        275                 280                 285

Arg Pro His Gln Lys Gly Trp Leu Ser Ile Thr Leu Gly Ser His Trp
    290                 295                 300

Ile Glu Pro Asn Arg Ser Glu Asn Thr Met Asp Ile Phe Lys Cys Gln
305                 310                 315                 320

Gln Ser Met Val Ser Val Leu Gly Trp Phe Ala Asn Pro Ile His Gly
                325                 330                 335

Asp Gly Asp Tyr Pro Glu Gly Met Arg Lys Lys Leu Phe Ser Val Leu
                340                 345                 350

Pro Ile Phe Ser Glu Ala Glu Lys His Glu Met Arg Gly Thr Ala Asp
        355                 360                 365

Phe Phe Ala Phe Ser Phe Gly Pro Asn Asn Phe Lys Pro Leu Asn Thr
    370                 375                 380

Met Ala Lys Met Gly Gln Asn Val Ser Leu Asn Leu Arg Glu Ala Leu
385                 390                 395                 400

Asn Trp Ile Lys Leu Glu Tyr Asn Asn Pro Arg Ile Leu Ile Ala Glu
                405                 410                 415

Asn Gly Trp Phe Thr Asp Ser Arg Val Lys Thr Glu Asp Thr Thr Ala
                420                 425                 430

Ile Tyr Met Met Lys Asn Phe Leu Ser Gln Val Leu Gln Ala Ile Arg
        435                 440                 445

Leu Asp Glu Ile Arg Val Phe Gly Tyr Thr Ala Trp Ser Leu Leu Asp
    450                 455                 460

Gly Phe Glu Trp Gln Asp Ala Tyr Thr Ile Arg Arg Gly Leu Phe Tyr
465                 470                 475                 480

Val Asp Phe Asn Ser Lys Gln Lys Glu Arg Lys Pro Lys Ser Ser Ala
                485                 490                 495

His Tyr Tyr Lys Gln Ile Ile Arg Glu Asn Gly Phe Ser Leu Lys Glu
                500                 505                 510

Ser Thr Pro Asp Val Gln Gly Gln Phe Pro Cys Asp Phe Ser Trp Gly
        515                 520                 525

Val Thr Glu Ser Val Leu Lys Pro Glu Ser Val Ala Ser Ser Pro Gln
    530                 535                 540

Phe Ser Asp Pro His Leu Tyr Val Trp Asn Ala Thr Gly Asn Arg Leu
545                 550                 555                 560

Leu His Arg Val Glu Gly Val Arg Leu Lys Thr Arg Pro Ala Gln Cys
```

-continued

```
                565                 570                 575

Thr Asp Phe Val Asn Ile Lys Lys Gln Leu Glu Met Leu Ala Arg Met
            580                 585                 590

Lys Val Thr His Tyr Arg Phe Ala Leu Asp Trp Ala Ser Val Leu Pro
            595                 600                 605

Thr Gly Asn Leu Ser Ala Val Asn Arg Gln Ala Leu Arg Tyr Tyr Arg
            610                 615                 620

Cys Val Val Ser Glu Gly Leu Lys Leu Gly Ile Ser Ala Met Val Thr
625                 630                 635                 640

Leu Tyr Tyr Pro Thr His Ala His Leu Gly Leu Pro Glu Pro Leu Leu
            645                 650                 655

His Ala Asp Gly Trp Leu Asn Pro Ser Thr Ala Glu Ala Phe Gln Ala
            660                 665                 670

Tyr Ala Gly Leu Cys Phe Gln Glu Leu Gly Asp Leu Val Lys Leu Trp
            675                 680                 685

Ile Thr Ile Asn Glu Pro Asn Arg Leu Ser Asp Ile Tyr Asn Arg Ser
            690                 695                 700

Gly Asn Asp Thr Tyr Gly Ala Ala His Asn Leu Leu Val Ala His Ala
705                 710                 715                 720

Leu Ala Trp Arg Leu Tyr Asp Arg Gln Phe Arg Pro Ser Gln Arg Gly
            725                 730                 735

Ala Val Ser Leu Ser Leu His Ala Asp Trp Ala Glu Pro Ala Asn Pro
            740                 745                 750

Tyr Ala Asp Ser His Trp Arg Ala Ala Glu Arg Phe Leu Gln Phe Glu
            755                 760                 765

Ile Ala Trp Phe Ala Glu Pro Leu Phe Lys Thr Gly Asp Tyr Pro Ala
            770                 775                 780

Ala Met Arg Glu Tyr Ile Ala Ser Lys His Arg Arg Gly Leu Ser Ser
785                 790                 795                 800

Ser Ala Leu Pro Arg Leu Thr Glu Ala Glu Arg Arg Leu Leu Lys Gly
            805                 810                 815

Thr Val Asp Phe Cys Ala Leu Asn His Phe Thr Thr Arg Phe Val Met
            820                 825                 830

His Glu Gln Leu Ala Gly Ser Arg Tyr Asp Ser Asp Arg Asp Ile Gln
            835                 840                 845

Phe Leu Gln Asp Ile Thr Arg Leu Ser Ser Pro Thr Arg Leu Ala Val
            850                 855                 860

Ile Pro Trp Gly Val Arg Lys Leu Leu Arg Trp Val Arg Arg Asn Tyr
865                 870                 875                 880

Gly Asp Met Asp Ile Tyr Ile Thr Ala Ser Gly Ile Asp Asp Gln Ala
            885                 890                 895

Leu Glu Asp Asp Arg Leu Arg Lys Tyr Tyr Leu Gly Lys Tyr Leu Gln
            900                 905                 910

Glu Val Leu Lys Ala Tyr Leu Ile Asp Lys Val Arg Ile Lys Gly Tyr
            915                 920                 925

Tyr Ala Phe Lys Leu Ala Glu Glu Lys Ser Lys Pro Arg Phe Gly Phe
            930                 935                 940

Phe Thr Ser Asp Phe Lys Ala Lys Ser Ser Ile Gln Phe Tyr Asn Lys
945                 950                 955                 960

Val Ile Ser Ser Arg Gly Phe Pro Phe Glu Asn Ser Ser Arg Cys
            965                 970                 975

Ser Gln Thr Gln Glu Asn Thr Glu Cys Thr Val Cys Leu Phe Leu Val
            980                 985                 990
```

-continued

Gln Lys Lys Pro Leu Ile Phe Leu Gly Cys Cys Phe Ser Thr Leu
            995                 1000                1005

Val Leu Leu Ser Ile Ala Ile Phe Gln Arg Gln Lys Arg Arg Lys
    1010                1015                1020

Phe Trp Lys Ala Lys Asn Leu Gln His Ile Pro Leu Lys Gly Lys
1025                1030                1035                1040

Arg Val Val Ser Tyr Pro Tyr Asp Val Pro Asp Tyr Ala His His His
            1045                1050                1055

His His His

<210> SEQ ID NO 439
<211> LENGTH: 753
<212> TYPE: PRT
<213> ORGANISM: Artificial Sequence
<220> FEATURE:
<223> OTHER INFORMATION: synthetic

<400> SEQUENCE: 439

Met Trp Ser Trp Lys Cys Leu Leu Phe Trp Ala Val Leu Val Thr Ala
1               5                   10                  15

Thr Leu Cys Thr Ala Arg Pro Ser Pro Thr Leu Pro Glu Gln Asp Ala
            20                  25                  30

Leu Pro Ser Ser Glu Asp Asp Asp Asp Asp Asp Ser Ser Ser Glu
        35                  40                  45

Glu Lys Glu Thr Asp Asn Thr Lys Pro Asn Arg Met Pro Val Ala Pro
    50                  55                  60

Tyr Trp Thr Ser Pro Glu Lys Met Glu Lys Lys Leu His Ala Val Pro
65              70                  75                  80

Ala Ala Lys Thr Val Lys Phe Lys Cys Pro Ser Ser Gly Thr Pro Asn
                85                  90                  95

Pro Thr Leu Arg Trp Leu Lys Asn Gly Lys Glu Phe Lys Pro Asp His
            100                 105                 110

Arg Ile Gly Gly Tyr Lys Val Arg Tyr Ala Thr Trp Ser Ile Ile Met
        115                 120                 125

Asp Ser Val Val Pro Ser Asp Lys Gly Asn Tyr Thr Cys Ile Val Glu
    130                 135                 140

Asn Glu Tyr Gly Ser Ile Asn His Thr Tyr Gln Leu Asp Val Val Glu
145                 150                 155                 160

Arg Ser Pro His Arg Pro Ile Leu Gln Ala Gly Leu Pro Ala Asn Lys
                165                 170                 175

Thr Val Ala Leu Gly Ser Asn Val Glu Phe Met Cys Lys Val Tyr Ser
            180                 185                 190

Asp Pro Gln Pro His Ile Gln Trp Leu Lys His Ile Glu Val Asn Gly
        195                 200                 205

Ser Lys Ile Gly Pro Asp Asn Leu Pro Tyr Val Gln Ile Leu Lys Thr
    210                 215                 220

Ala Gly Val Asn Thr Thr Asp Lys Glu Met Glu Val Leu His Leu Arg
225                 230                 235                 240

Asn Val Ser Phe Glu Asp Ala Gly Glu Tyr Thr Cys Leu Ala Gly Asn
                245                 250                 255

Ser Ile Gly Leu Ser His His Ser Ala Trp Leu Thr Val Leu Glu Ala
            260                 265                 270

Leu Glu Glu Arg Pro Ala Val Met Thr Ser Pro Leu Tyr Leu Glu Ile
        275                 280                 285

```
Ile Ile Tyr Cys Thr Gly Ala Phe Leu Ile Ser Cys Met Val Gly Ser
    290                 295                 300
Val Ile Val Tyr Lys Met Lys Ser Gly Thr Lys Lys Ser Asp Phe His
305                 310                 315                 320
Ser Gln Met Ala Val His Lys Leu Ala Lys Ser Ile Pro Leu Arg Arg
                325                 330                 335
Gln Val Thr Val Ser Ala Asp Ser Ser Ala Ser Met Asn Ser Gly Val
                340                 345                 350
Leu Leu Val Arg Pro Ser Arg Leu Ser Ser Ser Gly Thr Pro Met Leu
            355                 360                 365
Ala Gly Val Ser Glu Tyr Glu Leu Pro Glu Asp Pro Arg Trp Glu Leu
370                 375                 380
Pro Arg Asp Arg Leu Val Leu Gly Lys Pro Leu Gly Glu Gly Cys Phe
385                 390                 395                 400
Gly Gln Val Val Leu Ala Glu Ala Ile Gly Leu Asp Lys Asp Lys Pro
                405                 410                 415
Asn Arg Val Thr Lys Val Ala Val Lys Met Leu Lys Ser Asp Ala Thr
                420                 425                 430
Glu Lys Asp Leu Ser Asp Leu Ile Ser Glu Met Glu Met Met Lys Met
            435                 440                 445
Ile Gly Lys His Lys Asn Ile Ile Asn Leu Leu Gly Ala Cys Thr Gln
450                 455                 460
Asp Gly Pro Leu Tyr Val Ile Val Glu Tyr Ala Ser Lys Gly Asn Leu
465                 470                 475                 480
Arg Glu Tyr Leu Gln Ala Arg Arg Pro Pro Gly Leu Glu Tyr Cys Tyr
                485                 490                 495
Asn Pro Ser His Asn Pro Glu Glu Gln Leu Ser Ser Lys Asp Leu Val
                500                 505                 510
Ser Cys Ala Tyr Gln Val Ala Arg Gly Met Glu Tyr Leu Ala Ser Lys
            515                 520                 525
Lys Cys Ile His Arg Asp Leu Ala Ala Arg Asn Val Leu Val Thr Glu
530                 535                 540
Asp Asn Val Met Lys Ile Ala Asp Phe Gly Leu Ala Arg Asp Ile His
545                 550                 555                 560
His Ile Asp Tyr Tyr Lys Lys Thr Thr Asn Gly Arg Leu Pro Val Lys
                565                 570                 575
Trp Met Ala Pro Glu Ala Leu Phe Asp Arg Ile Tyr Thr His Gln Ser
                580                 585                 590
Asp Val Trp Ser Phe Gly Val Leu Leu Trp Glu Ile Phe Thr Leu Gly
            595                 600                 605
Gly Ser Pro Tyr Pro Gly Val Pro Val Glu Glu Leu Phe Lys Leu Leu
610                 615                 620
Lys Glu Gly His Arg Met Asp Lys Pro Ser Asn Cys Thr Asn Glu Leu
625                 630                 635                 640
Tyr Met Met Met Arg Asp Cys Trp His Ala Val Pro Ser Gln Arg Pro
                645                 650                 655
Thr Phe Lys Gln Leu Val Glu Asp Leu Asp Arg Ile Val Ala Leu Thr
                660                 665                 670
Ser Asn Gln Glu Tyr Leu Asp Leu Ser Met Pro Leu Asp Gln Tyr Ser
            675                 680                 685
Pro Ser Phe Pro Asp Thr Arg Ser Ser Thr Cys Ser Ser Gly Glu Asp
690                 695                 700
Ser Val Phe Ser His Glu Pro Leu Pro Glu Glu Pro Cys Leu Pro Arg
```

```
                705                 710                 715                 720
His Pro Ala Gln Leu Ala Asn Gly Gly Leu Lys Arg Arg Gly Lys Pro
                    725                 730                 735

Ile Pro Asn Pro Leu Leu Gly Leu Asp Ser Thr His His His His
                    740                 745                 750

His

<210> SEQ ID NO 440
<211> LENGTH: 1012
<212> TYPE: PRT
<213> ORGANISM: Artificial Sequence
<220> FEATURE:
<223> OTHER INFORMATION: synthetic

<400> SEQUENCE: 440

Met Pro Ala Ser Ala Pro Pro Arg Arg Pro Arg Pro Pro Pro Pro Ser
1               5                   10                  15

Leu Ser Leu Leu Leu Val Leu Leu Gly Leu Gly Gly Arg Arg Leu Arg
                20                  25                  30

Ala Glu Pro Gly Asp Gly Ala Gln Thr Trp Ala Arg Phe Ser Arg Pro
            35                  40                  45

Pro Ala Pro Glu Ala Ala Gly Leu Phe Gln Gly Thr Phe Pro Asp Gly
        50                  55                  60

Phe Leu Trp Ala Val Gly Ser Ala Ala Tyr Gln Thr Glu Gly Gly Trp
65              70                  75                  80

Gln Gln His Gly Lys Gly Ala Ser Ile Trp Asp Thr Phe Thr His His
                85                  90                  95

Pro Leu Ala Pro Pro Gly Asp Ser Arg Asn Ala Ser Leu Pro Leu Gly
            100                 105                 110

Ala Pro Ser Pro Leu Gln Pro Ala Thr Gly Asp Val Ala Ser Asp Ser
        115                 120                 125

Tyr Asn Asn Val Phe Arg Asp Thr Glu Ala Leu Arg Glu Leu Gly Val
130                 135                 140

Thr His Tyr Arg Phe Ser Ile Ser Trp Ala Arg Val Leu Pro Asn Gly
145                 150                 155                 160

Ser Ala Gly Val Pro Asn Arg Glu Gly Leu Arg Tyr Tyr Arg Arg Leu
                165                 170                 175

Leu Glu Arg Leu Arg Glu Leu Gly Val Gln Pro Val Val Thr Leu Tyr
            180                 185                 190

His Trp Asp Leu Pro Gln Arg Leu Gln Asp Ala Tyr Gly Gly Trp Ala
        195                 200                 205

Asn Arg Ala Leu Ala Asp His Phe Arg Asp Tyr Ala Glu Leu Cys Phe
    210                 215                 220

Arg His Phe Gly Gly Gln Val Lys Tyr Trp Ile Thr Ile Asp Asn Pro
225                 230                 235                 240

Tyr Val Val Ala Trp His Gly Tyr Ala Thr Gly Arg Leu Ala Pro Gly
                245                 250                 255

Ile Arg Gly Ser Pro Arg Leu Gly Tyr Leu Val Ala His Asn Leu Leu
            260                 265                 270

Leu Ala His Ala Lys Val Trp His Leu Tyr Asn Thr Ser Phe Arg Pro
        275                 280                 285

Thr Gln Gly Gly Gln Val Ser Ile Ala Leu Ser Ser His Trp Ile Asn
    290                 295                 300

Pro Arg Arg Met Thr Asp His Ser Ile Lys Glu Cys Gln Lys Ser Leu
305                 310                 315                 320
```

-continued

```
Asp Phe Val Leu Gly Trp Phe Ala Lys Pro Val Phe Ile Asp Gly Asp
            325                 330                 335
Tyr Pro Glu Ser Met Lys Asn Asn Leu Ser Ser Ile Leu Pro Asp Phe
        340                 345                 350
Thr Glu Ser Glu Lys Lys Phe Ile Lys Gly Thr Ala Asp Phe Phe Ala
    355                 360                 365
Leu Cys Phe Gly Pro Thr Leu Ser Phe Gln Leu Leu Asp Pro His Met
370                 375                 380
Lys Phe Arg Gln Leu Glu Ser Pro Asn Leu Arg Gln Leu Leu Ser Trp
385                 390                 395                 400
Ile Asp Leu Glu Phe Asn His Pro Gln Ile Phe Ile Val Glu Asn Gly
            405                 410                 415
Trp Phe Val Ser Gly Thr Thr Lys Arg Asp Asp Ala Lys Tyr Met Tyr
        420                 425                 430
Tyr Leu Lys Lys Phe Ile Met Glu Thr Leu Lys Ala Ile Lys Leu Asp
    435                 440                 445
Gly Val Asp Val Ile Gly Tyr Thr Ala Trp Ser Leu Met Asp Gly Phe
450                 455                 460
Glu Trp His Arg Gly Tyr Ser Ile Arg Arg Gly Leu Phe Tyr Val Asp
465                 470                 475                 480
Phe Leu Ser Gln Asp Lys Met Leu Pro Lys Ser Ser Ala Leu Phe
            485                 490                 495
Tyr Gln Lys Leu Ile Glu Lys Asn Gly Phe Pro Pro Leu Pro Glu Asn
        500                 505                 510
Gln Pro Leu Glu Gly Thr Phe Pro Cys Asp Phe Ala Trp Gly Val Val
    515                 520                 525
Asp Asn Tyr Ile Gln Val Asp Thr Thr Leu Ser Gln Phe Thr Asp Leu
530                 535                 540
Asn Val Tyr Leu Trp Asp Val His His Ser Lys Arg Leu Ile Lys Val
545                 550                 555                 560
Asp Gly Val Val Thr Lys Lys Arg Lys Ser Tyr Cys Val Asp Phe Ala
            565                 570                 575
Ala Ile Gln Pro Gln Ile Ala Leu Leu Gln Glu Met His Val Thr His
        580                 585                 590
Phe Arg Phe Ser Leu Asp Trp Ala Leu Ile Leu Pro Leu Gly Asn Gln
    595                 600                 605
Ser Gln Val Asn His Thr Ile Leu Gln Tyr Tyr Arg Cys Met Ala Ser
610                 615                 620
Glu Leu Val Arg Val Asn Ile Thr Pro Val Val Ala Leu Trp Gln Pro
625                 630                 635                 640
Met Ala Pro Asn Gln Gly Leu Pro Arg Leu Leu Ala Arg Gln Gly Ala
            645                 650                 655
Trp Glu Asn Pro Tyr Thr Ala Leu Ala Phe Ala Glu Tyr Ala Arg Leu
        660                 665                 670
Cys Phe Gln Glu Leu Gly His His Val Lys Leu Trp Ile Thr Met Asn
    675                 680                 685
Glu Pro Tyr Thr Arg Asn Met Thr Tyr Ser Ala Gly His Asn Leu Leu
690                 695                 700
Lys Ala His Ala Leu Ala Trp His Val Tyr Asn Glu Lys Phe Arg His
705                 710                 715                 720
Ala Gln Asn Gly Lys Ile Ser Ile Ala Leu Gln Ala Asp Trp Ile Glu
            725                 730                 735
```

Pro Ala Cys Pro Phe Ser Gln Lys Asp Lys Glu Val Ala Glu Arg Val
                740                 745                 750

Leu Glu Phe Asp Ile Gly Trp Leu Ala Glu Pro Ile Phe Gly Ser Gly
            755                 760                 765

Asp Tyr Pro Trp Val Met Arg Asp Trp Leu Asn Gln Arg Asn Asn Phe
        770                 775                 780

Leu Leu Pro Tyr Phe Thr Glu Asp Glu Lys Lys Leu Ile Gln Gly Thr
785                 790                 795                 800

Phe Asp Phe Leu Ala Leu Ser His Tyr Thr Thr Ile Leu Val Asp Ser
                805                 810                 815

Glu Lys Glu Asp Pro Ile Lys Tyr Asn Asp Tyr Leu Gly Val Gln Glu
            820                 825                 830

Met Thr Asp Ile Thr Trp Leu Asn Ser Pro Ser Gln Val Ala Val Val
        835                 840                 845

Pro Trp Gly Leu Arg Lys Val Leu Asn Trp Leu Lys Phe Lys Tyr Gly
850                 855                 860

Asp Leu Pro Met Tyr Ile Ile Ser Asn Gly Ile Asp Asp Gly Leu His
865                 870                 875                 880

Ala Glu Asp Asp Gln Leu Arg Val Tyr Tyr Met Gln Asn Tyr Ile Asn
                885                 890                 895

Glu Ala Leu Lys Ala His Ile Leu Asp Gly Ile Asn Leu Cys Gly Tyr
            900                 905                 910

Phe Ala Tyr Ser Phe Asn Asp Arg Thr Ala Pro Arg Phe Gly Leu Tyr
        915                 920                 925

Arg Tyr Ala Ala Asp Gln Phe Glu Pro Lys Ala Ser Met Lys His Tyr
930                 935                 940

Arg Lys Ile Ile Asp Ser Asn Gly Phe Pro Gly Pro Glu Thr Leu Glu
945                 950                 955                 960

Arg Phe Cys Pro Glu Glu Phe Thr Val Cys Thr Glu Cys Ser Phe Phe
                965                 970                 975

His Thr Arg Lys Ser Leu Leu Ala Phe Ile Ala Phe Leu Phe Phe Ala
            980                 985                 990

Ser Ile Ile Ser Leu Ser Leu Ile Phe Tyr Tyr Ser Lys Lys Gly Arg
        995                 1000                1005

Arg Ser Tyr Lys
    1010

<210> SEQ ID NO 441
<211> LENGTH: 1043
<212> TYPE: PRT
<213> ORGANISM: Artificial Sequence
<220> FEATURE:
<223> OTHER INFORMATION: synthetic

<400> SEQUENCE: 441

Met Lys Thr Gly Cys Ala Ala Gly Ser Pro Gly Asn Glu Trp Ile Phe
1               5                   10                  15

Phe Ser Ser Asp Glu Arg Asn Thr Arg Ser Arg Lys Thr Met Ser Asn
                20                  25                  30

Arg Ala Leu Gln Arg Ser Ala Val Leu Ser Ala Phe Val Leu Leu Arg
            35                  40                  45

Ala Val Thr Gly Phe Ser Gly Asp Gly Lys Ala Ile Trp Asp Lys Lys
        50                  55                  60

Gln Tyr Val Ser Pro Val Asn Pro Ser Gln Leu Phe Leu Tyr Asp Thr
65                  70                  75                  80

Phe Pro Lys Asn Phe Ser Trp Gly Val Gly Thr Gly Ala Phe Gln Val
                85                  90                  95

Glu Gly Ser Trp Lys Thr Asp Gly Arg Gly Pro Ser Ile Trp Asp Arg
            100                 105                 110

Tyr Val Tyr Ser His Leu Arg Gly Val Asn Gly Thr Asp Arg Ser Thr
        115                 120                 125

Asp Ser Tyr Ile Phe Leu Glu Lys Asp Leu Leu Ala Leu Asp Phe Leu
    130                 135                 140

Gly Val Ser Phe Tyr Gln Phe Ser Ile Ser Trp Pro Arg Leu Phe Pro
145                 150                 155                 160

Asn Gly Thr Val Ala Ala Val Asn Ala Gln Gly Leu Arg Tyr Tyr Arg
                165                 170                 175

Ala Leu Leu Asp Ser Leu Val Leu Arg Asn Ile Glu Pro Ile Val Thr
            180                 185                 190

Leu Tyr His Trp Asp Leu Pro Leu Thr Leu Gln Glu Glu Tyr Gly Gly
        195                 200                 205

Trp Lys Asn Ala Thr Met Ile Asp Leu Phe Asn Asp Tyr Ala Thr Tyr
    210                 215                 220

Cys Phe Gln Thr Phe Gly Asp Arg Val Lys Tyr Trp Ile Thr Ile His
225                 230                 235                 240

Asn Pro Tyr Leu Val Ala Trp His Gly Phe Gly Thr Gly Met His Ala
                245                 250                 255

Pro Gly Glu Lys Gly Asn Leu Thr Ala Val Tyr Thr Val Gly His Asn
            260                 265                 270

Leu Ile Lys Ala His Ser Lys Val Trp His Asn Tyr Asp Lys Asn Phe
        275                 280                 285

Arg Pro His Gln Lys Gly Trp Leu Ser Ile Thr Leu Gly Ser His Trp
    290                 295                 300

Ile Glu Pro Asn Arg Thr Asp Asn Met Glu Asp Val Ile Asn Cys Gln
305                 310                 315                 320

His Ser Met Ser Ser Val Leu Gly Trp Phe Ala Asn Pro Ile His Gly
                325                 330                 335

Asp Gly Asp Tyr Pro Glu Phe Met Lys Thr Gly Ala Met Ile Pro Glu
            340                 345                 350

Phe Ser Glu Ala Glu Lys Glu Val Arg Gly Thr Ala Asp Phe Phe
        355                 360                 365

Ala Phe Ser Phe Gly Pro Asn Asn Phe Arg Pro Ser Asn Thr Val Val
    370                 375                 380

Lys Met Gly Gln Asn Val Ser Leu Asn Leu Arg Gln Val Leu Asn Trp
385                 390                 395                 400

Ile Lys Leu Glu Tyr Asp Asp Pro Gln Ile Leu Ile Ser Glu Asn Gly
                405                 410                 415

Trp Phe Thr Asp Ser Tyr Ile Lys Thr Glu Asp Thr Thr Ala Ile Tyr
            420                 425                 430

Met Met Lys Asn Phe Leu Asn Gln Val Leu Gln Ala Ile Lys Phe Asp
        435                 440                 445

Glu Ile Arg Val Phe Gly Tyr Thr Ala Trp Thr Leu Leu Asp Gly Phe
    450                 455                 460

Glu Trp Gln Asp Ala Tyr Thr Thr Arg Arg Gly Leu Phe Tyr Val Asp
465                 470                 475                 480

Phe Asn Ser Glu Gln Lys Glu Arg Lys Pro Lys Ser Ser Ala His Tyr
                485                 490                 495

Tyr Lys Gln Ile Ile Gln Asp Asn Gly Phe Pro Leu Lys Glu Ser Thr

```
                500             505             510
Pro Asp Met Lys Gly Arg Phe Pro Cys Asp Phe Ser Trp Gly Val Thr
        515                 520                 525
Glu Ser Val Leu Lys Pro Glu Phe Thr Val Ser Ser Pro Gln Phe Thr
        530                 535                 540
Asp Pro His Leu Tyr Val Trp Asn Val Thr Gly Asn Arg Leu Leu Tyr
545                 550                 555                 560
Arg Val Glu Gly Val Arg Leu Lys Thr Arg Pro Ser Gln Cys Thr Asp
                565                 570                 575
Tyr Val Ser Ile Lys Lys Arg Val Glu Met Leu Ala Lys Met Lys Val
            580                 585                 590
Thr His Tyr Gln Phe Ala Leu Asp Trp Thr Ser Ile Leu Pro Thr Gly
        595                 600                 605
Asn Leu Ser Lys Val Asn Arg Gln Val Leu Arg Tyr Tyr Arg Cys Val
        610                 615                 620
Val Ser Glu Gly Leu Lys Leu Gly Val Phe Pro Met Val Thr Leu Tyr
625                 630                 635                 640
His Pro Thr His Ser His Leu Gly Leu Pro Leu Pro Leu Leu Ser Ser
                645                 650                 655
Gly Gly Trp Leu Asn Met Asn Thr Ala Lys Ala Phe Gln Asp Tyr Ala
                660                 665                 670
Glu Leu Cys Phe Arg Glu Leu Gly Asp Leu Val Lys Leu Trp Ile Thr
            675                 680                 685
Ile Asn Glu Pro Asn Arg Leu Ser Asp Met Tyr Asn Arg Thr Ser Asn
        690                 695                 700
Asp Thr Tyr Arg Ala Ala His Asn Leu Met Ile Ala His Ala Gln Val
705                 710                 715                 720
Trp His Leu Tyr Asp Arg Gln Tyr Arg Pro Val Gln His Gly Ala Val
                725                 730                 735
Ser Leu Ser Leu His Cys Asp Trp Ala Glu Pro Ala Asn Pro Phe Val
                740                 745                 750
Asp Ser His Trp Lys Ala Ala Glu Arg Phe Leu Gln Phe Glu Ile Ala
            755                 760                 765
Trp Phe Ala Asp Pro Leu Phe Lys Thr Gly Asp Tyr Pro Ser Val Met
        770                 775                 780
Lys Glu Tyr Ile Ala Ser Lys Asn Gln Arg Gly Leu Ser Ser Ser Val
785                 790                 795                 800
Leu Pro Arg Phe Thr Ala Lys Glu Ser Arg Leu Val Lys Gly Thr Val
                805                 810                 815
Asp Phe Tyr Ala Leu Asn His Phe Thr Thr Arg Phe Val Ile His Lys
                820                 825                 830
Gln Leu Asn Thr Asn Arg Ser Val Ala Asp Arg Asp Val Gln Phe Leu
            835                 840                 845
Gln Asp Ile Thr Arg Leu Ser Ser Pro Ser Arg Leu Ala Val Thr Pro
        850                 855                 860
Trp Gly Val Arg Lys Leu Leu Ala Trp Ile Arg Arg Asn Tyr Arg Asp
865                 870                 875                 880
Arg Asp Ile Tyr Ile Thr Ala Asn Gly Ile Asp Asp Leu Ala Leu Glu
                885                 890                 895
Asp Asp Gln Ile Arg Lys Tyr Tyr Leu Glu Lys Tyr Val Gln Glu Ala
                900                 905                 910
Leu Lys Ala Tyr Leu Ile Asp Lys Val Lys Ile Lys Gly Tyr Tyr Ala
            915                 920                 925
```

```
Phe Lys Leu Thr Glu Glu Lys Ser Lys Pro Arg Phe Gly Phe Phe Thr
    930                 935                 940
Ser Asp Phe Arg Ala Lys Ser Val Gln Phe Tyr Ser Lys Leu Ile
945                 950                 955                 960
Ser Ser Ser Gly Leu Pro Ala Glu Asn Arg Ser Pro Ala Cys Gly Gln
                965                 970                 975
Pro Ala Glu Asp Thr Asp Cys Thr Ile Cys Ser Phe Leu Val Glu Lys
            980                 985                 990
Lys Pro Leu Ile Phe Phe Gly Cys Cys Phe Ile Ser Thr Leu Ala Val
        995                 1000                1005
Leu Leu Ser Ile Thr Val Phe His His Gln Lys Arg Arg Lys Phe Gln
    1010                1015                1020
Lys Ala Arg Asn Leu Gln Asn Ile Pro Leu Lys Lys Gly His Ser Arg
1025                1030                1035                1040
Val Phe Ser
```

<210> SEQ ID NO 442
<211> LENGTH: 229
<212> TYPE: PRT
<213> ORGANISM: Artificial Sequence
<220> FEATURE:
<223> OTHER INFORMATION: synthetic

<400> SEQUENCE: 442

```
Glu Ser Lys Tyr Gly Pro Pro Cys Pro Ser Cys Pro Ala Pro Glu Phe
1               5                   10                  15
Leu Gly Gly Pro Ser Val Phe Leu Phe Pro Pro Lys Pro Lys Asp Thr
            20                  25                  30
Leu Met Ile Ser Arg Thr Pro Glu Val Thr Cys Val Val Val Asp Val
        35                  40                  45
Ser Gln Glu Asp Pro Glu Val Gln Phe Asn Trp Tyr Val Asp Gly Val
    50                  55                  60
Glu Val His Asn Ala Lys Thr Lys Pro Arg Glu Glu Gln Phe Asn Ser
65                  70                  75                  80
Thr Tyr Arg Val Val Ser Val Leu Thr Val Leu His Gln Asp Trp Leu
                85                  90                  95
Asn Gly Lys Glu Tyr Lys Cys Lys Val Ser Asn Lys Gly Leu Pro Ser
            100                 105                 110
Ser Ile Glu Lys Thr Ile Ser Lys Ala Lys Gly Gln Pro Arg Glu Pro
        115                 120                 125
Gln Val Tyr Thr Leu Pro Pro Ser Gln Glu Glu Met Thr Lys Asn Gln
    130                 135                 140
Val Ser Leu Thr Cys Leu Val Lys Gly Phe Tyr Pro Ser Asp Ile Ala
145                 150                 155                 160
Val Glu Trp Glu Ser Asn Gly Gln Pro Glu Asn Asn Tyr Lys Thr Thr
                165                 170                 175
Pro Pro Val Leu Asp Ser Asp Gly Ser Phe Phe Leu Tyr Ser Arg Leu
            180                 185                 190
Thr Val Asp Lys Ser Arg Trp Gln Glu Gly Asn Val Phe Ser Cys Ser
        195                 200                 205
Val Met His Glu Ala Leu His Asn His Tyr Thr Gln Lys Ser Leu Ser
    210                 215                 220
Leu Ser Leu Gly Lys
225
```

<210> SEQ ID NO 443
<211> LENGTH: 229
<212> TYPE: PRT
<213> ORGANISM: Artificial Sequence
<220> FEATURE:
<223> OTHER INFORMATION: synthetic

<400> SEQUENCE: 443

```
Glu Ser Lys Tyr Gly Pro Pro Cys Pro Ser Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn Arg Phe Thr Gln Lys Ser Leu Ser
    210                 215                 220

Leu Ser Leu Gly Lys
225
```

<210> SEQ ID NO 444
<211> LENGTH: 232
<212> TYPE: PRT
<213> ORGANISM: Artificial Sequence
<220> FEATURE:
<223> OTHER INFORMATION: synthetic

<400> SEQUENCE: 444

```
Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80
```

Tyr Asn Ser Thr Tyr Arg Val Val Ser Val Leu Thr Val Leu His Gln
            85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
            115                 120                 125

Arg Glu Pro Gln Val Tyr Thr Leu Pro Pro Ser Arg Asp Glu Leu Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
            165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
            195                 200                 205

Ser Cys Ser Val Met His Glu Ala Leu His Asn His Tyr Thr Gln Lys
            210                 215                 220

Ser Leu Ser Leu Ser Pro Gly Lys
225                 230

<210> SEQ ID NO 445
<211> LENGTH: 232
<212> TYPE: PRT
<213> ORGANISM: Artificial Sequence
<220> FEATURE:
<223> OTHER INFORMATION: synthetic

<400> SEQUENCE: 445

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
            35                  40                  45

Val Asp Val Ser His Glu Asp Pro Glu Val Lys Phe Asn Trp Tyr Val
50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
            85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
            115                 120                 125

Arg Glu Pro Gln Val Tyr Thr Leu Pro Pro Ser Arg Asp Glu Leu Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
            165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
            195                 200                 205

```
Ser Cys Ser Val Met His Glu Ala Leu His Asn Arg Phe Thr Gln Lys
    210                 215                 220

Ser Leu Ser Leu Ser Pro Gly Lys
225                 230
```

<210> SEQ ID NO 446
<211> LENGTH: 16
<212> TYPE: PRT
<213> ORGANISM: Artificial Sequence
<220> FEATURE:
<223> OTHER INFORMATION: synthetic

<400> SEQUENCE: 446

```
Gly Gly Gly Ser Gly Gly Gly Ser Gly Gly Ser Gly Gly Gly Ser
1               5                   10                  15
```

<210> SEQ ID NO 447
<211> LENGTH: 209
<212> TYPE: PRT
<213> ORGANISM: Artificial Sequence
<220> FEATURE:
<223> OTHER INFORMATION: synthetic

<400> SEQUENCE: 447

```
Met Asp Ser Asp Glu Thr Gly Phe Glu His Ser Gly Leu Trp Val Ser
1               5                   10                  15

Val Leu Ala Gly Leu Leu Leu Gly Ala Cys Gln Ala His Pro Ile Pro
            20                  25                  30

Asp Ser Ser Pro Leu Leu Gln Phe Gly Gly Gln Val Arg Gln Arg Tyr
        35                  40                  45

Leu Tyr Thr Asp Asp Ala Gln Gln Thr Glu Ala His Leu Glu Ile Arg
    50                  55                  60

Glu Asp Gly Thr Val Gly Gly Ala Ala Asp Gln Ser Pro Glu Ser Leu
65                  70                  75                  80

Leu Gln Leu Lys Ala Leu Lys Pro Gly Val Ile Gln Ile Leu Gly Val
                85                  90                  95

Lys Thr Ser Arg Phe Leu Cys Gln Arg Pro Asp Gly Ala Leu Tyr Gly
            100                 105                 110

Ser Leu His Phe Asp Pro Glu Ala Cys Ser Phe Arg Glu Leu Leu Leu
        115                 120                 125

Glu Asp Gly Tyr Asn Val Tyr Gln Ser Glu Ala His Gly Leu Pro Leu
    130                 135                 140

His Leu Pro Gly Asn Lys Ser Pro His Arg Asp Pro Ala Pro Arg Gly
145                 150                 155                 160

Pro Ala Arg Phe Leu Pro Leu Pro Gly Leu Pro Pro Ala Pro Pro Glu
                165                 170                 175

Pro Pro Gly Ile Leu Ala Pro Gln Pro Pro Asp Val Gly Ser Ser Asp
            180                 185                 190

Pro Leu Ser Met Val Gly Pro Ser Gln Gly Arg Ser Pro Ser Tyr Ala
        195                 200                 205

Ser
```

<210> SEQ ID NO 448
<211> LENGTH: 173
<212> TYPE: PRT
<213> ORGANISM: Artificial Sequence
<220> FEATURE:
<223> OTHER INFORMATION: synthetic

<400> SEQUENCE: 448

Leu Leu Gln Phe Gly Gly Gln Val Arg Gln Arg Tyr Leu Tyr Thr Asp
1               5                   10                  15

Asp Ala Gln Gln Thr Glu Ala His Leu Glu Ile Arg Glu Asp Gly Thr
            20                  25                  30

Val Gly Gly Ala Ala Asp Gln Ser Pro Glu Ser Leu Leu Gln Leu Lys
        35                  40                  45

Ala Leu Lys Pro Gly Val Ile Gln Ile Leu Gly Val Lys Thr Ser Arg
    50                  55                  60

Phe Leu Cys Gln Arg Pro Asp Gly Ala Leu Tyr Gly Ser Leu His Phe
65                  70                  75                  80

Asp Pro Glu Ala Cys Ser Phe Arg Glu Leu Leu Leu Glu Asp Gly Tyr
                85                  90                  95

Asn Val Tyr Gln Ser Glu Ala His Gly Leu Pro Leu His Leu Pro Gly
            100                 105                 110

Asn Lys Ser Pro His Arg Asp Pro Ala Pro Arg Gly Pro Ala Arg Phe
        115                 120                 125

Leu Pro Leu Pro Gly Leu Pro Pro Ala Pro Pro Glu Pro Pro Gly Ile
    130                 135                 140

Leu Ala Pro Gln Pro Pro Asp Val Gly Ser Ser Asp Pro Leu Ser Met
145                 150                 155                 160

Val Gly Pro Ser Gln Gly Arg Ser Pro Ser Tyr Ala Ser
                165                 170

<210> SEQ ID NO 449
<211> LENGTH: 42
<212> TYPE: PRT
<213> ORGANISM: Artificial Sequence
<220> FEATURE:
<223> OTHER INFORMATION: synthetic

<400> SEQUENCE: 449

Pro Gly Leu Pro Pro Ala Pro Pro Glu Pro Pro Gly Ile Leu Ala Pro
1               5                   10                  15

Gln Pro Pro Asp Val Gly Ser Ser Asp Pro Leu Ser Met Val Gly Pro
            20                  25                  30

Ser Gln Gly Arg Ser Pro Ser Tyr Ala Ser
        35                  40

<210> SEQ ID NO 450
<211> LENGTH: 45
<212> TYPE: PRT
<213> ORGANISM: Artificial Sequence
<220> FEATURE:
<223> OTHER INFORMATION: synthetic

<400> SEQUENCE: 450

Leu Pro Leu Pro Gly Leu Pro Pro Ala Pro Pro Glu Pro Pro Gly Ile
1               5                   10                  15

Leu Ala Pro Gln Pro Pro Asp Val Gly Ser Ser Asp Pro Leu Ser Met
            20                  25                  30

Val Gly Pro Ser Gln Gly Arg Ser Pro Ser Tyr Ala Ser
        35                  40                  45

<210> SEQ ID NO 451
<211> LENGTH: 17
<212> TYPE: PRT
<213> ORGANISM: Artificial Sequence
<220> FEATURE:

<223> OTHER INFORMATION: synthetic

<400> SEQUENCE: 451

His Pro Ile Pro Asp Ser Ser Pro Leu Leu Gln Phe Gly Gly Gln Val
1               5                   10                  15
Arg

<210> SEQ ID NO 452
<211> LENGTH: 8
<212> TYPE: PRT
<213> ORGANISM: Artificial Sequence
<220> FEATURE:
<223> OTHER INFORMATION: synthetic

<400> SEQUENCE: 452

His Pro Ile Pro Asp Ser Ser Pro
1               5

<210> SEQ ID NO 453
<211> LENGTH: 187
<212> TYPE: PRT
<213> ORGANISM: Artificial Sequence
<220> FEATURE:
<223> OTHER INFORMATION: synthetic

<400> SEQUENCE: 453

His His His His His His Pro Ile Pro Asp Ser Ser Pro Leu Leu
1               5                   10                  15

Gln Phe Gly Gly Gln Val Arg Gln Arg Tyr Leu Tyr Thr Asp Asp Ala
                20                  25                  30

Gln Gln Thr Glu Ala His Leu Glu Ile Arg Glu Asp Gly Thr Val Gly
            35                  40                  45

Gly Ala Ala Asp Gln Ser Pro Glu Ser Leu Leu Gln Leu Lys Ala Leu
        50                  55                  60

Lys Pro Gly Val Ile Gln Ile Leu Gly Val Lys Thr Ser Arg Phe Leu
65                  70                  75                  80

Cys Gln Arg Pro Asp Gly Ala Leu Tyr Gly Ser Leu His Phe Asp Pro
                85                  90                  95

Glu Ala Cys Ser Phe Arg Glu Leu Leu Leu Glu Asp Gly Tyr Asn Val
                100                 105                 110

Tyr Gln Ser Glu Ala His Gly Leu Pro Leu His Leu Pro Gly Asn Lys
            115                 120                 125

Ser Pro His Arg Asp Pro Ala Pro Arg Gly Pro Ala Arg Phe Leu Pro
        130                 135                 140

Leu Pro Gly Leu Pro Pro Ala Pro Pro Glu Pro Pro Gly Ile Leu Ala
145                 150                 155                 160

Pro Gln Pro Pro Asp Val Gly Ser Ser Asp Pro Leu Ser Met Val Gly
                165                 170                 175

Pro Ser Gln Gly Arg Ser Pro Ser Tyr Ala Ser
            180                 185

<210> SEQ ID NO 454
<211> LENGTH: 229
<212> TYPE: PRT
<213> ORGANISM: Artificial Sequence
<220> FEATURE:
<223> OTHER INFORMATION: synthetic

<400> SEQUENCE: 454

Glu Ser Lys Tyr Gly Pro Pro Cys Pro Pro Cys Pro Ala Pro Glu Phe

```
1               5                   10                  15
Leu Gly Gly Pro Ser Val Phe Leu Phe Pro Pro Lys Pro Lys Asp Thr
                20                  25                  30
Leu Met Ile Ser Arg Thr Pro Glu Val Thr Cys Val Val Val Asp Val
                35                  40                  45
Ser Gln Glu Asp Pro Glu Val Gln Phe Asn Trp Tyr Val Asp Gly Val
        50                  55                  60
Glu Val His Asn Ala Lys Thr Lys Pro Arg Glu Glu Gln Phe Asn Ser
65                  70                  75                  80
Thr Tyr Arg Val Val Ser Val Leu Thr Val Leu His Gln Asp Trp Leu
                    85                  90                  95
Asn Gly Lys Glu Tyr Lys Cys Lys Val Ser Asn Lys Gly Leu Pro Ser
                100                 105                 110
Ser Ile Glu Lys Thr Ile Ser Lys Ala Lys Gly Gln Pro Arg Glu Pro
                115                 120                 125
Gln Val Tyr Thr Leu Pro Pro Ser Gln Glu Glu Met Thr Lys Asn Gln
            130                 135                 140
Val Ser Leu Thr Cys Leu Val Lys Gly Phe Tyr Pro Ser Asp Ile Ala
145                 150                 155                 160
Val Glu Trp Glu Ser Asn Gly Gln Pro Glu Asn Asn Tyr Lys Thr Thr
                    165                 170                 175
Pro Pro Val Leu Asp Ser Asp Gly Ser Phe Phe Leu Tyr Ser Arg Leu
                180                 185                 190
Thr Val Asp Lys Ser Arg Trp Gln Glu Gly Asn Val Phe Ser Cys Ser
                195                 200                 205
Val Met His Glu Ala Leu His Asn His Tyr Thr Gln Lys Ser Leu Ser
        210                 215                 220
Leu Ser Leu Gly Lys
225

<210> SEQ ID NO 455
<211> LENGTH: 229
<212> TYPE: PRT
<213> ORGANISM: Artificial Sequence
<220> FEATURE:
<223> OTHER INFORMATION: synthetic

<400> SEQUENCE: 455

Glu Ser Lys Tyr Gly Pro Pro Cys Pro Pro Cys Pro Ala Pro Glu Phe
1               5                   10                  15
Leu Gly Gly Pro Ser Val Phe Leu Phe Pro Pro Lys Pro Lys Asp Thr
                20                  25                  30
Leu Met Ile Ser Arg Thr Pro Glu Val Thr Cys Val Val Val Asp Val
                35                  40                  45
Ser Gln Glu Asp Pro Glu Val Gln Phe Asn Trp Tyr Val Asp Gly Val
        50                  55                  60
Glu Val His Asn Ala Lys Thr Lys Pro Arg Glu Glu Gln Phe Asn Ser
65                  70                  75                  80
Thr Tyr Arg Val Val Ser Val Leu Thr Val Leu His Gln Asp Trp Leu
                    85                  90                  95
Asn Gly Lys Glu Tyr Lys Cys Lys Val Ser Asn Lys Gly Leu Pro Ser
                100                 105                 110
Ser Ile Glu Lys Thr Ile Ser Lys Ala Lys Gly Gln Pro Arg Glu Pro
                115                 120                 125
Gln Val Tyr Thr Leu Pro Pro Ser Gln Glu Glu Met Thr Lys Asn Gln
```

```
            130             135             140
Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
                195                 200                 205

Val Met His Glu Ala Leu His Asn Arg Phe Thr Gln Lys Ser Leu Ser
            210                 215                 220

Leu Ser Leu Gly Lys
225

<210> SEQ ID NO 456
<211> LENGTH: 487
<212> TYPE: PRT
<213> ORGANISM: Artificial Sequence
<220> FEATURE:
<223> OTHER INFORMATION: synthetic

<400> SEQUENCE: 456

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
                20                  25                  30

Tyr Trp Ser Trp Ile Arg Gln Pro Pro Gly Lys Gly Leu Asp Trp Ile
            35                  40                  45

Gly His Ile Tyr Tyr Ser Gly Thr Thr Tyr Tyr Asn Pro Ser Leu Lys
        50                  55                  60

Ser Arg Val Ser Ile Ser Leu Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg His Leu Arg Gly Tyr Ser Ser Gly Arg Glu Phe Asp Tyr Trp Gly
            100                 105                 110

Gln Gly Thr Leu Val Thr Val Ser Gly Gly Gly Ser Gly Gly
            115                 120                 125

Gly Gly Ser Gly Gly Gly Ser Asp Ile Gln Met Thr Gln Ser Pro
        130                 135                 140

Ser Ser Leu Ser Ala Ser Val Gly Gly Arg Val Ser Leu Thr Cys Arg
145                 150                 155                 160

Ala Ser Gln Ser Ile Phe Ser Tyr Leu Asn Trp Tyr Gln Gln Lys Pro
                165                 170                 175

Gly Lys Ala Pro Lys Leu Leu Ile Tyr Ala Ala Ser Asn Leu Gln Ser
            180                 185                 190

Gly Val Pro Ser Arg Phe Ser Gly Ser Gly Ser Gly Thr Asp Phe Thr
            195                 200                 205

Leu Thr Ile Ser Ser Leu Gln Pro Glu Asp Phe Ala Thr Tyr Ser Cys
            210                 215                 220

Gln Gln Ser Tyr Asn Ile Pro Tyr Thr Phe Gly Gln Gly Thr Lys Leu
225                 230                 235                 240

Glu Ile Lys Gly Gly Gly Gly Ser Gly Gly Gly Ser Gly Gly
                245                 250                 255

Gly Ser Glu Ser Lys Tyr Gly Pro Pro Cys Pro Pro Cys Pro Ala Pro
```

```
            260                 265                 270
Glu Phe Leu Gly Gly Pro Ser Val Phe Leu Phe Pro Pro Lys Pro Lys
            275                 280                 285

Asp Thr Leu Met Ile Ser Arg Thr Pro Glu Val Thr Cys Val Val Val
        290                 295                 300

Asp Val Ser Gln Glu Asp Pro Glu Val Gln Phe Asn Trp Tyr Val Asp
305                 310                 315                 320

Gly Val Glu Val His Asn Ala Lys Thr Lys Pro Arg Glu Glu Gln Phe
                325                 330                 335

Asn Ser Thr Tyr Arg Val Val Ser Val Leu Thr Val Leu His Gln Asp
            340                 345                 350

Trp Leu Asn Gly Lys Glu Tyr Lys Cys Lys Val Ser Asn Lys Gly Leu
        355                 360                 365

Pro Ser Ser Ile Glu Lys Thr Ile Ser Lys Ala Lys Gly Gln Pro Arg
    370                 375                 380

Glu Pro Gln Val Tyr Thr Leu Pro Pro Ser Gln Glu Glu Met Thr Lys
385                 390                 395                 400

Asn Gln Val Ser Leu Thr Cys Leu Val Lys Gly Phe Tyr Pro Ser Asp
                405                 410                 415

Ile Ala Val Glu Trp Glu Ser Asn Gly Gln Pro Glu Asn Asn Tyr Lys
            420                 425                 430

Thr Thr Pro Pro Val Leu Asp Ser Asp Gly Ser Phe Phe Leu Tyr Ser
        435                 440                 445

Arg Leu Thr Val Asp Lys Ser Arg Trp Gln Glu Gly Asn Val Phe Ser
    450                 455                 460

Cys Ser Val Met His Glu Ala Leu His Asn His Tyr Thr Gln Lys Ser
465                 470                 475                 480

Leu Ser Leu Ser Leu Gly Lys
                485

<210> SEQ ID NO 457
<211> LENGTH: 484
<212> TYPE: PRT
<213> ORGANISM: Artificial Sequence
<220> FEATURE:
<223> OTHER INFORMATION: synthetic

<400> SEQUENCE: 457

Glu Val Gln Leu Val Glu Ser Gly Gly Gly Val Val Arg Pro Gly Gly
1               5                   10                  15

Ser Leu Arg Leu Ser Cys Ala Ala Ser Gly Phe Lys Phe Asp Val Tyr
            20                  25                  30

Gly Met Ser Trp Val Arg Gln Leu Pro Gly Lys Gly Leu Glu Trp Val
        35                  40                  45

Ser Gly Ile Ser Trp Thr Gly Gly Ser Gly Tyr Ala Asp Ser Val
    50                  55                  60

Lys Gly Arg Phe Thr Ile Ser Arg Asp Asn Gly Lys Lys Ser Leu Tyr
65                  70                  75                  80

Leu Gln Met Asn Ser Leu Arg Ala Glu Asp Thr Ala Leu Tyr Tyr Cys
                85                  90                  95

Thr Arg Glu Glu Asp Tyr Trp Gly Gln Gly Thr Leu Val Thr Val Ser
            100                 105                 110

Ser Gly Gly Gly Gly Ser Gly Gly Gly Gly Ser Gly Gly Gly Gly Ser
        115                 120                 125

Asp Val Val Met Thr Gln Ser Pro Leu Ser Leu Pro Val Thr Leu Gly
```

```
                130                 135                 140
Gln Pro Ala Ser Ile Ser Cys Arg Ser Ser Gln Ser Leu Val Tyr Ser
145                 150                 155                 160

Asp Gly Asn Thr Tyr Leu Asn Trp Phe Gln Gln Arg Pro Gly Gln Ser
                165                 170                 175

Pro Arg Arg Leu Ile Tyr Lys Val Ser Asn Arg Asp Ser Gly Val Pro
            180                 185                 190

Asp Arg Phe Ser Gly Ser Gly Ser Gly Thr Asp Phe Thr Leu Lys Ile
            195                 200                 205

Ser Arg Val Glu Ala Glu Asp Val Gly Ile Tyr Tyr Cys Met Gln Gly
            210                 215                 220

Thr Gln Trp Pro Leu Thr Phe Gly Gly Gly Thr Lys Val Glu Ile Lys
225                 230                 235                 240

Gly Gly Gly Gly Ser Gly Gly Gly Ser Gly Gly Gly Gly Ser Glu
                245                 250                 255

Ser Lys Tyr Gly Pro Pro Cys Pro Pro Cys Pro Ala Pro Glu Phe Leu
            260                 265                 270

Gly Gly Pro Ser Val Phe Leu Phe Pro Pro Lys Pro Lys Asp Thr Leu
            275                 280                 285

Met Ile Ser Arg Thr Pro Glu Val Thr Cys Val Val Val Asp Val Ser
            290                 295                 300

Gln Glu Asp Pro Glu Val Gln Phe Asn Trp Tyr Val Asp Gly Val Glu
305                 310                 315                 320

Val His Asn Ala Lys Thr Lys Pro Arg Glu Glu Gln Phe Asn Ser Thr
                325                 330                 335

Tyr Arg Val Val Ser Val Leu Thr Val Leu His Gln Asp Trp Leu Asn
            340                 345                 350

Gly Lys Glu Tyr Lys Cys Lys Val Ser Asn Lys Gly Leu Pro Ser Ser
            355                 360                 365

Ile Glu Lys Thr Ile Ser Lys Ala Lys Gly Gln Pro Arg Glu Pro Gln
            370                 375                 380

Val Tyr Thr Leu Pro Pro Ser Gln Glu Glu Met Thr Lys Asn Gln Val
385                 390                 395                 400

Ser Leu Thr Cys Leu Val Lys Gly Phe Tyr Pro Ser Asp Ile Ala Val
                405                 410                 415

Glu Trp Glu Ser Asn Gly Gln Pro Glu Asn Asn Tyr Lys Thr Thr Pro
            420                 425                 430

Pro Val Leu Asp Ser Asp Gly Ser Phe Phe Leu Tyr Ser Arg Leu Thr
            435                 440                 445

Val Asp Lys Ser Arg Trp Gln Glu Gly Asn Val Phe Ser Cys Ser Val
            450                 455                 460

Met His Glu Ala Leu His Asn Arg Phe Thr Gln Lys Ser Leu Ser Leu
465                 470                 475                 480

Ser Pro Gly Lys

<210> SEQ ID NO 458
<211> LENGTH: 493
<212> TYPE: PRT
<213> ORGANISM: Artificial Sequence
<220> FEATURE:
<223> OTHER INFORMATION: synthetic

<400> SEQUENCE: 458

Gln Val Gln Leu Val Glu Ser Gly Gly Gly Val Val Gln Pro Gly Arg
1               5                   10                  15
```

```
Ser Leu Arg Leu Ser Cys Val Ala Ser Gly Phe Thr Phe Ser Ser Tyr
            20                  25                  30

Gly Met His Trp Val Arg Gln Ala Pro Gly Lys Gly Leu Glu Trp Val
            35                  40                  45

Ala Val Ile Ser Phe Asp Gly Ser Asn Lys Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Pro Ala Asp Thr Ala Val Tyr Tyr Cys
                85                  90                  95

Ala Lys Asp Arg Ser Asn Tyr Tyr Phe Gly Met Asp Val Trp Gly
            100                 105                 110

Gln Gly Thr Thr Val Thr Val Ser Ser Gly Gly Gly Ser Gly Gly
            115                 120                 125

Gly Gly Ser Gly Gly Gly Ser Asp Ile Val Met Thr Gln Thr Pro
 130                 135                 140

Leu Ser Leu Pro Val Thr Pro Gly Glu Pro Ala Ser Ile Ser Cys Arg
145                 150                 155                 160

Ser Ser Gln Ser Leu Leu Asp Ser Asp Gly Asn Thr Tyr Leu Asp
            165                 170                 175

Trp Tyr Leu Gln Lys Pro Gly Gln Ser Pro Gln Leu Leu Ile Tyr Thr
            180                 185                 190

Leu Ser Tyr Arg Ala Ser Gly Val Pro Asp Arg Phe Ser Gly Ser Gly
            195                 200                 205

Ser Gly Thr Asp Phe Thr Leu Lys Ile Ser Arg Val Glu Ala Glu Asp
            210                 215                 220

Val Gly Val Tyr Tyr Cys Met Gln Arg Ile Glu Phe Pro Leu Thr Phe
225                 230                 235                 240

Gly Gly Gly Thr Lys Val Glu Ile Lys Gly Gly Gly Ser Gly Gly
            245                 250                 255

Gly Gly Ser Gly Gly Gly Ser Glu Ser Lys Tyr Gly Pro Pro Cys
            260                 265                 270

Pro Pro Cys Pro Ala Pro Glu Phe Leu Gly Gly Pro Ser Val Phe Leu
            275                 280                 285

Phe Pro Pro Lys Pro Lys Asp Thr Leu Met Ile Ser Arg Thr Pro Glu
290                 295                 300

Val Thr Cys Val Val Val Asp Val Ser Gln Glu Asp Pro Glu Val Gln
305                 310                 315                 320

Phe Asn Trp Tyr Val Asp Gly Val Glu Val His Asn Ala Lys Thr Lys
            325                 330                 335

Pro Arg Glu Glu Gln Phe Asn Ser Thr Tyr Arg Val Val Ser Val Leu
            340                 345                 350

Thr Val Leu His Gln Asp Trp Leu Asn Gly Lys Glu Tyr Lys Cys Lys
            355                 360                 365

Val Ser Asn Lys Gly Leu Pro Ser Ser Ile Glu Lys Thr Ile Ser Lys
            370                 375                 380

Ala Lys Gly Gln Pro Arg Glu Pro Gln Val Tyr Thr Leu Pro Pro Ser
385                 390                 395                 400

Gln Glu Glu Met Thr Lys Asn Gln Val Ser Leu Thr Cys Leu Val Lys
                405                 410                 415

Gly Phe Tyr Pro Ser Asp Ile Ala Val Glu Trp Glu Ser Asn Gly Gln
            420                 425                 430
```

```
Pro Glu Asn Asn Tyr Lys Thr Thr Pro Val Leu Asp Ser Asp Gly
                435                 440                 445

Ser Phe Phe Leu Tyr Ser Arg Leu Thr Val Asp Lys Ser Arg Trp Gln
450                 455                 460

Glu Gly Asn Val Phe Ser Cys Ser Val Met His Glu Ala Leu His Asn
465                 470                 475                 480

Arg Phe Thr Gln Lys Ser Leu Ser Leu Ser Pro Gly Lys
                485                 490

<210> SEQ ID NO 459
<211> LENGTH: 742
<212> TYPE: PRT
<213> ORGANISM: Artificial Sequence
<220> FEATURE:
<223> OTHER INFORMATION: synthetic

<400> SEQUENCE: 459

Glu Val Gln Leu Val Glu Ser Gly Gly Gly Val Val Arg Pro Gly Gly
1               5                   10                  15

Ser Leu Arg Leu Ser Cys Ala Ala Ser Gly Phe Lys Phe Asp Val Tyr
            20                  25                  30

Gly Met Ser Trp Val Arg Gln Leu Pro Gly Lys Gly Leu Glu Trp Val
        35                  40                  45

Ser Gly Ile Ser Trp Thr Gly Gly Ser Gly Tyr Ala Asp Ser Val
    50                  55                  60

Lys Gly Arg Phe Thr Ile Ser Arg Asp Asn Gly Lys Lys Ser Leu Tyr
65                  70                  75                  80

Leu Gln Met Asn Ser Leu Arg Ala Glu Asp Thr Ala Leu Tyr Tyr Cys
                85                  90                  95

Thr Arg Glu Glu Asp Tyr Trp Gly Gln Gly Thr Leu Val Thr Val Ser
            100                 105                 110

Ser Gly Gly Gly Gly Ser Gly Gly Gly Ser Gly Gly Gly Gly Ser
        115                 120                 125

Asp Val Val Met Thr Gln Ser Pro Leu Ser Leu Pro Val Thr Leu Gly
130                 135                 140

Gln Pro Ala Ser Ile Ser Cys Arg Ser Ser Gln Ser Leu Val Tyr Ser
145                 150                 155                 160

Asp Gly Asn Thr Tyr Leu Asn Trp Phe Gln Gln Arg Pro Gly Gln Ser
                165                 170                 175

Pro Arg Arg Leu Ile Tyr Lys Val Ser Asn Arg Asp Ser Gly Val Pro
            180                 185                 190

Asp Arg Phe Ser Gly Ser Gly Ser Gly Thr Asp Phe Thr Leu Lys Ile
        195                 200                 205

Ser Arg Val Glu Ala Glu Asp Val Gly Ile Tyr Tyr Cys Met Gln Gly
    210                 215                 220

Thr Gln Trp Pro Leu Thr Phe Gly Gly Gly Thr Lys Val Glu Ile Lys
225                 230                 235                 240

Gly Gly Gly Gly Ser Gly Gly Gly Ser Gly Gly Gly Gly Ser Glu
                245                 250                 255

Ser Lys Tyr Gly Pro Pro Cys Pro Pro Cys Pro Ala Pro Glu Phe Leu
            260                 265                 270

Gly Gly Pro Ser Val Phe Leu Phe Pro Pro Lys Pro Lys Asp Thr Leu
        275                 280                 285

Met Ile Ser Arg Thr Pro Glu Val Thr Cys Val Val Val Asp Val Ser
    290                 295                 300
```

```
Gln Glu Asp Pro Glu Val Gln Phe Asn Trp Tyr Val Asp Gly Val Glu
305                 310                 315                 320
Val His Asn Ala Lys Thr Lys Pro Arg Glu Glu Gln Phe Asn Ser Thr
                325                 330                 335
Tyr Arg Val Val Ser Val Leu Thr Val Leu His Gln Asp Trp Leu Asn
            340                 345                 350
Gly Lys Glu Tyr Lys Cys Lys Val Ser Asn Lys Gly Leu Pro Ser Ser
        355                 360                 365
Ile Glu Lys Thr Ile Ser Lys Ala Lys Gly Gln Pro Arg Glu Pro Gln
    370                 375                 380
Val Tyr Thr Leu Pro Pro Ser Gln Glu Glu Met Thr Lys Asn Gln Val
385                 390                 395                 400
Ser Leu Thr Cys Leu Val Lys Gly Phe Tyr Pro Ser Asp Ile Ala Val
                405                 410                 415
Glu Trp Glu Ser Asn Gly Gln Pro Glu Asn Asn Tyr Lys Thr Thr Pro
            420                 425                 430
Pro Val Leu Asp Ser Asp Gly Ser Phe Phe Leu Tyr Ser Arg Leu Thr
        435                 440                 445
Val Asp Lys Ser Arg Trp Gln Glu Gly Asn Val Phe Ser Cys Ser Val
    450                 455                 460
Met His Glu Ala Leu His Asn His Tyr Thr Gln Lys Ser Leu Ser Leu
465                 470                 475                 480
Ser Leu Gly Lys Gly Gly Gly Ser Gly Gly Gly Ser Gly Gly
                485                 490                 495
Gly Gly Ser Gln Val Gln Leu Gln Glu Ser Gly Pro Gly Leu Val Lys
            500                 505                 510
Pro Ser Glu Thr Leu Ser Leu Thr Cys Thr Val Ser Gly Gly Ser Ile
        515                 520                 525
Ser Ser Tyr Tyr Trp Ser Trp Ile Arg Gln Pro Pro Gly Lys Gly Leu
    530                 535                 540
Asp Trp Ile Gly His Ile Tyr Tyr Ser Gly Thr Thr Tyr Tyr Asn Pro
545                 550                 555                 560
Ser Leu Lys Ser Arg Val Ser Ile Ser Leu Asp Thr Ser Lys Asn Gln
                565                 570                 575
Phe Ser Leu Lys Leu Ser Ser Val Thr Ala Ala Asp Thr Ala Val Tyr
            580                 585                 590
Tyr Cys Ala Arg His Leu Arg Gly Tyr Ser Ser Gly Arg Glu Phe Asp
        595                 600                 605
Tyr Trp Gly Gln Gly Thr Leu Val Thr Val Ser Ser Gly Gly Gly Gly
    610                 615                 620
Ser Gly Gly Gly Gly Ser Gly Gly Gly Gly Ser Asp Ile Gln Met Thr
625                 630                 635                 640
Gln Ser Pro Ser Ser Leu Ser Ala Ser Val Gly Gly Arg Val Ser Leu
                645                 650                 655
Thr Cys Arg Ala Ser Gln Ser Ile Phe Ser Tyr Leu Asn Trp Tyr Gln
            660                 665                 670
Gln Lys Pro Gly Lys Ala Pro Lys Leu Leu Ile Tyr Ala Ala Ser Asn
        675                 680                 685
Leu Gln Ser Gly Val Pro Ser Arg Phe Ser Gly Ser Gly Ser Gly Thr
    690                 695                 700
Asp Phe Thr Leu Thr Ile Ser Ser Leu Gln Pro Glu Asp Phe Ala Thr
705                 710                 715                 720
Tyr Ser Cys Gln Gln Ser Tyr Asn Ile Pro Tyr Thr Phe Gly Gln Gly
```

```
                        725                 730                 735
Thr Lys Leu Glu Ile Lys
            740

<210> SEQ ID NO 460
<211> LENGTH: 751
<212> TYPE: PRT
<213> ORGANISM: Artificial Sequence
<220> FEATURE:
<223> OTHER INFORMATION: synthetic

<400> SEQUENCE: 460

Gln Val Gln Leu Val Glu Ser Gly Gly Val Val Gln Pro Gly Arg
1               5                   10                  15

Ser Leu Arg Leu Ser Cys Val Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Ile Ser Phe Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Ala Asp Thr Ala Val Tyr Tyr Cys
                85                  90                  95

Ala Lys Asp Arg Ser Asn Tyr Tyr Phe Gly Met Asp Val Trp Gly
            100                 105                 110

Gln Gly Thr Thr Val Thr Val Ser Ser Gly Gly Gly Ser Gly Gly
            115                 120                 125

Gly Gly Ser Gly Gly Gly Ser Asp Ile Val Met Thr Gln Thr Pro
            130                 135                 140

Leu Ser Leu Pro Val Thr Pro Gly Glu Pro Ala Ser Ile Ser Cys Arg
145                 150                 155                 160

Ser Ser Gln Ser Leu Leu Asp Ser Asp Gly Asn Thr Tyr Leu Asp
                165                 170                 175

Trp Tyr Leu Gln Lys Pro Gly Gln Ser Pro Gln Leu Leu Ile Tyr Thr
                180                 185                 190

Leu Ser Tyr Arg Ala Ser Gly Val Pro Asp Arg Phe Ser Gly Ser Gly
            195                 200                 205

Ser Gly Thr Asp Phe Thr Leu Lys Ile Ser Arg Val Glu Ala Glu Asp
        210                 215                 220

Val Gly Val Tyr Tyr Cys Met Gln Arg Ile Glu Phe Pro Leu Thr Phe
225                 230                 235                 240

Gly Gly Gly Thr Lys Val Glu Ile Lys Gly Gly Gly Ser Gly Gly
                245                 250                 255

Gly Gly Ser Gly Gly Gly Ser Glu Ser Lys Tyr Gly Pro Pro Cys
            260                 265                 270

Pro Pro Cys Pro Ala Pro Glu Phe Leu Gly Gly Pro Ser Val Phe Leu
            275                 280                 285

Phe Pro Pro Lys Pro Lys Asp Thr Leu Met Ile Ser Arg Thr Pro Glu
        290                 295                 300

Val Thr Cys Val Val Val Asp Val Ser Gln Glu Asp Pro Glu Val Gln
305                 310                 315                 320

Phe Asn Trp Tyr Val Asp Gly Val Glu Val His Asn Ala Lys Thr Lys
                325                 330                 335

Pro Arg Glu Glu Gln Phe Asn Ser Thr Tyr Arg Val Val Ser Val Leu
```

```
                340                 345                 350
Thr Val Leu His Gln Asp Trp Leu Asn Gly Lys Glu Tyr Lys Cys Lys
            355                 360                 365
Val Ser Asn Lys Gly Leu Pro Ser Ser Ile Glu Lys Thr Ile Ser Lys
        370                 375                 380
Ala Lys Gly Gln Pro Arg Glu Pro Gln Val Tyr Thr Leu Pro Pro Ser
385                 390                 395                 400
Gln Glu Glu Met Thr Lys Asn Gln Val Ser Leu Thr Cys Leu Val Lys
                405                 410                 415
Gly Phe Tyr Pro Ser Asp Ile Ala Val Glu Trp Glu Ser Asn Gly Gln
            420                 425                 430
Pro Glu Asn Asn Tyr Lys Thr Thr Pro Pro Val Leu Asp Ser Asp Gly
        435                 440                 445
Ser Phe Phe Leu Tyr Ser Arg Leu Thr Val Asp Lys Ser Arg Trp Gln
    450                 455                 460
Glu Gly Asn Val Phe Ser Cys Ser Val Met His Glu Ala Leu His Asn
465                 470                 475                 480
His Tyr Thr Gln Lys Ser Leu Ser Leu Ser Leu Gly Lys Gly Gly Gly
                485                 490                 495
Gly Ser Gly Gly Gly Gly Ser Gly Gly Gly Gly Ser Gln Val Gln Leu
            500                 505                 510
Gln Glu Ser Gly Pro Gly Leu Val Lys Pro Ser Glu Thr Leu Ser Leu
        515                 520                 525
Thr Cys Thr Val Ser Gly Gly Ser Ile Ser Ser Tyr Tyr Trp Ser Trp
    530                 535                 540
Ile Arg Gln Pro Pro Gly Lys Gly Leu Asp Trp Ile Gly His Ile Tyr
545                 550                 555                 560
Tyr Ser Gly Thr Thr Tyr Tyr Asn Pro Ser Leu Lys Ser Arg Val Ser
                565                 570                 575
Ile Ser Leu Asp Thr Ser Lys Asn Gln Phe Ser Leu Lys Leu Ser Ser
            580                 585                 590
Val Thr Ala Ala Asp Thr Ala Val Tyr Tyr Cys Ala Arg His Leu Arg
        595                 600                 605
Gly Tyr Ser Ser Gly Arg Glu Phe Asp Tyr Trp Gly Gln Gly Thr Leu
    610                 615                 620
Val Thr Val Ser Ser Gly Gly Gly Gly Ser Gly Gly Gly Gly Ser Gly
625                 630                 635                 640
Gly Gly Gly Ser Asp Ile Gln Met Thr Gln Ser Pro Ser Ser Leu Ser
                645                 650                 655
Ala Ser Val Gly Gly Arg Val Ser Leu Thr Cys Arg Ala Ser Gln Ser
            660                 665                 670
Ile Phe Ser Tyr Leu Asn Trp Tyr Gln Gln Lys Pro Gly Lys Ala Pro
        675                 680                 685
Lys Leu Leu Ile Tyr Ala Ala Ser Asn Leu Gln Ser Gly Val Pro Ser
    690                 695                 700
Arg Phe Ser Gly Ser Gly Ser Gly Thr Asp Phe Thr Leu Thr Ile Ser
705                 710                 715                 720
Ser Leu Gln Pro Glu Asp Phe Ala Thr Tyr Ser Cys Gln Gln Ser Tyr
                725                 730                 735
Asn Ile Pro Tyr Thr Phe Gly Gln Gly Thr Lys Leu Glu Ile Lys
            740                 745                 750

<210> SEQ ID NO 461
```

```
<211> LENGTH: 411
<212> TYPE: PRT
<213> ORGANISM: Artificial Sequence
<220> FEATURE:
<223> OTHER INFORMATION: synthetic

<400> SEQUENCE: 461

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
    130                 135                 140

Ala Pro Pro Glu Pro Pro Gly Ile Leu Ala Pro Gln Pro Pro Asp Val
145                 150                 155                 160

Gly Ser Ser Asp Pro Leu Ser Gly Gly Gly Ser Gly Gly Gly Gly Gly
                165                 170                 175

Ser Gly Gly Gly Gly Ser Glu Ser Lys Tyr Gly Pro Pro Cys Pro Pro
            180                 185                 190

Cys Pro Ala Pro Glu Phe Leu Gly Gly Pro Ser Val Phe Leu Phe Pro
        195                 200                 205

Pro Lys Pro Lys Asp Thr Leu Met Ile Ser Arg Thr Pro Glu Val Thr
    210                 215                 220

Cys Val Val Val Asp Val Ser Gln Glu Asp Pro Glu Val Gln Phe Asn
225                 230                 235                 240

Trp Tyr Val Asp Gly Val Glu Val His Asn Ala Lys Thr Lys Pro Arg
                245                 250                 255

Glu Glu Gln Phe Asn Ser Thr Tyr Arg Val Val Ser Val Leu Thr Val
            260                 265                 270

Leu His Gln Asp Trp Leu Asn Gly Lys Glu Tyr Lys Cys Lys Val Ser
        275                 280                 285

Asn Lys Gly Leu Pro Ser Ser Ile Glu Lys Thr Ile Ser Lys Ala Lys
    290                 295                 300

Gly Gln Pro Arg Glu Pro Gln Val Tyr Thr Leu Pro Pro Ser Gln Glu
305                 310                 315                 320

Glu Met Thr Lys Asn Gln Val Ser Leu Thr Cys Leu Val Lys Gly Phe
                325                 330                 335

Tyr Pro Ser Asp Ile Ala Val Glu Trp Glu Ser Asn Gly Gln Pro Glu
            340                 345                 350

Asn Asn Tyr Lys Thr Thr Pro Pro Val Leu Asp Ser Asp Gly Ser Phe
        355                 360                 365

Phe Leu Tyr Ser Arg Leu Thr Val Asp Lys Ser Arg Trp Gln Glu Gly
    370                 375                 380
```

-continued

```
Asn Val Phe Ser Cys Ser Val Met His Glu Ala Leu His Asn Arg Phe
385                 390                 395                 400

Thr Gln Lys Ser Leu Ser Leu Ser Pro Gly Lys
                405                 410
```

<210> SEQ ID NO 462
<211> LENGTH: 672
<212> TYPE: PRT
<213> ORGANISM: Artificial Sequence
<220> FEATURE:
<223> OTHER INFORMATION: synthetic

<400> SEQUENCE: 462

```
Glu Val Gln Leu Val Glu Ser Gly Gly Gly Val Val Arg Pro Gly Gly
1               5                   10                  15

Ser Leu Arg Leu Ser Cys Ala Ala Ser Gly Phe Lys Phe Asp Val Tyr
            20                  25                  30

Gly Met Ser Trp Val Arg Gln Leu Pro Gly Lys Gly Leu Glu Trp Val
        35                  40                  45

Ser Gly Ile Ser Trp Thr Gly Ser Ser Gly Tyr Ala Asp Ser Val
    50                  55                  60

Lys Gly Arg Phe Thr Ile Ser Arg Asp Asn Gly Lys Lys Ser Leu Tyr
65                  70                  75                  80

Leu Gln Met Asn Ser Leu Arg Ala Glu Asp Thr Ala Leu Tyr Tyr Cys
                85                  90                  95

Thr Arg Glu Glu Asp Tyr Trp Gly Gln Gly Thr Leu Val Thr Val Ser
            100                 105                 110

Ser Gly Gly Gly Gly Ser Gly Gly Gly Gly Ser Gly Gly Gly Gly Ser
        115                 120                 125

Asp Val Val Met Thr Gln Ser Pro Leu Ser Leu Pro Val Thr Leu Gly
    130                 135                 140

Gln Pro Ala Ser Ile Ser Cys Arg Ser Ser Gln Ser Leu Val Tyr Ser
145                 150                 155                 160

Asp Gly Asn Thr Tyr Leu Asn Trp Phe Gln Gln Arg Pro Gly Gln Ser
                165                 170                 175

Pro Arg Arg Leu Ile Tyr Lys Val Ser Asn Arg Asp Ser Gly Val Pro
            180                 185                 190

Asp Arg Phe Ser Gly Ser Gly Ser Gly Thr Asp Phe Thr Leu Lys Ile
        195                 200                 205

Ser Arg Val Glu Ala Glu Asp Val Gly Ile Tyr Tyr Cys Met Gln Gly
    210                 215                 220

Thr Gln Trp Pro Leu Thr Phe Gly Gly Gly Thr Lys Val Glu Ile Lys
225                 230                 235                 240

Gly Gly Gly Gly Ser Gly Gly Gly Ser Gly Gly Gly Gly Ser Glu
                245                 250                 255

Ser Lys Tyr Gly Pro Pro Cys Pro Pro Cys Pro Ala Pro Glu Phe Leu
            260                 265                 270

Gly Gly Pro Ser Val Phe Leu Phe Pro Pro Lys Pro Lys Asp Thr Leu
        275                 280                 285

Met Ile Ser Arg Thr Pro Glu Val Thr Cys Val Val Val Asp Val Ser
    290                 295                 300

Gln Glu Asp Pro Glu Val Gln Phe Asn Trp Tyr Val Asp Gly Val Glu
305                 310                 315                 320

Val His Asn Ala Lys Thr Lys Pro Arg Glu Glu Gln Phe Asn Ser Thr
                325                 330                 335
```

Tyr Arg Val Val Ser Val Leu Thr Val Leu His Gln Asp Trp Leu Asn
            340                 345                 350

Gly Lys Glu Tyr Lys Cys Lys Val Ser Asn Lys Gly Leu Pro Ser Ser
            355                 360                 365

Ile Glu Lys Thr Ile Ser Lys Ala Lys Gly Gln Pro Arg Glu Pro Gln
370                 375                 380

Val Tyr Thr Leu Pro Pro Ser Gln Glu Glu Met Thr Lys Asn Gln Val
385                 390                 395                 400

Ser Leu Thr Cys Leu Val Lys Gly Phe Tyr Pro Ser Asp Ile Ala Val
            405                 410                 415

Glu Trp Glu Ser Asn Gly Gln Pro Glu Asn Asn Tyr Lys Thr Thr Pro
            420                 425                 430

Pro Val Leu Asp Ser Asp Gly Ser Phe Phe Leu Tyr Ser Arg Leu Thr
            435                 440                 445

Val Asp Lys Ser Arg Trp Gln Glu Gly Asn Val Phe Ser Cys Ser Val
450                 455                 460

Met His Glu Ala Leu His Asn His Tyr Thr Gln Lys Ser Leu Ser Leu
465                 470                 475                 480

Ser Leu Gly Lys Gly Gly Gly Ser Gly Gly Gly Ser Gly Gly
            485                 490                 495

Gly Gly Ser Leu Leu Gln Phe Gly Gly Gln Val Arg Gln Arg Tyr Leu
            500                 505                 510

Tyr Thr Asp Asp Ala Gln Gln Thr Glu Ala His Leu Glu Ile Arg Glu
            515                 520                 525

Asp Gly Thr Val Gly Gly Ala Asp Gln Ser Pro Glu Ser Leu Leu
            530                 535                 540

Gln Leu Lys Ala Leu Lys Pro Gly Val Ile Gln Ile Leu Gly Val Lys
545                 550                 555                 560

Thr Ser Arg Phe Leu Cys Gln Arg Pro Asp Gly Ala Leu Tyr Gly Ser
            565                 570                 575

Leu His Phe Asp Pro Glu Ala Cys Ser Phe Arg Glu Leu Leu Leu Glu
            580                 585                 590

Asp Gly Tyr Asn Val Tyr Gln Ser Glu Ala His Gly Leu Pro Leu His
            595                 600                 605

Leu Pro Gly Asn Lys Ser Pro His Arg Asp Pro Ala Pro Arg Gly Pro
            610                 615                 620

Ala Arg Phe Leu Pro Leu Pro Gly Leu Pro Pro Ala Pro Pro Glu Pro
625                 630                 635                 640

Pro Gly Ile Leu Ala Pro Gln Pro Pro Asp Val Gly Ser Ser Asp Pro
            645                 650                 655

Leu Ser Met Val Gly Pro Ser Gln Gly Arg Ser Pro Ser Tyr Ala Ser
            660                 665                 670

<210> SEQ ID NO 463
<211> LENGTH: 681
<212> TYPE: PRT
<213> ORGANISM: Artificial Sequence
<220> FEATURE:
<223> OTHER INFORMATION: synthetic

<400> SEQUENCE: 463

Gln Val Gln Leu Val Glu Ser Gly Gly Gly Val Val Gln Pro Gly Arg
1               5                   10                  15

Ser Leu Arg Leu Ser Cys Val Ala Ser Gly Phe Thr Phe Ser Ser Tyr
            20                  25                  30

-continued

```
Gly Met His Trp Val Arg Gln Ala Pro Gly Lys Gly Leu Glu Trp Val
        35                  40                  45

Ala Val Ile Ser Phe Asp Gly Ser Asn Lys Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Pro Ala Asp Thr Ala Val Tyr Tyr Cys
                 85                  90                  95

Ala Lys Asp Arg Ser Asn Tyr Tyr Phe Gly Met Asp Val Trp Gly
                100                 105                 110

Gln Gly Thr Thr Val Thr Val Ser Ser Gly Gly Gly Ser Gly Gly
            115                 120                 125

Gly Gly Ser Gly Gly Gly Ser Asp Ile Val Met Thr Gln Thr Pro
        130                 135                 140

Leu Ser Leu Pro Val Thr Pro Gly Glu Pro Ala Ser Ile Ser Cys Arg
145                 150                 155                 160

Ser Ser Gln Ser Leu Leu Asp Ser Asp Gly Asn Thr Tyr Leu Asp
                165                 170                 175

Trp Tyr Leu Gln Lys Pro Gly Gln Ser Pro Gln Leu Leu Ile Tyr Thr
                180                 185                 190

Leu Ser Tyr Arg Ala Ser Gly Val Pro Asp Arg Phe Ser Gly Ser Gly
                195                 200                 205

Ser Gly Thr Asp Phe Thr Leu Lys Ile Ser Arg Val Glu Ala Glu Asp
        210                 215                 220

Val Gly Val Tyr Tyr Cys Met Gln Arg Ile Glu Phe Pro Leu Thr Phe
225                 230                 235                 240

Gly Gly Gly Thr Lys Val Glu Ile Lys Gly Gly Gly Ser Gly Gly
                245                 250                 255

Gly Gly Ser Gly Gly Gly Gly Ser Glu Ser Lys Tyr Gly Pro Pro Cys
        260                 265                 270

Pro Pro Cys Pro Ala Pro Glu Phe Leu Gly Gly Pro Ser Val Phe Leu
        275                 280                 285

Phe Pro Pro Lys Pro Lys Asp Thr Leu Met Ile Ser Arg Thr Pro Glu
        290                 295                 300

Val Thr Cys Val Val Val Asp Val Ser Gln Glu Asp Pro Glu Val Gln
305                 310                 315                 320

Phe Asn Trp Tyr Val Asp Gly Val Glu Val His Asn Ala Lys Thr Lys
                325                 330                 335

Pro Arg Glu Glu Gln Phe Asn Ser Thr Tyr Arg Val Val Ser Val Leu
            340                 345                 350

Thr Val Leu His Gln Asp Trp Leu Asn Gly Lys Glu Tyr Lys Cys Lys
            355                 360                 365

Val Ser Asn Lys Gly Leu Pro Ser Ser Ile Glu Lys Thr Ile Ser Lys
370                 375                 380

Ala Lys Gly Gln Pro Arg Glu Pro Gln Val Tyr Thr Leu Pro Pro Ser
385                 390                 395                 400

Gln Glu Glu Met Thr Lys Asn Gln Val Ser Leu Thr Cys Leu Val Lys
                405                 410                 415

Gly Phe Tyr Pro Ser Asp Ile Ala Val Glu Trp Glu Ser Asn Gly Gln
            420                 425                 430

Pro Glu Asn Asn Tyr Lys Thr Thr Pro Pro Val Leu Asp Ser Asp Gly
            435                 440                 445
```

```
Ser Phe Phe Leu Tyr Ser Arg Leu Thr Val Asp Lys Ser Arg Trp Gln
450                 455                 460
Glu Gly Asn Val Phe Ser Cys Ser Val Met His Glu Ala Leu His Asn
465                 470                 475                 480
His Tyr Thr Gln Lys Ser Leu Ser Leu Ser Leu Gly Lys Gly Gly Gly
            485                 490                 495
Gly Ser Gly Gly Gly Gly Ser Gly Gly Gly Gly Ser Leu Leu Gln Phe
        500                 505                 510
Gly Gly Gln Val Arg Gln Arg Tyr Leu Tyr Thr Asp Asp Ala Gln Gln
            515                 520                 525
Thr Glu Ala His Leu Glu Ile Arg Glu Asp Gly Thr Val Gly Gly Ala
530                 535                 540
Ala Asp Gln Ser Pro Glu Ser Leu Leu Gln Leu Lys Ala Leu Lys Pro
545                 550                 555                 560
Gly Val Ile Gln Ile Leu Gly Val Lys Thr Ser Arg Phe Leu Cys Gln
            565                 570                 575
Arg Pro Asp Gly Ala Leu Tyr Gly Ser Leu His Phe Asp Pro Glu Ala
            580                 585                 590
Cys Ser Phe Arg Glu Leu Leu Leu Glu Asp Gly Tyr Asn Val Tyr Gln
            595                 600                 605
Ser Glu Ala His Gly Leu Pro Leu His Leu Pro Gly Asn Lys Ser Pro
610                 615                 620
His Arg Asp Pro Ala Pro Arg Gly Pro Ala Arg Phe Leu Pro Leu Pro
625                 630                 635                 640
Gly Leu Pro Pro Ala Pro Pro Glu Pro Gly Ile Leu Ala Pro Gln
            645                 650                 655
Pro Pro Asp Val Gly Ser Ser Asp Pro Leu Ser Met Val Gly Pro Ser
            660                 665                 670
Gln Gly Arg Ser Pro Ser Tyr Ala Ser
            675                 680

<210> SEQ ID NO 464
<211> LENGTH: 317
<212> TYPE: PRT
<213> ORGANISM: Artificial Sequence
<220> FEATURE:
<223> OTHER INFORMATION: synthetic

<400> SEQUENCE: 464

His Pro Ile Pro Asp Ser Ser Pro Gly Gly Gly Ser Gly Gly Gly
1               5                   10                  15
Gly Ser Gly Gly Gly Gly Ser Gly Gly Gly Gly Ser Asp Lys Thr His
            20                  25                  30
Thr Cys Pro Pro Cys Pro Ala Pro Glu Leu Leu Gly Gly Pro Ser Val
        35                  40                  45
Phe Leu Phe Pro Pro Lys Pro Lys Asp Thr Leu Met Ile Ser Arg Thr
50                  55                  60
Pro Glu Val Thr Cys Val Val Val Asp Val Ser His Glu Asp Pro Glu
65                  70                  75                  80
Val Lys Phe Asn Trp Tyr Val Asp Gly Val Glu Val His Asn Ala Lys
            85                  90                  95
Thr Lys Pro Arg Glu Glu Gln Tyr Asn Ser Thr Tyr Arg Val Val Ser
            100                 105                 110
Val Leu Thr Val Leu His Gln Asp Trp Leu Asn Gly Lys Glu Tyr Lys
        115                 120                 125
```

Cys Lys Val Ser Asn Lys Ala Leu Pro Ala Pro Ile Glu Lys Thr Ile
130                 135                 140

Ser Lys Ala Lys Gly Gln Pro Arg Glu Pro Gln Val Tyr Thr Leu Pro
145                 150                 155                 160

Pro Ser Arg Asp Glu Leu Thr Lys Asn Gln Val Ser Leu Thr Cys Leu
                165                 170                 175

Val Lys Gly Phe Tyr Pro Ser Asp Ile Ala Val Glu Trp Glu Ser Asn
            180                 185                 190

Gly Gln Pro Glu Asn Asn Tyr Lys Thr Thr Pro Val Leu Asp Ser
        195                 200                 205

Asp Gly Ser Phe Phe Leu Tyr Ser Lys Leu Thr Val Asp Lys Ser Arg
210                 215                 220

Trp Gln Gln Gly Asn Val Phe Ser Cys Ser Val Met His Glu Ala Leu
225                 230                 235                 240

His Asn His Tyr Thr Gln Lys Ser Leu Ser Leu Ser Pro Gly Lys Gly
                245                 250                 255

Gly Gly Gly Ser Gly Gly Gly Ser Gly Gly Gly Ser Gly Gly
            260                 265                 270

Gly Gly Ser Pro Gly Leu Pro Ala Pro Glu Pro Gly Ile
            275                 280                 285

Leu Ala Pro Gln Pro Pro Asp Val Gly Ser Ser Asp Pro Leu Ser Met
290                 295                 300

Val Gly Pro Ser Gln Gly Arg Ser Pro Ser Tyr Ala Ser
305                 310                 315

<210> SEQ ID NO 465
<211> LENGTH: 326
<212> TYPE: PRT
<213> ORGANISM: Artificial Sequence
<220> FEATURE:
<223> OTHER INFORMATION: synthetic

<400> SEQUENCE: 465

His Pro Ile Pro Asp Ser Ser Pro Leu Leu Gln Phe Gly Gly Gln Val
1               5                   10                  15

Arg Gly Gly Gly Gly Ser Gly Gly Gly Ser Gly Gly Gly Ser
            20                  25                  30

Gly Gly Gly Gly Ser Asp Lys Thr His Thr Cys Pro Pro Cys Pro Ala
            35                  40                  45

Pro Glu Leu Leu Gly Gly Pro Ser Val Phe Leu Phe Pro Pro Lys Pro
        50                  55                  60

Lys Asp Thr Leu Met Ile Ser Arg Thr Pro Glu Val Thr Cys Val Val
65                  70                  75                  80

Val Asp Val Ser His Glu Asp Pro Glu Val Lys Phe Asn Trp Tyr Val
                85                  90                  95

Asp Gly Val Glu Val His Asn Ala Lys Thr Lys Pro Arg Glu Glu Gln
            100                 105                 110

Tyr Asn Ser Thr Tyr Arg Val Val Ser Val Leu Thr Val Leu His Gln
        115                 120                 125

Asp Trp Leu Asn Gly Lys Glu Tyr Lys Cys Lys Val Ser Asn Lys Ala
130                 135                 140

Leu Pro Ala Pro Ile Glu Lys Thr Ile Ser Lys Ala Lys Gly Gln Pro
145                 150                 155                 160

Arg Glu Pro Gln Val Tyr Thr Leu Pro Pro Ser Arg Asp Glu Leu Thr
                165                 170                 175

```
Lys Asn Gln Val Ser Leu Thr Cys Leu Val Lys Gly Phe Tyr Pro Ser
                180                 185                 190

Asp Ile Ala Val Glu Trp Glu Ser Asn Gly Gln Pro Glu Asn Asn Tyr
            195                 200                 205

Lys Thr Thr Pro Pro Val Leu Asp Ser Asp Gly Ser Phe Phe Leu Tyr
        210                 215                 220

Ser Lys Leu Thr Val Asp Lys Ser Arg Trp Gln Gln Gly Asn Val Phe
225                 230                 235                 240

Ser Cys Ser Val Met His Glu Ala Leu His Asn His Tyr Thr Gln Lys
                245                 250                 255

Ser Leu Ser Leu Ser Pro Gly Lys Gly Gly Gly Gly Ser Gly Gly Gly
            260                 265                 270

Gly Ser Gly Gly Gly Gly Ser Gly Gly Gly Gly Ser Pro Gly Leu Pro
        275                 280                 285

Pro Ala Pro Pro Glu Pro Pro Gly Ile Leu Ala Pro Gln Pro Pro Asp
        290                 295                 300

Val Gly Ser Ser Asp Pro Leu Ser Met Val Gly Pro Ser Gln Gly Arg
305                 310                 315                 320

Ser Pro Ser Tyr Ala Ser
                325

<210> SEQ ID NO 466
<211> LENGTH: 493
<212> TYPE: PRT
<213> ORGANISM: Artificial Sequence
<220> FEATURE:
<223> OTHER INFORMATION: synthetic

<400> SEQUENCE: 466

Gln Val Gln Leu Val Glu Ser Gly Gly Gly Val Val Gln Pro Gly Arg
1               5                   10                  15

Ser Leu Arg Leu Ser Cys Val Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Phe Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Ala Asp Thr Ala Val Tyr Tyr Cys
                85                  90                  95

Ala Lys Asp Arg Ser Asn Tyr Tyr Tyr Phe Gly Met Asp Val Trp Gly
            100                 105                 110

Gln Gly Thr Thr Val Thr Val Ser Ser Gly Gly Gly Gly Ser Gly Gly
        115                 120                 125

Gly Gly Ser Gly Gly Gly Gly Ser Asp Ile Val Met Thr Gln Thr Pro
    130                 135                 140

Leu Ser Leu Pro Val Thr Pro Gly Glu Pro Ala Ser Ile Ser Cys Arg
145                 150                 155                 160

Ser Ser Gln Ser Leu Leu Asp Ser Asp Asp Gly Asn Thr Tyr Leu Asp
                165                 170                 175

Trp Tyr Leu Gln Lys Pro Gly Gln Ser Pro Gln Leu Leu Ile Tyr Thr
            180                 185                 190

Leu Ser Tyr Arg Ala Ser Gly Val Pro Asp Arg Phe Ser Gly Ser Gly
        195                 200                 205
```

```
Ser Gly Thr Asp Phe Thr Leu Lys Ile Ser Arg Val Glu Ala Glu Asp
210                 215                 220
Val Gly Val Tyr Tyr Cys Met Gln Arg Ile Glu Phe Pro Leu Thr Phe
225                 230                 235                 240
Gly Gly Gly Thr Lys Val Glu Ile Lys Gly Gly Gly Ser Gly Gly
                245                 250                 255
Gly Gly Ser Gly Gly Gly Ser Glu Ser Lys Tyr Gly Pro Pro Cys
            260                 265                 270
Pro Pro Cys Pro Ala Pro Glu Phe Leu Gly Gly Pro Ser Val Phe Leu
            275                 280                 285
Phe Pro Pro Lys Pro Lys Asp Thr Leu Met Ile Ser Arg Thr Pro Glu
    290                 295                 300
Val Thr Cys Val Val Val Asp Val Ser Gln Glu Asp Pro Glu Val Gln
305                 310                 315                 320
Phe Asn Trp Tyr Val Asp Gly Val Glu Val His Asn Ala Lys Thr Lys
                325                 330                 335
Pro Arg Glu Glu Gln Phe Asn Ser Thr Tyr Arg Val Val Ser Val Leu
            340                 345                 350
Thr Val Leu His Gln Asp Trp Leu Asn Gly Lys Glu Tyr Lys Cys Lys
            355                 360                 365
Val Ser Asn Lys Gly Leu Pro Ser Ser Ile Glu Lys Thr Ile Ser Lys
370                 375                 380
Ala Lys Gly Gln Pro Arg Glu Pro Gln Val Tyr Thr Leu Pro Pro Ser
385                 390                 395                 400
Gln Glu Glu Met Thr Lys Asn Gln Val Ser Leu Thr Cys Leu Val Lys
                405                 410                 415
Gly Phe Tyr Pro Ser Asp Ile Ala Val Glu Trp Glu Ser Asn Gly Gln
            420                 425                 430
Pro Glu Asn Asn Tyr Lys Thr Thr Pro Pro Val Leu Asp Ser Asp Gly
            435                 440                 445
Ser Phe Phe Leu Tyr Ser Arg Leu Thr Val Asp Lys Ser Arg Trp Gln
    450                 455                 460
Glu Gly Asn Val Phe Ser Cys Ser Val Met His Glu Ala Leu His Asn
465                 470                 475                 480
His Tyr Thr Gln Lys Ser Leu Ser Leu Ser Leu Gly Lys
                485                 490

<210> SEQ ID NO 467
<211> LENGTH: 417
<212> TYPE: PRT
<213> ORGANISM: Artificial Sequence
<220> FEATURE:
<223> OTHER INFORMATION: synthetic

<400> SEQUENCE: 467

Glu Ser Lys Tyr Gly Pro Pro Cys Pro Pro Cys Pro Ala Pro Glu Phe
1               5                   10                  15
Leu Gly Gly Pro Ser Val Phe Leu Phe Pro Pro Lys Pro Lys Asp Thr
                20                  25                  30
Leu Met Ile Ser Arg Thr Pro Glu Val Thr Cys Val Val Val Asp Val
            35                  40                  45
Ser Gln Glu Asp Pro Glu Val Gln Phe Asn Trp Tyr Val Asp Gly Val
    50                  55                  60
Glu Val His Asn Ala Lys Thr Lys Pro Arg Glu Glu Gln Phe Asn Ser
65                  70                  75                  80
```

```
Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
            115                 120                 125

Gln Val Tyr Thr Leu Pro Pro Ser Gln Glu Glu Met Thr Lys Asn Gln
            130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
            165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
            195                 200                 205

Val Met His Glu Ala Leu His Asn His Tyr Thr Gln Lys Ser Leu Ser
210                 215                 220

Leu Ser Leu Gly Lys Gly Gly Gly Ser Gly Gly Gly Ser Gly
225                 230                 235                 240

Gly Gly Gly Ser Leu Leu Gln Phe Gly Gln Val Arg Gln Arg Tyr
            245                 250                 255

Leu Tyr Thr Asp Asp Ala Gln Gln Thr Glu Ala His Leu Glu Ile Arg
            260                 265                 270

Glu Asp Gly Thr Val Gly Gly Ala Ala Asp Gln Ser Pro Glu Ser Leu
            275                 280                 285

Leu Gln Leu Lys Ala Leu Lys Pro Gly Val Ile Gln Ile Leu Gly Val
            290                 295                 300

Lys Thr Ser Arg Phe Leu Cys Gln Arg Pro Asp Gly Ala Leu Tyr Gly
305                 310                 315                 320

Ser Leu His Phe Asp Pro Glu Ala Cys Ser Phe Arg Glu Leu Leu Leu
            325                 330                 335

Glu Asp Gly Tyr Asn Val Tyr Gln Ser Glu Ala His Gly Leu Pro Leu
            340                 345                 350

His Leu Pro Gly Asn Lys Ser Pro His Arg Asp Pro Ala Pro Arg Gly
            355                 360                 365

Pro Ala Arg Phe Leu Pro Leu Pro Gly Leu Pro Pro Ala Pro Pro Glu
            370                 375                 380

Pro Pro Gly Ile Leu Ala Pro Gln Pro Pro Asp Val Gly Ser Ser Asp
385                 390                 395                 400

Pro Leu Ser Met Val Gly Pro Ser Gln Gly Arg Ser Pro Ser Tyr Ala
            405                 410                 415

Ser
```

<210> SEQ ID NO 468
<211> LENGTH: 4
<212> TYPE: PRT
<213> ORGANISM: Artificial Sequence
<220> FEATURE:
<223> OTHER INFORMATION: synthetic

<400> SEQUENCE: 468

Gly Gly Gly Ser
1

```
<210> SEQ ID NO 469
<211> LENGTH: 4
<212> TYPE: PRT
<213> ORGANISM: Artificial Sequence
<220> FEATURE:
<223> OTHER INFORMATION: synthetic

<400> SEQUENCE: 469

Ser Gly Gly Gly
1

<210> SEQ ID NO 470
<211> LENGTH: 5
<212> TYPE: PRT
<213> ORGANISM: Artificial Sequence
<220> FEATURE:
<223> OTHER INFORMATION: synthetic

<400> SEQUENCE: 470

Gly Gly Gly Gly Ser
1               5

<210> SEQ ID NO 471
<211> LENGTH: 5
<212> TYPE: PRT
<213> ORGANISM: Artificial Sequence
<220> FEATURE:
<223> OTHER INFORMATION: synthetic

<400> SEQUENCE: 471

Ser Gly Gly Gly Gly
1               5

<210> SEQ ID NO 472
<211> LENGTH: 6
<212> TYPE: PRT
<213> ORGANISM: Artificial Sequence
<220> FEATURE:
<223> OTHER INFORMATION: synthetic

<400> SEQUENCE: 472

Gly Gly Gly Gly Gly Ser
1               5

<210> SEQ ID NO 473
<211> LENGTH: 6
<212> TYPE: PRT
<213> ORGANISM: Artificial Sequence
<220> FEATURE:
<223> OTHER INFORMATION: synthetic

<400> SEQUENCE: 473

Ser Gly Gly Gly Gly Gly
1               5

<210> SEQ ID NO 474
<211> LENGTH: 7
<212> TYPE: PRT
<213> ORGANISM: Artificial Sequence
<220> FEATURE:
<223> OTHER INFORMATION: synthetic

<400> SEQUENCE: 474

Gly Gly Gly Gly Gly Gly Ser
1               5
```

```
<210> SEQ ID NO 475
<211> LENGTH: 7
<212> TYPE: PRT
<213> ORGANISM: Artificial Sequence
<220> FEATURE:
<223> OTHER INFORMATION: synthetic

<400> SEQUENCE: 475

Ser Gly Gly Gly Gly Gly Gly
1               5

<210> SEQ ID NO 476
<211> LENGTH: 12
<212> TYPE: PRT
<213> ORGANISM: Artificial Sequence
<220> FEATURE:
<223> OTHER INFORMATION: synthetic

<400> SEQUENCE: 476

Gly Gly Gly Ser Gly Gly Gly Ser Gly Gly Gly Ser
1               5                   10
```